(12) United States Patent
Old et al.

(10) Patent No.: US 7,589,180 B2
(45) Date of Patent: Sep. 15, 2009

(54) SPECIFIC BINDING PROTEINS AND USES THEREOF

(75) Inventors: Lloyd J. Old, New York, NY (US); Terrance Grant Johns, Melbourne (AU); Con Panousis, Melbourne (AU); Andrew Mark Scott, Kew (AU); Christoph Renner, Homburg/Saar (DE); Gerd Ritter, New York, NY (US); Achim Jungbluth, New York, NY (US); Elisabeth Stockert, New York, NY (US); Peter Collins, Cambridge (GB); Webster K. Cavenee, Del Mar, CA (US); Huei-Jen Su Huang, Rancho Santa Fe, CA (US); Antony Wilks Burgess, Camberwell (AU); Edouard Collins Nice, St Kilda (AU)

(73) Assignee: Abbott Laboratories Inc., Abbott Park, IL (US)

( * ) Notice: Subject to any disclaimer, the term of this patent is extended or adjusted under 35 U.S.C. 154(b) by 413 days.

(21) Appl. No.: 10/145,598

(22) Filed: May 13, 2002

(65) Prior Publication Data

US 2009/0137782 A1    May 28, 2009

Related U.S. Application Data

(60) Provisional application No. 60/290,410, filed on May 11, 2001, provisional application No. 60/326,019, filed on Sep. 28, 2001, provisional application No. 60/342,258, filed on Dec. 21, 2001.

(51) Int. Cl.
*C07K 16/28* (2006.01)
(52) U.S. Cl. ............... 530/387.3; 530/350; 530/387.1; 530/387.7; 530/388.8
(58) Field of Classification Search ............ 530/387.9, 530/387.7, 387.3, 388.22, 388.8, 389.7, 300, 530/350, 387.1
See application file for complete search history.

(56) References Cited

U.S. PATENT DOCUMENTS

| 5,457,105 A | 10/1995 | Barker |
| 5,942,602 A | 8/1999 | Wels et al. |
| 6,217,866 B1 | 4/2001 | Schlessinger et al. |

OTHER PUBLICATIONS

Greenspan et al. (Nature Biotechnology. 1999; 7: 936-937).*
Jungbluth et al. (Proc. Natl. Acad. Sci. USA. Jan. 21, 2003; 100 (2): 639-644).*
Stancoviski et al. (Proceedings of the National Academy of Science USA. 1991; 88: 8691-8695).*
Mariuzza et al. (Annu. Rev. Biophys. Biophys. Chem. 1987; 16: 139-159).*
Gussow et al. (Methods in Enzymology. 1991; 203: 99-121).*
Giusti et al. (Proc. Natl. Acad. Sci. USA. May 1987; 84 (9): 2926-2930).*
Chien et al. (Proc. Natl. Acad. Sci. USA. Jul. 1989; 86 (14): 5532-5534).*
Caldas et al. (Mol. Immunol. May 2003; 39 (15): 941-952).*
Mishima et al. (Cancer Res. Jul. 15, 2001; 61: 5349-5354).*
Gill et al. (Somat. Cell Mol. Genet. Jul. 1985; 11 (4): 309-318).*
Buss et al. (Proc. Natl. Acad. Sci. U S A. Apr. 1982; 79 (8): 2574-2578).*
Casset et al. (Biochem. Biophys. Res. Commun. Jul. 18, 2003; 307 (1): 198-205).*
MacCallum et al. (J. Mol. Biol. Oct. 11, 1996; 262 (5): 732-745).*
Holm et al. (Mol. Immunol. Feb. 2007; 44 (6): 1075-1084).*
De Pascalis et al. (J. Immunol. 2002; 169 (6): 3076-3084).*
Wu et al. (J. Mol. Biol. Nov. 19, 1999; 294 (1): 151-162).*
Luwor et al. (Cancer Res. Jul. 15, 2001; 61: 5355-5361).*
George et al. (Circulation, 1998; 97: 900-906).*
Chao et al. (J. Mol. Biol. 2004; 342: 539-550).*
Johns et al. (J. Biol. Chem. Jul. 16, 2004; 279 (20): 30375-30384).*
Johns et al. (FASEB J. May 2005; Epub. Mar. 17, 2005, pp. 1-18).*
Henry et al. (Cancer Res. Nov. 1, 2004; 64: 7995-8001).*
Riemer et al. (Mol. Immunol. 2005; 42: 1121-1124).*
Xu et al. (Int. J. Cancer. 1993; 53: 401-408).*
Jiang et al. (J. Biol. Chem. Feb. 11, 2005; 280 (6): 4656-4662).*
Boyer et al. (Int. J. Cancer. 1999; 82: 525-531).*
Press et al. (J. Immunol. Dec. 15, 1988; 141 (12): 4410-4417).*
Cochran et al. (J. Immunol. Meth. 2004; 287: 147-158).*
Reiter et al. (Genomics. 2001; 71: 1-20).*
Sivasubramanian et al. (Structure. Mar. 2006; 14 (3): 401-414).*
Perera et al. (Neoplasia. Dec. 2007; 9 (12): 1099-1110).*
Baselga, J. et al (1993) J Natl. Cancer Inst. 85:1327-1333.
Baselga, J. et al (2000) J Clin Oncol. 18:904-914.
Ekstrand, A.J. et al (1992) Proc Natl Acad Sci U.S.A. 89:4309-4313.
Faillot, T. et al (1996) Neurosurgery. 39:478-483.
Fan, Z. et al (1993) Cancer Res. 53:4637-4642.
Foulon, C.F. et al (2000) Cancer Res. 60(16):4453-4460.
Garcia de Palazzo, I.E. et al (1993) Cancer Res. 53:3217-3220.
Goldstein, N.I. et al (1995) Clin Cancer Res. 1:1311-1318.
Hills, D. et al (1995) Int J Cancer. 63:537-543.
Huang et al (2000) Clin Cancer Res. 6(6):2166-2174.
Humphrey, P.A. et al (1990) Proc Natl Acad Sci U.S.A. 87:4207-4211.

(Continued)

*Primary Examiner*—Stephen L Rawlings
(74) *Attorney, Agent, or Firm*—Irene M. Reininger

(57) ABSTRACT

The invention relates to specific binding members, particularly antibodies and active fragments thereof, which recognize an aberrant post-translationally modified, particularly an aberrant glycosylated form of the EGFR. The binding members, particularly antibodies and fragments thereof, of the invention do not bind to EGFR on normal cells in the absence of amplification of the wild-type gene and are capable of binding the de2-7 EGFR at an epitope which is distinct from the junctional peptide. Antibodies of this type are exemplified by the novel antibody 806 whose VH and VL sequences are illustrated as SEQ ID NOs: 2 and 4 and chimeric antibodies thereof as exemplified by ch806.

4 Claims, 52 Drawing Sheets

OTHER PUBLICATIONS

Masui, H. et al (1984) Cancer Res. 44:1002-1007.
Milas, L. et al (2000) Clin Cancer Res. 6(2):701-708.
Moscatello, D.K. et al (1995) Cancer Res. 55:5536-5539.
Okamoto, S. et al (1996) Br J Cancer. 73:1366-1372.
Olapade-Olaopa, E.O. et al (2000) Br J Cancer 82:186-194.
Reist, C.J. et al (1995) Cancer Res. 55:4375-4382.
Sato, J.D. et al (1983) Mol Biol Med 1(5):511-539.
Seymour, L. et al (1999) Cancer Treat Rev. 25:301-312.
Sturgis, E.M. et al (1994) Otolaryngol Head Neck Surg. 111:633-643.
Sugawa, N. et al (1990) Proc Natl Acad Sci U.S.A. 87:8602-8606.
Waterfield, M.D. et al (1982) J. Cell. Biochem 20(2):149-161.
Wikstrand, C.J. et al (1995) Cancer Res. 55:3140-3148.
Wikstrand, C.J. et al (1997) Cancer Res. 57:4130-4140.
Wikstrand, C.J. et al (1998) J Neurovirol. 4:148-158.
Wong, A.J. et al (1992) Proc Natl Acad Sci U.S.A. 89:2965-2969.
Yamazaki, H. et al (1988) Mol Cell Biol. 8:1816-1820.
Yamazaki, H. et al (1990) Jpn J Cancer Res. 81:773-779.
Johns et al; Ludwig Annual Branch Report; pp. 118-119; Mar. 4, 2000, Ludwig Institute for Cancer Research The 1998 Annual Report Available on the Internet.

* cited by examiner

D806

DH8.3

528

D806

DH8.3

528

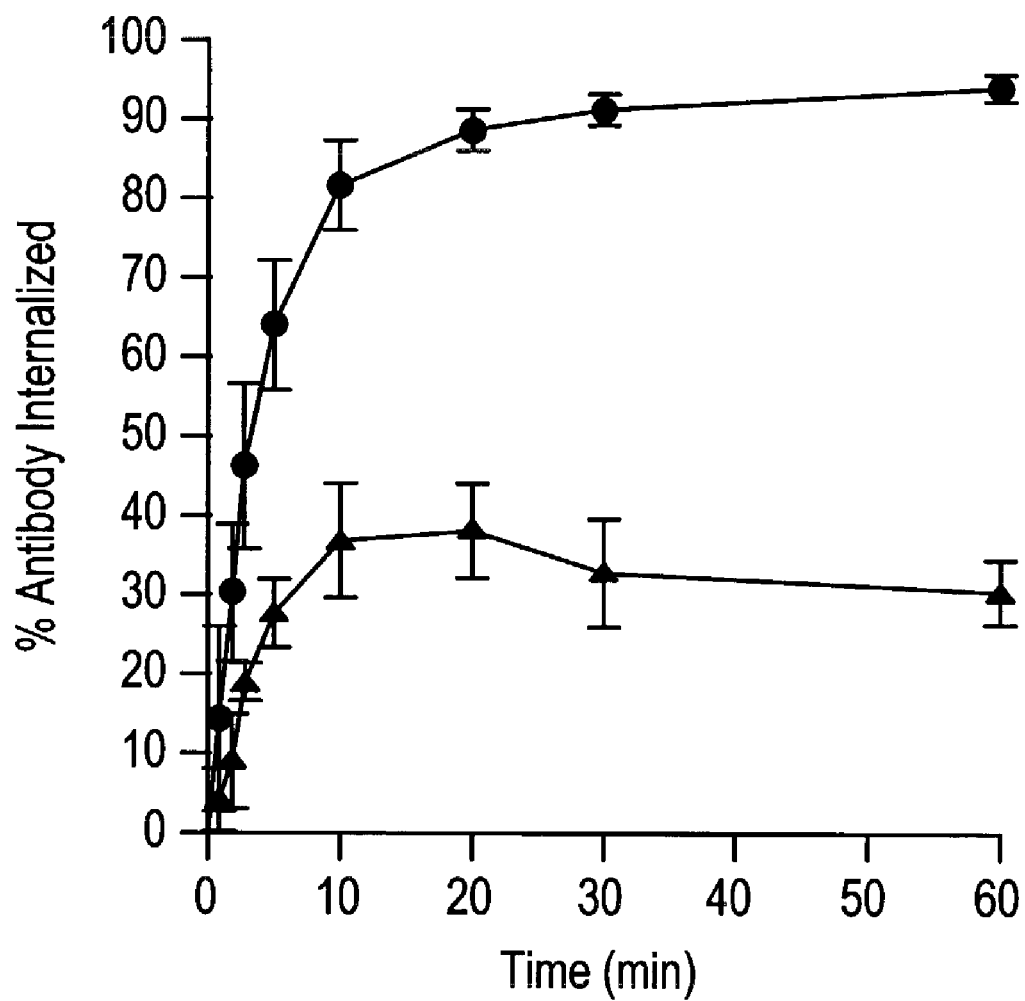

mAb 806

DH8.3

528

Days Post Inoculation

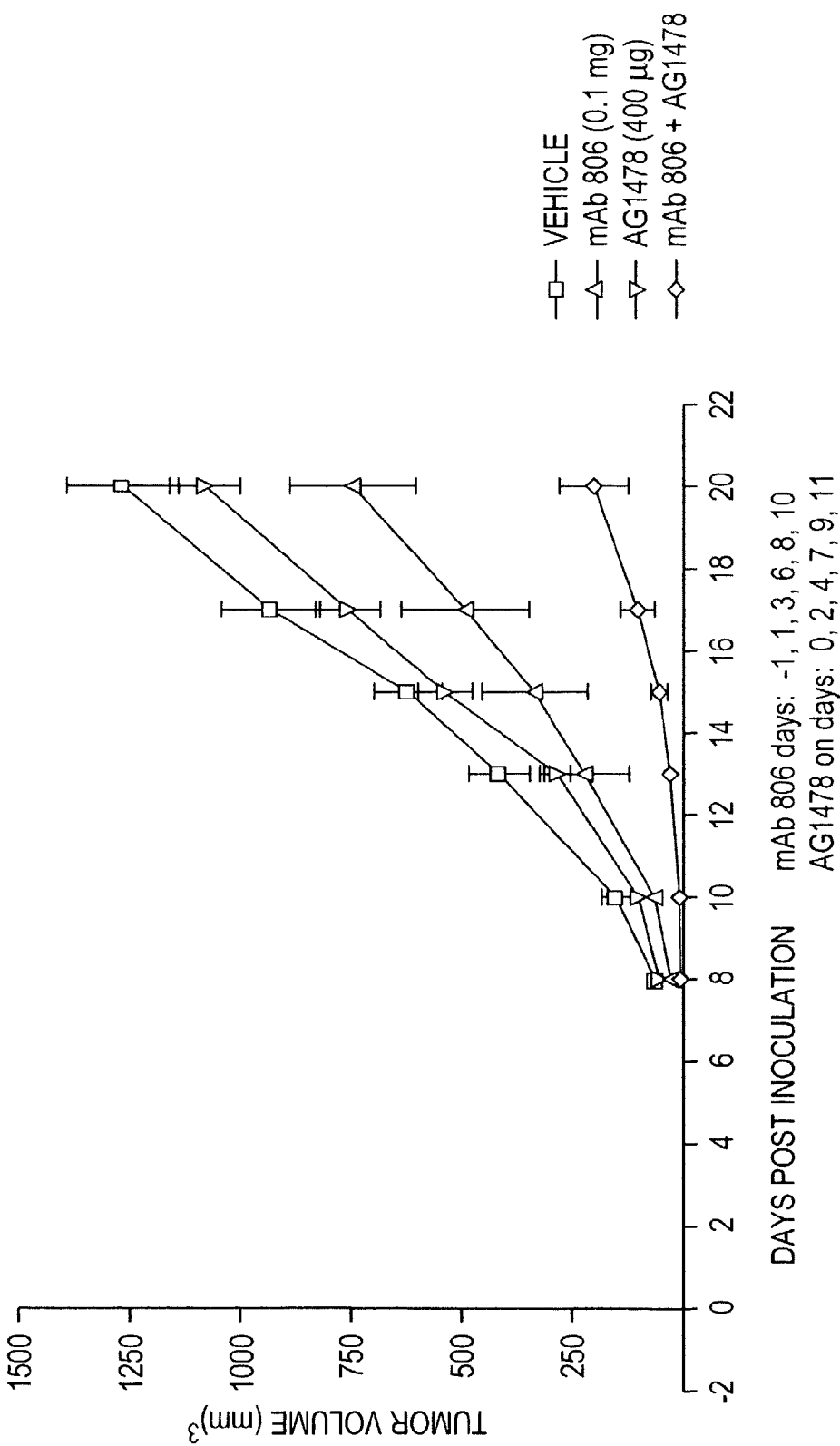

FIG. 14

DNA and Protein Sequence of 806 VH and Signal Peptide

DNA Sequence

<u>ATGAGAGTGCTGATTCTTTTGTGGCTGTTCACAGCCTTCCTGGTGTCCTGTCT</u>
<u>GATGTGC</u>AGCTTCAGGAGTCGGGACCTAGCCTGGTGAAACCTTCTCAGTCTCT
GTCCCTCACCTGCACTGTCACTGGCTACTCAATCACCAGTGATTTTGCCTGGA
ACTGGATCCGGCAGTTTCCAGGAAACAAGCTGGAGTGGATGGGCTACATAAG
TTATAGTGGTAACACTAGGTAACAACCCATCTCCAAAAGTCGAATCTCTATCA
CTCGAGACACATCCAAGAACCAATTCTTCCTGCAGTTGAATTCTGTGACTATT
GAGGACACAGCCACCATATTACTGTGTAACGGCGGGACGCGGGTTTCCTTATT
GGGGCCAAGGGACTCTGGTCACACTGTCTCTGCA

Underlined area is signal peptide.

Remaining sequence is 806 VH region.

Protein Sequence

⌐→ VH

<u>MRVLILLWLFTAFPGVLS</u>DVQLQESGPSLVKPSQSLSLTC
TVTGYSITSDFAWNWIRQFPGNKLEWMGYISYSGNTRYN
PSLKSRISITRDTSKNQFFLQLNSVTIEDTATYYCVTAGRG
FPYWGQGTLVTVSA

FIG. 15

DNA and Protein Sequence of 806 VL and Signal Peptide

DNA Sequence

<u>ATGGTGTCCACAGCTCAGTTCCTTGCATTCTTGTTGCTTTGGTTTCCAGGTGCA</u>
<u>AGATGT</u>GACATCCTGATGACCCAAATCTCCATCCTCCATGTCTGTATCTCTGGG
AGACACAGTCAGCATCACTTGCCATTCAAGTCAGGACATTAACAGTAATATA
GGGTGGTTGCAGCAGAGACCAGGGAAATCATTTAAGGGCCTGATCTATCATG
GAACCAACTTGGACGATGAAGTTCCATCAAGGTTCAGTGGCAGTGGATCTGG
AGCCGATTATTCTCTCACCATCAGCAGCCTGGAATCTGAAGATTTTGCAGACT
ATTACTGTGTACAGTATGCTCAGTTTCCGTGGACGTTCGGTGGAGGCACCAAG
CTGGAAATCAAACGT

Underlined area is signal peptide.

Remaining sequence is 806 VL region.

Protein Sequence

<u>MVSTAQFLAFLLLWFPGARC</u>DILMTQSPSSMSVSLGDTVS
ITCHSSQDINSNIGWLQQRPGKSFKGLIYHGTNLDDEVPSR
FSGSGSGADYSLTISSLESEDFADYYCVQYAQFPWTFGGG
TKLEIKR (VL arrow points to D after signal peptide)

M806: DVQLQESGPSLVKPSQSLSLTCTVTGYSITSDFAWNW (1-36), with H1 = GYSITSDFAWN (26-35A)

M806: IRQFPGNKLEWMGYIS-YSGNTRYNPSLKSRISITRD (37-72), with H2 = GYIS-YSGNTRYNPSLK (49-64)

M806: TSKNQFFLQLNSVTIEDTATYYCVTAGRGFPYWGQGT (73-107), with H3 = VTAGRGFPYW (93-103)

M806: LVTVSA (108-113)

FIG. 17 mAb-806 V_L

M806 (positions 1–37): D I L M T Q S P S S M S V S L G D T V S I T C [H S S Q D I N S N I G] W L Q (H1: residues 24–34)

M806 (positions 38–74): Q R P G K S F K G L I Y [H G I N L D D] E V P S R F S G S G S G A D Y S L T (H2: residues 50–56)

M806 (positions 75–108): I S S L E S E D F A D Y Y C [V Q Y A Q F P W T] F G G G T K L E I K R (H3: residues 89–97)

FIG. 20
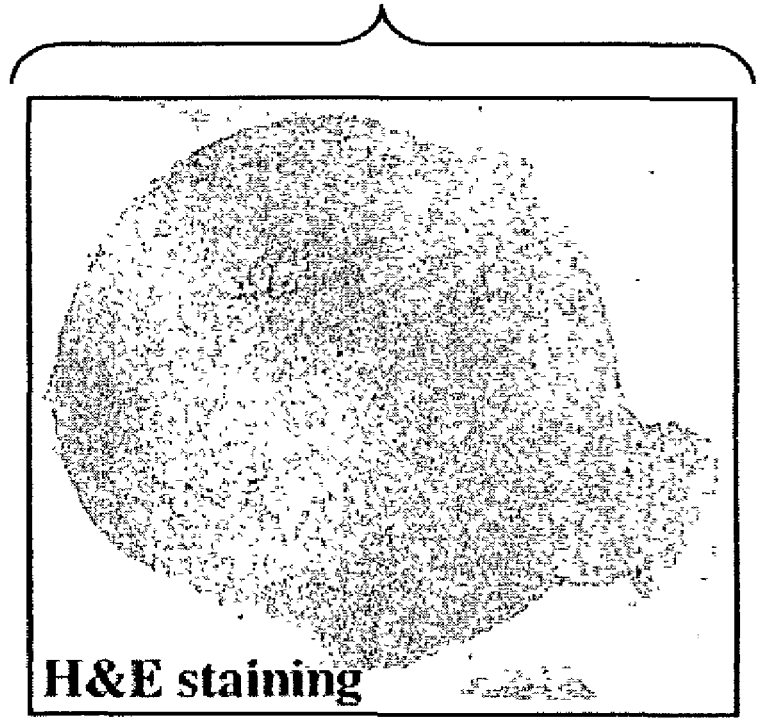
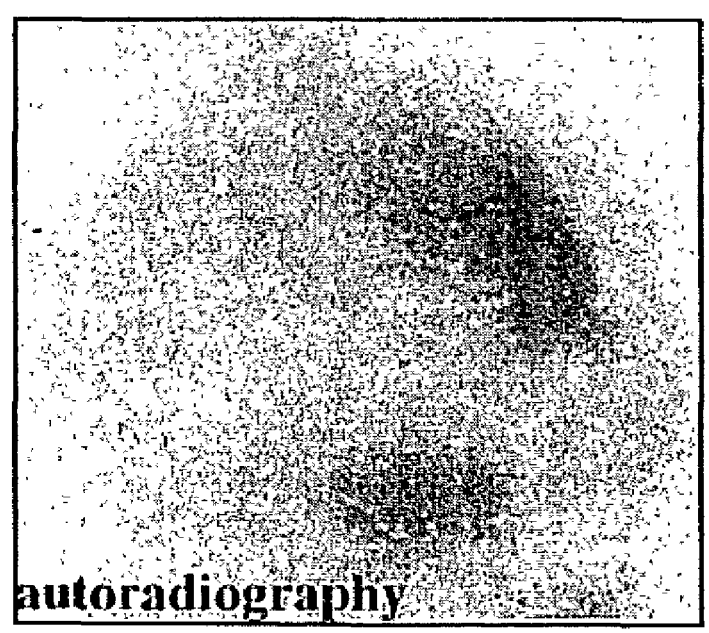

U87MG.ΔEGFR — Control / mAb 806
100 ± 17.0%   11.2 ± 3.2%***

LN-Z308.ΔEGFR — Control / mAb 806
100 ± 13.0%   4.7 ± 0.5%***

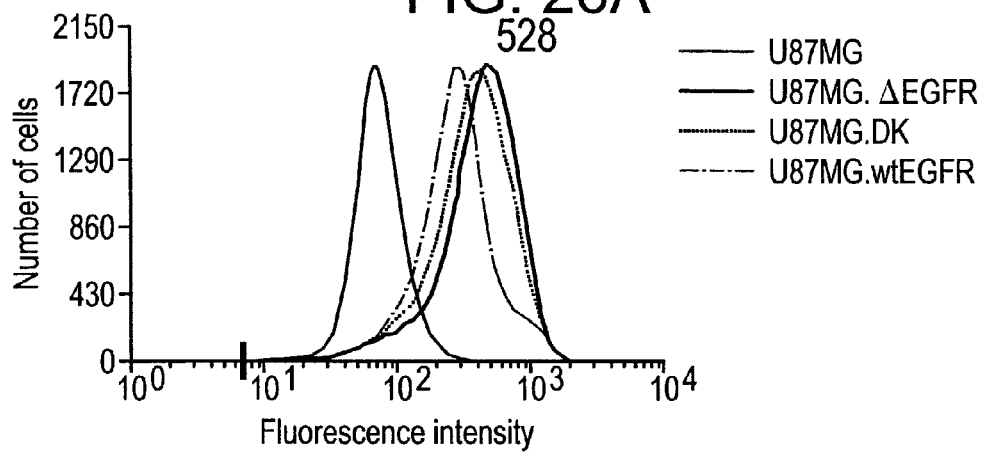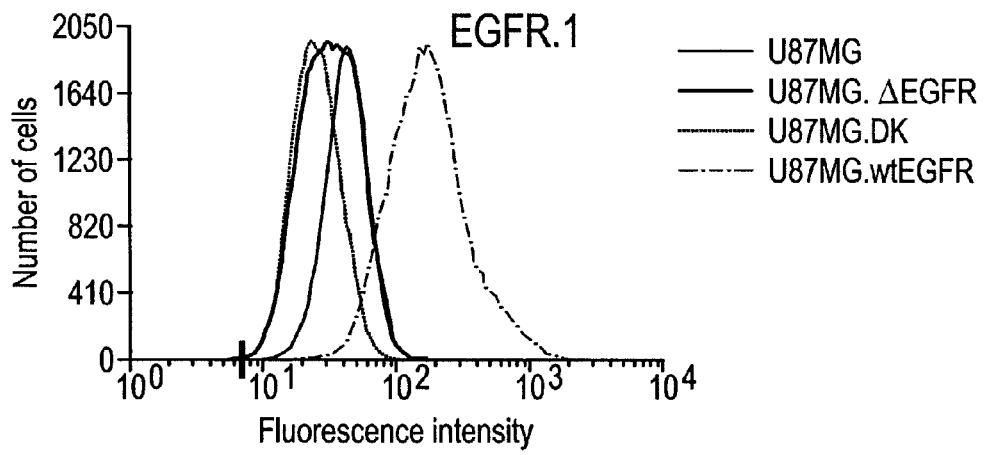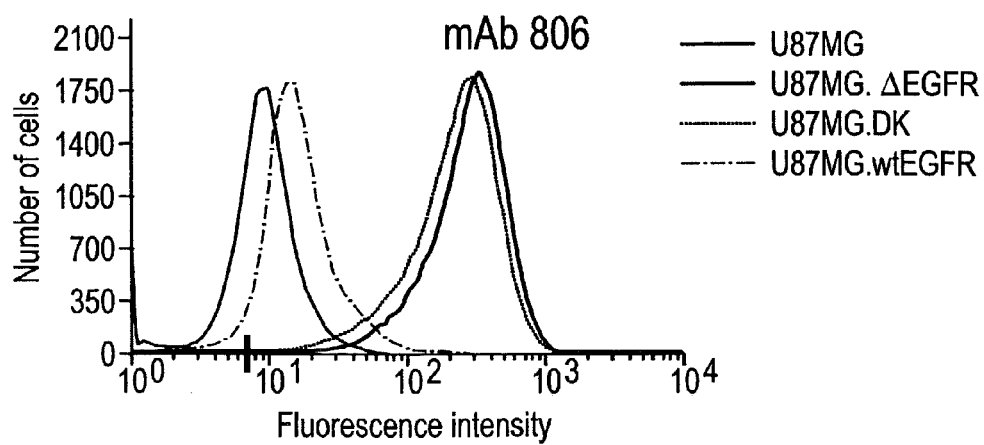

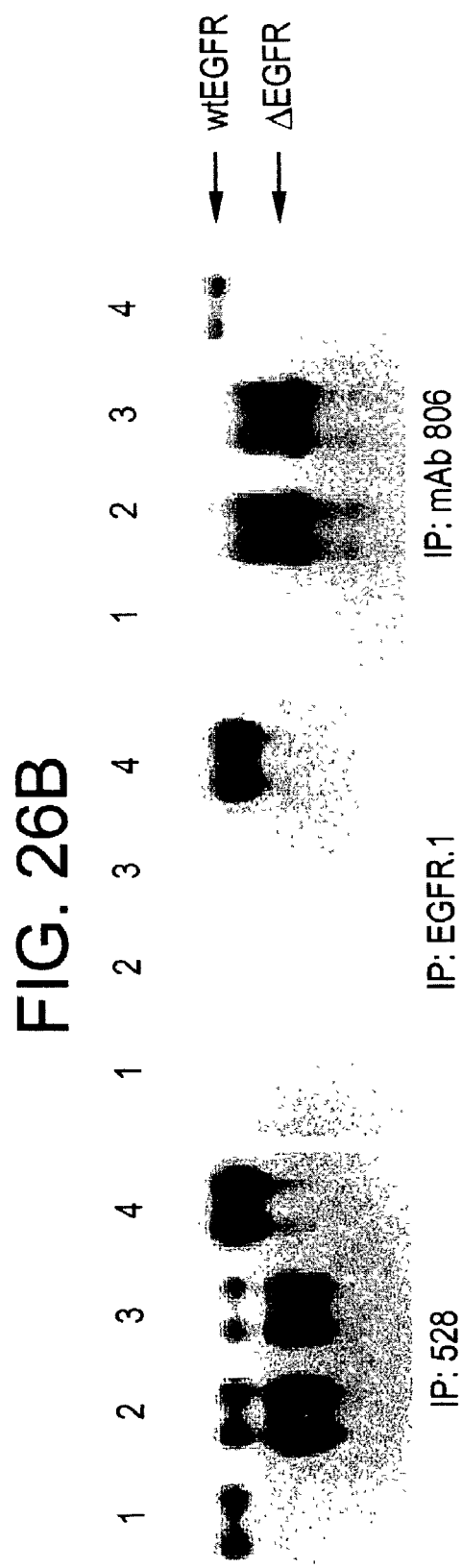

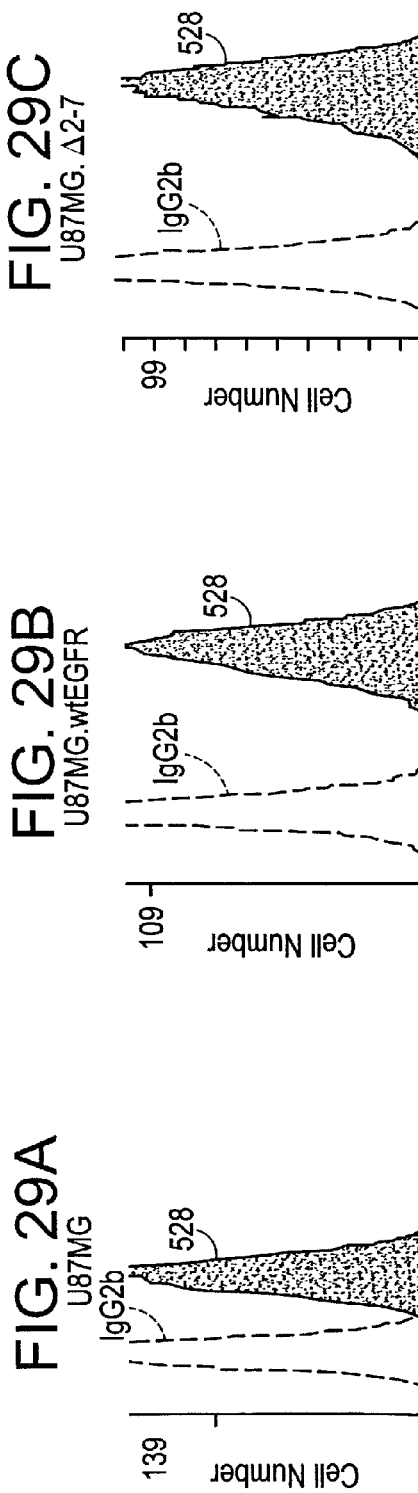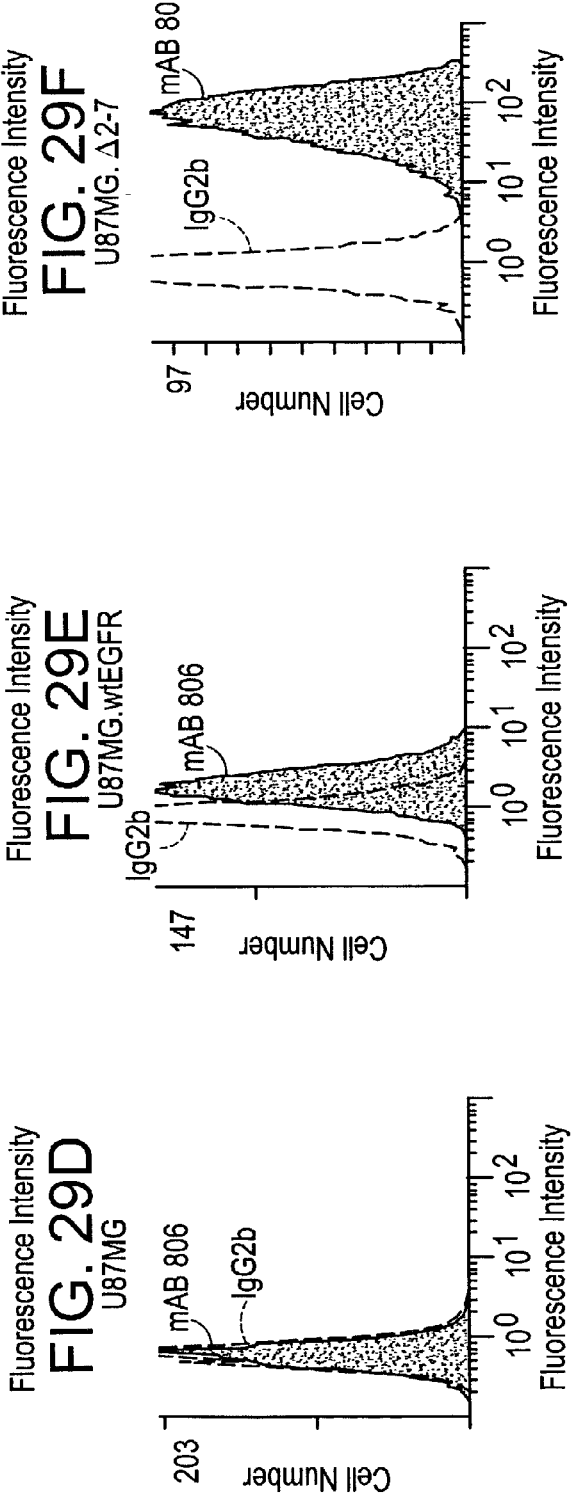

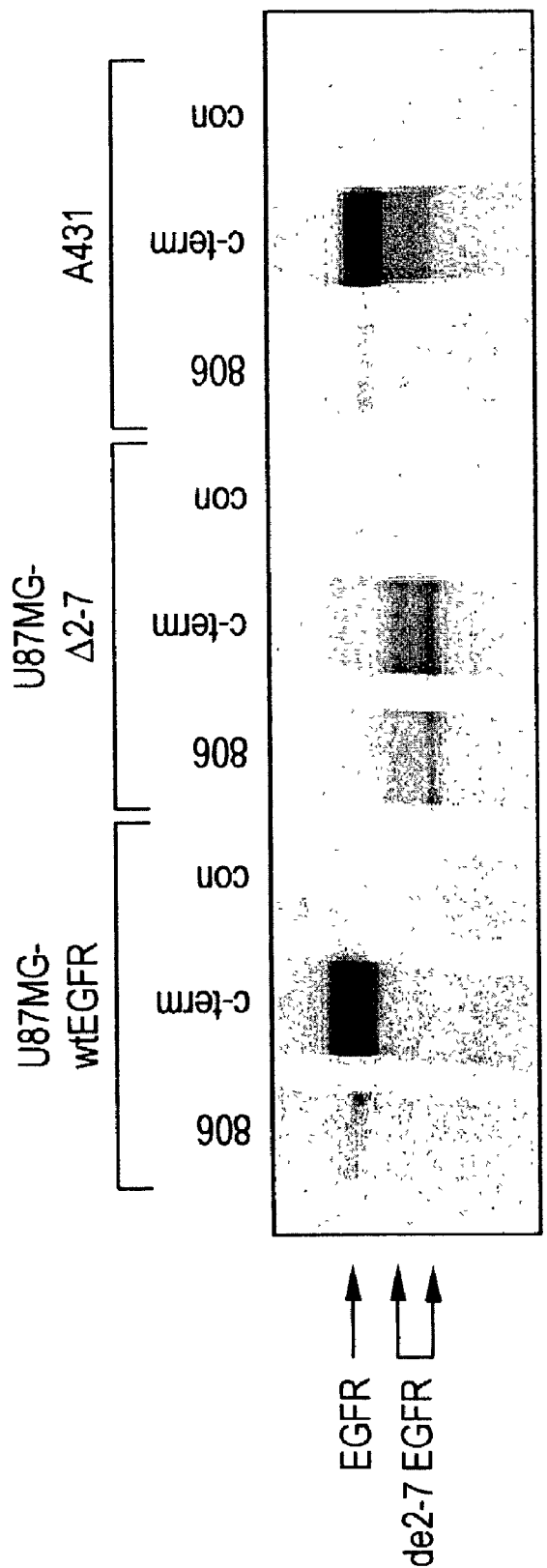

- ○ LMH-11 pre
- ▽ LMH-14 pre
- □ LMH-12 pre
- ◇ LMH-13 pre
- △ ch806 alone
- ○ Conjugate
- ○ Substrate

- ○ LMH-11 clone
- ▽ LMH-12 clone
- □ LMH-13 clone
- ◇ ch806 alone
- △ Conjugate
- ○ Substrate ○ sEGFR Y ch806

Y Anti-idiotype mAb

Y Goat anti-hIgG-HRP

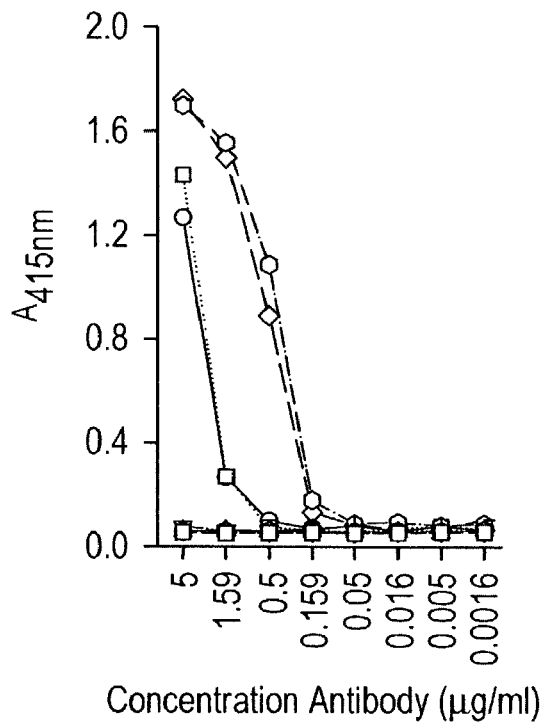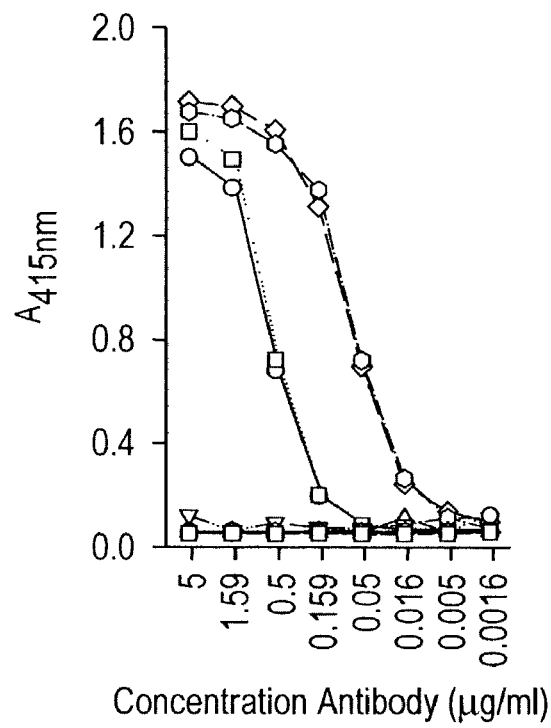
FIG. 42A
FIG. 42B

- ch806-Serum
- ch806-1%FCS/Media
- h3S193-Serum
- h3S193-1%FCS/mediaM
- m806-Serum
- m806-1%FCS/Media
- m3S193-Serum
- m3S193-1%FCS/MediaM
- Avidin-HRP
- ABTS Substrate

SEQUENCE LISTING

<160> NUMBER OF SEQ ID NOS: 14

<210> SEQ ID NO 1
<211> LENGTH: 402
<212> TYPE: DNA
<213> ORGANISM: Mus musculus

<400> SEQUENCE: 1

```
atgagagtgc tgattctttt gtggctgttc acagcctttc ctggtgtcct gtctgatgtg      60
cagcttcagg agtcgggacc tagcctggtg aaaccttctc agtctctgtc cctcacctgc     120
actgtcactg gctactcaat caccagtgat tttgcctgga actggatccg gcagtttcca     180
ggaaacaagc tggagtggat gggctacata agttatagtg gtaacactag gtacaaccca     240
tctctcaaaa gtcgaatctc tatcactcga gacacatcca agaaccaatt cttcctgcag     300
ttgaattctg tgactattga ggacacagcc acatattact gtgtaacggc gggacgcggg     360
tttccttatt ggggccaagg gactctggtc actgtctctg ca                        402
```

<210> SEQ ID NO 2
<211> LENGTH: 134
<212> TYPE: PRT
<213> ORGANISM: Mus musculus

<400> SEQUENCE: 2

Met Arg Val Leu Ile Leu Leu Trp Leu Phe Thr Ala Phe Pro Gly Val
 1               5                  10                  15

Leu Ser Asp Val Gln Leu Gln Glu Ser Gly Pro Ser Leu Val Lys Pro
            20                  25                  30

Ser Gln Ser Leu Ser Leu Thr Cys Thr Val Thr Gly Tyr Ser Ile Thr

-continued

```
            35                  40                  45
Ser Asp Phe Ala Trp Asn Trp Ile Arg Gln Phe Pro Gly Asn Lys Leu
    50                  55                  60

Glu Trp Met Gly Tyr Ile Ser Tyr Ser Gly Asn Thr Arg Tyr Asn Pro
 65                  70                  75                  80

Ser Leu Lys Ser Arg Ile Ser Ile Thr Arg Asp Thr Ser Lys Asn Gln
                85                  90                  95

Phe Phe Leu Gln Leu Asn Ser Val Thr Ile Glu Asp Thr Ala Thr Tyr
            100                 105                 110

Tyr Cys Val Thr Ala Gly Arg Gly Phe Pro Tyr Trp Gly Gln Gly Thr
        115                 120                 125

Leu Val Thr Val Ser Ala
    130
```

<210> SEQ ID NO 3
<211> LENGTH: 384
<212> TYPE: DNA
<213> ORGANISM: Mus musculus

<400> SEQUENCE: 3

```
atggtgtcca cagctcagtt ccttgcattc ttgttgcttt ggtttccagg tgcaagatgt    60
gacatcctga tgacccaatc tccatcctcc atgtctgtat ctctgggaga cacagtcagc   120
atcacttgcc attcaagtca ggacattaac agtaatatag ggtggttgca gcagagacca   180
gggaaatcat ttaagggcct gatctatcat ggaaccaact tggacgatga agttccatca   240
aggttcagtg gcagtggatc tggagccgat tattctctca ccatcagcag cctggaatct   300
gaagattttg cagactatta ctgtgtacag tatgctcagt ttccgtggac gttcggtgga   360
ggcaccaagc tggaaatcaa acgt                                          384
```

<210> SEQ ID NO 4
<211> LENGTH: 128
<212> TYPE: PRT
<213> ORGANISM: Mus musculus

<400> SEQUENCE: 4

```
Met Val Ser Thr Ala Gln Phe Leu Ala Phe Leu Leu Trp Phe Pro
  1               5                  10                  15

Gly Ala Arg Cys Asp Ile Leu Met Thr Gln Ser Pro Ser Ser Met Ser
                20                  25                  30

Val Ser Leu Gly Asp Thr Val Ser Ile Thr Cys His Ser Ser Gln Asp
            35                  40                  45

Ile Asn Ser Asn Ile Gly Trp Leu Gln Gln Arg Pro Gly Lys Ser Phe
    50                  55                  60

Lys Gly Leu Ile Tyr His Gly Thr Asn Leu Asp Asp Glu Val Pro Ser
 65                  70                  75                  80

Arg Phe Ser Gly Ser Gly Ser Gly Ala Asp Tyr Ser Leu Thr Ile Ser
                85                  90                  95

Ser Leu Glu Ser Glu Asp Phe Ala Asp Tyr Tyr Cys Val Gln Tyr Ala
            100                 105                 110

Gln Phe Pro Trp Thr Phe Gly Gly Thr Lys Leu Glu Ile Lys Arg
    115                 120                 125
```

<210> SEQ ID NO 5
<211> LENGTH: 13
<212> TYPE: PRT
<213> ORGANISM: Artificial Sequence

```
<220> FEATURE:
<223> OTHER INFORMATION: synthetic
      biotinylated at position 1

<400> SEQUENCE: 5

Leu Glu Glu Lys Lys Gly Asn Tyr Val Val Thr Asp His
 1               5                  10

<210> SEQ ID NO 6
<211> LENGTH: 13
<212> TYPE: PRT
<213> ORGANISM: Artificial Sequence
<220> FEATURE:
<223> OTHER INFORMATION: synthetic
      biotinylated at position 13

<400> SEQUENCE: 6

Leu Glu Glu Lys Lys Gly Asn Tyr Val Val Thr Asp His
 1               5                  10

<210> SEQ ID NO 7
<211> LENGTH: 6149
<212> TYPE: DNA
<213> ORGANISM: Artificial Sequence
<220> FEATURE:
<223> OTHER INFORMATION: synthetic vector

<400> SEQUENCE: 7
ctcgagagcg ggcagtgagc gcaacgcaat taatgtgagt tagctcactc attaggcacc      60
ccaggcttta cactttatgc tcccggctcg tatgttgtgt ggagattgtg agcggataac     120
aatttcacac agaattcgtg aggctccggt gcccgtcagt gggcagagcg cacatcgccc     180
acagtccccg agaagttggg gggaggggtc ggcaattgaa ccggtgccta gagaaggtgg     240
cgcggggtaa actgggaaag tgatgtcgtg tactggctcc gcctttttcc cgagggtggg     300
ggagaaccgt atataagtgc agtagtcgcc gtgaacgttc tttttcgcaa cgggtttgcc     360
gccagaacac aggtaagtgc cgtgtgtggt tcccgcgggc ctggcctctt tacgggttat     420
ggcccttgcg tgccttgaat tacttccacg ccctggctg cagtacgtga ttcttgatcc      480
cgagcttcgg gttggaagtg ggtgggagag ttcgaggcct tgcgcttaag gagccccttc     540
gcctcgtgct tgagttgagg cctggcctgg gcgctgggc cgccgcgtgc gaatctggtg      600
gcaccttcgc gcctgtctcg ctgctttcga taagtctcta gccatttaaa attttttgatg   660
acctgctgcg acgctttttt tctggcaaga tagtcttgta aatgcgggcc aagatctgca     720
cactggtatt tcggtttttg gggccgcggg cggcgacggg gcccgtgcgt cccagcgcac     780
atgttcggcg aggcggggcc tgcgagcgcg gccaccgaga tcggacgggg gtagtctca     840
agctggccgg cctgctctgg tgcctggcct cgcgccgccg tgtatcgccc cgccctgggc     900
ggcaaggctg gcccggtcgg caccagttgc gtgagcggaa agatgccgc ttccggccc       960
tgctgcaggg agctcaaaat ggaggacgcg gcgctcggga gagcgggcgg gtgagtcacc    1020
cacacaaagg aaaagggcct ttccgtcctc agccgtcgct tcatgtgact ccacggagta    1080
ccgggcgccg tccaggcacc tcgattagtt ctcgagcttt tggagtacgt cgtctttagg    1140
ttggggggag gggttttatg cgatggagtt tccccacact gagtgggtgg agactgaagt    1200
taggccagct tggcacttga tgtaattctc cttggaattt gccctttttg agtttggatc    1260
ttggttcatt ctcaagcctc agacagtggt tcaaagtttt tttcttccat ttcaggtgta    1320
cgcgtctcgg gaagctttag tttaaacgcc gccaccatgg tgtccacagc tcagttcctt    1380
```

```
gcattcttgt tgctttggtt tccaggtgca agatgtgaca tcctgatgac ccaatctcca   1440
tcctccatgt ctgtatctct gggagacaca gtcagcatca cttgccattc aagtcaggac   1500
attaacagta atataggggtg gttgcagcag agaccaggga atcatttaa gggcctgatc   1560
tatcatggaa ccaacttgga cgatgaagtt ccatcaaggt tcagtggcag tggatctgga   1620
gccgattatt ctctcaccat cagcagcctg aatctgaag attttgcaga ctattactgt   1680
gtacagcatg ctcagtttcc gtggacgttc ggtggaggca ccaagctgga aatcaaacgg   1740
gtgagtggat ccatctggga taagcatgct gttttctgtc tgtccctaac atgccctgtg   1800
attatgcgca acaacacac ccaagggcag aactttgtta cttaaacacc atcctgtttg   1860
cttctttcct caggaactgt ggctgcacca tctgtcttca tcttcccgcc atctgatgag   1920
cagttgaaat ctggaactgc ctctgttgtg tgcctgctga ataacttcta tcccagagag   1980
gccaaagtac agtggaaggt ggataacgcc ctccaatcgg gtaactccca ggagagtgtc   2040
acagagcagg acagcaagga cagcacctac agcctcagca gcaccctgac gctgagcaaa   2100
gcagactacg agaaacacaa agtctacgcc tgcgaagtca cccatcaggg cctgagctcg   2160
cccgtcacaa agagcttcaa caggggagag tgttgagcta gaactaacta actaagctag   2220
caacggtttc cctctagcgg gatcaattcc gcccccccc cctaacgtta ctggccgaag   2280
ccgcttggaa taaggccggt gtgcgtttgt ctatatgtta ttttccacca tattgccgtc   2340
ttttggcaat gtgagggccc ggaaacctgg ccctgtcttc ttgacgagca ttcctagggg   2400
tctttcccct ctcgccaaag gaatgcaagg tctgttgaat gtcgtgaagg aagcagttcc   2460
tctggaagct tcttgaagac aaacaacgtc tgtagcgacc ctttgcaggc agcggaaccc   2520
cccacctggc gacaggtgcc tctgcggcca aaagccacgt gtataagata cacctgcaaa   2580
ggcggcacaa ccccagtgcc acgttgtgag ttggatagtt gtggaaagag tcaaatggct   2640
ctcctcaagc gtattcaaca aggggctgaa ggatgcccag aaggtacccc attgtatggg   2700
atctgatctg gggcctcggt gcacatgctt tacgtgtgtt tagtcgaggt taaaaaacgt   2760
ctaggccccc cgaaccacgg ggacgtggtt ttccttttga aaaacacgata taccatggtg   2820
tgaacaagat ggattgcacg caggttctcc ggccgcttgg gtggagaggc tattcggcta   2880
tgactgggca acagacaaa tcggctgctc tgatgccgcc gtgttccggc tgtcagcgca   2940
ggggcgcccg gttcttttg tcaagaccga cctgtccggt gccctgaatg aactgcagga   3000
cgaggcagcg cggctatcgt ggctggccac gacgggcgtt ccttgcgcag ctgtgctcga   3060
cgttgtcact gaagcgggaa gggactggct gctattgggc gaagtgccgg ggcaggatct   3120
cctgtcatct caccttgctc ctgccgagaa agtatccatc atggctgatg caatgcggcg   3180
gctgcatacg cttgatccgg ctacctgccc attcgaccac caagcgaaac atcgcatcga   3240
gcgagcacgt actcggatgg aagccggtct tgtcgatcag gatgatctgg acgaagagca   3300
tcagggctc gcgccagccg aactgttcgc caggctcaag gcgcgcatgc ccgacggcga   3360
ggatctcgtc gtgacccatg gcgatgcctg cttgccgaat atcatggtgg aaaatggccg   3420
cttttctgga ttcatcgact gtggccggct gggtgtggcg gaccgctatc aggacatagc   3480
gttggctacc cgtgatattg ctgaagagct tggcggcgaa tgggctgacc gcttcctcgt   3540
gctttacggt atcgccgctc ccgattcgca gcgcatcgcc ttctatcgcc ttcttgacga   3600
gttcttctga gtcgatcgac ctggcgtaat agcgaagagg cccgcaccga tcgcccttcc   3660
caacagttgc gcagcctgaa tggcgaatgg gacgcgccct gtagcggcgc attaagcgcg   3720
gcgggtgtgg tggttacgcg cagcgtgacc gctacacttg ccagcgccct agcgcccgct   3780
```

```
cctttcgctt tcttcccttc ctttctcgcc acgttcgccg gctttccccg tcaagctcta    3840
aatcggggc tccctttagg gttccgattt agtgctttac ggcacctcga ccccaaaaaa     3900
cttgattagg gtgatggttc acgtagtggg ccatcgccct gatagacggt ttttcgcctt    3960
tgacgttgga gtccacgttc tttaatagtg gactcttgtt ccaaactgga acaacactca    4020
accctatctc ggtctattta aagggattt tgccgatttc ggcctattgg ttaaaaaatg     4080
agctgattta acaaaattta acgcgaattt taacaaaata ttaacgctta caatttaggt    4140
ggcacttttc ggggaaatgt gcgcggaacc cctatatttg tttattttc taaatacatt     4200
caaatatgta tccgctcatg agacaataac cctgataaat gcttcaataa tattgaaaaa    4260
ggaagagtat gagtattcaa catttccgtg tcgcccttat ccctttttt gcggcatttt     4320
gccttactgt ttttgctcac ccagaaacgc tggtgaaagt aaaagatgct gaagatcagt    4380
tgggtgcacg agtgggttac atcgaactgg atctcaacag cggtaagatc cttgagagtt    4440
ttcgccccga agaacgtttt ccaatgatga gcacttttaa agttctgcta tgtggcgcgg    4500
tattatcccg tattgacgcc gggcaagagc aactcggtcg ccgcatacac tattctcaga    4560
atgacttggt tgagtactca ccagtcacag aaaagcatat tacggatggc atgacagtaa    4620
gagaattatg cagtgctgcc ataaccatga gtgataacac tgcggccaac ttacttctga    4680
caacgatcgg aggaccgaag gagctaaccg cttttttgca acatggggg atcatgtaa     4740
ctcgccttga tcgttgggaa ccggagctga atgaagccat accaaacgac gagcgtgaca    4800
ccacgatgcc tgtagcaatg gcaacaacgt tgcgcaaact attaactggc gaactactta    4860
ctctagcttc ccggcaacaa ttaatagact ggatggaggc ggataaagtt gcaggaccac    4920
ttctgcgctc ggcccttccg gctggctggt ttattgctga taaatctgga gccggtgagc    4980
gtgggtctcg cggtatcatt gcagcactgg ggccagatgg taagccctcc cgtatcgtag    5040
ttatctacac gacggggagt caggcaacta tggatgaacg aaatagacag atcgctgaga    5100
taggtgcctc actgattaag cattggtaac tgtcagacca agtttactca tatatacttt    5160
agattgattt aaaacttcat ttttaattta aaaggatcta ggtgaagatc cttttgata    5220
atctcatgac caaaatccct taacgtgagt tttcgttcca ctgagcgtca gaccccgtag    5280
aaaagatcaa aggatgttct tgagatcctt ttttctgca cgtaatctgc tgcttgcaaa    5340
caaaaaacca ccgctaccag cggtggtttg tttgccggat caagagctac caactctttt    5400
tccgaaggta actggcttca gcagagcgca gataccaaat actgtccttc tagtgtagcc    5460
gtagttaggc caccacttca agaactctgt agcaccgcct acatacctcg ctctgctaat    5520
cctgttacca gtggctgctg ccagtggcga taagtcgtgt cttaccgggt tggactcaag    5580
acgatagtta ccggataagg cgcagcggtc gggctgaacg ggggggttcgt gcacacagcc    5640
cagcttggag cgaacgacct acaccgaact gagatacta cagcgtgagc tatgagaaag    5700
cgccacgctt cccgaaggga gaaaggcgga caggtatccg gtaagcggca gggtcggaac    5760
aggagagcgc acgagggagc ttccagggg aaacgcctgg tatctttata gtcctgtcgg    5820
gtttcgccac ctctgacttg agcgtcgatt tttgtgatgc tcgtcagggg ggcggagcct    5880
atggaaaaac gccagcaacg cggcctttt acggttcctg gccttttgct ggccttttgc    5940
tcacatgttc tttcctgcgt tatcccctga ttctgtggat aaccgtatta ccgcctttga    6000
gtgagctgat accgctcgcc gcagccgaac gaccgagcgc agcgagtcag tgagcgagga    6060
agcggaagag cgcccaatac gcaaaccgcc tctccccgcg cgttggccga ttcattaatg    6120
```

```
caggtatcac gaggcccttt cgtcttcac                                       6149

<210> SEQ ID NO 8
<211> LENGTH: 6625
<212> TYPE: DNA
<213> ORGANISM: Artificial Sequence
<220> FEATURE:
<223> OTHER INFORMATION: synthetic vector

<400> SEQUENCE: 8
ctcgagagcg ggcagtgagc gcaacgcaat taatgtgagt tagctcactc attaggcacc       60
ccaggcttta cactttatgc tcccggctcg tatgttgtgt ggagattgtg agcggataac      120
aatttcacac agaattcgtg aggctccggt gcccgtcagt gggcagagcg cacatcgccc      180
acagtccccg agaagttggg gggaggggtc ggcaattgaa ccggtgccta gagaaggtgg      240
cgcggggtaa actgggaaag tgatgtcgtg tactggctcc gccttttttcc cgagggtggg      300
ggagaaccgt ataaagtgc agtagtcgcc gtgaacgttc tttttcgcaa cgggtttgcc      360
gccagaacac aggtaagtgc cgtgtgtggt tcccgcgggc ctggcctctt tacgggttat      420
ggcccttgcg tgccttgaat tacttccacg ccctggctg cagtacgtga ttcttgatcc      480
cgagcttcgg gttggaagtg ggtgggagag ttcgaggcct gcgcttaag gagccccttc      540
gcctcgtgct tgagttgagg cctggcctgg gcgctgggc cgccgcgtgc gaatctggtg      600
gcaccttcgc gcctgtctcg ctgctttcga taagtctcta gccattaaa attttttgatg      660
acctgctgcg acgcttttttt tctggcaaga tagtcttgta aatgcgggcc aagatctgca      720
cactggtatt tcggtttttg gggccgcggg cggcgacggg gcccgtgcgt cccagcgcac      780
atgttcggcg aggcggggcc tgcgagcgcg gccaccgaga atcggacggg ggtagtctca      840
agctggccgg cctgctctgg tgcctggcct cgcgccgccg tgtatcgccc cgccctgggc      900
ggcaaggctg gcccggtcgg caccagttgc gtgagcggaa agatggccgc ttcccggccc      960
tgctgcaggg agctcaaaat ggaggacgcg gcgctcggga gagcgggcgg gtgagtcacc     1020
cacacaaagg aaaagggcct ttccgtcctc agccgtcgct tcatgtgact ccacggagta     1080
ccgggcgccg tccaggcacc tcgattagtt ctcgagcttt tggagtacgt cgtctttagg     1140
ttgggggggag gggtttatg cgatggagtt tccccacact gagtgggtgg agactgaagt     1200
taggccagct tggcacttga tgtaattctc cttggaattt gcccttttg agtttggatc     1260
ttggttcatt ctcaagcctc agacagtggt tcaaagtttt ttctcttccat ttcaggtgta     1320
cgcgtctcgg gaagctttag tttaaacgcc gccaccatga gagtgctgat tcttttgtgg     1380
ctgttcacag ccttttcctgg tgtcctgtct gatgtgcagc ttcaggagtc gggacctagc     1440
ctggtgaaac cttctcagac tctgtccctc acctgcactg tcactggcta ctcaatcacc     1500
agtgattttg cctggaactg gatccggcag tttccaggaa acaagctgga gtggatgggc     1560
tacataagtt atagtggtaa cactaggtac aacccatctc tcaaaagtcg aatctctatc     1620
actcgagaca catccaagaa ccaattcttc ctgcagttga attctgtgac tattgaggac     1680
acagccacat attactgtgt aacgcgggga cgcgggtttc cttattgggg ccaagggact     1740
ctggtcactg tctctgcaca gtgagtggat cctctgcgcc tgggcccagc tctgtcccac     1800
accgcggtca catggcacca cctctcttgc agcctccacc aagggcccat cggtcttccc     1860
cctggcaccc tcctccaaga gcacctctgg gggcacagcg gccctgggct gcctggtcaa     1920
ggactacttc cccgaaccgg tgacggtgtc gtggaactca ggcgccctga ccagcggcgt     1980
gcacaccttc ccggctgtcc tacagtcctc aggactctac tccctcagca gcgtggtgac     2040
```

-continued

```
cgtgccctcc agcagcttgg gcacccagac ctacatctgc aacgtgaatc acaagcccag    2100
caacaccaag gtggacaaga aagttgagcc caaatcttgt gacaaaactc acacatgccc    2160
accgtgccca gcacctgaac tcctgggggg accgtcagtc ttcctcttcc ccccaaaacc    2220
caaggacacc ctcatgatct cccggacccc tgaggtcaca tgcgtggtgg tggacgtgag    2280
ccacgaagac cctgaggtca agttcaactg gtacgtggac ggcgtggagg tgcataacgc    2340
caagacaaag ccgcgggagg agcagtacaa cagcacgtac cgggtggtca gcgtcctcac    2400
cgtcctgcac caggactggc tgaatggcaa ggagtacaag tgcaaggtct ccaacaaagc    2460
cctcccagcc cccatcgaga aaccatctc caaagccaaa gggcagcccc gagaaccaca    2520
ggtgtacacc ctgcccccat cccgggagga gatgaccaag aaccaggtca gcctgacctg    2580
cctggtcaaa ggcttctatc ccagcgacat cgccgtggag tgggagagca atgggcagcc    2640
ggagaacaac tacaagacca cgcctcccgt gctggactcc gacggctcct tcttcctcta    2700
cagcaagctc accgtggaca agagcaggtg gcagcagggg aacgtcttct catgctccgt    2760
gatgcatgag gctctgcaca accactacac gcagaagagc ctctccctgt ctccgggtaa    2820
atgagctaga aactaactaa gctagcaacg gtttccctct agcgggatca attccgcccc    2880
ccccccctaa cgttactggc cgaagccgct tggaataagg ccggtgtgcg tttgtctata    2940
tgttattttc caccatattg ccgtcttttg gcaatgtgag ggcccggaaa cctggccctg    3000
tcttcttgac gagcattcct aggggtcttt cccctctcgc caaggaatg caaggtctgt    3060 tgaatgtcgt gaaggaagca gttcctctgg aagcttcttg aagacaaaca acgtctgtag    3120
cgaccctttg caggcagcgg aaccccccac ctggcgacag gtgcctctgc ggccaaaagc    3180
cacgtgtata agatacacct gcaaaggcgg cacaaccca gtgccacgtt gtgagttgga    3240
tagttgtgga aagagtcaaa tggctctcct caagcgtatt caacaagggg ctgaaggatg    3300
cccagaaggt acccccattgt atgggatctg atctggggcc tcggtgcaca tgctttacgt    3360
gtgtttagtc gaggttaaaa aacgtctagg cccccgaac cacggggacg tggttttcct    3420
ttgaaaaaca cgataatacc atggttcgac cattgaactg catcgtcgcc gtgtcccaaa    3480
atatggggat tggcaagaac ggagacctac cctggcctcc gctcaggaac gagttcaagt    3540
acttccaaag aatgaccaca acctcttcag tggaaggtaa acagaatctg gtgattatgg    3600
gtaggaaaac ctggttctcc attcctgaga agaatcgacc tttaaaggac agaattaatg    3660
gttcgatata gttctcagta gagaactcaa agaaccacca cgaggagctc attttcttgc    3720
caaaagtttg gatgatgcct taagacttat tgaacaaccg gaattggcaa gtaaagtaga    3780
catggtttgg atagtcggag gcagttctgt ttaccaggaa gccatgaatc aaccaggcca    3840
cctcagactc tttgtgacaa ggatcatgca ggaatttgaa agtgacacgt ttttcccaga    3900
aattgatttg gggaaatata aacttctccc agaatacca ggcgtcctct ctgaggtcca    3960
ggaggaaaaa ggcatcaagt ataagtttga agtctacgag aagaaagact aacaggaaga    4020
tgctttcaag ttctctgctc ccctcctaaa gctatgcatt tttataagac catgggactt    4080
ttgctggtcg atcgacctgg cgtaatagcg aagaggcccg caccgatcgc ccttcccaac    4140
agttgcgcag cctgaatggc gaatgggacg cgccctgtag cggcgcatta agcgcggcgg    4200
gtgtggtggt tacgcgcagc gtgaccgcta cacttgccag cgccctagcg cccgctcctt    4260
tcgctttctt cccttccttt ctcgccacgt tcgccggctt tccccgtcaa gctctaaatc    4320
gggggctccc tttagggttc cgatttagtg ctttacggca cctcgacccc aaaaaacttg    4380
```

```
attagggtga tggttcacgt agtgggccat cgccctgata gacggttttt cgcctttgac    4440
gttggagtcc acgttcttta atagtggact cttgttccaa actggaacaa cactcaaccc    4500
tatctcggtc tatttataag ggattttgcc gatttcggcc tattggttaa aaaatgagct    4560
gatttaacaa aatttaacgc gaattttaac aaaatattaa cgcttacaat ttaggtggca    4620
cttttcgggg aaatgtgcgc ggaacccta tatttgttta ttttctaaa tacattcaaa      4680
tatgtatccg ctcatgagac aataaccctg ataaatgctt caataatatt gaaaaggaa     4740
gagtatgagt attcaacatt tccgtgtcgc ccttattccc ttttttgcgg cattttgcct    4800
tactgttttt gctcacccag aaacgctggt gaaagtaaaa gatgctgaag atcagttggg    4860
tgcacgagtg ggttacatcg aactggatct caacagcggt aagatccttg agagttttcg    4920
ccccgaagaa cgttttccaa tgatgagcac ttttaaagtt ctgctatgtg gcgcggtatt    4980
atcccgtatt gacgccgggc aagagcaact cggtcgccgc atacactatt ctcagaatga    5040
cttggttgag tactcaccag tcacagaaaa gcatattacg gatggcatga cagtaagaga    5100
attatgcagt gctgccataa ccatgagtga taacactgcg gccaacttac ttctgacaac    5160
gatcggagga ccgaaggagc taaccgcttt tttgcacaac atgggggatc atgtaactcg    5220
ccttgatcgt tgggaaccgg agctgaatga agccatacca aacgacgagc gtgacaccac    5280
gatgcctgta gcaatggcaa caacgttgcg caaactatta actggcgaac tacttactct    5340
agcttcccgg caacaattaa tagactggat ggaggcggat aaagttgcag gaccacttct    5400
gcgctcggcc cttccggctg gctggtttat tgctgataaa tctggagccg gtgagcgtgg    5460
gtctcgcggt atcattgcag cactggggcc agatggtaag ccctcccgta tcgtagttat    5520
ctacacgacg gggagtcagg caactatgga tgaacgaaat agacagatcg ctgagatagg    5580
tgcctcactg attaagcatt ggtaactgtc agaccaagtt tactcatata ctttagat     5640
tgatttaaaa cttcattttt aatttaaaag gatctaggtg aagatccttt ttgataatct    5700
catgaccaaa atcccttaac gtgagttttc gttccactga gcgtcagacc ccgtagaaaa    5760
gatcaaagga tgttcttgag atcctttttt tctgcacgta atctgctgct tgcaaacaaa    5820
aaaccaccgc taccagcggt ggtttgtttg ccggatcaag agctaccaac tctttttccg    5880
aaggtaactg gcttcagcag agcgcagata ccaaatactg tccttctagt gtagccgtag    5940
ttaggccacc acttcaagaa ctctgtagca ccgcctacat acctcgctct gctaatcctg    6000
ttaccagtgg ctgctgccag tggcgataag tcgtgtctta ccgggttgga ctcaagacga    6060
tagttaccgg ataaggcgca gcggtcgggc tgaacggggg gttcgtgcac acagcccagc    6120
ttggagcgaa cgacctacac cgaactgaga tacctacagc gtgagctatg agaaagcgcc    6180
acgcttcccg aagggagaaa ggcggacagg tatccggtaa gcggcagggt cggaacagga    6240
gagcgcacga gggagcttcc agggggaaac gcctggtatc tttatagtcc tgtcgggttt    6300
cgccacctct gacttgagcg tcgatttttg tgatgctcgt caggggggcg gagcctatgg    6360
aaaaacgcca gcaacgcggc cttttacgg ttcctggcct tttgctggcc ttttgctcac     6420
atgttctttc ctgcgttatc ccctgattct gtggataacc gtattaccgc ctttgagtga    6480
gctgataccg ctcgccgcag ccgaacgacc gagcgcagcg agtcagtgag cgaggaagcg    6540
gaagagcgcc caatacgcaa accgcctctc cccgcgcgtt ggccgattca ttaatgcagg    6600
tatcacgagg ccctttcgtc ttcac                                         6625
```

<210> SEQ ID NO 9
<211> LENGTH: 234

```
<212> TYPE: PRT
<213> ORGANISM: Artificial Sequence
<220> FEATURE:
<223> OTHER INFORMATION: synthetic vector

<400> SEQUENCE: 9

Met Val Ser Thr Ala Gln Phe Leu Ala Phe Leu Leu Leu Trp Phe Pro
1               5                   10                  15

Gly Ala Arg Cys Asp Ile Leu Met Thr Gln Ser Pro Ser Ser Met Ser
            20                  25                  30

Val Ser Leu Gly Asp Thr Val Ser Ile Thr Cys His Ser Ser Gln Asp
        35                  40                  45

Ile Asn Ser Asn Ile Gly Trp Leu Gln Gln Arg Pro Gly Lys Ser Phe
50                  55                  60

Lys Gly Leu Ile Tyr His Gly Thr Asn Leu Asp Glu Val Pro Ser
65                  70                  75                  80

Arg Phe Ser Gly Ser Gly Ser Gly Ala Asp Tyr Ser Leu Thr Ile Ser
                85                  90                  95

Ser Leu Glu Ser Glu Asp Phe Ala Asp Tyr Tyr Cys Val Gln His Ala
            100                 105                 110

Gln Phe Pro Trp Thr Phe Gly Gly Gly Thr Lys Leu Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 10
<211> LENGTH: 463
<212> TYPE: PRT
<213> ORGANISM: Artificial Sequence
<220> FEATURE:
<223> OTHER INFORMATION: synthetic vector

<400> SEQUENCE: 10

Met Arg Val Leu Ile Leu Leu Trp Leu Phe Thr Ala Phe Pro Gly Val
1               5                   10                  15

Leu Ser Asp Val Gln Leu Gln Glu Ser Gly Pro Ser Leu Val Lys Pro
            20                  25                  30

Ser Gln Thr Leu Ser Leu Thr Cys Thr Val Thr Gly Tyr Ser Ile Thr
        35                  40                  45

Ser Asp Phe Ala Trp Asn Trp Ile Arg Gln Phe Pro Gly Asn Lys Leu
50                  55                  60

Glu Trp Met Gly Tyr Ile Ser Tyr Ser Gly Asn Thr Arg Tyr Asn Pro
65                  70                  75                  80

Ser Leu Lys Ser Arg Ile Ser Ile Thr Arg Asp Thr Ser Lys Asn Gln
                85                  90                  95
```

```
Phe Phe Leu Gln Leu Asn Ser Val Thr Ile Glu Asp Thr Ala Thr Tyr
            100                 105                 110
Tyr Cys Val Thr Ala Gly Arg Gly Phe Pro Tyr Trp Gly Gln Gly Thr
        115                 120                 125
Leu Val Thr Val Ser Ala Ser Thr Lys Gly Pro Ser Val Phe Pro Leu
    130                 135                 140
Ala Pro Ser Ser Lys Ser Thr Ser Gly Gly Thr Ala Ala Leu Gly Cys
145                 150                 155                 160
Leu Val Lys Asp Tyr Phe Pro Glu Pro Val Thr Val Ser Trp Asn Ser
                165                 170                 175
Gly Ala Leu Thr Ser Gly Val His Thr Phe Pro Ala Val Leu Gln Ser
            180                 185                 190
Ser Gly Leu Tyr Ser Leu Ser Ser Val Val Tyr Val Pro Ser Ser Ser
        195                 200                 205
Leu Gly Thr Gln Thr Tyr Ile Cys Asn Val Asn His Lys Pro Ser Asn
    210                 215                 220
Thr Lys Val Asp Lys Lys Val Glu Pro Lys Ser Cys Asp Lys Thr His
225                 230                 235                 240
Thr Cys Pro Pro Cys Pro Ala Pro Glu Leu Leu Gly Gly Pro Ser Val
                245                 250                 255
Phe Leu Phe Pro Pro Lys Pro Lys Asp Thr Leu Met Ile Ser Arg Thr
            260                 265                 270
Pro Glu Val Thr Cys Val Val Val Asp Val Ser His Glu Asp Pro Glu
        275                 280                 285
Val Lys Phe Asn Trp Tyr Val Asp Gly Val Glu Val His Asn Ala Lys
    290                 295                 300
Thr Lys Pro Arg Glu Glu Gln Tyr Asn Ser Thr Tyr Arg Val Val Ser
305                 310                 315                 320
Val Leu Thr Val Leu His Gln Asp Trp Leu Asn Gly Lys Glu Tyr Lys
                325                 330                 335
Cys Lys Val Ser Asn Lys Ala Leu Pro Ala Pro Ile Glu Lys Thr Ile
            340                 345                 350
Ser Lys Ala Lys Gly Gln Pro Arg Glu Pro Gln Val Tyr Thr Leu Pro
        355                 360                 365
Pro Ser Arg Glu Glu Met Thr Lys Asn Gln Val Ser Leu Thr Cys Leu
    370                 375                 380
Val Lys Gly Phe Tyr Pro Ser Asp Ile Ala Val Glu Trp Glu Ser Asn
385                 390                 395                 400
Gly Gln Pro Glu Asn Asn Tyr Lys Thr Thr Pro Pro Val Leu Asp Ser
                405                 410                 415
Asp Gly Ser Phe Phe Leu Tyr Ser Lys Leu Thr Val Asp Lys Ser Arg
            420                 425                 430
Trp Gln Gln Gly Asn Val Phe Ser Cys Ser Val Met His Glu Ala Leu
        435                 440                 445
His Asn His Tyr Thr Gln Lys Ser Leu Ser Leu Ser Pro Gly Lys
    450                 455                 460

<210> SEQ ID NO 11
<211> LENGTH: 116
<212> TYPE: PRT
<213> ORGANISM: Mus musculus

<400> SEQUENCE: 11

Asp Val Gln Leu Gln Glu Ser Gly Pro Ser Leu Val Lys Pro Ser Gln
```

```
                1               5                   10                  15
Ser Leu Ser Leu Thr Cys Thr Val Thr Gly Tyr Ser Ile Thr Ser Asp
                    20                  25                  30

Phe Ala Trp Asn Trp Ile Arg Gln Phe Pro Gly Asn Lys Leu Glu Trp
                    35                  40                  45

Met Gly Tyr Ile Ser Tyr Ser Gly Asn Thr Arg Tyr Asn Pro Ser Leu
        50                  55                  60

Lys Ser Arg Ile Ser Ile Thr Arg Asp Thr Ser Lys Asn Gln Phe Phe
65                      70                  75                  80

Leu Gln Leu Asn Ser Val Thr Ile Glu Asp Thr Ala Thr Tyr Tyr Cys
                    85                  90                  95

Val Thr Ala Gly Arg Gly Phe Pro Tyr Trp Gly Gln Gly Thr Leu Val
                    100                 105                 110

Thr Val Ser Ala
        115

<210> SEQ ID NO 12
<211> LENGTH: 108
<212> TYPE: PRT
<213> ORGANISM: Mus musculus

<400> SEQUENCE: 12

Asp Ile Leu Met Thr Gln Ser Pro Ser Ser Met Ser Val Ser Leu Gly
1               5                   10                  15

Asp Thr Val Ser Ile Thr Cys His Ser Ser Gln Asp Ile Asn Ser Asn
                    20                  25                  30

Ile Gly Trp Leu Gln Gln Arg Pro Gly Lys Ser Phe Lys Gly Leu Ile
            35                  40                  45

Tyr His Gly Thr Asn Leu Asp Asp Glu Val Pro Ser Arg Phe Ser Gly
        50                  55                  60

Ser Gly Ser Gly Ala Asp Tyr Ser Leu Thr Ile Ser Ser Leu Glu Ser
65                      70                  75                  80

Glu Asp Phe Ala Asp Tyr Tyr Cys Val Gln Tyr Ala Gln Phe Pro Trp
                    85                  90                  95

Thr Phe Gly Gly Gly Thr Lys Leu Glu Ile Lys Arg
                100                 105

<210> SEQ ID NO 13
<211> LENGTH: 13
<212> TYPE: PRT
<213> ORGANISM: Artificial Sequence
<220> FEATURE:
<223> OTHER INFORMATION: synthetic

<400> SEQUENCE: 13

Leu Glu Glu Lys Lys Gly Asn Tyr Val Val Thr Asp His
1               5                   10

<210> SEQ ID NO 14
<211> LENGTH: 14
<212> TYPE: PRT
<213> ORGANISM: Artificial Sequence
<220> FEATURE:
<223> OTHER INFORMATION: synthetic
      biotinylated at position 14

<400> SEQUENCE: 14

Leu Glu Glu Lys Lys Gly Asn Tyr Val Val Thr Asp His Lys
1               5                   10
```

SPECIFIC BINDING PROTEINS AND USES THEREOF

CROSS REFERENCE TO RELATED APPLICATIONS

The present application claims priority from U.S. Provisional Application Ser. No. 60/290,410, filed May 11, 2001, Ser. No. 60/326,019, filed Sep. 28, 2001, and Ser. No. 60/342,258, filed Dec. 21, 2001, each of which is incorporated by reference herein in its entirety.

FIELD OF THE INVENTION

The present invention relates to specific binding members, particularly antibodies and fragments thereof, which bind to amplified epidermal growth factor receptor (EGFR) and to the de2-7 EGFR truncation of the EGFR. In particular, the epitope recognized by the specific binding members, particularly antibodies and fragments thereof, is enhanced or evident upon aberrant post-translational modification. These specific binding members are useful in the diagnosis and treatment of cancer. The binding members of the present invention may also be used in therapy in combination with chemotherapeutics or anti-cancer agents and/or with other antibodies or fragments thereof.

BACKGROUND OF THE INVENTION

The treatment of proliferative disease, particularly cancer, by chemotherapeutic means often relies upon exploiting differences in target proliferating cells and other normal cells in the human or animal body. For example, many chemical agents are designed to be taken up by rapidly replicating DNA so that the process of DNA replication and cell division is disrupted. Another approach is to identify antigens on the surface of tumor cells or other abnormal cells which are not normally expressed in developed human tissue, such as tumor antigens or embryonic antigens. Such antigens can be targeted with binding proteins such as antibodies which can block or neutralize the antigen. In addition, the binding proteins, including antibodies and fragments thereof, may deliver a toxic agent or other substance which is capable of directly or indirectly activating a toxic agent at the site of a tumor.

The EGFR is an attractive target for tumor-targeted antibody therapy because it is over-expressed in many types of epithelial tumors (27,28). Moreover, expression of the EGFR is associated with poor prognosis in a number of tumor types including stomach, colon, urinary bladder, breast, prostate, endometrium, kidney and brain (e.g., glioma). Consequently, a number of EGFR antibodies have been reported in the literature with several undergoing clinical evaluation (18, 19, 29). Results from studies using EGFR mAbs in patients with head and neck cancer, squamous cell lung cancer, brain gliomas and malignant astrocytomas have been encouraging. The anti-tumor activity of most EGFR antibodies is enhanced by their ability to block ligand binding (30, 31). Such antibodies may mediate their efficacy through both modulation of cellular proliferation and antibody dependent immune functions (e.g. complement activation). The use of these antibodies, however, may be limited by uptake in organs that have high endogenous levels of EGFR such as the liver and skin (18, 19).

A significant proportion of tumors containing amplifications of the EGFR gene (i.e., multiple copies of the EGFR gene) also co-express a truncated version of the receptor (13) known as de2-7 EGFR, ΔEGFR, or Δ2-7 (terms used interchangeably herein) (2). The rearrangement seen in the de2-7 EGFR results in an in-frame mature mRNA lacking 801 nucleotides spanning exons 2-7 (6-9). The corresponding EGFR protein has a 267 amino acid deletion comprising residues 6-273 of the extracellular domain and a novel glycine residue at the fusion junction (9). This deletion, together with the insertion of a glycine residue, produces a unique junctional peptide at the deletion interface (9). The de2-7 EGFR (2) has been reported in a number of tumor types including glioma, breast, lung, ovarian and prostate (1-4). While this truncated receptor does not bind ligand, it possesses low constitutive activity and imparts a significant growth advantage to glioma cells grown as tumor xenografts in nude mice (10) and is able to transform NIH3T3 cells (11) and MCF-7 cells. The cellular mechanisms utilized by the de2-7 EGFR in glioma cells are not fully defined but are reported to include a decrease in apoptosis (12) and a small enhancement of proliferation (12).

As expression of this truncated receptor is restricted to tumor cells it represents a highly specific target for antibody therapy. Accordingly, a number of laboratories have reported the generation of both polyclonal (14) and monoclonal (3, 15, 16) antibodies specific to the unique peptide of de2-7 EGFR. A series of mouse mAbs, isolated following immunization with the unique de2-7 peptide, all showed selectivity and specificity for the truncated receptor and targeted de2-7 EGFR positive xenografts grown in nude mice (3, 25, 32).

However, one potential shortcoming of de2-7 EGFR antibodies is that only a proportion of tumors exhibiting amplification of the EGFR gene also express the de 2-7 EGFR (5). The exact percentage of tumors containing the de2-7 EGFR is not completely established, because the use of different techniques (i.e. PCR versus immunohistochemistry) and various antibodies, has produced a wide range of reported values for the frequency of its presence. Published data indicates that approximately 25-30% of gliomas express de2-7 EGFR with expression being lowest in anaplastic astrocytomas and highest in glioblastoma multiforme (6,13,17). The proportion of positive cells within de2-7 EGFR expressing gliomas has been reported to range from 37-86% (1). 27% of breast carcinomas and 17% of lung cancers were found to be positive for the de2-7 EGFR (1, 3, 13, 16). Thus, de2-7 EGFR specific antibodies would be expected to be useful in only a percentage of EGFR positive tumors.

Thus, while the extant evidence of activity of EGFR antibodies is encouraging, the observed limitations on range of applicability and efficacy reflected above remain. Accordingly, it would be desirable to develop antibodies and like agents that demonstrate efficacy with a broad range of tumors, and it is toward the achievement of that objective that the present invention is directed.

The citation of references herein shall not be construed as an admission that such is prior art to the present invention.

SUMMARY OF THE INVENTION

In a broad aspect, the present invention provides an isolated specific binding member, particularly an antibody or fragment thereof, which recognizes an EGFR epitope which does not demonstrate any amino acid sequence alterations or substitutions from wild type EGFR and which is found in tumorigenic, hyperproliferative or abnormal cells and is not detectable in normal or wild type cells (the term "wild type cell" as used herein contemplates a cell that expresses endogenous EGFR but not the de 2-7 EGFR and the term specifically excludes a cell that overexpresses the EGFR gene; the term "wild type" refers to a genotype or phenotype or other characteristic present in a normal cell rather than in an abnormal or tumorigenic cell). In a further aspect, the present invention provides a specific binding member, particularly an antibody or fragment thereof, which recognizes an EGFR epitope which is found in tumorigenic, hyperproliferative or abnormal cells and is not detectable in normal or wild type cells, wherein the epitope is enhanced or evident upon aberrant post translational modification or aberrant expression. In a particular nonlimiting exemplification provided herein, the EGFR epitope is enhanced or evident wherein post-translational modification is not complete or full to the extent seen with normal expression of EGFR in wild type cells. In one aspect, the EGFR epitope is enhanced or evident upon initial or simple carbohydrate modification or early glycosylation, particularly high mannose modification, and is reduced or not evident in the presence of complex carbohydrate modification.

The specific binding member, which may be an antibody or a fragment thereof, such as an immunogenic fragment thereof, does not bind to or recognize normal or wild type cells containing normal or wild type EGFR epitope in the absence of aberrant expression and in the presence of normal EGFR post-translational modification. More particularly, the specific binding member of the invention, may be an antibody or fragment thereof, which recognizes an EGFR epitope which is present in cells overexpressing EGFR (e.g., EGFR gene is amplified) or expressing the de2-7 EGFR, particularly in the presence of aberrant post-translational modification, and that is not detectable in cells expressing EGFR under normal conditions, particularly in the presence of normal post-translational modification.

The present inventors have discovered novel monoclonal antibodies, exemplified herein by the antibody designated mAb 806, which specifically recognize aberrantly expressed EGFR. In particular, the antibodies of the present invention recognize an EGFR epitope which is found in tumorigenic, hyperproliferative or abnormal cells and is not detectable in normal or wild type cells, wherein the epitope is enhanced or evident upon aberrant post-translational modification. The antibodies of the present invention are further exemplified by the antibodies mAb 124 and mAb 1133 described herein. The novel antibodies of the invention also recognize amplified wild type EGFR and the de2-7 EGFR, yet bind to an epitope distinct from the unique junctional peptide of the de2-7 EGFR mutation. The antibodies of the present invention specifically recognize aberrantly expressed EGFR, including amplified EGFR and mutant EGFR (exemplified herein by the de2-7 mutation), particularly upon aberrant post-translational modification. Additionally, while mAb 806 does not recognize the EGFR when expressed on the cell surface of a glioma cell line expressing normal amounts of EGFR, it does bind to the extracellular domain of the EGFR (sEGFR) immobilized on the surface of ELISA plates, indicating the recognition of a conformational epitope. MAb 806 binds to the surface of A431 cells, which have an amplification of the EGFR gene but do not express the de2-7 EGFR. Importantly, mAb 806 did not bind significantly to normal tissues such as liver and skin, which express levels of endogenous, wild type (wt) EGFR that are higher than in most other normal tissues, but wherein EGFR is not aberrantly expressed or amplified.

The antibodies of the present invention can specifically categorize the nature of EGFR tumors or tumorigenic cells, by staining or otherwise recognizing those tumors or cells wherein aberrant EGFR expression, including EGFR amplification and/or EGFR mutation, particularly de2-7EGFR, is present. Further, the antibodies of the present invention, as exemplified by mAb 806, demonstrate significant in vivo anti-tumor activity against tumors containing amplified EGFR and against de2-7 EGFR positive xenografts.

The unique specificity of mAb 806, whereby mAb 806 binds to the de2-7 EGFR and amplified EGFR but not the normal, wild type EGFR, provides diagnostic and therapeutic uses to identify, characterize and target a number of tumor types, for example, head and neck, breast, or prostate tumors and glioma, without the problems associated with normal tissue uptake that may be seen with previously known EGFR antibodies.

Accordingly, the invention provides specific binding proteins, such as antibodies, which bind to the de2-7 EGFR at an epitope which is distinct from the junctional peptide but which do not bind to EGFR on normal cells in the absence of amplification of the EGFR gene. By amplification, it is meant to include that the cell comprises multiple copies of the EGFR gene.

Preferably the epitope recognized by mAb 806 is located within the region comprising residues 273-501 of the mature normal or wild type EGFR sequence. Therefore, also provided are specific binding proteins, such as antibodies, which bind to the de2-7 EGFR at an epitope located within the region comprising residues 273-501 of the EGFR sequence. The epitope may be determined by any conventional epitope mapping techniques known to the person skilled in the art. Alternatively, the DNA sequence encoding residues 273-501 could be digested, and the resultant fragments expressed in a suitable host. Antibody binding could be determined as mentioned above.

In a preferred aspect, the antibody is one which has the characteristics of the antibody which the inventors have identified and characterized, in particular recognizing aberrantly expressed EGFR, as found in amplified EGFR and de2-7EGFR. In a particularly preferred aspect the antibody is the mAb 806, or active fragments thereof. In a further preferred aspect the antibody of the present invention comprises the VH and VL amino acid sequences depicted in FIG. 14 (SEQ ID NO:2) and FIG. 15 (SEQ ID NO:4) respectively.

In another aspect, the invention provides an antibody capable of competing with the 806 antibody, under conditions in which at least 10% of an antibody having the VH and VL sequences of the 806 antibody is blocked from binding to de2-7EGFR by competition with such an antibody in an ELISA assay. In particular, anti-idiotype antibodies are contemplated and are exemplified herein. The anti-idiotype antibodies LMH-11, LMH-12 and LMH-13 are provided herein.

An isolated polypeptide consisting essentially of the epitope comprising residues 273-501 of the mature normal, wild type EGFR (residues 6-234 of mature de2-7 EGFR) forms another aspect of the present invention. The peptide of the invention is particularly useful in diagnostic assays or kits and therapeutically or prophylactically, including as a tumor or anticancer vaccine. Thus compositions of the peptide of the present invention include pharmaceutical compositions and immunogenic compositions.

The binding of an antibody to its target antigen is mediated through the complementarity-determining regions (CDRs) of its heavy and light chains, with the role of CDR3 being of particular importance. Accordingly, specific binding members based on the CDR3 regions of the heavy or light chain, and preferably both, of mAb806 will be useful specific binding members for in vivo therapy. The CDRs of the mAb 806 antibody are shown in FIGS. 16 and 17.

Accordingly, specific binding proteins such as antibodies which are based on the CDRs of the mAb 806 antibody identified, particularly the CDR 3 regions, will be useful for targeting tumors with amplified EGFR regardless of their de2-7 EGFR status. As mAb 806 does not bind significantly to normal, wild type receptor, there would be no significant uptake in normal tissue, a limitation of EGFR antibodies currently being developed (18, 19).

In the accompanying drawings, the nucleic acid sequence (SEQ ID NO:1) and translation (SEQ ID NO:2) thereof of the 806 VH gene is shown in FIG. 14. The VL gene of the 806 antibody is shown as FIG. 15 as nucleic acid sequence (SEQ ID NO:3) and predicted amino acid sequence (SEQ ID NO:4). In FIGS. 16 and 17, depicting the VH and VL polypeptide sequences of mAb 806, the CDRs are indicated in boxes.

In a further aspect, the present invention provides an isolated specific binding member capable of binding an antigen, wherein said specific binding member comprises a polypeptide binding domain comprising an amino acid sequence substantially as set out as residues 93-102 of SEQ ID NO:2. The invention further provides said isolated specific binding member which further comprises one or both of the polypeptide binding domains substantially as set out as residues 26-35A and 49-64 of SEQ ID NO:2, preferably both. One example of such an embodiment is the sequence substantially as shown in SEQ ID NO:2. In a preferred embodiment, the binding domains are carried by a human antibody framework.

In another aspect, the invention provides an isolated specific binding member capable of binding a tumor antigen, wherein said specific binding member comprises a polypeptide binding domain comprising a heavy chain sequence comprising at least the CDR3 sequence of SEQ ID NO:2, together with a light chain comprising CDRs whose amino acid sequences are substantially as found within SEQ ID NO:4. One example of such an embodiment is the sequence substantially as shown in SEQ ID NO:4. In a preferred embodiment, the CDRs are carried by a human antibody framework.

In further aspects, the invention provides an isolated nucleic acid which comprises a sequence encoding a specific binding member as defined above, and methods of preparing specific binding members of the invention which comprise expressing said nucleic acids under conditions to bring about expression of said binding member, and recovering the binding member.

Yet a further aspect of the invention are compositions of such binding proteins with additional binding proteins, such as binding proteins which bind to EGFR, preferably inhibiting ligand binding thereto. Such compositions can be "one pot" cocktails, kits, and so forth, preferably formulated for ease of administration.

Specific binding members according to the invention may be used in a method of treatment or diagnosis of the human or animal body, such as a method of treatment of a tumor in a human patient which comprises administering to said patient an effective amount of a specific binding member of the invention.

The present invention also relates to a recombinant DNA molecule or cloned gene, or a degenerate variant thereof, which encodes an antibody of the present invention; preferably a nucleic acid molecule, in particular a recombinant DNA molecule or cloned gene, encoding the antibody VH which has a nucleotide sequence or is complementary to a DNA sequence shown in FIG. 14 (SEQ ID NO:1). In another embodiment, the present invention also relates to a recombinant DNA molecule or cloned gene, or a degenerate variant thereof, preferably a nucleic acid molecule, in particular a recombinant DNA molecule or cloned gene, encoding the antibody VL which has a nucleotide sequence or is complementary to a DNA sequence shown in FIG. 15 (SEQ ID NO:3).

The present invention also includes polypeptides or antibodies having the activities noted herein, and that display the amino acid sequences set forth and described above and in FIGS. 14 and 15 hereof and selected from SEQ ID NO:2 and 4.

In a further embodiment of the invention, the full DNA sequence of the recombinant DNA molecule or cloned gene provided herein may be operatively linked to an expression control sequence which may be introduced into an appropriate host. The invention accordingly extends to unicellular hosts transformed with the cloned gene or recombinant DNA molecule comprising a DNA sequence encoding the present VH and/or VL, or portions thereof, of the antibody, and more particularly, the VH and/or VL set forth above and in SEQ ID NO:1 and 3.

The present invention naturally contemplates several means for preparation of the antibodies and active fragments thereof, including as illustrated herein known recombinant techniques, and the invention is accordingly intended to cover such synthetic or chimeric antibody preparations within its scope. The isolation of the cDNA and amino acid sequences disclosed herein facilitates the reproduction of the antibody of the present invention by such recombinant techniques, and accordingly, the invention extends to expression vectors prepared from the disclosed DNA sequences for expression in host systems by recombinant DNA techniques, and to the resulting transformed hosts.

The present invention provides drugs or other entities, including antibodies such as anti-idiotype antibodies, that are capable of binding to the antibody thereby modulating, inhibiting or potentiating the antibody activity. Thus, anti-idiotype antibodies to mAb806 are provided and exemplified herein. Such anti-idiotype antibodies would be useful in the development of drugs that would specifically bind the antibodies such as mAb806 or its epitope or that would potentiate its activity.

The diagnostic utility of the present invention extends to the use of the antibodies of the present invention in assays to characterize tumors or cellular samples or to screen for tumors or cancer, including in vitro and in vivo diagnostic assays.

In an immunoassay, a control quantity of the antibodies, or the like may be prepared and labeled with an enzyme, a specific binding partner and/or a radioactive element, and may then be introduced into a cellular sample. After the labeled material or its binding partner(s) has had an opportunity to react with sites within the sample, the resulting mass may be examined by known techniques, which may vary with the nature of the label attached.

Specific binding members of the invention may carry a detectable or functional label. The specific binding members may carry a radioactive label, such as the isotopes $^{3}$H, $^{14}$C, $^{32}$P, $^{35}$S, $^{36}$Cl, $^{57}$Co, $^{58}$Co $^{59}$Fe, $^{90}$Y, $^{121}$I, $^{124}$I, $^{125}$I, $^{131}$I, $^{111}$In, $^{211}$At, $^{198}$Au, $^{67}$Cu, $^{225}$Ac, $^{213}$Bi, $^{99}$Tc and $^{186}$Re. When radioactive labels are used, known currently available counting procedures may be utilized to identify and quantitate the specific binding members. In the instance where the label is an enzyme, detection may be accomplished by any of the presently utilized calorimetric, spectrophotometric, fluorospectrophotometric, amperometric or gasometric techniques known in the art.

The radiolabelled specific binding members, particularly antibodies and fragments thereof, are useful in in vitro diagnostics techniques and in in vivo radioimaging techniques. In a further aspect of the invention, radiolabelled specific binding members, particularly antibodies and fragments thereof, particularly radioimmunoconjugates, are useful in radioimmunotherapy, particularly as radiolabelled antibodies for cancer therapy. In a still further aspect, the radiolabelled specific binding members, particularly antibodies and fragments thereof, are useful in radioimmuno-guided surgery techniques, wherein they can identify and indicate the presence and/or location of cancer cells, precancerous cells, tumor cells, and hyperproliferative cells, prior to, during or following surgery to remove such cells.

Immunoconjugates or antibody fusion proteins of the present invention, wherein the specific binding members, particularly antibodies and fragments thereof, of the present invention are conjugated or attached to other molecules or agents further include, but are not limited to binding members conjugated to a chemical ablation agent, toxin, immunomodulator, cytokine, cytotoxic agent, chemotherapeutic agent or drug.

The present invention includes an assay system which may be prepared in the form of a test kit for the quantitative analysis of the extent of the presence of, for instance, amplified EGFR or de2-7EGFR. The system or test kit may comprise a labeled component prepared by one of the radioactive and/or enzymatic techniques discussed herein, coupling a label to the antibody, and one or more additional immunochemical reagents, at least one of which is a free or immobilized components to be determined or their binding partner(s).

In a further embodiment, the present invention relates to certain therapeutic methods which would be based upon the activity of the binding member, antibody, or active fragments thereof, or upon agents or other drugs determined to possess the same activity. A first therapeutic method is associated with the prevention or treatment of cancer, including but not limited to head and neck, breast, prostate and glioma.

In particular, the binding members and antibodies of the present invention, and in a particular embodiment the 806 antibody whose sequences are presented in SEQ ID NOS: 2 and 4 herein, or active fragments thereof, and chimeric (bispecific) or synthetic antibodies derived therefrom can be prepared in pharmaceutical compositions, including a suitable vehicle, carrier or diluent, for administration in instances wherein therapy is appropriate, such as to treat cancer. Such pharmaceutical compositions may also include methods of modulating the half-life of the binding members, antibodies or fragments by methods known in the art such as pegylation. Such pharmaceutical compositions may further comprise additional antibodies or therapeutic agents.

Thus, a composition of the present invention may be administered alone or in combination with other treatments, therapeutics or agents, either simultaneously or sequentially dependent upon the condition to be treated. In addition, the present invention contemplates and includes compositions comprising the binding member, particularly antibody or fragment thereof, herein described and other agents or therapeutics such as anti-cancer agents or therapeutics, anti-EGFR agents or antibodies, or immune modulators. More generally these anti-cancer agents may be tyrosine kinase inhibitors or phosphorylation cascade inhibitors, post-translational modulators, cell growth or division inhibitors (e.g. anti-mitotics), PDGFR inhibitors or signal transduction inhibitors. Other treatments or therapeutics may include the administration of suitable doses of pain relief drugs such as non-steroidal anti-inflammatory drugs (e.g. aspirin, paracetamol, ibuprofen or ketoprofen) or opiates such as morphine, or anti-emetics. Thus, these agents may be anti-EGFR specific agents, such as AG1478, or may be more general anti-cancer and anti-neoplastic agents, non limiting examples including doxorubicin, carboplatin and cisplatin. In addition, the composition may be administered with immune modulators, such as interleukins, tumor necrosis factor (TNF) or other growth factors, cytokines or hormones such as dexamethasone which stimulate the immune response and reduction or elimination of cancer cells or tumors. The composition may also be administered with, or may include combinations along with other anti-EGFR antibodies, including but not limited to the anti-EGFR antibodies 528; 225; SC-03; 108 (ATCC HB9764) U.S. Pat. No. 6,217,866; 14E1 (U.S. Pat. No. 5,942,602); DH8.3; L8A4; Y10; HuMAX-EGFr (Genmab/Medarex); ICR62; and ABX-EGF (Abgenix).

The present invention also includes binding members, including antibodies and fragments thereof, which are covalently attached to or otherwise associated with other molecules or agents. These other molecules or agents include, but are not limited to, molecules (including antibodies or antibody fragments) with distinct recognition characteristics, toxins, ligands, and chemotherapeutic agents.

Other objects and advantages will become apparent to those skilled in the art from a review of the ensuing detailed description, which proceeds with reference to the following illustrative drawings, and the attendant claims.

BRIEF DESCRIPTION OF THE DRAWINGS

FIG. 3 depicts the internalization of MAb 806 and the DH8.3 antibody. U87MG.Δ2-7 cells were pre-incubated with MAb 806 (▲) or DH8.3 (●) at 4° C., transferred to 37° C. and internalization determined by FACS. Data represents mean internalization at each time point ±SE of 3 (DH8.3) or 4 (MAb 806) separate experiments.

FIG. 12 illustrates the anti-tumor effect of treatment with mAb 806 combined with treatment with AG1478 on A431 xenografts in a preventative model. Data are expressed as mean tumor volume ±S.E.

FIG. 14 illustrates the nucleic acid sequence and the amino acid translation thereof of the 806 VH gene (SEQ ID NO:1 and SEQ ID NO:2, respectively).

FIG. 15 illustrates the nucleic acid sequence and the amino acid translation thereof of the 806 VL gene (SEQ ID NO:3 and SEQ ID NO:4, respectively).

FIG. 16 shows the VH sequence (SEQ ID NO:11) numbered according to Kabat, with the CDRs boxed. Key residues of the VH are 24, 37, 48, 67 and 78.

FIG. 17 shows the VL sequence (SEQ ID NO:12) numbered according to Kabat, with the CDRs boxed. Key residues of the VL are 36, 46, 57 and 71.

FIG. 20 Autoradiography of a U87MG.Δ2-7 xenograft section collected 8 hr after injection of $^{125}$I-MAb 806.

FIG. 26 A, FACS analysis of mAb 806 reactivity with U87 MG cell lines. U87 MG, U87 MG.ΔEGFR, U87 MG. DK, and U87 MG.wtEGFR cells were stained with anti-EGFR mAbs 528, EGFR.1, and anti-ΔEGFR antibody, mAb 806. Monoclonal EGFR. 1 antibody recognized wtEGFR exclusively and monoclonal 528 antibody reacted with both wtEGFR and ΔEGFR. mAb 806 reacted intensively with U87 MG.ΔEGFR and U87 MG. DK and weakly with U87 MG.wtEGFR. Bars on the abscissa, maximum staining of cells in the absence of primary antibody. Results were reproduced in three independent experiments. B, mAb 806 immunoprecipitation of EGFR forms. Mutant and wtEGFR were immunoisolated with anti-EGFR antibodies, 528, or EGFR.1, or anti-ΔEGFR antibody, mAb 806, from (Lane 1) U87 MG, (Lane 2)

U87Δ.EGFR, (Lane 3) U87 MG. DK, and (Lane 4) U87 MG.wtEGFR cells and were then detected by Western blotting with anti-pan EGFR antibody, C13.

Figure 27A:
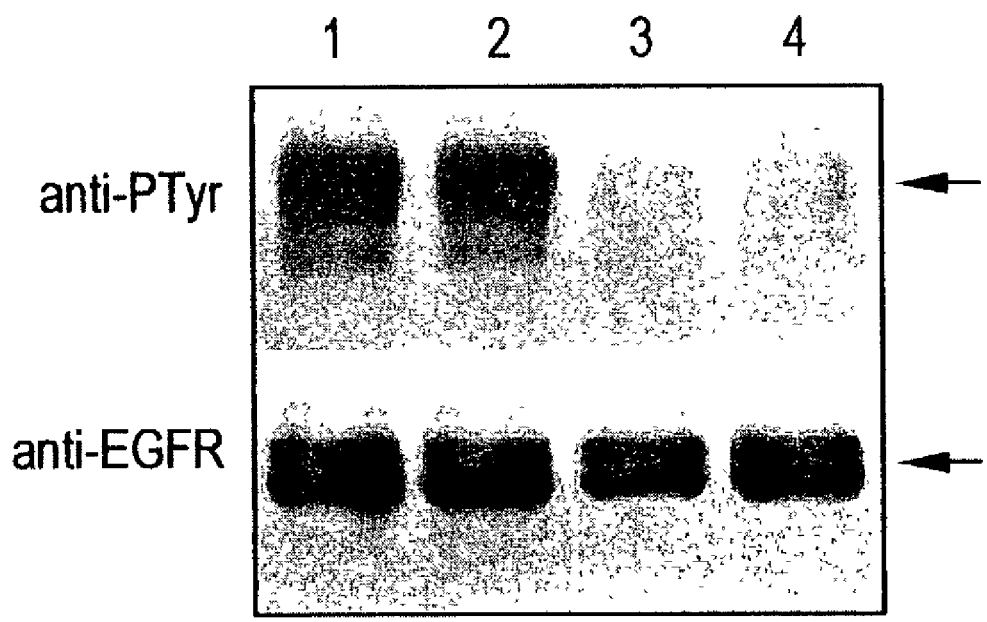
Figure 27B:
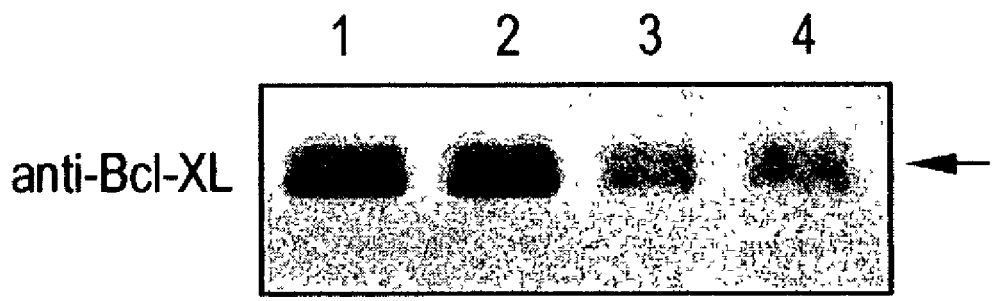

FIG. 27 Systemic treatment with mAb 806 decreases the phosphorylation of ΔEGFR and Bcl-X$_L$ expression in U87 MG.ΔEGFR brain tumors. U87 MG.ΔEGFR tumors were resected at day 9 of mAb 806 treatment, immediately frozen in liquid nitrogen and stored at −80° C. before tumor lysate preparation. A, Western blot analysis of expression and the degree of autophosphorylation of ΔEGFR. Thirty Ξg of tumor lysates were subjected to SDS-polyacrylamide gels, transferred to nitrocellulose membranes, and probed with antiphosphotyrosine mAb, then were stripped and reprobed with anti-EGFR antibody, C13. B, Western blotting of Bcl-X$_L$ by using the same tumor lysates as in A. Membranes were probed with antihuman Bcl-X polyclonal antibody. Lanes 1 and 2, U87 MG.ΔEGFR brain tumors treated with isotype control; Lanes 3 and 4, U87 MG.ΔEGFR brain tumors treated with mAb 806.

Figure 28:
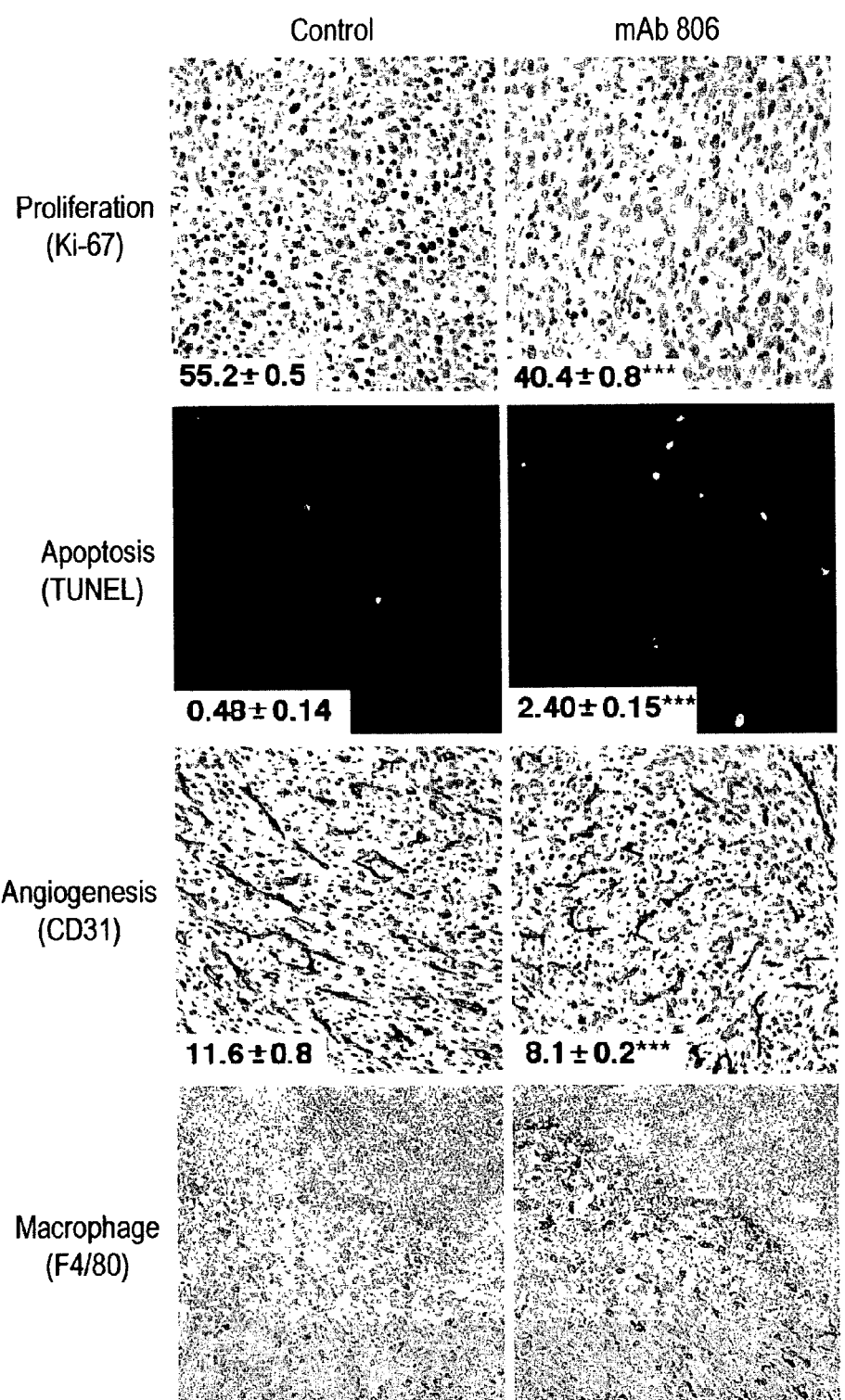

FIG. 28 MAb 806 treatment leads to a decrease in growth and vasculogenesis and to increases in apoptosis and accumulating macrophages in U87 MG.ΔEGFR tumors. Tumor sections were stained for Ki-67. Cell proliferative index was assessed by the percentage of total cells that were Ki-67 positive from four randomly selected high-power fields (×400) in intracranial tumors from four mice of each group. Data are the mean±SE. Apoptotic cells were detected by TUNEL assay. Apoptotic index was assessed by the ratio of TUNEL-positive cells:total number of cells from four randomly selected high-power fields (×400) in intracranial tumors from four mice of each group. Data are the mean±SE. Tumor sections were immunostained with anti-CD31 antibody. MVAs were analyzed by computerized image analysis from four randomly selected fields (×200) from intracranial tumors from four mice of each group. Peritumoral infiltrates of macrophages in mAb 806-treated U87MG.ΔEGFR tumors. Tumor sections were stained with anti-F4/80 antibody.

FIG. 29 Flow cytometric analysis of parental and transfected U87 MG glioma cell lines. Cells were stained with either an irrelevant IgG2b antibody (open histograms) or the 528 antibody or mAb 806 (filled histograms) as indicated.

FIG. 30 Immunoprecipitation of EGFR from cell lines. The EGFR was immunoprecipitated from $^{35}$S-labeled U87 MG.wtEGFR, U87 MG. Δ2-7, and A431 cells with mAb806 (806), sc-03 antibody (c-term), or a IgG2b isotype control (con). Arrows, position of the de2-7 and wt EGFR.

Figure 31:
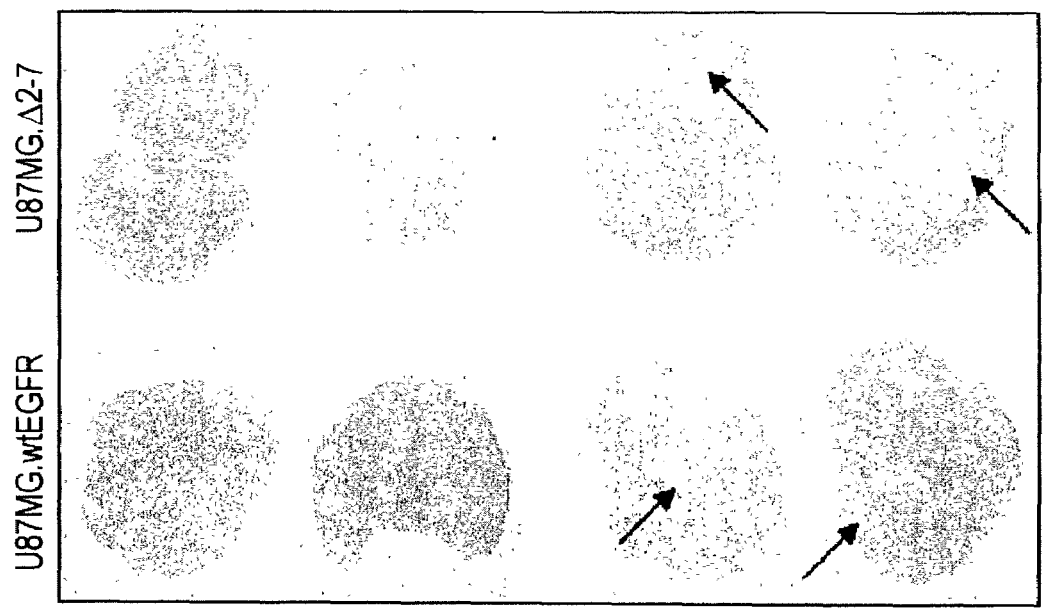

FIG. 31 Representative H&E-stained paraffin sections of U87 MG.Δ2-7 and U87MG.wtEGFR xenografts. U87 MG.Δ2-7 (collected 24 days after tumor inoculation) and U87 MG.wtEGFR (collected 42 days after tumor inoculation) xenografts were excised from mice treated as described in FIG. 10 above, and stained with H&E. Vehicle-treated U87 MG.Δ2-7 (collected 18 days after tumor inoculation) and U87 MG.wtEGFR (collected 37 days after tumor inoculation) xenografts showed very few areas of necrosis (left panel), whereas extensive necrosis (arrows) was observed in both U87 MG.Δ2-7 and U87 MG.wtEGFR xenografts treated with mAb 806 (right panel).

Figure 32:
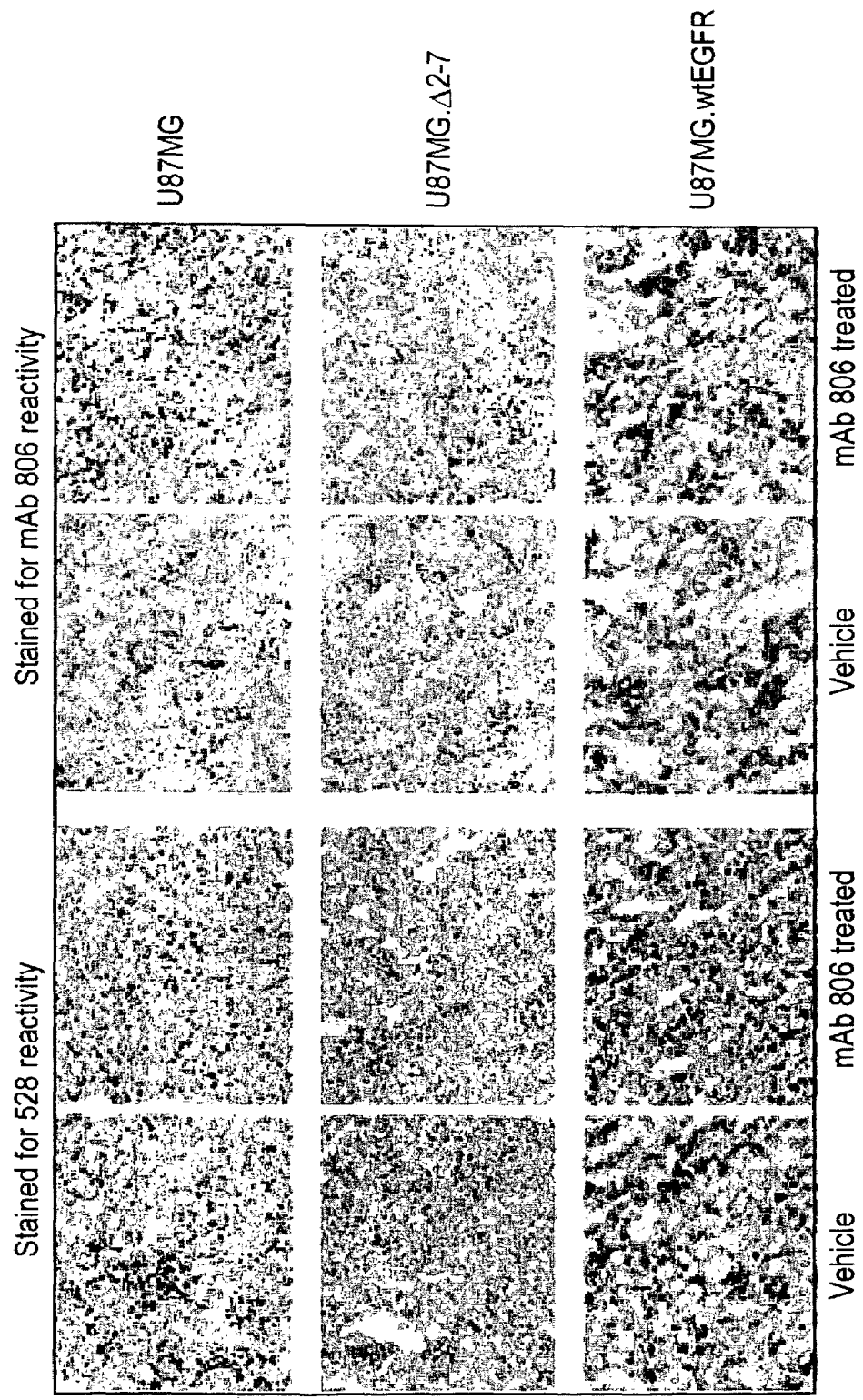

FIG. 32 Immunohistochemical analysis of EGFR expression in frozen sections derived from U87 MG, U87 MG.Δ2-7, and U87 MG.wtEGFR xenografts. Sections were collected at the time points described in FIG. 31 above. Xenograft sections were immunostained with the 528 antibody (left panel) and mAb 806 (right panel). No decreased immunoreactivity to either wt EGFR, amplified EGFR, or de2-7 EGFR was observed in xenografts treated with mAb 806. Consistent with the in vitro data, parental U87 MG xenografts were positive for 528 antibody but were negative for mAb 806 staining.

Figure 33A:
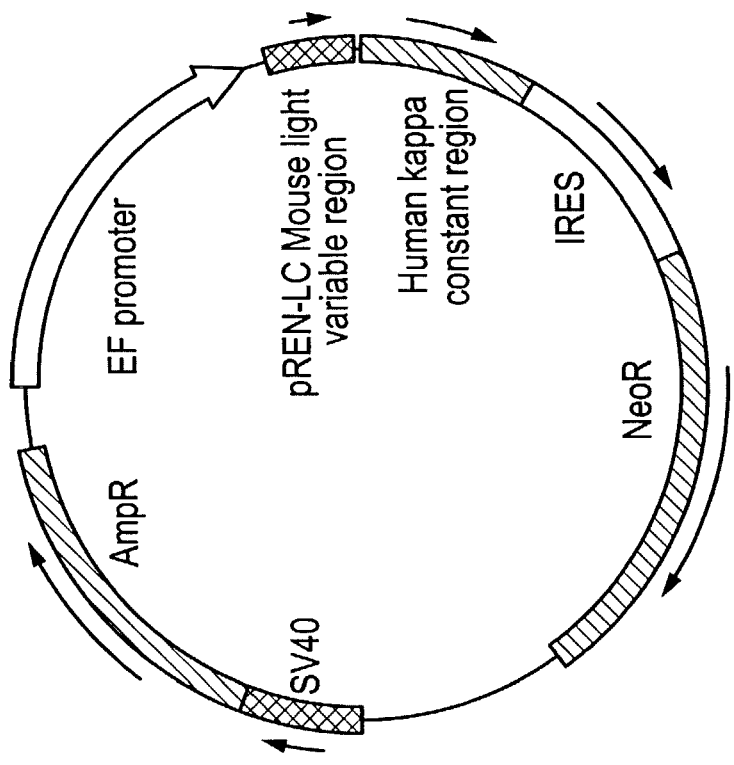
Figure 33B:
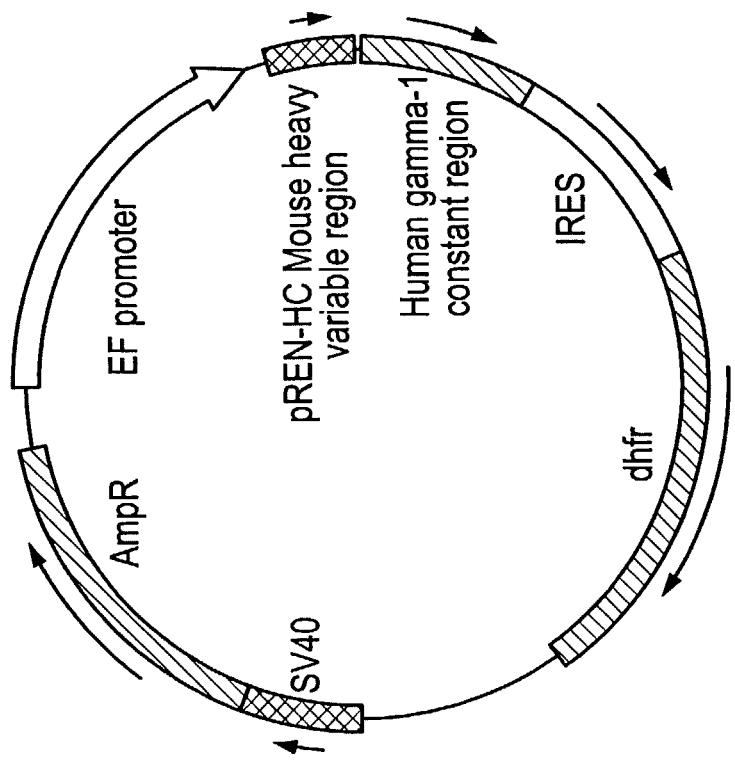

FIG. 33. Schematic representation of generated bicistronic expression constructs. Transcription of the chimeric antibody chains is initiated by Elongation Factor-1 promoter and terminated by a strong artificial termination sequence. IRES sequences were introduced between coding regions of light chain and NeoR and heavy chain and dhfr gene.

Figure 34B:
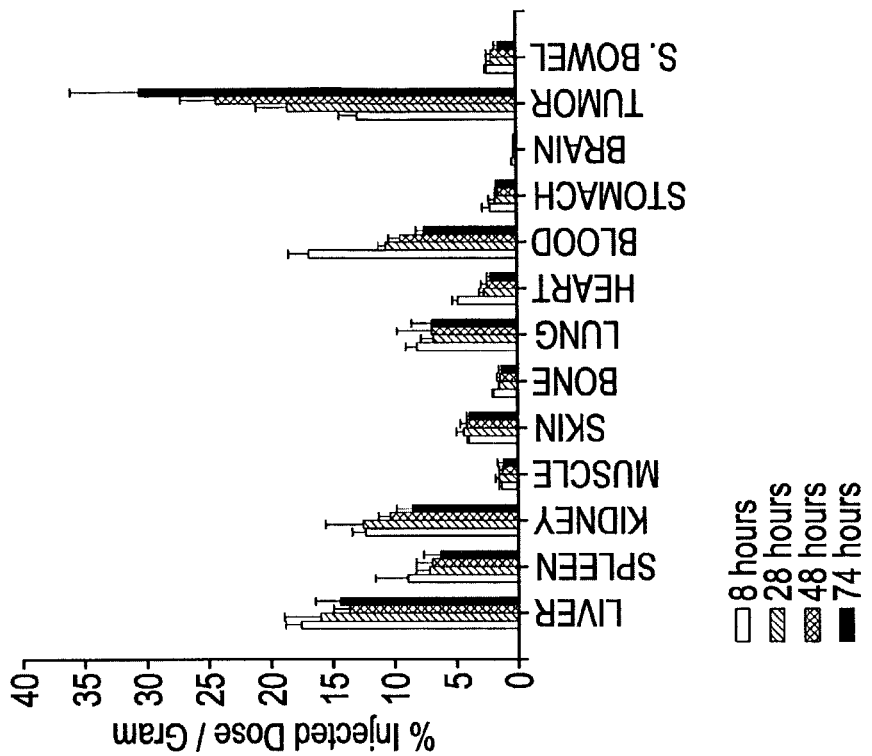
Figure 34A:
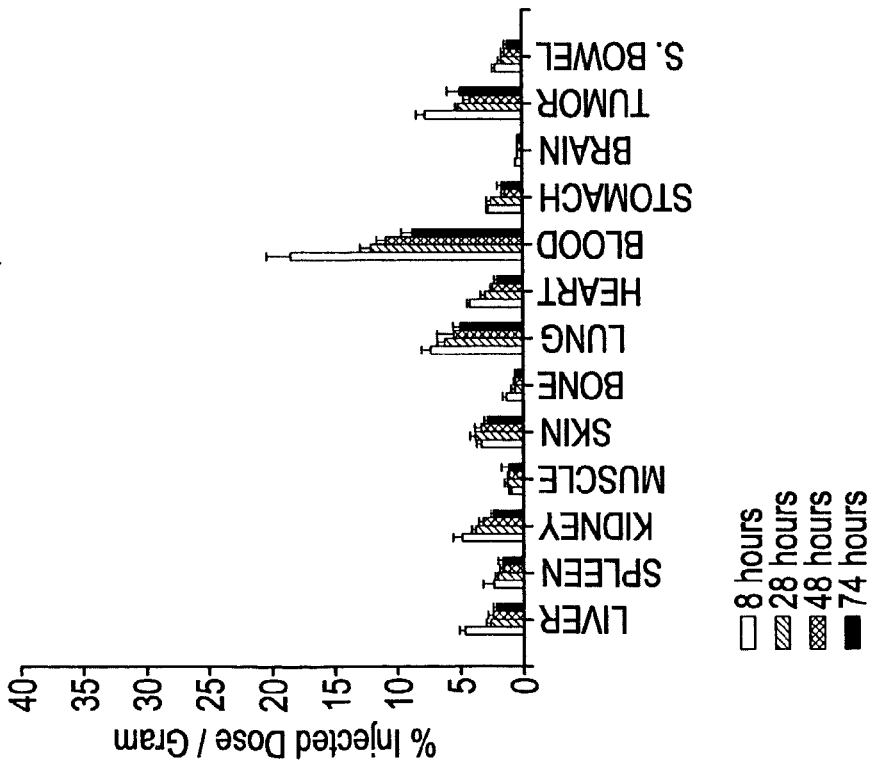

FIG. 34. Biodistribution analysis of the ch806 radiolabeled with either A) $^{125}$I or B) $^{111}$I was performed in BALB/c nude mice bearing U87MG-de2-7 xenograft tumors. Mice were injected with 5 ug of radiolabeled antibody and in groups of 4 mice per time point, sacrificed at either 8, 28, 48 or 74 hours. Organs were collected, weighed and radioactivity measured in a gamma counter.

Figure 35A:
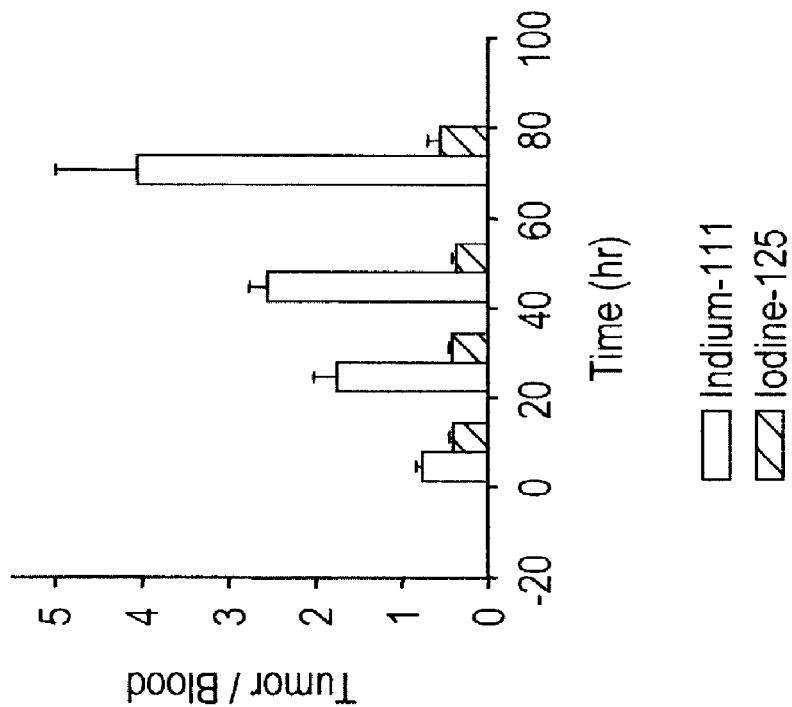
Figure 35B:
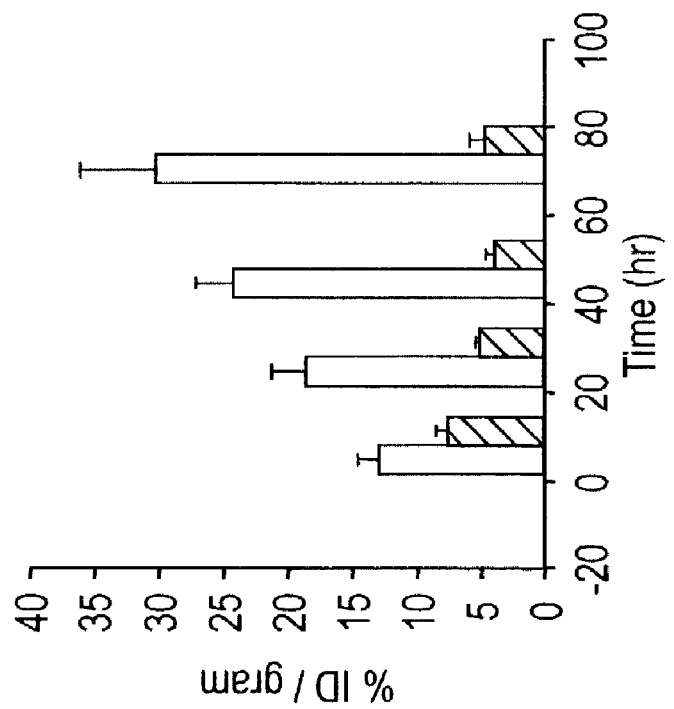

FIG. 35. Depicts (A) the % ID gram tumor tissue and (B) the tumor to blood ratio. Indium-111 antibody shows approximately 30% ID/gram tissue and a tumor to blood ratio of 4.0.

Figure 36:
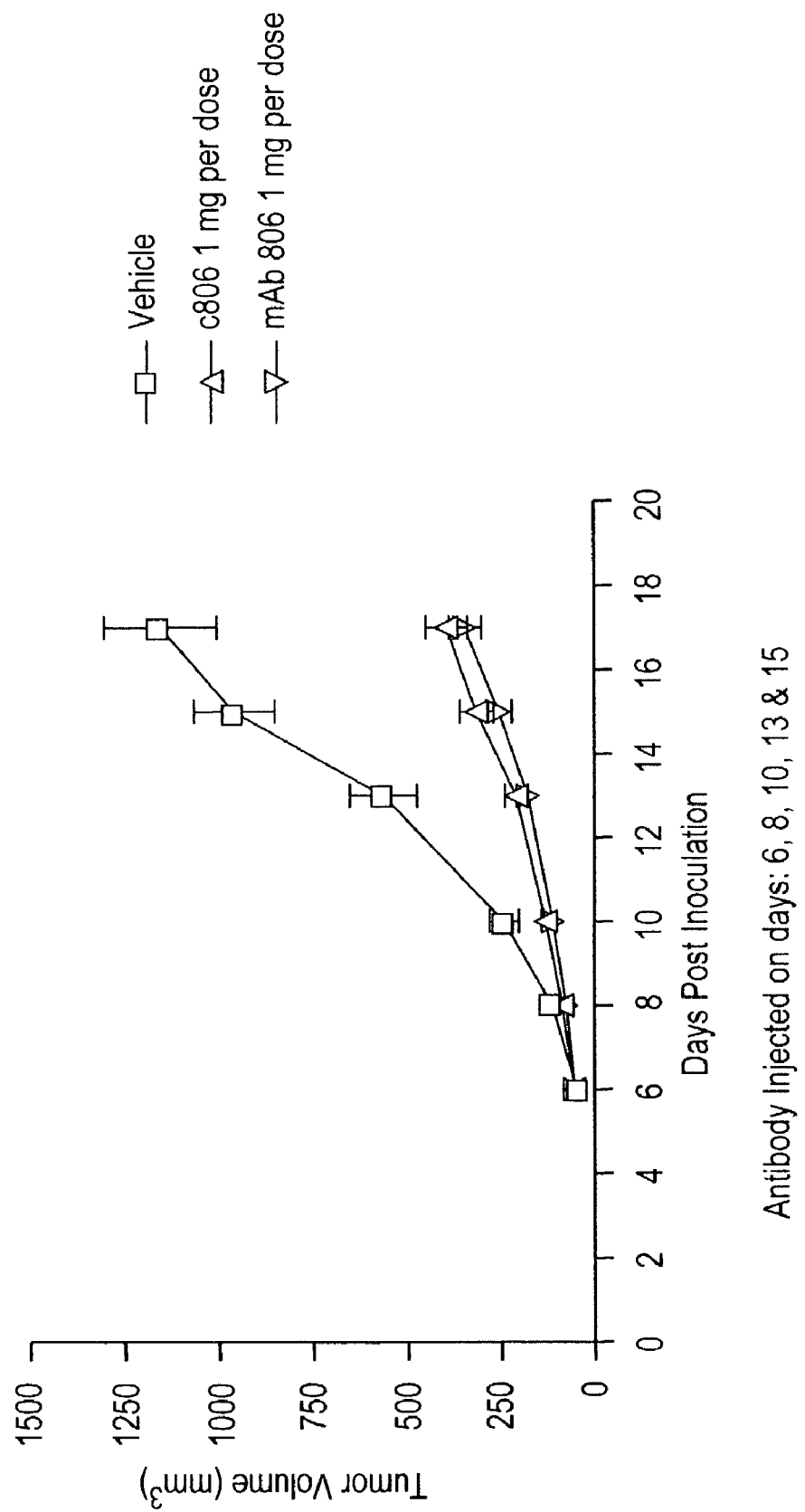

FIG. 36 depicts the therapeutic efficacy of chimeric antibody ch806 in an established tumor model. 3×10$^6$ U87MG.Δ2-7 cells in 100 ul of PBS were inoculated s.c. into both flanks of 4-6 week old female nude mice. The mAb806 was included as a positive control. Treatment was started when tumors had reached a mean volume of 50 mm$^3$ and consisted of 1 mg of ch806 or mAb806 given i.p. for a total of 5 injections on the days indicated. Data was expressed as mean tumor volume +/−S.E. for each treatment group.

Figure 37A:
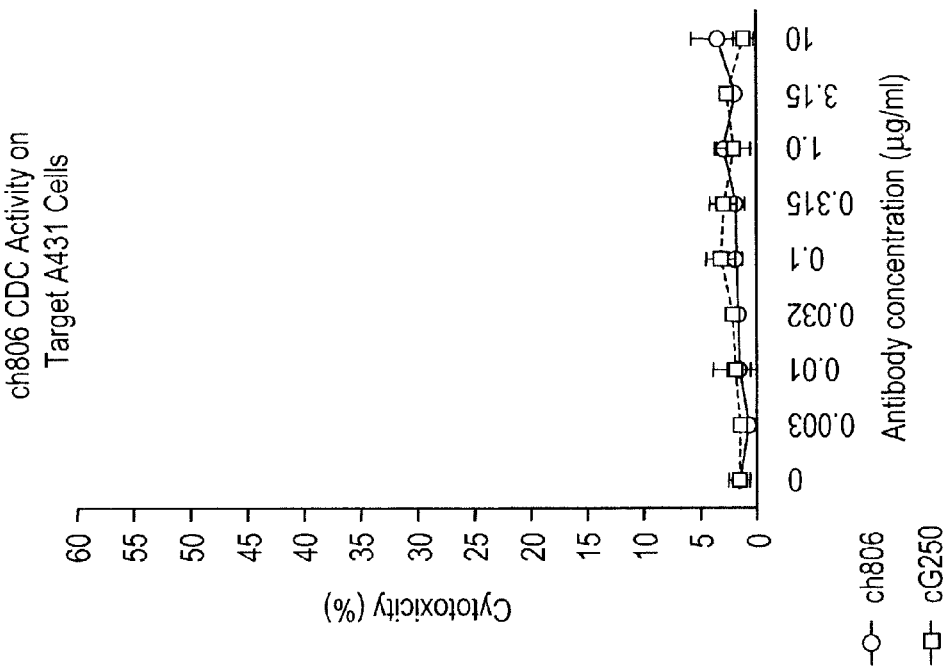
Figure 37B:
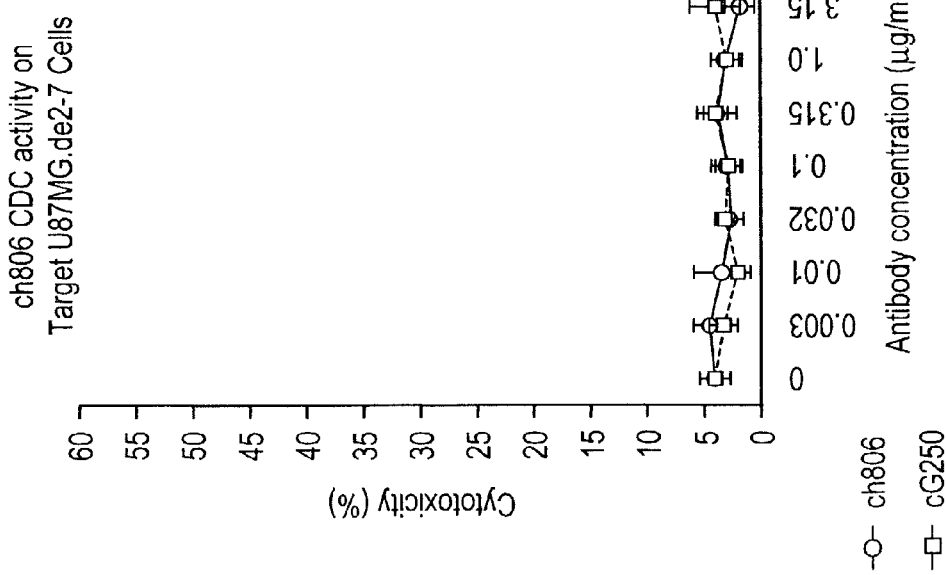

FIG. 37. CDC Activity on Target A) U87MG.de2-7 and B) A431 cells for anti-EGFR chimeric IgG1 antibodies ch806 and control cG250. Mean (bars; ±SD) percent cytotoxicity of triplicate determinations are presented.

Figure 38B:
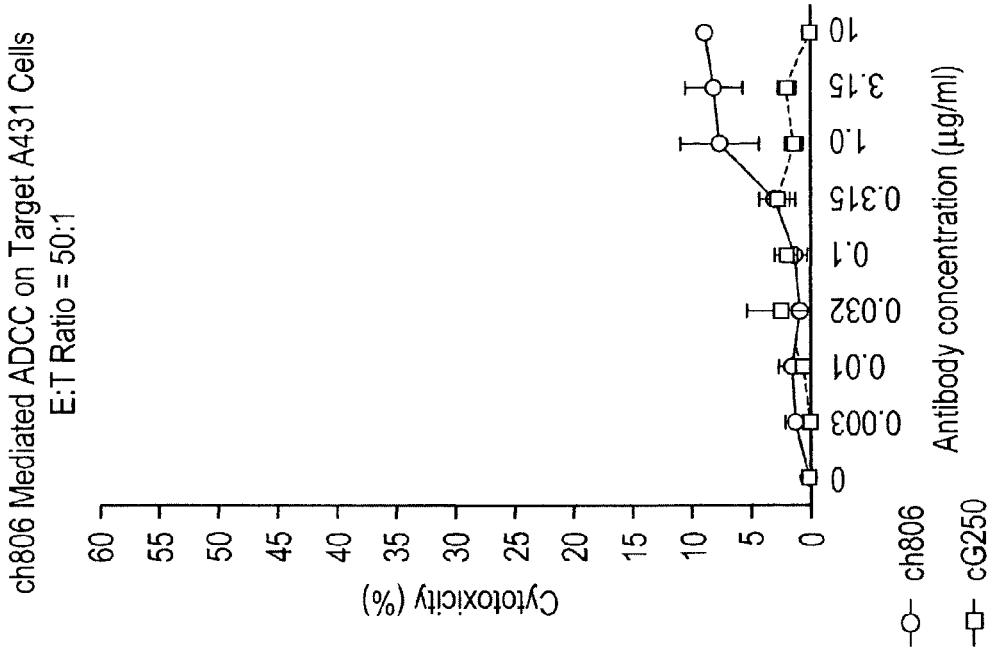
Figure 38A:
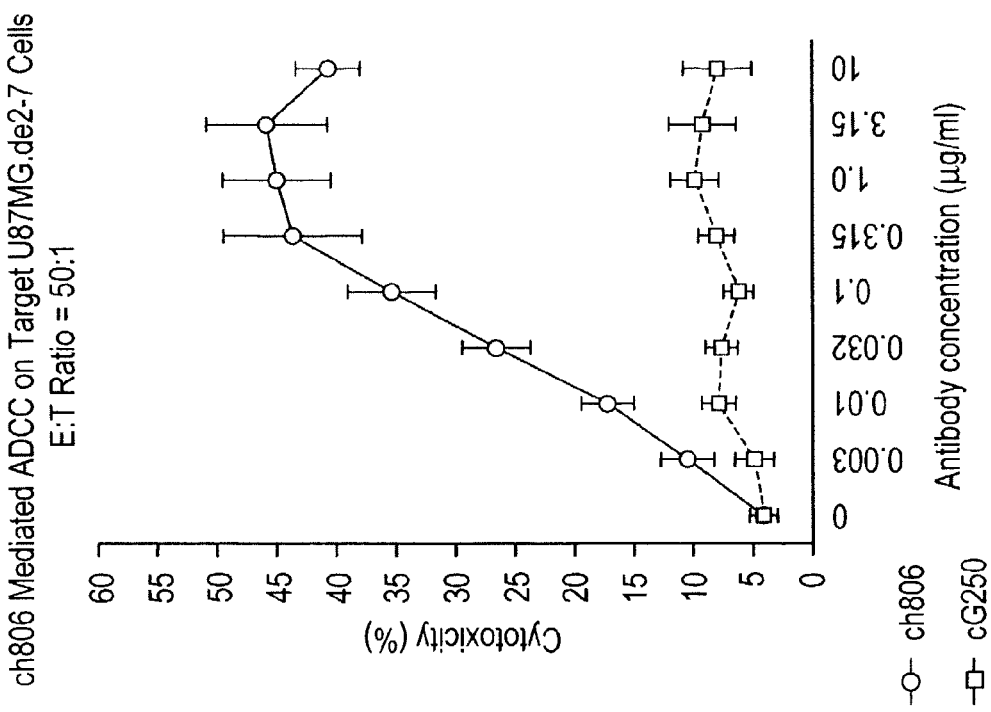

FIG. 38. ADCC on target A) U87MG.de2-7 and B) A431 cells at Effector:Target cell ratio of 50:1 mediated by ch806 and isotype control cG250 (0-10 ug/ml). Results are expressed as mean (bars; ±SD) percent cytotoxicity of triplicate determinations.

Figure 39:
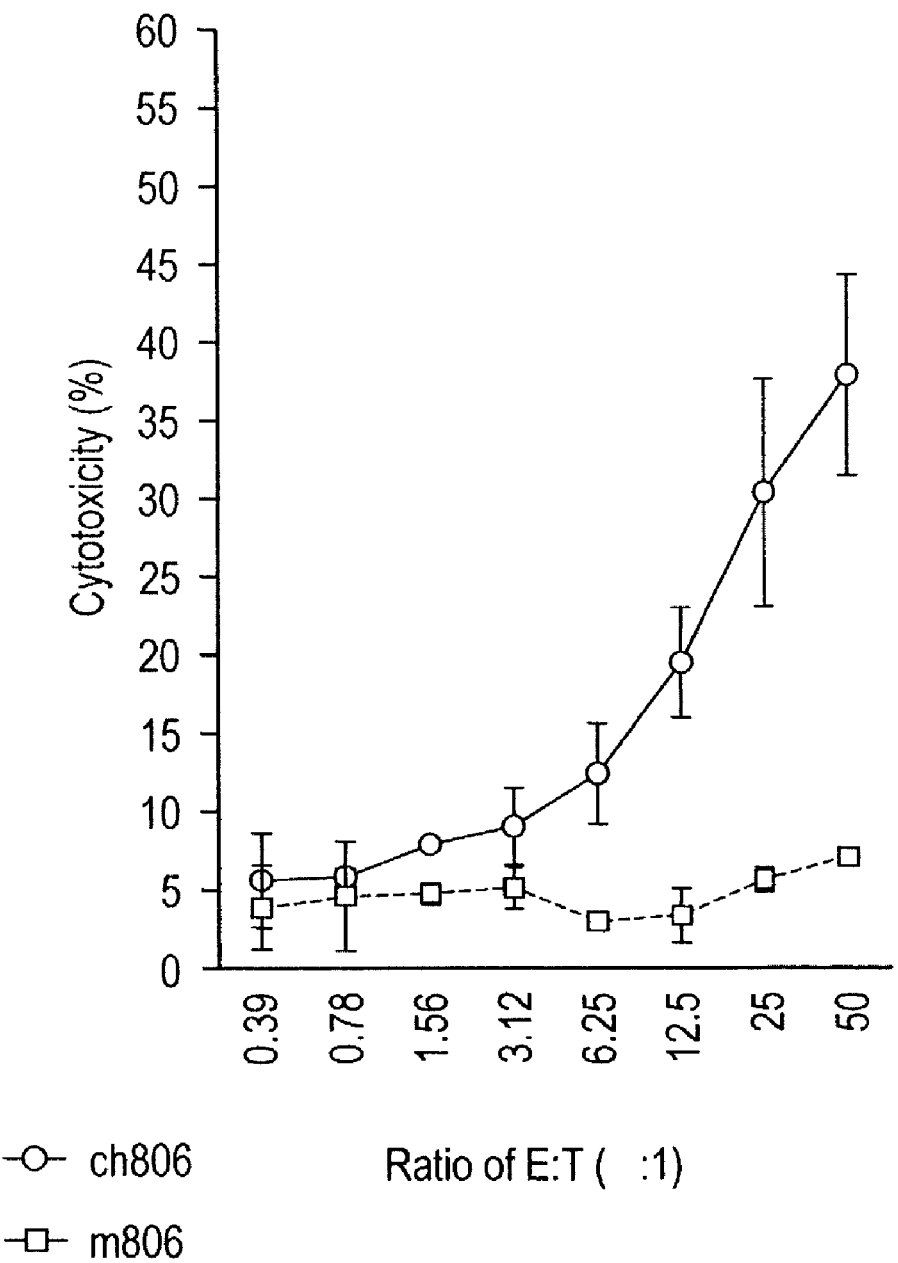

FIG. 39. ADCC mediated by 1 ug/ml parental mAb 806 and ch806 on target U87MG.de2-7 cells over a range of Effector: Target ratios. Mean (bars; ±SD) of triplicate determinations are presented.

Figure 40B:
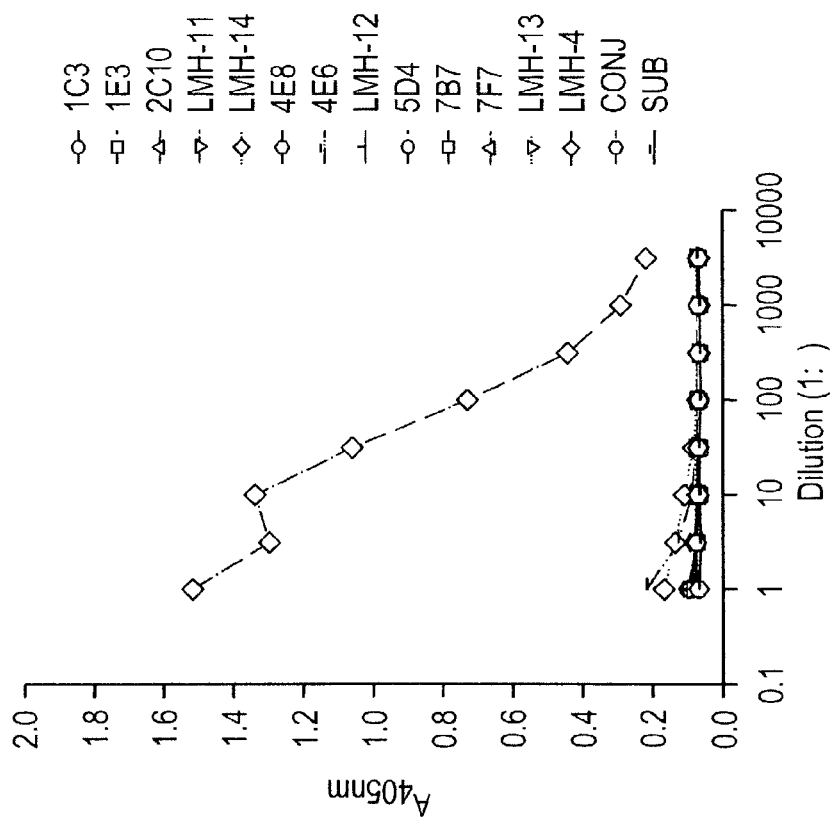
Figure 40A:
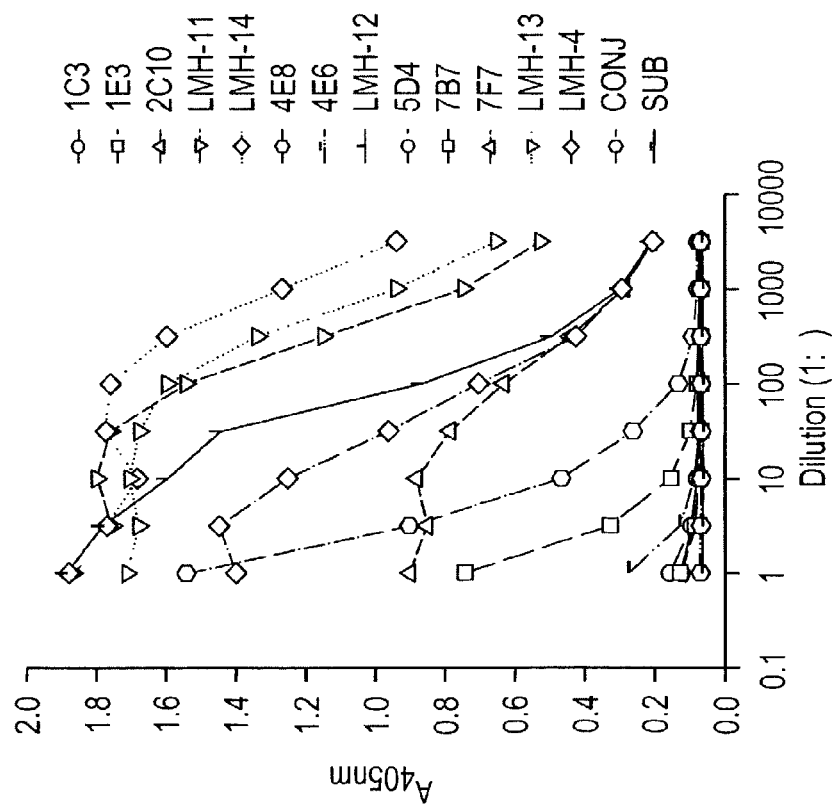

FIG. 40. Twenty-five hybridomas producing antibodies that bound ch806 but not huIgG were initially selected. Four of these anti-ch806 hybridomas with high affinity binding (clones 3E3, 5B8, 9D6 and 4D8) were subsequently pursued for clonal expansion from single cells by limiting dilution and designated Ludwig Institute for Cancer Research Melbourne Hybridoma (LMH)-11, -12, -13 and -14, respectively. In addition, two hybridomas that produced mAbs specific for huIgG were also cloned and characterized further: clones 2C10 (LMH-15) and 2B8 (LMH-16).

Figure 41A:
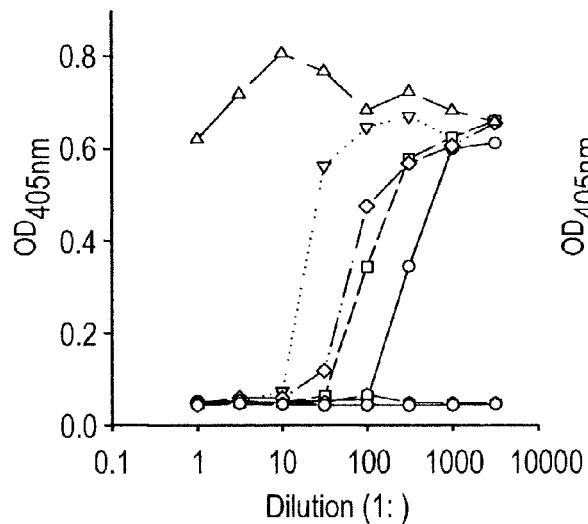
Figure 41B:
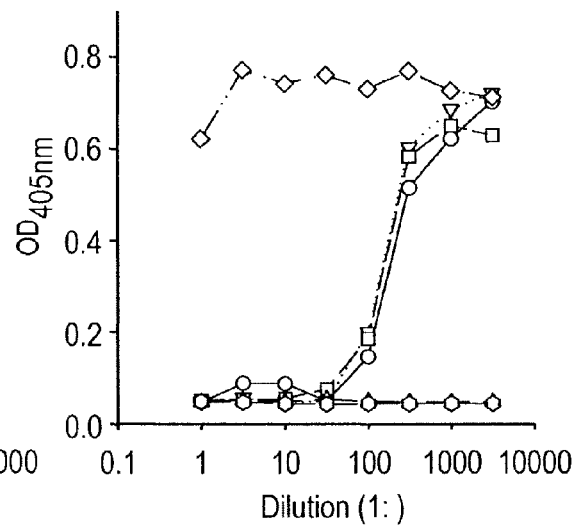
Figure 41C:
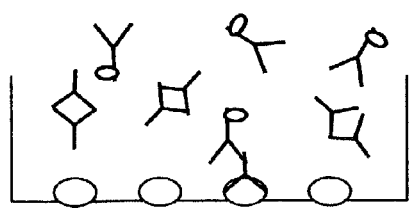

FIG. 41. After clonal expansion, the hybridoma culture supernatants were examined in triplicate by ELISA for the ability to neutralize ch806 or mAb 806 antigen binding activity with sEGFR621. Mean (±SD) results demonstrated the antagonist activity of anti-idiotype mAbs LMH-11, -12, -13 and -14 with the blocking in solution of both ch806 and murine mAb 806 binding to plates coated with sEGFR (LMH-14 not shown).

Figure 42C:
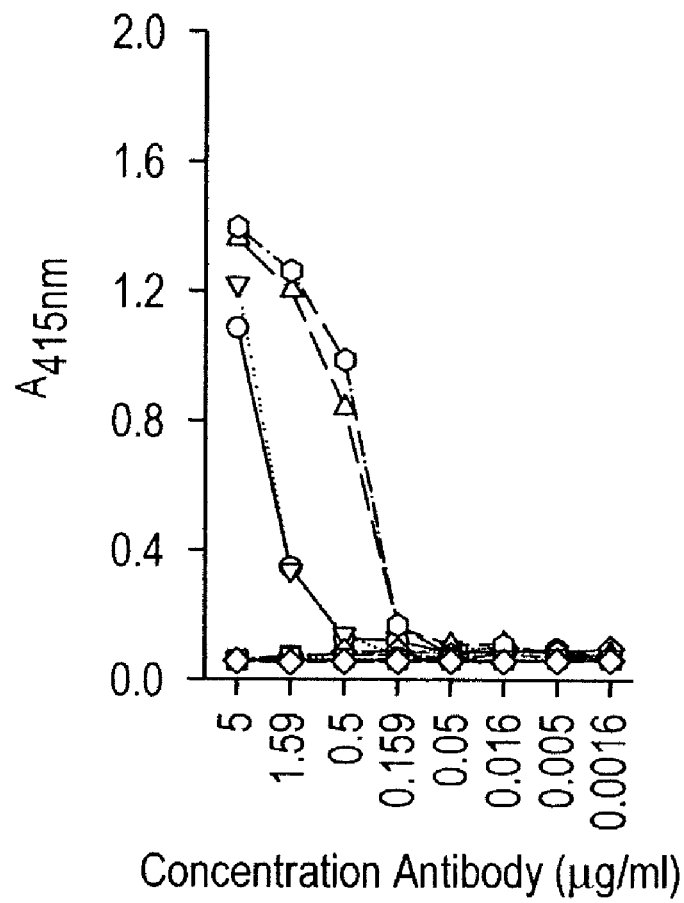

FIG. 42. Microtitre plates were coated with 10 μg/ml purified A) LMH-11, B) LMH-12 and C) LMH-13. The three purified clones were compared for their ability to capture ch806 or mAb 806 in sera or 1% FCS/Media and then detect bound ch806 or mAb806. Isotype control antibodies hu3S193 and m3S193 in serum and 1% FCS/Media were included in addition to controls for secondary conjugate avidin-HRP and ABTS substrate. Results are presented as mean (±SD) of triplicate samples using biotinylated-LMH-12 (10 μg/ml) for detection and indicate LMH-12 used for capture and detection had the highest sensitivity for ch806 in serum (3 ng/ml) with negligible background binding.

Figure 43:
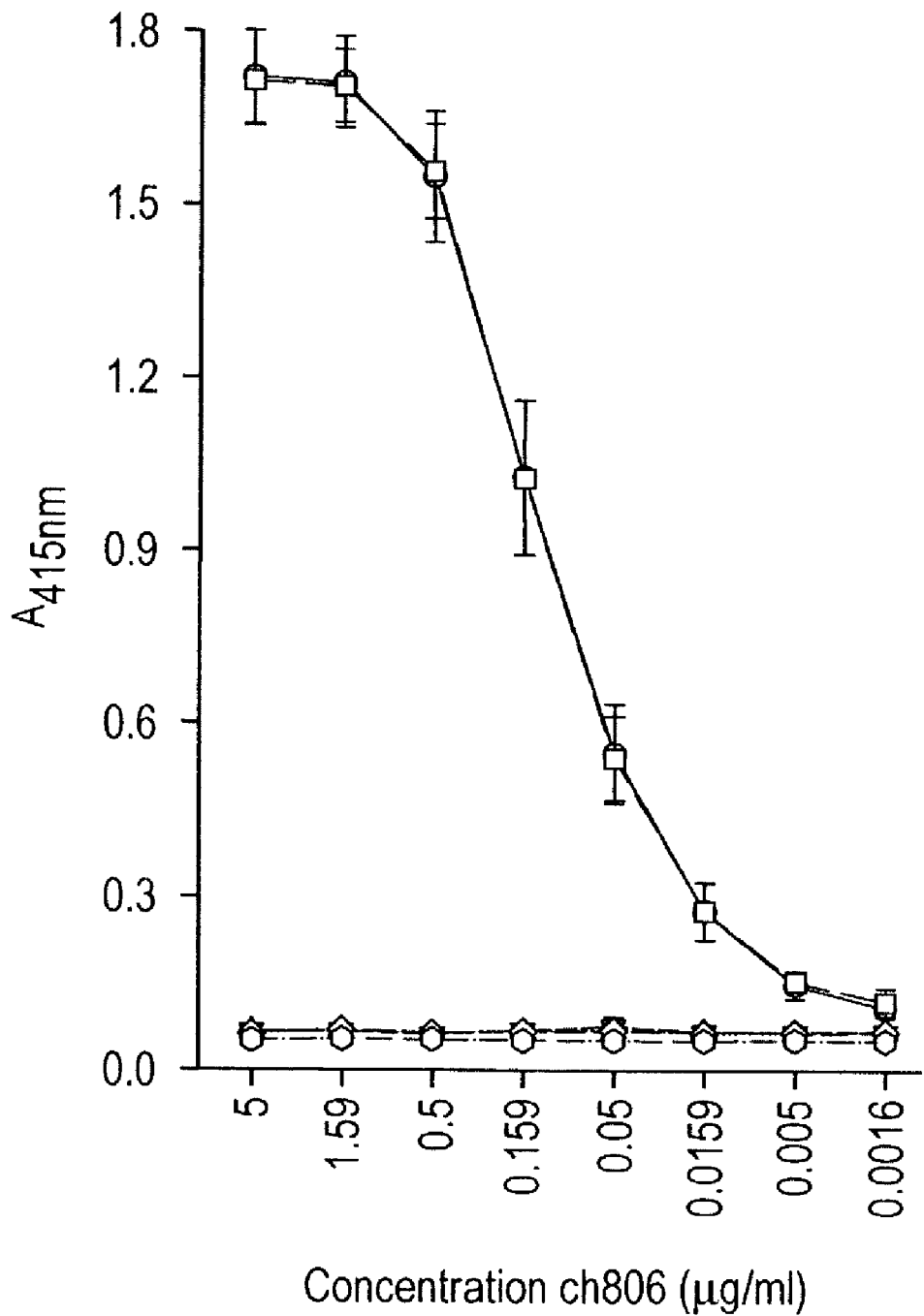

FIG. 43. Validation of the optimal pharmacokinetic ELISA conditions using 1 μg/ml anti-idiotype LMH-12 and 1 μg/ml biotinylated LMH-12 for capture and detection, respectively. Three separate ELISAs were performed in quadruplicate to measure ch806 in donor serum (•) from three healthy donors or 1% BSA/media (■) with isotype control hu3S193 in serum (▲) or 1% BSA/media (▼). Controls for secondary conjugate avidin-HRP (♦) and ABTS substrate (hexagon) alone were also included with each ELISA. Mean (±SD) results demonstrate highly reproducible binding curves for measuring ch806 (2 μg/ml-1.6 ng/ml) in sera with a 3 ng/ml limit of detection. (n=12; 1-100 ng/ml, Coefficient of Variation<25%; 100 ng/ml-5 μg/ml, Coefficient of Variation<15%). No background binding was evident with any of the three sera tested and negligible binding was observed with isotype control hu3S193.

Figure 44:
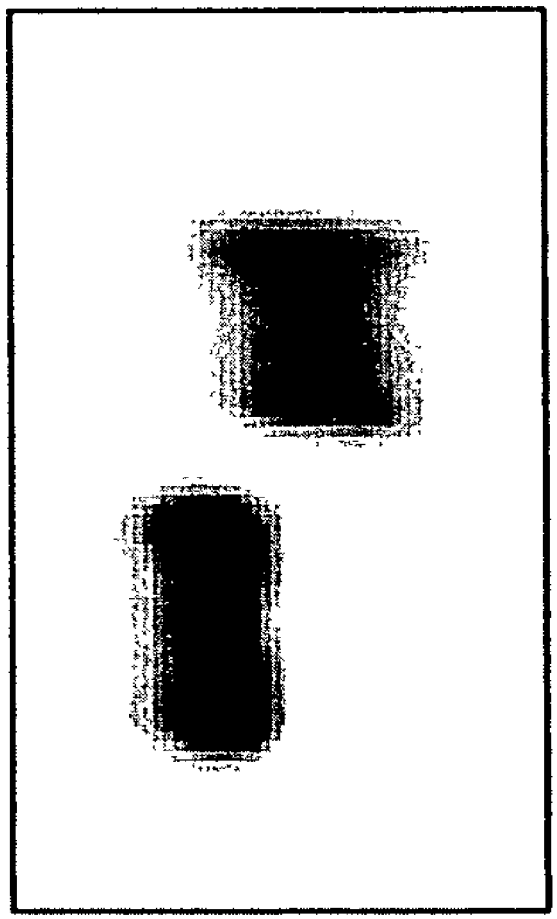

FIG. 44 depicts an immunoblot of recombinant sEGFR expressed in CHO cells, blotted with mAb806. Recombinant sEGFR was treated with PNGaseF to remove N-linked glycosylation (deglycosylated), or untreated (untreated), the protein was run on SDS-PAGE, transferred to membrane and immunoblotted with mAb 806.

Figure 45:
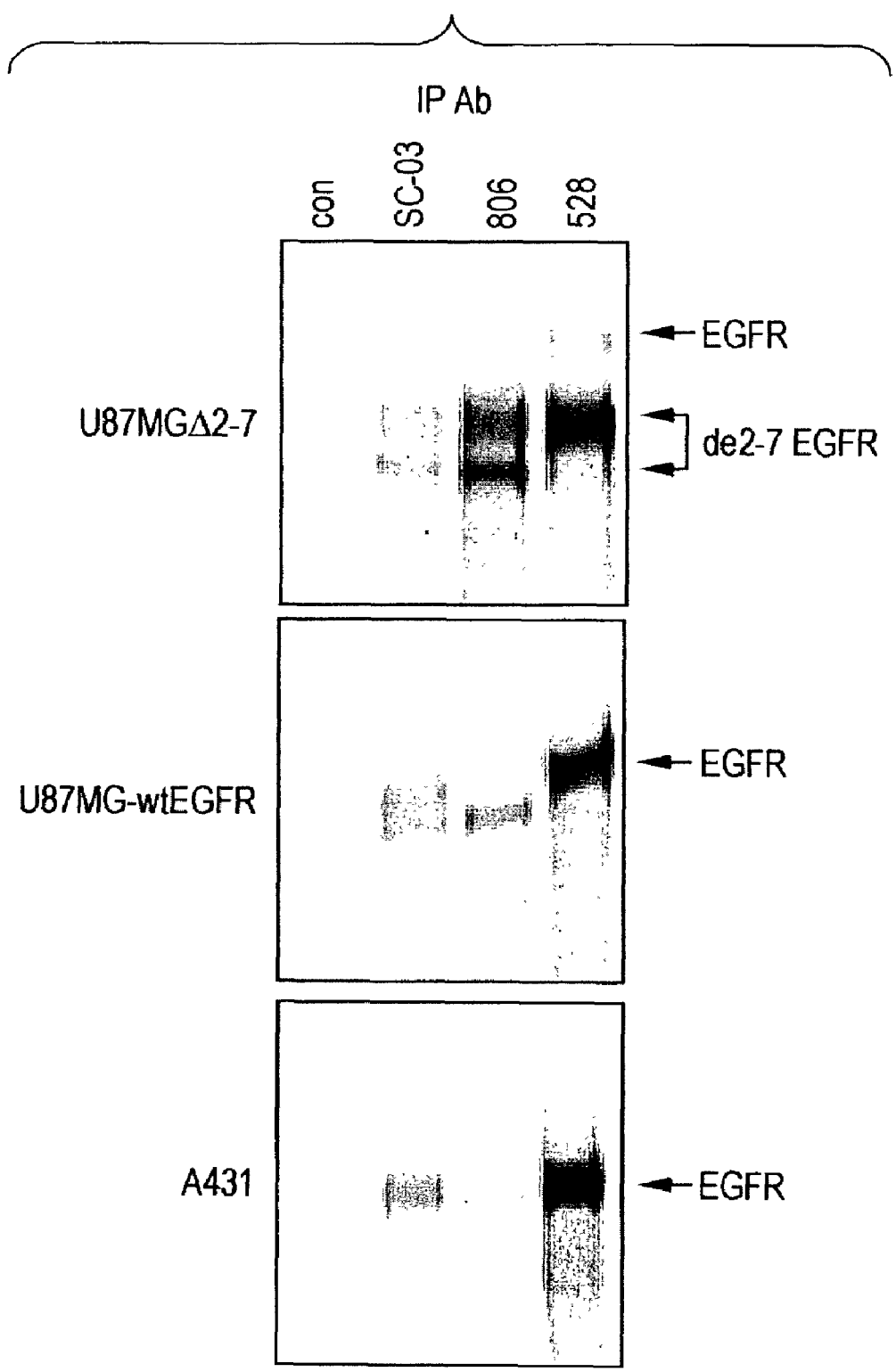

FIG. 45 depicts immunoprecipitation of EGFR from $^{35}$S-labelled cell lines (U87MG Δ2-7, U87MG-wtEGFR, and A431) with different antibodies (SC-03, 806 and 528 antibodies).

Figure 46:
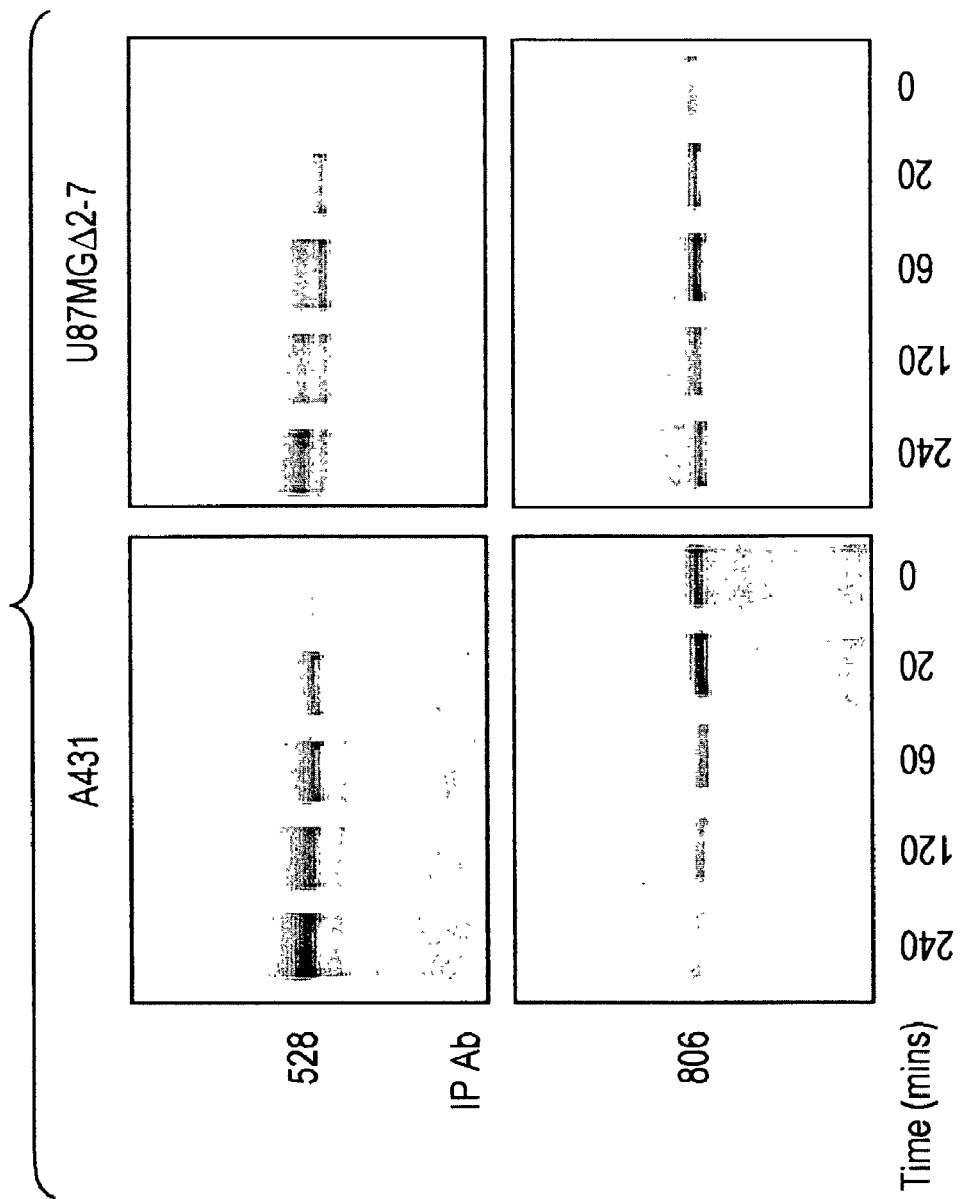

FIG. 46 depicts immunoprecipitation of EGFR from different cells (A431 and U87MGΔ2-7) at different time points (time 0 to 240 minutes) after pulse-labelling with $^{35}$S methionine/cysteine. Antibodies 528 and 806 are used for immunoprecipitation.

Figure 47:
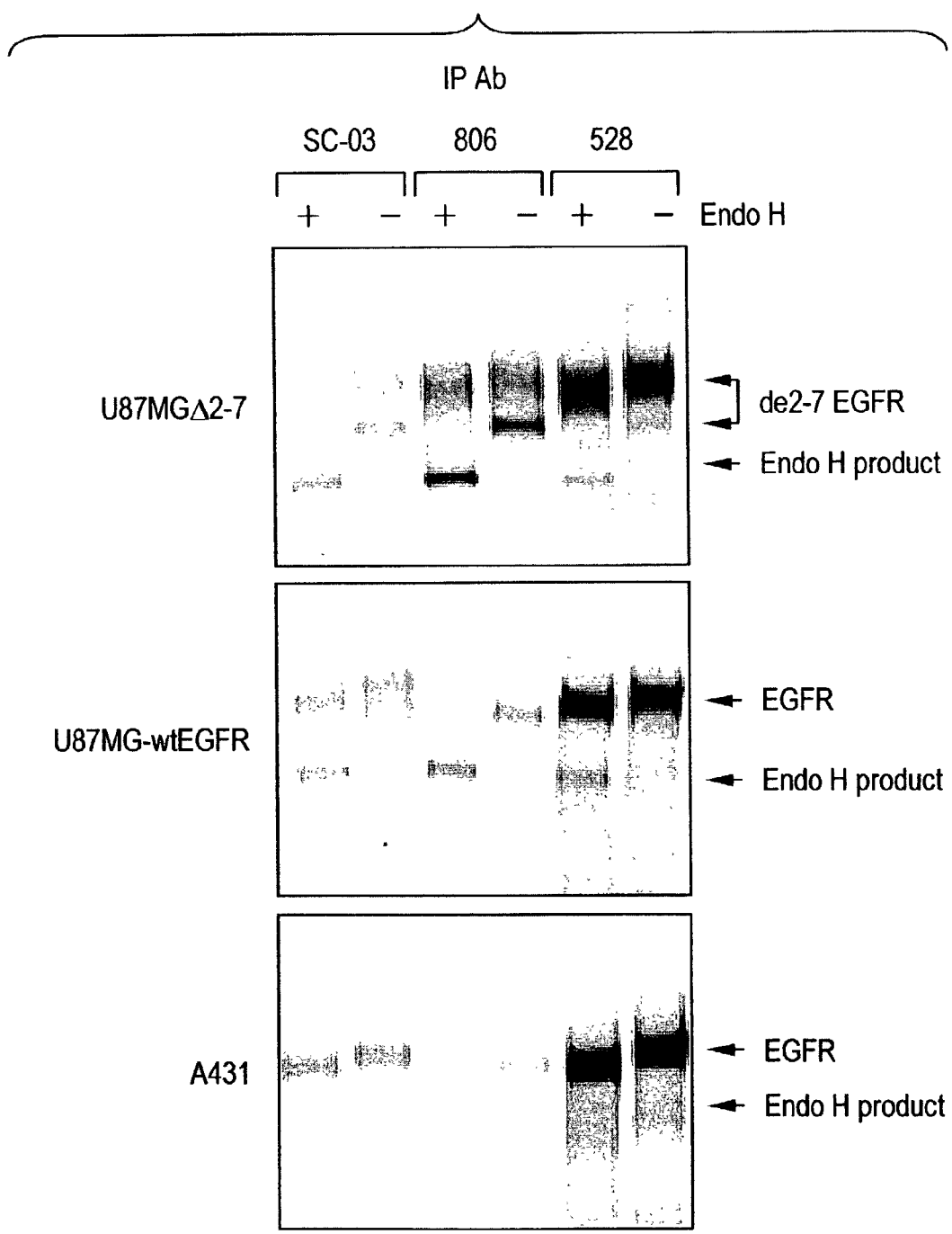

FIG. 47 depicts immunoprecipitation of EGFR from various cell lines (U87MGΔ2-7, U87MG-wtEGFR and A431) with various antibodies (SC-03, 806 and 528) in the absence of (−) and after Endo H digestion (+) to remove high mannose type carbohydrates.

Figure 48:
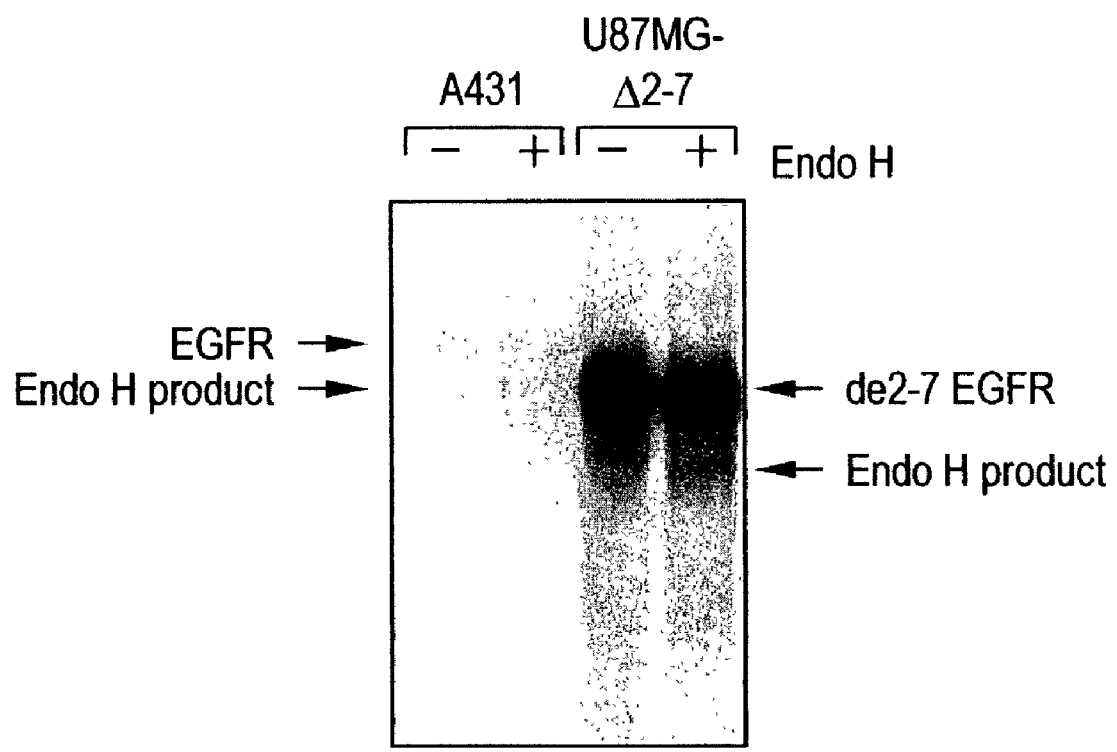

FIG. 48 depicts cell surface iodination of the A431 and U87MGΔ2-7 cell lines followed by immunoprecipitation with the 806 antibody, and with or without Endo H digestion, confirming that the EGFR bound by mAb 806 on the cell surface of A431 cells is an EndoH sensitive form.

DETAILED DESCRIPTION

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I-III [Ausubel, R. M., ed. (1994)]; "Cell Biology: A Laboratory Handbook" Volumes I-III [J. E. Celis, ed. (1994))]; "Current Protocols in Immunology" Volumes I-III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Therefore, if appearing herein, the following terms shall have the definitions set out below.

A. Terminology

The term "specific binding member" describes a member of a pair of molecules which have binding specificity for one another. The members of a specific binding pair may be naturally derived or wholly or partially synthetically produced. One member of the pair of molecules has an area on its surface, or a cavity, which specifically binds to and is therefore complementary to a particular spatial and polar organisation of the other member of the pair of molecules. Thus the members of the pair have the property of binding specifically to each other. Examples of types of specific binding pairs are antigen-antibody, biotin-avidin, hormone-hormone receptor, receptor-ligand, enzyme-substrate. This application is concerned with antigen-antibody type reactions.

The term "aberrant expression" in its various grammatical forms may mean and include any heightened or altered expression or overexpression of a protein in a tissue, e.g. an increase in the amount of a protein, caused by any means including enhanced expression or translation, modulation of the promoter or a regulator of the protein, amplification of a gene for a protein, or enhanced half-life or stability, such that more of the protein exists or can be detected at any one time, in contrast to a non-overexpressed state. Aberrant expression includes and contemplates any scenario or alteration wherein the protein expression or post-translational modification machinery in a cell is taxed or otherwise disrupted due to enhanced expression or increased levels or amounts of a protein, including wherein an altered protein, as in mutated protein or variant due to sequence alteration, deletion or insertion, or altered folding is expressed.

It is important to appreciate that the term "aberrant expression" has been specifically chosen herein to encompass the state where abnormal (usually increased) quantities/levels of the protein are present, irrespective of the efficient cause of that abnormal quantity or level. Thus, abnormal quantities of protein may result from overexpression of the protein in the absence of gene amplification, which is the case e.g. in many cellular/tissue samples taken from the head and neck of subjects with cancer, while other samples exhibit abnormal protein levels attributable to gene amplification.

In this latter connection, certain of the work of the inventors that is presented herein to illustrate the invention includes the analysis of samples certain of which exhibit abnormal protein levels resulting from amplification of EFGR. This therefore accounts for the presentation herein of experimental findings where reference is made to amplification and for the use of the terms "amplification/amplified" and the like in describing abnormal levels of EFGR. However, it is the observation of abnormal quantities or levels of the protein that defines the environment or circumstance where clinical intervention as by resort to the binding members of the invention is contemplated, and for this reason, the present specification considers that the term "aberrant expression" more broadly captures the causal environment that yields the corresponding abnormality in EFGR levels.

Accordingly, while the terms "overexpression" and "amplification" in their various grammatical forms are understood to have distinct technical meanings, they are to be considered equivalent to each other, insofar as they represent the state where abnormal EFGR protein levels are present in the context of the present invention. Consequently, the term "aberrant expression" has been chosen as it is believed to subsume the terms "overexpression" and "amplification" within its scope for the purposes herein, so that all terms may be considered equivalent to each other as used herein.

The term "antibody" describes an immunoglobulin whether natural or partly or wholly synthetically produced.

The term also covers any polypeptide or protein having a binding domain which is, or is homologous to, an antibody binding domain. CDR grafted antibodies are also contemplated by this term.

As antibodies can be modified in a number of ways, the term "antibody" should be construed as covering any specific binding member or substance having a binding domain with the required specificity. Thus, this term covers antibody fragments, derivatives, functional equivalents and homologues of antibodies, including any polypeptide comprising an immunoglobulin binding domain, whether natural or wholly or partially synthetic. Chimeric molecules comprising an immunoglobulin binding domain, or equivalent, fused to another polypeptide are therefore included. Cloning and expression of chimeric antibodies are described in EP-A-0120694 and EP-A-0125023 and U.S. Pat. Nos. 4,816,397 and 4,816,567.

It has been shown that fragments of a whole antibody can perform the function of binding antigens. Examples of binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment (Ward, E. S. et al., Nature 341, 544-546 (1989)) which consists of a VH domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al, Science, 242, 423-426, 1988; Huston et al, PNAS USA, 85, 5879-5883, 1988); (viii) multivalent antibody fragments (scFv dimers, trimers and/or tetramers (Power and Hudson, J Immunol. Methods 242: 193-204 9 (2000)) (ix) bispecific single chain Fv dimers (PCT/JS92/09965) and (x) "diabodies", multivalent or multispecific fragments constructed by gene fusion (WO94/13804; P. Holliger et al Proc. Natl. Acad. Sci. USA 90 6444-6448, (1993)).

An "antibody combining site" is that structural portion of an antibody molecule comprised of light chain or heavy and light chain variable and hypervariable regions that specifically binds antigen.

The phrase "antibody molecule" in its various grammatical forms as used herein contemplates both an intact immunoglobulin molecule and an immunologically active portion of an immunoglobulin molecule.

Exemplary antibody molecules are intact immunoglobulin molecules, substantially intact immunoglobulin molecules and those portions of an immunoglobulin molecule that contains the paratope, including those portions known in the art as Fab, Fab', F(ab')$_2$ and F(v), which portions are preferred for use in the therapeutic methods described herein.

Antibodies may also be bispecific, wherein one binding domain of the antibody is a specific binding member of the invention, and the other binding domain has a different specificity, e.g. to recruit an effector function or the like. Bispecific antibodies of the present invention include wherein one binding domain of the antibody is a specific binding member of the present invention, including a fragment thereof, and the other binding domain is a distinct antibody or fragment thereof, including that of a distinct anti-EGFR antibody, for instance antibody 528 (U.S. Pat. No. 4,943,533), the chimeric and humanized 225 antibody (U.S. Pat. No. 4,943,533 and WO/9640210), an anti-de2-7 antibody such as DH8.3 (Hills, D. et al (1995) Int. J. Cancer 63(4):537-543), antibody L8A4 and Y10 (Reist, C J et al (1995) Cancer Res. 55(19):4375-4382; Foulon C F et al. (2000) Cancer Res. 60(16):4453-4460), ICR62 (Modjtahedi H et al (1993) Cell Biophys. January-June; 22(1-3):129-46; Modjtahedi et al (2002) P.A.A.C.R. 55(14):3140-3148, or the antibody of Wikstrand et al (Wikstrand C. et al (1995) Cancer Res. 55(14):3140-3148). The other binding domain may be an antibody that recognizes or targets a particular cell type, as in a neural or glial cell-specific antibody. In the bispecific antibodies of the present invention the one binding domain of the antibody of the invention may be combined with other binding domains or molecules which recognize particular cell receptors and/or modulate cells in a particular fashion, as for instance an immune modulator (e.g., interleukin(s)), a growth modulator or cytokine (e.g. tumor necrosis factor (TNF), and particularly, the TNF bispecific modality demonstrated in U.S. Ser. No. 60/355,838 filed Feb. 13, 2002 incorporated herein in its entirety) or a toxin (e.g., ricin) or anti-mitotic or apoptotic agent or factor.

Fab and F(ab')$_2$ portions of antibody molecules may be prepared by the proteolytic reaction of papain and pepsin, respectively, on substantially intact antibody molecules by methods that are well-known. See for example, U.S. Pat. No. 4,342,566 to Theofilopolous et al. Fab' antibody molecule portions are also well-known and are produced from F(ab')$_2$ portions followed by reduction of the disulfide bonds linking the two heavy chain portions as with mercaptoethanol, and followed by alkylation of the resulting protein mercaptan with a reagent such as iodoacetamide. An antibody containing intact antibody molecules is preferred herein.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may also contain an antibody molecule having a plurality of antibody combining sites, each immunospecific for a different antigen; e.g., a bispecific (chimeric) monoclonal antibody.

The term "antigen binding domain" describes the part of an antibody which comprises the area which specifically binds to and is complementary to part or all of an antigen. Where an antigen is large, an antibody may bind to a particular part of the antigen only, which part is termed an epitope. An antigen binding domain may be provided by one or more antibody variable domains. Preferably, an antigen binding domain comprises an antibody light chain variable region (VL) and an antibody heavy chain variable region (VH).

"Post-translational modification" may encompass any one of or combination of modification(s), including covalent modification, which a protein undergoes after translation is complete and after being released from the ribosome or on the nascent polypeptide cotranslationally. Post-translational modification includes but is not limited to phosphorylation, myristylation, ubiquitination, glycosylation, coenzyme attachment, methylation and acetylation. Post-translational modification can modulate or influence the activity of a protein, its intracellular or extracellular destination, its stability or half-life, and/or its recognition by ligands, receptors or other proteins Post-translational modification can occur in cell organelles, in the nucleus or cytoplasm or extracellularly.

The term "specific" may be used to refer to the situation in which one member of a specific binding pair will not show any significant binding to molecules other than its specific binding partner(s). The term is also applicable where e.g. an antigen binding domain is specific for a particular epitope which is carried by a number of antigens, in which case the specific binding member carrying the antigen binding domain will be able to bind to the various antigens carrying the epitope.

The term "comprise" generally used in the sense of include, that is to say permitting the presence of one or more features or components.

The term "consisting essentially of" refers to a product, particularly a peptide sequence, of a defined number of residues which is not covalently attached to a larger product. In the case of the peptide of the invention referred to above, those of skill in the art will appreciate that minor modifications to the N- or C-terminal of the peptide may however be contemplated, such as the chemical modification of the terminal to add a protecting group or the like, e.g. the amidation of the C-terminus.

The term "isolated" refers to the state in which specific binding members of the invention, or nucleic acid encoding such binding members will be, in accordance with the present invention. Members and nucleic acid will be free or substantially free of material with which they are naturally associated such as other polypeptides or nucleic acids with which they are found in their natural environment, or the environment in which they are prepared (e.g. cell culture) when such preparation is by recombinant DNA technology practised in vitro or in vivo. Members and nucleic acid may be formulated with diluents or adjuvants and still for practical purposes be isolated—for example the members will normally be mixed with gelatin or other carriers if used to coat microtitre plates for use in immunoassays, or will be mixed with pharmaceutically acceptable carriers or diluents when used in diagnosis or therapy. Specific binding members may be glycosylated, either naturally or by systems of heterologous eukaryotic cells, or they may be (for example if produced by expression in a prokaryotic cell) unglycosylated.

Also, as used herein, the terms "glycosylation" and "glycosylated" includes and encompasses the post-translational modification of proteins, termed glycoproteins, by addition of oligosaccharides. Oligosaccharides are added at glycosylation sites in glycoproteins, particularly including N-linked oligosaccharides and O-linked oligosaccharides. N-linked oligosaccharides are added to an Asn residue, particularly wherein the Asn residue is in the sequence N-X-S/T, where X cannot be Pro or Asp, and are the most common ones found in glycoproteins. In the biosynthesis of N-linked glycoproteins, a high mannose type oligosaccharide (generally comprised of dolichol, N-Acetylglucosamine, mannose and glucose is first formed in the endoplasmic reticulum (ER). The high mannose type glycoproteins are then transported from the ER to the Golgi, where further processing and modification of the oligosaccharides occurs. O-linked oligosaccharides are added to the hydroxyl group of Ser or Thr residues. In O-linked oligosaccharides, N-Acetylglucosamine is first transferred to the Ser or Thr residue by N-Acetylglucosaminyltransferase in the ER. The protein then moves to the Golgi where further modification and chain elongation occurs. O-linked modifications can occur with the simple addition of the OG1cNAc monosaccharide alone at those Ser or Thr sites which can also under different conditions be phosphorylated rather than glycosylated.

As used herein, "pg" means picogram, "ng" means nanogram, "ug" or "μg" mean microgram, "mg" means milligram, "ul" or "μl" mean microliter, "ml" means milliliter, "l" means liter.

The terms "806 antibody", "mAb806", "ch806" and any variants not specifically listed, may be used herein interchangeably, and as used throughout the present application and claims refer to proteinaceous material including single or multiple proteins, and extends to those proteins having the amino acid sequence data described herein and presented in SEQ ID NO:2 and SEQ ID NO:4, and the chimeric antibody ch806 which is incorporated in and forms a part of SEQ ID NOS: 7 and 8, and the profile of activities set forth herein and in the Claims. Accordingly, proteins displaying substantially equivalent or altered activity are likewise contemplated. These modifications may be deliberate, for example, such as modifications obtained through site-directed mutagenesis, or may be accidental, such as those obtained through mutations in hosts that are producers of the complex or its named subunits. Also, the terms "806 antibody", "mAb806" and "ch806" are intended to include within their scope proteins specifically recited herein as well as all substantially homologous analogs and allelic variations.

The amino acid residues described herein are preferred to be in the "L" isomeric form. However, residues in the "D" isomeric form can be substituted for any L-amino acid residue, as long as the desired functional property of immunoglobulin-binding is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature, *J. Biol. Chem.*, 243:3552-59 (1969), abbreviations for amino acid residues are shown in the following Table of Correspondence:

| TABLE OF CORRESPONDENCE | | |
|---|---|---|
| SYMBOL | | |
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues. The above Table is presented to correlate the three-letter and one-letter notations which may appear alternately herein.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix.

This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the -10 and -35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide," as used herein in referring to the probe of the present invention, is defined as a molecule comprised of two or more ribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15-25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

As used herein, the terms "restriction endonucleases" and "restriction enzymes" refer to bacterial enzymes, each of which cut double-stranded DNA at or near a specific nucleotide sequence.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

Two DNA sequences are "substantially homologous" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

It should be appreciated that also within the scope of the present invention are DNA sequences encoding specific binding members (antibodies) of the invention which code for e.g. an antibody having the same amino acid sequence as SEQ ID NO:2 or SEQ ID NO:4, but which are degenerate to SEQ ID NO:2 or SEQ ID NO:4. By "degenerate to" is meant that a different three-letter codon is used to specify a particular amino acid. It is well known in the art that the following codons can be used interchangeably to code for each specific amino acid:

| | |
|---|---|
| Phenylalanine (Phe or F) | UUU or UUC |
| Leucine (Leu or L) | UUA or UUG or CUU or CUC or CUA or CUG |
| Isoleucine (Ile or I) | AUU or AUC or AUA |
| Methionine (Met or M) | AUG |
| Valine (Val or V) | GUU or GUC of GUA or GUG |
| Serine (Ser or S) | UCU or UCC or UCA or UCG or AGU or AGC |
| Proline (Pro or P) | CCU or CCC or CCA or CCG |
| Threonine (Thr or T) | ACU or ACC or ACA or ACG |
| Alanine (Ala or A) | GCU or GCG or GCA or GCG |
| Tyrosine (Tyr or Y) | UAU or UAC |
| Histidine (His or H) | CAU or CAC |
| Glutamine (Gln or Q) | CAA or CAG |
| Asparagine (Asn or N) | AAU or AAC |
| Lysine (Lys or K) | AAA or AAG |
| Aspartic Acid (Asp or D) | GAU or GAC |
| Glutamic Acid (Glu or E) | GAA or GAG |
| Cysteine (Cys or C) | UGU or UGC |
| Arginine (Arg or R) | CGU or CGC or CGA or CGG or AGA or AGG |
| Glycine (Gly or G) | GGU or GGC or GGA or GGG |
| Tryptophan (Trp or W) | UGG |
| Termination codon | UAA (ochre) or UAG (amber) or UGA (opal) |

It should be understood that the codons specified above are for RNA sequences. The corresponding codons for DNA have a T substituted for U.

Mutations can be made in SEQ ID NO:2 or SEQ ID NO:4 such that a particular codon is changed to a codon which codes for a different amino acid. Such a mutation is generally made by making the fewest nucleotide changes possible. A substitution mutation of this sort can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. A non-conservative change is more likely to alter the structure, activity or function of the resulting protein. The present invention should be considered to include sequences containing conservative changes which do not significantly alter the activity or binding characteristics of the resulting protein.

The following is one example of various groupings of amino acids:

Amino Acids with Nonpolar R Groups

Alanine, Valine, Leucine, Isoleucine, Proline, Phenylalanine, Tryptophan, Methionine Amino Acids with Uncharged Polar R Groups Glycine, Serine, Threonine, Cysteine, Tyrosine, Asparagine, Glutamine Amino Acids with Charged Polar R Groups (Negatively Charged at pH 6.0)

Aspartic acid, Glutamic acid

Basic Amino Acids (Positively Charged at pH 6.0)

Lysine, Arginine, Histidine (at pH 6.0)

Another grouping may be those amino acids with phenyl groups:

Phenylalanine, Tryptophan, Tyrosine

Another grouping may be according to molecular weight (i.e., size of R groups):

| | |
|---|---|
| Glycine | 75 |
| Alanine | 89 |
| Serine | 105 |
| Proline | 115 |
| Valine | 117 |
| Threonine | 119 |
| Cysteine | 121 |
| Leucine | 131 |
| Isoleucine | 131 |
| Asparagine | 132 |
| Aspartic acid | 133 |
| Glutamine | 146 |
| Lysine | 146 |
| Glutamic acid | 147 |
| Methionine | 149 |
| Histidine (at pH 6.0) | 155 |
| Phenylalanine | 165 |
| Arginine | 174 |
| Tyrosine | 181 |
| Tryptophan | 204 |

Particularly preferred substitutions are:

Lys for Arg and vice versa such that a positive charge may be maintained;

Glu for Asp and vice versa such that a negative charge may be maintained;

Ser for Thr such that a free —OH can be maintained; and

Gln for Asn such that a free $NH_2$ can be maintained.

Amino acid substitutions may also be introduced to substitute an amino acid with a particularly preferable property. For example, a Cys may be introduced a potential site for disulfide bridges with another Cys. A His may be introduced as a particularly "catalytic" site (i.e., His can act as an acid or base and is the most common amino acid in biochemical catalysis). Pro may be introduced because of its particularly planar structure, which induces. β-turns in the protein's structure.

Two amino acid sequences are "substantially homologous" when at least about 70% of the amino acid residues preferably at least about 80%, and most preferably at least about 90 or 95%) are identical, or represent conservative substitutions.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

The phrase "pharmaceutically acceptable" refers to molecular entities and compositions that are physiologically tolerable and do not typically produce an allergic or similar untoward reaction, such as gastric upset, dizziness and the like, when administered to a human.

The phrase "therapeutically effective amount" is used herein to mean an amount sufficient to prevent, and preferably reduce by at least about 30 percent, preferably by at least 50 percent, preferably by at least 70 percent, preferably by at least 80 percent, preferably by at least 90%, a clinically significant change in the growth or progression or mitotic activity of a target cellular mass, group of cancer cells or tumor, or other feature of pathology. For example, the degree of EGFR activation or activity or amount or number of EGFR positive cells, particularly of antibody or binding member reactive or positive cells may be reduced.

A DNA sequence is "operatively linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene.

The term "standard hybridization conditions" refers to salt and temperature conditions substantially equivalent to 5×SSC and 65° C. for both hybridization and wash. However, one skilled in the art will appreciate that such "standard hybridization conditions" are dependent on particular conditions including the concentration of sodium and magnesium in the buffer, nucleotide sequence length and concentration, percent mismatch, percent formamide, and the like. Also important in the determination of "standard hybridization conditions" is whether the two sequences hybridizing are RNA-RNA, DNA-DNA or RNA-DNA. Such standard hybridization conditions are easily determined by one skilled in the art according to well known formulae, wherein hybridization is typically 10-20° C. below the predicted or determined $T_m$ with washes of higher stringency, if desired.

B. Detailed Disclosure.

The present invention provides a novel specific binding member, particularly an antibody or fragment thereof, including immunogenic fragments, which recognizes an EGFR epitope which is found in tumorigenic, hyperproliferative or abnormal cells wherein the epitope is enhanced or evident upon aberrant post-translational modification and not detectable in normal or wild type cells. In a particular but non-limiting embodiment, the binding member, such as the antibody, recognizes an EGFR epitope which is enhanced or evident upon simple carbohydrate modification or early glycosylation and is reduced or not evident in the presence of complex carbohydrate modification or glycosylation. The specific binding member, such as the antibody or fragment thereof, does not bind to or recognize normal or wild type cells containing normal or wild type EGFR epitope in the absence of overexpression and in the presence of normal EGFR post-translational modification.

The invention relates to a specific binding member, particularly an antibody or a fragment thereof, which recognizes an EGFR epitope which is present in cells expressing amplified EGFR or expressing the de2-7 EGFR and not detectable in cells expressing normal or wild type EGFR, particularly in the presence of normal post-translational modification.

It is further noted and herein demonstrated that an additional non-limiting observation or characteristic of the antibodies of the present invention is their recognition of their epitope in the presence of high mannose groups, which is a characteristic of early glycosylation or simple carbohydrate modification. Thus, altered or aberrant glycosylation facilitates the presence and/or recognition of the antibody epitope or comprises a portion of the antibody epitope.

Glycosylation includes and encompasses the post-translational modification of proteins, termed glycoproteins, by addition of oligosaccarides. Oligosaccharides are added at glycosylation sites in glycoproteins, particularly including N-linked oligosaccharides and O-linked oligosaccharides. N-linked oligosaccharides are added to an Asn residue, particularly wherein the Asn residue is in the sequence N-X-S/T, where X cannot be Pro or Asp, and are the most common ones found in glycoproteins. In the biosynthesis of N-linked glycoproteins, a high mannose type oligosaccharide (generally comprised of dolichol, N-Acetylglucosamine, mannose and glucose is first formed in the endoplasmic reticulum (ER). The high mannose type glycoproteins are then transported from the ER to the Golgi, where further processing and modification of the oligosaccharides normally occurs. O-linked oligosaccharides are added to the hydroxyl group of Ser or Thr residues. In O-linked oligosaccharides, N-Acetylglucosamine is first transferred to the Ser or Thr residue by N-Acetylgucosaminyltransferase in the ER. The protein then moves to the Golgi where further modification and chain elongation occurs.

In a particular aspect of the invention and as stated above, the present inventors have discovered novel monoclonal antibodies, exemplified herein by the antibody designated mAb 806 and its chimeric ch806, which specifically recognize amplified wild type EGFR and the de2-7 EGFR, yet bind to an epitope distinct from the unique junctional peptide of the de2-7 EGFR mutation. The antibodies of the present invention specifically recognize overexpressed EGFR, including amplified EGFR and mutant EGFR (exemplified herein by the de2-7 mutation), particularly upon aberrant post-translational modification. Additionally, while mAb 806 does not recognize the normal, wild type EGFR expressed on the cell surface of glioma cells, it does bind to the extracellular domain of the EGFR immobilized on the surface of ELISA plates, indicating a conformational epitope with a polypeptide aspect. Importantly, mAb 806 did not bind significantly to normal tissues such as liver and skin, which express levels of endogenous wt EGFR that are higher than in most other normal tissues, but wherein EGFR is not overexpressed or amplified. Thus, mAb806 demonstrates novel and useful specificity, recognizing de2-7 EGFR and amplified EGFR, while not recognizing normal, wild type EGFR or the unique junctional peptide which is characteristic of de2-7 EGFR.

In a preferred aspect, the antibody is one which has the characteristics of the antibody which the inventors have identified and characterized, in particular recognizing amplified EGFR and de2-7EGFR. In a particularly preferred aspect the antibody is the mAb 806, or active fragments thereof. In a further preferred aspect the antibody of the present invention comprises the VH and VL amino acid sequences depicted in FIG. 14 (SEQ ID NO:2) and FIG. 15 (SEQ ID NO:4) respectively. The mature amino acid sequences (without the signal sequence) are depicted, respectively, in FIG. 16 with respect to the VH (SEQ ID NO:11) and in FIG. 17 with respect to the VL (SEQ ID NO:12).

Preferably the epitope of the specific binding member or antibody is located within the region comprising residues 273-501 of the mature normal or wild type EGFR sequence. Therefore, also provided are specific binding proteins, such as antibodies, which bind to the de2-7 EGFR at an epitope located within the region comprising residues 273-501 of the EGFR sequence. The epitope may be determined by any conventional epitope mapping techniques known to the person skilled in the art. Alternatively, the DNA sequence encoding residues 273-501 could be digested, and the resultant fragments expressed in a suitable host. Antibody binding could be determined as mentioned above.

In particular, the member will bind to an epitope comprising residues 273-501 of the mature normal or wild type EGFR. However other antibodies which show the same or a substantially similar pattern of reactivity also form an aspect of the invention. This may be determined by comparing such members with an antibody comprising the VH and VL domains shown in SEQ ID NO:2 and SEQ ID NO:4 respectively. The comparison will typically be made using a Western blot in which binding members are bound to duplicate blots prepared from a nuclear preparation of cells so that the pattern of binding can be directly compared.

In another aspect, the invention provides an antibody capable of competing with the 806 antibody, under conditions in which at least 10% of an antibody having the VH and VL sequences of the 806 antibody is blocked from binding to de2-7EGFR by competition with such an antibody in an ELISA assay. As set forth above, anti-idiotype antibodies are contemplated and are illustrated herein.

An isolated polypeptide consisting essentially of the epitope comprising residues 273-501 of the mature wild type EGFR (residues 6-234 of mature de2-7 EGFR) forms another aspect of the present invention. The peptide of the invention is particularly useful in diagnostic assays or kits and therapeutically or prophylactically, including as an anti-tumor or anti-cancer vaccine. Thus compositions of the peptide of the present invention include pharmaceutical composition and immunogenic compositions.

Diagnostic and Therapeutic Uses

The unique specificity of the specific binding members, particularly antibodies or fragments thereof, of the present invention, whereby the binding member(s) recognize an EGFR epitope which is found in tumorigenic, hyperproliferative or abnormal cells and not detectable in normal or wild type cells and wherein the epitope is enhanced or evident upon aberrant post-translational modification and wherein the member(s) bind to the de2-7 EGFR and amplified EGFR but not the wt EGFR, provides diagnostic and therapeutic uses to identify, characterize, target and treat, reduce or eliminate a number of tumorigenic cell types and tumor types, for example head and neck, breast, lung, bladder or prostate tumors and glioma, without the problems associated with normal tissue uptake that may be seen with previously known EGFR antibodies. Thus, cells overexpressing EGFR (e.g. by amplification or expression of a mutant or variant EGFR), particularly those demonstrating aberrant post-translational modification may be recognized, isolated, characterized, targeted and treated or eliminated utilizing the binding member(s), particularly antibody(ies) or fragments thereof of the present invention.

The antibodies of the present invention can thus specifically categorize the nature of EGFR tumors or tumorigenic cells, by staining or otherwise recognizing those tumors or cells wherein EGFR overexpression, particularly amplification and/or EGFR mutation, particularly de2-7EGFR, is present. Further, the antibodies of the present invention, as exemplified by mAb 806 and chimeric antibody ch806, demonstrate significant in vivo anti-tumor activity against tumors containing amplified EGFR and against de2-7 EGFR positive xenografts.

As outlined above, the inventors have found that the specific binding member of the invention recognises tumor-associated forms of the EGFR (de2-7 EGFR and amplified EGFR) but not the normal, wild-type receptor when expressed in normal cells. It is believed that antibody recognition is dependent upon an aberrant post-translational modification (e.g., a unique glycosylation, acetylation or phosphorylation variant) of the EGFR expressed in cells exhibiting overexpression of the EGFR gene.

As described below, mAb 806 and ch806 have been used in therapeutic studies. mAb 806 and ch806 are shown to inhibit growth of overexpressing (e.g. amplified) EGFR xenografts and human de2-7 EGFR expressing xenografts of human tumors and to induce significant necrosis within such tumors.

Moreover, the antibodies of the present invention inhibit the growth of intracranial tumors in a preventative model. This model involves injecting glioma cells expressing de2-7 EGFR into nude mice and then injecting the antibody intracranially either on the same day or within 1 to 3 days, optionally with repeated doses. The doses of antibody are suitably about 10 µg. Mice injected with antibody are compared to controls, and it has been found that survival of the treated mice is significantly increased.

Therefore, in a further aspect of the invention, there is provided a method of treatment of a tumor, a cancerous condition, a precancerous condition, and any condition related to or resulting from hyperproliferative cell growth comprising administration of a specific binding member of the invention.

Antibodies of the present invention are designed to be used in methods of diagnosis and treatment of tumors in human or animal subjects, particularly epithelial tumors. These tumors may be primary or secondary solid tumors of any type including, but not limited to, glioma, breast, lung, prostate, head or neck tumors.

Binding Member and Antibody Generation

The general methodology for making monoclonal antibodies by hybridomas is well known. Immortal, antibody-producing cell lines can also be created by techniques other than fusion, such as direct transformation of B lymphocytes with oncogenic DNA, or transfection with Epstein-Barr virus. See, e.g., M. Schreier et al., "Hybridoma Techniques" (1980); Hammerling et al., "Monoclonal Antibodies And T-cell Hybridomas" (1981); Kennett et al., "Monoclonal Antibodies" (1980); see also U.S. Pat. Nos. 4,341,761; 4,399,121; 4,427,783; 4,444,887; 4,451,570; 4,466,917; 4,472,500; 4,491,632; 4,493,890.

Panels of monoclonal antibodies produced against EFGR can be screened for various properties; i.e., isotype, epitope, affinity, etc. Of particular interest are monoclonal antibodies that mimic the activity of EFGR or its subunits. Such monoclonals can be readily identified in specific binding member activity assays. High affinity antibodies are also useful when immunoaffinity purification of native or recombinant specific binding member is possible.

Methods for producing polyclonal anti-EFGR antibodies are well-known in the art. See U.S. Pat. No. 4,493,795 to Nestor et al. A monoclonal antibody, typically containing Fab and/or F(ab')$_2$ portions of useful antibody molecules, can be prepared using the hybridoma technology described in *Antibodies—A Laboratory Manual*, Harlow and Lane, eds., Cold Spring Harbor Laboratory, New York (1988), which is incorporated herein by reference. Briefly, to form the hybridoma from which the monoclonal antibody composition is produced, a myeloma or other self-perpetuating cell line is fused with lymphocytes obtained from the spleen of a mammal hyperimmunized with an appropriate EGFR.

Splenocytes are typically fused with myeloma cells using polyethylene glycol (PEG) 6000. Fused hybrids are selected by their sensitivity to HAT. Hybridomas producing a monoclonal antibody useful in practicing this invention are identified by their ability to immunoreact with the present antibody or binding member and their ability to inhibit specified tumorigenic or hyperproliferative activity in target cells.

A monoclonal antibody useful in practicing the present invention can be produced by initiating a monoclonal hybridoma culture comprising a nutrient medium containing a hybridoma that secretes antibody molecules of the appropriate antigen specificity. The culture is maintained under conditions and for a time period sufficient for the hybridoma to secrete the antibody molecules into the medium. The antibody-containing medium is then collected. The antibody molecules can then be further isolated by well-known techniques.

Media useful for the preparation of these compositions are both well-known in the art and commercially available and include synthetic culture media, inbred mice and the like. An exemplary synthetic medium is Dulbecco's minimal essential medium (DMEM; Dulbecco et al., *Virol.* 8:396 (1959)) supplemented with 4.5 gm/l glucose, 20 mm glutamine, and 20% fetal calf serum. An exemplary inbred mouse strain is the Balb/c.

Methods for producing monoclonal anti-EGFR antibodies are also well-known in the art. See Niman et al., *Proc. Natl. Acad. Sci. USA,* 80:4949-4953 (1983). Typically, the EGFR or a peptide analog is used either alone or conjugated to an immunogenic carrier, as the immunogen in the before described procedure for producing anti-EGFR monoclonal antibodies. The hybridomas are screened for the ability to produce an antibody that immunoreacts with the EGFR present in tumorigenic, abnormal or hyperproliferative cells. Other anti-EGFR antibodies include but are not limited to the HuMAX-EGFr antibody from Genmab/Medarex, the 108 antibody (ATCC HB9764) and U.S. Pat. No. 6,217,866, and antibody 14E1 from Schering A G (U.S. Pat. No. 5,942,602).

Recombinant Binding Members, Chimerics, Bispecifics and Fragments

In general, the CDR3 regions, comprising amino acid sequences substantially as set out as the CDR3 regions of SEQ ID NO:2 and SEQ ID NO:4 will be carried in a structure which allows for binding of the CDR3 regions to an tumor antigen. In the case of the CDR3 region of SEQ ID NO:4, this is preferably carried by the VL region of SEQ ID NO:4.

By "substantially as set out" it is meant that that CDR3 regions of the invention will be either identical or highly homologous to the specified regions of SEQ ID NO:2 and SEQ ID NO:4. By "highly homologous" it is contemplated that only a few substitutions, preferably from 1 to 8, preferably from 1 to 5, preferably from 1 to 4, or from 1 to 3 or 1 or 2 substitutions may be made in the CDRs.

The structure for carrying the CDR3s of the invention will generally be of an antibody heavy or light chain sequence or substantial portion thereof in which the CDR3 regions are located at locations corresponding to the CDR3 region of naturally occurring VH and VL antibody variable domains encoded by rearranged immunoglobulin genes. The structures and locations of immunoglobulin variable domains may be determined by reference to Kabat, E. A. et al, Sequences of Proteins of Immunological Interest. 4th Edition. US Department of Health and Human Services. 1987, and updates thereof.

Preferably, the amino acid sequence substantially as set out as residues 93-102 of SEQ ID NO:2 is carried as the CDR3 in a human heavy chain variable domain or a substantial portion thereof, and the amino acid sequences substantially as set out as residues 24-34, 50-56 and 89-97 of SEQ ID NO:4 are carried as the CDRs 1-3 respectively in a human light chain variable domain or a substantial portion thereof.

The variable domains may be derived from any germline or rearranged human variable domain, or may be a synthetic variable domain based on consensus sequences of known human variable domains. The CDR3-derived sequences of the invention, as defined in the preceding paragraph, may be introduced into a repertoire of variable domains lacking CDR3 regions, using recombinant DNA technology.

For example, Marks et al (Bio/Technology, 1992, 10:779-783) describe methods of producing repertoires of antibody variable domains in which consensus primers directed at or adjacent to the 5' end of the variable domain area are used in conjunction with consensus primers to the third framework region of human VH genes to provide a repertoire of VH variable domains lacking a CDR3. Marks et al further describe how this repertoire may be combined with a CDR3 of a particular antibody. Using analogous techniques, the CDR3-derived sequences of the present invention may be shuffled with repertoires of VH or VL domains lacking a CDR3, and the shuffled complete VH or VL domains combined with a cognate VL or VH domain to provide specific binding members of the invention. The repertoire may then be displayed in a suitable host system such as the phage display system of WO92/01047 so that suitable specific binding members may be selected. A repertoire may consist of from anything from $10^4$ individual members upwards, for example from $10^6$ to $10^8$ or $10^{10}$ members.

Analogous shuffling or combinatorial techniques are also disclosed by Stemmer (Nature, 1994, 370:389-391), who describes the technique in relation to a β-lactamase gene but observes that the approach may be used for the generation of antibodies.

A further alternative is to generate novel VH or VL regions carrying the CDR3-derived sequences of the invention using random mutagenesis of, for example, the mAb806 VH or VL genes to generate mutations within the entire variable domain. Such a technique is described by Gram et al (1992, Proc. Natl. Acad. Sci., USA, 89:3576-3580), who used error-prone PCR.

Another method which may be used is to direct mutagenesis to CDR regions of VH or VL genes. Such techniques are disclosed by Barbas et al, (1994, Proc. Natl. Acad. Sci., USA, 91:3809-3813) and Schier et al (1996, J. Mol. Biol. 263:551-567).

All the above described techniques are known as such in the art and in themselves do not form part of the present invention. The skilled person will be able to use such techniques to provide specific binding members of the invention using routine methodology in the art.

A substantial portion of an immunoglobulin variable domain will comprise at least the three CDR regions, together with their intervening framework regions. Preferably, the portion will also include at least about 50% of either or both of the first and fourth framework regions, the 50% being the C-terminal 50% of the first framework region and the N-terminal 50% of the fourth framework region. Additional residues at the N-terminal or C-terminal end of the substantial part of the variable domain may be those not normally associated with naturally occurring variable domain regions. For example, construction of specific binding members of the present invention made by recombinant DNA techniques may result in the introduction of N- or C-terminal residues encoded by linkers introduced to facilitate cloning or other manipulation steps. Other manipulation steps include the introduction of linkers to join variable domains of the invention to further protein sequences including immunoglobulin heavy chains, other variable domains (for example in the production of diabodies) or protein labels as discussed in more detail below.

Although in a preferred aspect of the invention specific binding members comprising a pair of binding domains based on sequences substantially set out in SEQ ID NO:2 and SEQ ID NO:4 are preferred, single binding domains based on either of these sequences form further aspects of the invention. In the case of the binding domains based on the sequence substantially set out in SEQ ID NO:2, such binding domains may be used as targeting agents for tumor antigens since it is known that immunoglobulin VH domains are capable of binding target antigens in a specific manner.

In the case of either of the single chain specific binding domains, these domains may be used to screen for complementary domains capable of forming a two-domain specific binding member which has in vivo properties as good as or equal to the mAb806 antibody disclosed herein.

This may be achieved by phage display screening methods using the so-called hierarchical dual combinatorial approach as disclosed in U.S. Pat. No. 5,969,108 in which an individual colony containing either an H or L chain clone is used to infect a complete library of clones encoding the other chain (L or H) and the resulting two-chain specific binding member is selected in accordance with phage display techniques such as those described in that reference. This technique is also disclosed in Marks et al, ibid.

Specific binding members of the present invention may further comprise antibody constant regions or parts thereof. For example, specific binding members based on SEQ ID NO:4 may be attached at their C-terminal end to antibody light chain constant domains including human Cκ or Cλ chains, preferably Cλ chains. Similarly, specific binding members based on SEQ ID NO:2 may be attached at their C-terminal end to all or part of an immunoglobulin heavy chain derived from any antibody isotype, e.g. IgG, IgA, IgE, IgD and IgM and any of the isotype sub-classes, particularly IgG1, IgG2b, and IgG4. IgG1 is preferred.

The advent of monoclonal antibody (mAb) technology 25 years ago has provide an enormous repertoire of useful research reagents and created the opportunity to use antibodies as approved pharmaceutical reagents in cancer therapy, autoimmune disorders, transplant rejection, antiviral prophylaxis and as anti-thrombotics (Glennie and Johnson 2000). The application of molecular engineering to convert murine mAbs into chimeric mAbs (mouse V-region, human C-region) and humanised reagents where only the mAb complementarity-determining regions (CDR) are of murine origin has been critical to the clinical success of mAb therapy. The engineered mAbs have markedly reduced or absent immunogenicity, increased serum half-life and the human Fc portion of the mAb increases the potential to recruit the immune effectors of complement and cytotoxic cells (Clark 2000). Investigations into the biodistribution, pharmacokinetics and any induction of an immune response to clinically administered mAbs requires the development of analyses to discriminate between the pharmaceutical and endogenous proteins.

The antibodies, or any fragments thereof, may also be conjugated or recombinantly fused to any cellular toxin, bacterial or other, e.g. pseudomonas exotoxin, ricin, or diphtheria toxin. The part of the toxin used can be the whole toxin, or any particular domain of the toxin. Such antibody-toxin molecules have successfully been used for targeting and therapy of different kinds of cancers, see e.g. Pastan, Biochim Biophys Acta. 1997 Oct. 24; 1333(2):C1-6; Kreitman et al., N Engl J Med. 2001 Jul. 26; 345(4):241-7; Schnell et al., Leukemia. 2000 January; 14(1):129-35; Ghetie et al., Mol Biotechnol. 2001 July; 18(3):251-68.

Bi- and tri-specific multimers can be formed by association of different scFv molecules and have been designed as cross-linking reagents for T-cell recruitment into tumors (immunotherapy), viral retargeting (gene therapy) and as red blood cell agglutination reagents (immunodiagnostics), see e.g. Todorovska et al., J Immunol Methods. 2001 Feb. 1; 248(1-2):47-66; Tomlinson et al., Methods Enzymol. 2000; 326:461-79; McCall et al., J Immunol. 2001 May 15; 166(10):6112-7.

Fully human antibodies can be prepared by immunizing transgenic mice carrying large portions of the human immunoglobulin heavy and light chains. These mice, examples of such mice are the Xenomouse™ (Abgenix, Inc.) (U.S. Pat. Nos. 6,075,181 and 6,150,584), the HuMAb-Mouse™ (Medarex, Inc./GenPharm) (U.S. Pat. Nos. 5,545,806 and 5,569,825), the TransChromo Mouse™ (Kirin) and the KM Mouse™ (Medarex/Kirin), are well known within the art. Antibodies can then be prepared by, e.g. standard hybridoma technique or by phage display. These antibodies will then contain only fully human amino acid sequences.

Fully human antibodies can also be generated using phage display from human libraries. Phage display may be performed using methods well known to the skilled artisan, as in Hoogenboom et al and Marks et al (Hoogenboom H R and Winter G. (1992) J Mol Biol. 227(2):381-8; Marks J) et al (1991) J Mol Biol. 222(3):581-97; and also U.S. Pat. Nos. 5,885,793 and 5,969,108).

Therapeutic Antibodies and Uses

The in viva properties, particularly with regard to tumor: blood ratio and rate of clearance, of specific binding members of the invention will be at least comparable to mAb806. Following administration to a human or animal subject such a specific binding member will show a peak tumor to blood ratio of >1:1. Preferably at such a ratio the specific binding member will also have a tumor to organ ratio of greater than 1:1, preferably greater than 2:1, more preferably greater than 5:1. Preferably at such a ratio the specific binding member will also have an organ to blood ratio of <1:1 in organs away from the site of the tumor. These ratios exclude organs of catabolism and secretion of the administered specific binding member. Thus in the case of scFvs and Fabs (as shown in the accompanying examples), the binding members are secreted via the kidneys and there is greater presence here than other organs. In the case of whole IgGs, clearance will be at least in part, via the liver. The peak localisation ratio of the intact antibody will normally be achieved between 10 and 200 hours following administration of the specific binding member. More particularly, the ratio may be measured in a tumor xenograft of about 0.2-1.0 g formed subcutaneously in one flank of an athymic nude mouse.

Antibodies of the invention may be labelled with a detectable or functional label. Detectable labels include, but are not limited to, radiolabels such as the isotopes $^3$H, $^{14}$C, $^{32}$P, $^{35}$S, $^{36}$Cl, $^{57}$Cr, $^{57}$Co, $^{58}$Co, $^{59}$Fe, $^{90}$Y, $^{121}$I, $^{124}$I, $^{125}$I, $^{131}$I, $^{111}$In, $^{211}$At, $^{198}$Au, $^{67}$Cu, $^{225}$Ac, $^{213}$Bi, $^{99}$Tc and $^{186}$Re, which may be attached to antibodies of the invention using conventional chemistry known in the art of antibody imaging. Labels also include fluorescent labels and labels used conventionally in the art for MRI-CT imagine. They also include enzyme labels such as horseradish peroxidase. Labels further include chemical moieties such as biotin which may be detected via binding to a specific cognate detectable moiety, e.g. labelled avidin.

Functional labels include substances which are designed to be targeted to the site of a tumor to cause destruction of tumor tissue. Such functional labels include cytotoxic drugs such as 5-fluorouracil or ricin and enzymes such as bacterial carboxypeptidase or nitroreductase, which are capable of converting prodrugs into active drugs at the site of a tumor.

Also, antibodies including both polyclonal and monoclonal antibodies, and drugs that modulate the production or activity of the specific binding members, antibodies and/or their subunits may possess certain diagnostic applications and may for example, be utilized for the purpose of detecting and/or measuring conditions such as cancer, precancerous lesions, conditions related to or resulting from hyperproliferative cell growth or the like. For example, the specific binding members, antibodies or their subunits may be used to produce both polyclonal and monoclonal antibodies to themselves in a variety of cellular media, by known techniques such as the hybridoma technique utilizing, for example, fused mouse spleen lymphocytes and myeloma cells. Likewise, small molecules that mimic or antagonize the activity(ies) of the specific binding members of the invention may be discovered or synthesized, and may be used in diagnostic and/or therapeutic protocols.

The radiolabelled specific binding members, particularly antibodies and fragments thereof, are useful in in vitro diagnostics techniques and in in vivo radioimaging techniques and in radioimmunotherapy. In the instance of in vivo imaging, the specific binding members of the present invention may be conjugated to an imaging agent rather than a radioisotope(s), including but not limited to a magnetic resonance image enhancing agent, wherein for instance an antibody molecule is loaded with a large number of paramagnetic ions through chelating groups. Examples of chelating groups include EDTA, porphyrins, polyamines crown ethers and polyoximes. Examples of paramagnetic ions include gadolinium, iron, manganese, rhenium, europium, lanthanium, holmium and ferbium. In a further aspect of the invention, radiolabelled specific binding members, particularly antibodies and fragments thereof, particularly radioimmunoconjugates, are useful in radioimmunotherapy, particularly as radiolabelled antibodies for cancer therapy. In a still further aspect, the radiolabelled specific binding members, particularly antibodies and fragments thereof, are useful in radioimmuno-guided surgery techniques, wherein they can identify and indicate the presence and/or location of cancer cells, precancerous cells, tumor cells, and hyperproliferative cells, prior to, during or following surgery to remove such cells.

Immunoconjugates or antibody fusion proteins of the present invention, wherein the specific binding members, particularly antibodies and fragments thereof, of the present invention are conjugated or attached to other molecules or agents further include, but are not limited to binding members conjugated to a chemical ablation agent, toxin, immunomodulator, cytokine, cytotoxic agent, chemotherapeutic agent or drug.

Radioimmunotherapy (RAIT) has entered the clinic and demonstrated efficacy using various antibody immunoconjugates. $^{131}$I labeled humanized anti-carcinoembryonic antigen (anti-CEA) antibody hMN-14 has been evaluated in colorectal cancer (Behr T M et al (2002) Cancer 94(4Suppl):1373-81) and the same antibody with $^{90}$Y label has been assessed in medullary thyroid carcinoma (Stein R et al (2002) Cancer 94(1):51-61). Radioimmunotherapy using monoclonal antibodies has also been assessed and reported for non-Hodgkin's lymphoma and pancreatic cancer (Goldenberg D M (2001) Crit Rev Oncol Hematol 39(1-2):195-201; Gold D V et al (2001) Crit Rev Oncol Hematol 39 (1-2) 147-54). Radioimmunotherapy methods with particular antibodies are also described in U.S. Pat. Nos. 6,306,393 and 6,331,175. Radioimmunoguided surgery (RIGS) has also entered the clinic and demonstrated efficacy and usefulness, including using anti-CEA antibodies and antibodies directed against tumor-associated antigens (Kim J C et al (2002) Int J Cancer 97(4):542-7; Schneebaum S et al (2001) World J Surg 25(12): 1495-8; Avital S et al (2000) Cancer 89(8):1692-8; McIntosh D G et al (1997) Cancer Biother Radiopharm 12 (4):287-94).

Antibodies of the present invention may be administered to a patient in need of treatment via any suitable route, usually by injection into the bloodstream or CSF, or directly into the site of the tumor. The precise dose will depend upon a number of factors, including whether the antibody is for diagnosis or for treatment, the size and location of the tumor, the precise nature of the antibody (whether whole antibody, fragment, diabody, etc), and the nature of the detectable or functional label attached to the antibody. Where a radionuclide is used for therapy, a suitable maximum single dose is about 45 mCi/m$^2$, to a maximum of about 250 mCi/m$^2$. Preferable dosage is in the range of 15 to 40 mCi, with a further preferred dosage range of 20 to 30 mCi, or to 30 mCi. Such therapy may require bone marrow or stem cell replacement. A typical antibody dose for either tumor imaging or tumor treatment will be in the range of from 0.5 to 40 mg, preferably from 1 to 4 mg of antibody in F(ab')2 form. Naked antibodies are preferable administered in doses of 20 to 1000 mg protein per dose, or 20 to 500 mg protein per dose, or 20 to 100 mg protein per dose. This is a dose for a single treatment of an adult patient, which may be proportionally adjusted for children and infants, and also adjusted for other antibody formats in proportion to molecular weight. Treatments may be repeated at daily, twice-weekly, weekly or monthly intervals, at the discretion of the physician.

These formulations may include a second binding protein, such as the EGFR binding proteins described supra. In an especially preferred form, this second binding protein is a monoclonal antibody such as 528 or 225, discussed infra.

Pharmaceutical and Therapeutic Compositions

Specific binding members of the present invention will usually be administered in the form of a pharmaceutical composition, which may comprise at least one component in addition to the specific binding member.

Thus pharmaceutical compositions according to the present invention, and for use in accordance with the present invention, may comprise, in addition to active ingredient, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. intravenous.

Pharmaceutical compositions for oral administration may be in tablet, capsule, powder or liquid form. A tablet may comprise a solid carrier such as gelatin or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

A composition may be administered alone or in combination with other treatments, therapeutics or agents, either simultaneously or sequentially dependent upon the condition to be treated. In addition, the present invention contemplates and includes compositions comprising the binding member, particularly antibody or fragment thereof, herein described and other agents or therapeutics such as anti-cancer agents or therapeutics, hormones, anti-EGFR agents or antibodies, or immune modulators. More generally these anti-cancer agents may be tyrosine kinase inhibitors or phosphorylation cascade inhibitors, post-translational modulators, cell growth or division inhibitors (e.g. anti-mitotics), or signal transduction inhibitors. Other treatments or therapeutics may include the administration of suitable doses of pain relief drugs such as non-steroidal anti-inflammatory drugs (e.g. aspirin, paracetamol, ibuprofen or ketoprofen) or opiates such as morphine, or anti-emetics. The composition can be administered in combination (either sequentially (i.e. before or after) or simultaneously) with tyrosine kinase inhibitors (including, but not limited to AG1478 and ZD1839, ST1571, OSI-774, SU-6668), doxorubicin, temozolomide, cisplatin, carboplatin, nitrosoureas, procarbazine, vincristine, hydroxyurea, 5-fluoruracil, cytosine arabinoside, cyclophosphamide, epipodophyllotoxin, carmustine, lomustine, and/or other chemotherapeutic agents. Thus, these agents may be anti-EGFR specific agents, or tyrosine kinase inhibitors such as AG1478, ZD1839, ST1571, OSI-774, or SU-6668 or may be more general anti-cancer and anti-neoplastic agents such as doxorubicin, cisplatin, temozolomide, nitrosoureas, procarbazine, vincristine, hydroxyurea, 5-fluoruracil, cytosine arabinoside, cyclophosphamide, epipodophyllotoxin, carmustine, or lomustine. In addition, the composition may be administered with hormones such as dexamethasone, immune modulators, such as interleukins, tumor necrosis factor (TNF) or other growth factors or cytokines which stimulate the immune response and reduction or elimination of cancer cells or tumors.

An immune modulator such as TNF may be combined together with a member of the invention in the form of a bispecific antibody recognizing the 806 EGFR epitope as well as binding to TNF receptors. The composition may also be administered with, or may include combinations along with other anti-EGFR antibodies, including but not limited to the anti-EGFR antibodies 528, 225, SC-03, DH8.3 DR8.3, L8A4, Y10, ICR62 and ABX-EGF.

Previously the use of agents such as doxorubicin and cisplatin in conjunction with anti-EGFR antibodies have produced enhanced anti-tumor activity (Fan et al, 1993; Baselga et al, 1993). The combination of doxorubicin and mAb 528 resulted in total eradication of established A431 xenografts, whereas treatment with either agent alone caused only temporary in vivo growth inhibition (Baselga et al, 1993). Likewise, the combination of cisplatin and either mAb 528 or 225 also led to the eradication of well established A431 xenografts, which was not observed when treatment with either agent was used (Fan et al, 1993).

Conventional Radiotherapy

In addition, the present invention contemplates and includes therapeutic compositions for the use of the binding member in combination with conventional radiotherapy. It has been indicated that treatment with antibodies targeting EGF receptors can enhance the effects of conventional radiotherapy (Milas et al., Clin Cancer Res. 2000 February: 6 (2):701 8, Huang et al., Clin Cancer Res. 2000 June: 6(6): 2166 74).

As demonstrated herein, combinations of the binding member of the present invention, particularly an antibody or fragment thereof, preferably the mAb806, ch806 or a fragment thereof, and anti-cancer therapeutics, particularly anti-EGFR therapeutics, including other anti-EGFR antibodies, demonstrate effective therapy, and particularly synergy, against xenografted tumors. In the examples, it is demonstrated that the combination of AG1478 and in mAb 806 results in significantly enhanced reduction of A431 xenograft tumor volume in comparison with treatment with either agent alone. AG1478 (4-(3-chloroanilino)-6,7-dimethoxyquinazoline) is a potent and selective inhibitor of the EGF receptor kinase and is particularly described in U.S. Pat. No. 5,457, 105, incorporated by reference herein in its entirety (see also, Liu, W. et al (1999) J. Cell Sci. 112:2409; Eguchi, S. et al (1998) J. Biol. Chem. 273:8890; Levitsky, A. and Gazit, A. (1995) Science 267:1782). The specification examples further demonstrate therapeutic synergy of the 806 antibody with other anti-EGFR antibodies, particularly with the 528 anti-EGFR antibody.

The present invention further contemplates therapeutic compositions useful in practicing the therapeutic methods of this invention. A subject therapeutic composition includes, in admixture, a pharmaceutically acceptable excipient (carrier) and one or more of a specific binding member, polypeptide analog thereof or fragment thereof, as described herein as an active ingredient. In a preferred embodiment, the composition comprises an antigen capable of modulating the specific binding of the present binding member/antibody with a target cell.

The preparation of therapeutic compositions which contain polypeptides, analogs or active fragments as active ingredients is well understood in the art. Typically, such compositions are prepared as injectables, either as liquid solutions or suspensions. However, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

A polypeptide, analog or active fragment can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The therapeutic polypeptide-, analog- or active fragment-containing compositions are conventionally administered intravenously, as by injection of a unit dose, for example. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's immune system to utilize the active ingredient, and degree of EFGR binding capacity desired. Precise amounts of active ingredient required to be administered depend on the judgment of the practitioner and are peculiar to each individual. However, suitable dosages may range from about 0.1 to 20, preferably about 0.5 to about 10, and more preferably one to several, milligrams of active ingredient per kilogram body weight of individual per day and depend on the route of administration. Suitable regimes for initial administration and booster shots are also variable, but are typified by an initial administration followed by repeated doses at one or more hour intervals by a subsequent injection or other administration. Alternatively, continuous intravenous infusion sufficient to maintain concentrations of ten nanomolar to ten micromolar in the blood are contemplated.

Pharmaceutical compositions for oral administration may be in tablet, capsule, powder or liquid form. A tablet may comprise a solid carrier such as gelatin or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Diagnostic Assays

The present invention also relates to a variety of diagnostic applications, including methods for detecting the presence of stimuli such as aberrantly expressed EGFR, by reference to their ability to be recognized by the present specific binding member. As mentioned earlier, the EGFR can be used to produce antibodies to itself by a variety of known techniques, and such antibodies could then be isolated and utilized as in tests for the presence of particular EGFR activity in suspect target cells.

Diagnostic applications of the specific binding members of the present invention, particularly antibodies and fragments thereof, include in vitro and in vivo applications well known and standard to the skilled artisan and based on the present description. Diagnostic assays and kits for in vitro assessment and evaluation of EGFR status, particularly with regard to aberrant expression of EGFR, may be utilized to diagnose, evaluate and monitor patient samples including those known to have or suspected of having cancer, a precancerous condition, a condition related to hyperproliferative cell growth or from a tumor sample. The assessment and evaluation of EGFR status is also useful in determining the suitability of a patient for a clinical trial of a drug or for the administration of a particular chemotherapeutic agent or specific binding member, particularly an antibody, of the present invention, including combinations thereof, versus a different agent or binding member. This type of diagnostic monitoring and assessment is already in practice utilizing antibodies against the HER2 protein in breast cancer (Hercep Test, Dako Corporation), where the assay is also used to evaluate patients for antibody therapy using Herceptin. In vivo applications include imaging of tumors or assessing cancer status of individuals, including radioimaging.

As suggested earlier, the diagnostic method of the present invention comprises examining a cellular sample or medium by means of an assay including an effective amount of an antagonist to an EFGR/protein, such as an anti-EFGR antibody, preferably an affinity-purified polyclonal antibody, and more preferably a mAb. In addition, it is preferable for the anti-EFGR antibody molecules used herein be in the form of Fab, Fab', F(ab')$_2$ or F(v) portions or whole antibody molecules. As previously discussed, patients capable of benefiting from this method include those suffering from cancer, a pre-cancerous lesion, a viral infection, pathologies involving or resulting from hyperproliferative cell growth or other like pathological derangement. Methods for isolating EFGR and inducing anti-EFGR antibodies and for determining and optimizing the ability of anti-EFGR antibodies to assist in the examination of the target cells are all well-known in the art.

Preferably, the anti-EFGR antibody used in the diagnostic methods of this invention is an affinity purified polyclonal antibody. More preferably, the antibody is a monoclonal antibody (mAb). In addition, the anti-EFGR antibody molecules used herein can be in the form of Fab, Fab', F(ab')$_2$ or F(v) portions of whole antibody molecules.

As described in detail above, antibody(ies) to the EGFR can be produced and isolated by standard methods including the well known hybridoma techniques. For convenience, the antibody(ies) to the EGFR will be referred to herein as $Ab_1$ and antibody(ies) raised in another species as $Ab_2$.

The presence of EGFR in cells can be ascertained by the usual in vitro or in vivo immunological procedures applicable to such determinations. A number of useful procedures are known. Three such procedures which are especially useful utilize either the EGFR labeled with a detectable label, antibody $Ab_1$ labeled with a detectable label, or antibody $Ab_2$ labeled with a detectable label. The procedures may be summarized by the following equations wherein the asterisk indicates that the particle is labeled, and "R" stands for the EGFR:

$$R^* + Ab_1 = R^*Ab_1 \qquad \text{A.}$$

$$R + Ab^* = RAb_1^* \qquad \text{B.}$$

$$R + Ab_1 + Ab_2^* = RAb_1Ab_2^* \qquad \text{C.}$$

The procedures and their application are all familiar to those skilled in the art and accordingly may be utilized within the scope of the present invention. The "competitive" procedure, Procedure A, is described in U.S. Pat. Nos. 3,654,090 and 3,850,752. Procedure C, the "sandwich" procedure, is described in U.S. Pat. Nos. RE 31,006 and 4,016,043. Still other procedures are known such as the "double antibody," or "DASP" procedure.

In each instance above, the EGFR forms complexes with one or more antibody(ies) or binding partners and one member of the complex is labeled with a detectable label. The fact that a complex has formed and, if desired, the amount thereof, can be determined by known methods applicable to the detection of labels.

It will be seen from the above, that a characteristic property of $Ab_2$ is that it will react with $Ab_1$. This is because $Ab_1$ raised in one mammalian species has been used in another species as an antigen to raise the antibody $Ab_2$. For example, $Ab_2$ may be raised in goats using rabbit antibodies as antigens. $Ab_2$ therefore would be anti-rabbit antibody raised in goats. For purposes of this description and claims, $Ab_1$ will be referred to as a primary or anti-EGFR antibody, and $Ab_2$ will be referred to as a secondary or anti-$Ab_1$ antibody.

The labels most commonly employed for these studies are radioactive elements, enzymes, chemicals which fluoresce when exposed to ultraviolet light, and others.

A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate.

The EGFR or its binding partner(s) such as the present specific binding member, can also be labeled with a radioactive element or with an enzyme. The radioactive label can be detected by any of the currently available counting procedures. The preferred isotope may be selected from $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{121}I$, $^{124}I$, $^{125}I$, $^{131}I$, $^{111}In$, $^{211}At$, $^{198}Au$, $^{67}Cu$, $^{225}Ac$, $^{213}Bi$, $^{99}Tc$ and 186Re.

Enzyme labels are likewise useful, and can be detected by any of the presently utilized calorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090; 3,850,752; and 4,016,043 are referred to by way of example for their disclosure of alternate labeling material and methods.

A particular assay system that may be advantageously utilized in accordance with the present invention, is known as a receptor assay. In a receptor assay, the material to be assayed such as the specific binding member, is appropriately labeled and then certain cellular test colonies are inoculated with a quantity of both the labeled and unlabeled material after which binding studies are conducted to determine the extent to which the labeled material binds to the cell receptors. In this way, differences in affinity between materials can be ascertained.

Accordingly, a purified quantity of the specific binding member may be radiolabeled and combined, for example, with antibodies or other inhibitors thereto, after which binding studies would be carried out. Solutions would then be prepared that contain various quantities of labeled and unlabeled uncombined specific binding member, and cell samples would then be inoculated and thereafter incubated. The resulting cell monolayers are then washed, solubilized and then counted in a gamma counter for a length of time sufficient to yield a standard error of <5%. These data are then subjected to Scatchard analysis after which observations and conclusions regarding material activity can be drawn. While the foregoing is exemplary, it illustrates the manner in which a receptor assay may be performed and utilized, in the instance where the cellular binding ability of the assayed material may serve as a distinguishing characteristic.

An assay useful and contemplated in accordance with the present invention is known as a "cis/trans" assay. Briefly, this assay employs two genetic constructs, one of which is typically a plasmid that continually expresses a particular receptor of interest when transfected into an appropriate cell line, and the second of which is a plasmid that expresses a reporter such as luciferase, under the control of a receptor/ligand complex. Thus, for example, if it is desired to evaluate a compound as a ligand for a particular receptor, one of the plasmids would be a construct that results in expression of the receptor in the chosen cell line, while the second plasmid would possess a promoter linked to the luciferase gene in which the response element to the particular receptor is inserted. If the compound under test is an agonist for the receptor, the ligand will complex with the receptor, and the resulting complex will bind the response element and initiate transcription of the luciferase gene. The resulting chemiluminescence is then measured photometrically, and dose response curves are obtained and compared to those of known ligands. The foregoing protocol is described in detail in U.S. Pat. No. 4,981,784 and PCT International Publication No. WO 88/03168, for which purpose the artisan is referred.

In a further embodiment of this invention, commercial test kits suitable for use by a medical specialist may be prepared to determine the presence or absence of aberrant expression of EGFR, including but not limited to amplified EGFR and/or an EGFR mutation, in suspected target cells. In accordance with the testing techniques discussed above, one class of such kits will contain at least the labeled EGFR or its binding partner, for instance an antibody specific thereto, and directions, of course, depending upon the method selected, e.g., "competitive," "sandwich," "DASP" and the like. The kits may also contain peripheral reagents such as buffers, stabilizers, etc.

Accordingly, a test kit may be prepared for the demonstration of the presence or capability of cells for aberrant expression or post-translational modification of EGFR, comprising:

(a) a predetermined amount of at least one labeled immunochemically reactive component obtained by the direct or indirect attachment of the present specific binding member or a specific binding partner thereto, to a detectable label;

(b) other reagents; and (c) directions for use of said kit.

More specifically, the diagnostic test kit may comprise:

(a) a known amount of the specific binding member as described above (or a binding partner) generally bound to a solid phase to form an immunosorbent, or in the alternative, bound to a suitable tag, or plural such end products, etc. (or their binding partners) one of each;

(b) if necessary, other reagents; and (c) directions for use of said test kit.

In a further variation, the test kit may be prepared and used for the purposes stated above, which operates according to a predetermined protocol (e.g. "competitive," "sandwich," "double antibody," etc.), and comprises:

(a) a labeled component which has been obtained by coupling the specific binding member to a detectable label;

(b) one or more additional immunochemical reagents of which at least one reagent is a ligand or an immobilized ligand, which ligand is selected from the group consisting of:

(i) a ligand capable of binding with the labeled component (a);

(ii) a ligand capable of binding with a binding partner of the labeled component (a);

(iii) a ligand capable of binding with at least one of the component(s) to be determined; and (iv) a ligand capable of binding with at least one of the binding partners of at least one of the component(s) to be determined; and (c) directions for the performance of a protocol for the detection and/or determination of one or more components of an immunochemical reaction between the EFGR, the specific binding member, and a specific binding partner thereto.

In accordance with the above, an assay system for screening potential drugs effective to modulate the activity of the EFGR, the aberrant expression or post-translational modification of the EGFR, and/or the activity or binding of the specific binding member may be prepared. The receptor or the binding member may be introduced into a test system, and the prospective drug may also be introduced into the resulting cell culture, and the culture thereafter examined to observe any changes in the S-phase activity of the cells, due either to the addition of the prospective drug alone, or due to the effect of added quantities of the known agent(s).

Nucleic Acids

The present invention further provides an isolated nucleic acid encoding a specific binding member of the present invention. Nucleic acid includes DNA and RNA. In a preferred aspect, the present invention provides a nucleic acid which codes for a polypeptide of the invention as defined above, including a polypeptide as set out as residues 93-102 of SEQ ID NO:2 or 26-35A, 49-64 and 93-102 of SEQ ID NO:2, a polypeptide as set out in residues 24-34, 50-56 and 89-97 of SEQ ID NO:4, and the entire polypeptides of SEQ ID NO:2 and SEQ ID NO:4.

The present invention also provides constructs in the form of plasmids, vectors, transcription or expression cassettes which comprise at least one polynucleotide as above.

The present invention also provides a recombinant host cell which comprises one or more constructs as above. A nucleic acid encoding any specific binding member as provided itself forms an aspect of the present invention, as does a method of production of the specific binding member which method comprises expression from encoding nucleic acid therefor. Expression may conveniently be achieved by culturing under appropriate conditions recombinant host cells containing the nucleic acid. Following production by expression a specific binding member may be isolated and/or purified using any suitable technique, then used as appropriate.

Specific binding members and encoding nucleic acid molecules and vectors according to the present invention may be provided isolated and/or purified, e.g. from their natural environment, in substantially pure or homogeneous form, or, in the case of nucleic acid, free or substantially free of nucleic acid or genes origin other than the sequence encoding a polypeptide with the required function. Nucleic acid according to the present invention may comprise DNA or RNA and may be wholly or partially synthetic.

Systems for cloning and expression of a polypeptide in a variety of different host cells are well known. Suitable host cells include bacteria, mammalian cells, yeast and baculovirus systems. Mammalian cell lines available in the art for expression of a heterologous polypeptide include Chinese hamster ovary cells, HeLa cells, baby hamster kidney cells, NSO mouse melanoma cells and many others. A common, preferred bacterial host is *E. coli*.

The expression of antibodies and antibody fragments in prokaryotic cells such as *E. coli* is well established in the art. For a review, see for example Plückthun, A. Bio/Technology 9: 545-551 (1991). Expression in eukaryotic cells in culture is also available to those skilled in the art as an option for production of a specific binding member, see for recent reviews, for example Raff, M. E. (1993) Curr. Opinion Biotech. 4: 573-576; Trill J. J. et al. (1995) Curr. Opinion Biotech 6: 553-560.

Suitable vectors can be chosen or constructed, containing appropriate regulatory sequences, including promoter sequences, terminator sequences, polyadenylation sequences, enhancer sequences, marker genes and other sequences as appropriate. Vectors may be plasmids, viral e.g. 'phage, or phagemid, as appropriate. For further details see, for example, Molecular Cloning: a Laboratory Manual: 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Short Protocols in Molecular Biology, Second Edition, Ausubel et al. eds., John Wiley & Sons, 1992. The disclosures of Sambrook et al. and Ausubel et al. are incorporated herein by reference.

Thus, a further aspect of the present invention provides a host cell containing nucleic acid as disclosed herein. A still further aspect provides a method comprising introducing such nucleic acid into a host cell. The introduction may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. For bacterial cells, suitable techniques may include calcium chloride transformation, electroporation and transfection using bacteriophage.

The introduction may be followed by causing or allowing expression from the nucleic acid, e.g. by culturing host cells under conditions for expression of the gene.

In one embodiment, the nucleic acid of the invention is integrated into the genome (e.g. chromosome) of the host cell. Integration may be promoted by inclusion of sequences which promote recombination with the genome, in accordance with standard techniques.

The present invention also provides a method which comprises using a construct as stated above in an expression system in order to express a specific binding member or polypeptide as above.

As stated above, the present invention also relates to a recombinant DNA molecule or cloned gene, or a degenerate variant thereof, which encodes a specific binding member, particularly antibody or a fragment thereof, that possesses an amino acid sequence set forth in SEQ ID NO:2 and/or SEQ ID NO:4; preferably a nucleic acid molecule, in particular a recombinant DNA molecule or cloned gene, encoding the binding member or antibody has a nucleotide sequence or is complementary to a DNA sequence provided in SEQ ID NO: 1 and/or SEQ ID NO:3.

Another feature of this invention is the expression of the DNA sequences disclosed herein. As is well known in the art, DNA sequences may be expressed by operatively linking them to an expression control sequence in an appropriate expression vector and employing that expression vector to transform an appropriate unicellular host.

Such operative linking of a DNA sequence of this invention to an expression control sequence, of course, includes, if not already part of the DNA sequence, the provision of an initiation codon, ATG, in the correct reading frame upstream of the DNA sequence.

A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., *E. coli* plasmids col El, pCR1, pBR322, pMB9 and their derivatives, plasmids such as RP4; phage DNAs, e.g., the numerous derivatives of phage λ, e.g., NM989, and other phage DNA, e.g., M13 and filamentous single stranded phage DNA; yeast plasmids such as the 2 u plasmid or derivatives thereof, vectors useful in eukaryotic cells, such as vectors useful in insect or mammalian cells; vectors derived from combinations of plasmids and phage DNAs, such as plasmids that have been modified to employ phage DNA or other expression control sequences; and the like.

Any of a wide variety of expression control sequences—sequences that control the expression of a DNA sequence operatively linked to it—may be used in these vectors to express the DNA sequences of this invention. Such useful expression control sequences include, for example, the early or late promoters of SV40, CMV, vaccinia, polyoma or adenovirus, the lac system, the trp system, the TAC system, the TRC system, the LTR system, the major operator and promoter regions of phage λ, the control regions of fd coat protein, the promoter for 3-phosphoglycerate kinase or other glycolytic enzymes, the promoters of acid phosphatase (e.g., Pho5), the promoters of the yeast-mating factors, and other sequences known to control the expression of genes of prokaryotic or eukaryotic cells or their viruses, and various combinations thereof.

A wide variety of unicellular host cells are also useful in expressing the DNA sequences of this invention. These hosts may include well known eukaryotic and prokaryotic hosts, such as strains of *E. coli, Pseudomonas, Bacillus, Streptomyces*, fungi such as yeasts, and animal cells, such as CHO, YB/20, NSO, SP2/0, R1.1, B-W and L-M cells, African Green Monkey kidney cells (e.g., COS 1, COS 7, BSC1, BSC40, and BMT10), insect cells (e.g., Sf9), and human cells and plant cells in tissue culture.

It will be understood that not all vectors, expression control sequences and hosts will function equally well to express the DNA sequences of this invention. Neither will all hosts function equally well with the same expression system. However, one skilled in the art will be able to select the proper vectors, expression control sequences, and hosts without undue experimentation to accomplish the desired expression without departing from the scope of this invention. For example, in selecting a vector, the host must be considered because the vector must function in it. The vector's copy number, the ability to control that copy number, and the expression of any other proteins encoded by the vector, such as antibiotic markers, will also be considered.

In selecting an expression control sequence, a variety of factors will normally be considered. These include, for example, the relative strength of the system, its controllability, and its compatibility with the particular DNA sequence or gene to be expressed, particularly as regards potential secondary structures. Suitable unicellular hosts will be selected by consideration of, e.g., their compatibility with the chosen vector, their secretion characteristics, their ability to fold proteins correctly, and their fermentation requirements, as well as the toxicity to the host of the product encoded by the DNA sequences to be expressed, and the ease of purification of the expression products.

Considering these and other factors a person skilled in the art will be able to construct a variety of vector/expression control sequence/host combinations that will express the DNA sequences of this invention on fermentation or in large scale animal culture.

It is further intended that specific binding member analogs may be prepared from nucleotide sequences of the protein complex/subunit derived within the scope of the present invention. Analogs, such as fragments, may be produced, for example, by pepsin digestion of specific binding member material. Other analogs, such as muteins, can be produced by standard site-directed mutagenesis of specific binding member coding sequences. Analogs exhibiting "specific binding member activity" such as small molecules, whether functioning as promoters or inhibitors, may be identified by known in vivo and/or in vitro assays.

As mentioned above, a DNA sequence encoding a specific binding member can be prepared synthetically rather than cloned. The DNA sequence can be designed with the appropriate codons for the specific binding member amino acid sequence. In general, one will select preferred codons for the intended host if the sequence will be used for expression. The complete sequence is assembled from overlapping oligonucleotides prepared by standard methods and assembled into a complete coding sequence. See, e.g., Edge, *Nature,* 292:756 (1981); Nambair et al., *Science,* 223:1299 (1984); Jay et al., *J. Biol. Chem.,* 259:6311 (1984).

Synthetic DNA sequences allow convenient construction of genes which will express specific binding member analogs or "muteins". Alternatively, DNA encoding muteins can be made by site-directed mutagenesis of native specific binding member genes or cDNAs, and muteins can be made directly using conventional polypeptide synthesis.

A general method for site-specific incorporation of unnatural amino acids into proteins is described in Christopher J. Noren, Spencer J. Anthony-Cahill, Michael C. Griffith, Peter G. Schultz, *Science,* 244:182-188 (April 1989). This method may be used to create analogs with unnatural amino acids.

The present invention extends to the preparation of antisense oligonucleotides and ribozymes that may be used to interfere with the expression of the EGFR at the translational level. This approach utilizes antisense nucleic acid and ribozymes to block translation of a specific mRNA, either by masking that mRNA with an antisense nucleic acid or cleaving it with a ribozyme.

Antisense nucleic acids are DNA or RNA molecules that are complementary to at least a portion of a specific mRNA molecule. (See Weintraub, 1990; Marcus-Sekura, 1988.) In the cell, they hybridize to that mRNA, forming a double stranded molecule. The cell does not translate an mRNA in this double-stranded form. Therefore, antisense nucleic acids interfere with the expression of mRNA into protein. Oligomers of about fifteen nucleotides and molecules that hybridize to the AUG initiation codon will be particularly efficient, since they are easy to synthesize and are likely to pose fewer problems than larger molecules when introducing them into producing cells. Antisense methods have been used to inhibit the expression of many genes in vitro (Marcus-Sekura, 1988; Hambor et al., 1988).

Ribozymes are RNA molecules possessing the ability to specifically cleave other single stranded RNA molecules in a manner somewhat analogous to DNA restriction endonucleases. Ribozymes were discovered from the observation that certain mRNAs have the ability to excise their own introns. By modifying the nucleotide sequence of these RNAs, researchers have been able to engineer molecules that recognize specific nucleotide sequences in an RNA molecule and cleave it (Cech, 1988.). Because they are sequence-specific, only mRNAs with particular sequences are inactivated.

Investigators have identified two types of ribozymes, *Tetrahymena*-type and "hammerhead"-type. (Hasselhoff and Gerlach, 1988) *Tetrahymena*-type ribozymes recognize four-base sequences, while "hammerhead"-type recognize eleven- to eighteen-base sequences. The longer the recognition sequence, the more likely it is to occur exclusively in the target mRNA species. Therefore, hammerhead-type ribozymes are preferable to *Tetrahymena*-type ribozymes for inactivating a specific mRNA species, and eighteen base recognition sequences are preferable to shorter recognition sequences.

The DNA sequences described herein may thus be used to prepare antisense molecules against, and ribozymes that cleave mRNAs for EFGRs and their ligands.

The invention may be better understood by reference to the following non-limiting Examples, which are provided as exemplary of the invention. The following examples are presented in order to more fully illustrate the preferred embodiments of the invention and should in no way be construed, however, as limiting the broad scope of the invention.

EXAMPLE 1

Isolation of Antibodies

Materials

Cell Lines

For immunization and specificity analyses, several cell lines, native or transfected with either the normal, wild type or "wtEGFR" gene or the ΔEGFR gene carrying the Δ2-7 deletion mutation were used: Murine fibroblast cell line NR6, NR6$_{\Delta EGFR}$ (transfected with ΔEGFR) and NR6$_{wtEGFR}$ (transfected with wtEGFR), human glioblastoma cell line U87MG (expressing low levels of endogenous wtEGFR), U87MG$_{wtEGFR}$ (transfected with wtEGFR), U87MG$_{\Delta EGFR}$ (transfected with ΔEGFR), and human squamous cell carcinoma cell line A431 (expressing high levels of wtEGFR)[38]. Cell lines and transfections were described previously (Nishikawa R., et al. (1994) Proc. Natl. Acad. Sci. 91(16):7727-7731).

The U87MG astrocytoma cell line (20), which endogenously expresses low levels of the wt EGFR, was infected with a retrovirus containing the de2-7 EGFR to produce the U87MG.Δ2-7 cell line (10). The transfected cell line U87MG.wtEGFR was produced as described in Nagane et al 1996 (Cancer Res., 56: 5079-5086). Whereas U87MG cells express approximately 1×10$^5$ EGFR, U87MG.wtEGFR cells express approximately 1×10$^6$ EGFR, and thus mimic the situation seen with gene amplification.

Human squamous carcinoma A431 cells were obtained from ATCC (Rockville, Md.). All cell lines were cultured in DMEM/F-12 with GlutaMAX™ (Life Technologies, Melbourne, Australia) supplemented with 10% FCS (CSL, Melbourne, Australia).

Reagents

Biotinylated unique junctional peptides (Biotin-LEEKKGNYVVTDH (SEQ ID NO: 5) and LEEKKGNYVVTDH-Biotin (SEQ ID NO: 6)) from de2-7 EGFR were synthesized by standard Fmoc chemistry and purity (>96%) determined by reverse phase HPLC and mass spectral analysis (Auspep, Melbourne, Australia).

Antibodies Used in Studies

In order to compare our findings with other reagents, additional mAbs were included in our studies. These reagents were mAb 528 to the wtEGFR (Sato, J. D. et al. (1983) Mol. Biol. Med. 1(5):511-529) and DH8.3, which was generated against a synthetic peptide spanning the junctional sequence of the Δ2-7 EGFR deletion mutation. The DH8.3 antibody (IgG1) has been described previously (Hills et al, 1995, Int. J. Cancer 63(4); 537-543) and was obtained following immunization of mice with the unique junctional peptide found in de2-7 EGFR (16). The 528 antibody, which recognizes both de2-7 and wild type EGFR, has been described previously (21) and was produced in the Biological Production Facility (Ludwig Institute for Cancer Research, Melbourne) using a hybridoma obtained from ATCC HB-8509. SC-03 is an affinity purified rabbit polyclonal antibody raised against a carboxy terminal peptide of the EGFR (Santa Cruz Biotechnology Inc.).

Generation of Monoclonal Antibodies

The murine fibroblast line NR6$_{\Delta EGFR}$ was used as immunogen. Mouse hybridomas were generated by immunizing BALB/c mice five times subcutaneously at 2- to 3-week intervals, with 5×10$^5$-2×10$^6$ cells in adjuvant. Complete Freund's adjuvant was used for the first injection. Thereafter, incomplete Freund's adjuvant (Difco) was used. Spleen cells from immunized mice were fused with mouse myeloma cell line SP2/0. Supernatants of newly generated clones were screened in hemadsorption assays for reactivity with cell line NR6, NR6$_{wtEGFR}$, and NR6$_{\Delta EGFR}$ and then analyzed by hemadsorption assays with human glioblastoma cell lines U87MG, U87MG$_{wtEGFR}$, and U87MG$_{\Delta EGFR}$. Selected hybridoma supernatants were subsequently tested by western blotting and further analyzed by immunohistochemistry. Newly generated mAbs showing the expected reactivity pattern were purified.

Five hybridomas were established and three, clones 124 (IgG2a), 806 (IgG2b) and 1133 (IgG2a) were selected for further characterization based on high titer with NR6$_{\Delta EGFR}$ and low background on NR6 and NR6$_{wtEGFR}$ cells in the hemagglutination assay. In a subsequent hemagglutination analysis, these antibodies showed no reactivity (undiluted supernatant≦10%) with the native human glioblastoma cell line U87MG and U87MG$_{wtEGFR}$, but were strongly reactive with U87MG$_{\Delta EGFR}$; less reactivity was seen with A431. By contrast, in FACS analysis, 806 was unreactive with native U87MG and intensively stained U87MG$_{\Delta EGFR}$ and to a lesser degree U87MG$_{wtEGFR}$ indicating binding of 806 to both, ΔEGFR and wtEGFR (see below).

In Western blot assays, mAbs 124, 806 and 1133 were then analyzed for reactivity with wtEGFR and ΔEGFR. Detergent lysates were extracted from NR6$_{\Delta EGFR}$, U87MG$_{\Delta EGFR}$ as well as from A431. All three mAbs showed a similar reactivity pattern with cell lysates staining both the wtEGFR (170 kDa) and ΔEGFR protein (140 kDa). As a reference reagent, mAb R.I known to be reactive with the wtEGFR (Waterfield M. D. et al. (1982) J. Cell Biochem. 20(2):149-161) was used instead of mAb 528, which is known to be non-reactive in western blot analysis. Mab R.I showed reactivity with wt and ΔEGFR. All three newly generated clones showed reactivity with ΔEGFR and less intense with wtEGFR. DH8.3 was solely positive in the lysate of U87MG$_{\Delta EGFR}$ and NR6$_{\Delta EGFR}$.

The immunohistochemical analysis of clones 124, 806, and 1133 as well as mAb 528 and mAb DH8.3 on xenograft tumors U87MG, U87MG$_{\Delta EGFR}$, and A431 are shown in Table 1. All mAbs showed strong staining of xenograft U87MG$_{\Delta EGFR}$. Only mAb 528 showed weak reactivity in the native U87MG xenograft. In A431 xenografts, mAb 528 showed strong homogeneous reactivity. MAbs 124, 806, and 1133 revealed reactivity with mostly the basally located cells of the squamous cell carcinoma of A431 and did not react with the upper cell layers or the keratinizing component. DH8.3 was negative in A431 xenografts.

TABLE 1

Immunohistochemical Analysis of Antibodies 528, DH8.3, and 124, 806 and 1133

| Mab | xenograft ΔU87MG$_{ΔEGFR}$ | xenograft A431 | xenograft U87MG (native) |
|---|---|---|---|
| 528 | pos. | pos. | pos. (focal staining) |
| mAb-124 | pos. | pos. (predominantly basal cells) | — |
| mAb-806 | pos. | pos. (predominantly basal cells) | — |
| mAb-1133 | pos. | pos. (predominantly basal cells) | — |
| DH8.3 | pos. | — | — | minor stromal staining due to detection of endogenous mouse antibodies

EXAMPLE 2

Binding of Antibodies to Cell Lines by FACS

In order to determine the specificity of mAb 806, its binding to U87MG, U87MG.Δ2-7 and U87MG.wtEGFR cells was analyzed by flow activated cell sorting (FACS). Briefly, cells were labelled with the relevant antibody (10 μg/ml) followed by fluorescein-conjugated goat anti-mouse IgG (1:1100 dilution; Calbiochem San Diego, USA). FACS data was obtained on a Coulter Epics Elite ESP by observing a minimum of 5,000 events and analysed using EXPO (version 2) for Windows. An irrelevant IgG2b was included as an isotype control for mAb 806 and the 528 antibody was included as it recognizes both the de2-7 and wt EGFR.

Only the 528 antibody was able to stain the parental U87MG cell line (FIG. 1) consistent with previous reports demonstrating that these cells express the wt EGFR (Nishikawa et al, 1994). MAb 806 and DH8.3 had binding levels similar to the control antibody, clearly demonstrating that they are unable to bind the wt receptor (FIG. 1). Binding of the isotype control antibody to U87MG.Δ2-7 and U87MG.wtEGFR cells was similar as that observed for the U87MG cells.

MAb 806 stained U87MG.Δ2-7 and U87MG.wtEGFR cells, indicating that mAb 806 specifically recognizes the de2-7 EGFR and amplified EGFR (FIG. 1). DH8.3 antibody stained U87MG.Δ2-7 cells, confirming that DH8.3 antibody specifically recognizes the de2-7 EGFR (FIG. 1). As expected, the 528 antibody stained both the U87MG.Δ2-7 and U87MG.wtEGFR cell lines (FIG. 1). As expected, the 528 antibody stained U87MG.Δ2-7 with a higher intensity than the parental cell as it binds both the de2-7 and wild type receptors that are co-expressed in these cells (FIG. 1). Similar results were obtained using a protein A mixed hemadsorption which detects surface bound IgG by appearance of Protein A coated with human red blood cells (group O) to target cells. Monoclonal antibody 806 was reactive with U87MG.Δ2-7 cells but showed no significant reactivity (undiluted supernatant less than 10%) with U87MG expressing wid type EGF-R.

EXAMPLE 3

Binding of Antibodies in Assays

To further characterize the specificity of mAb 806 and the DH8.3 antibody, their binding was examined by ELISA. Two types of ELISA were used to determine the specificity of the antibodies. In the first assay, plates were coated with sEGFR (10 μg/ml in 0.1 M carbonate buffer pH 9.2) for 2 h and then blocked with 2% human serum albumin (HSA) in PBS. sEGFR is the recombinant extracellular domain (amino acids 1-621) of the wild type EGFR), and was produced as previously described (22). Antibodies were added to wells in triplicate at increasing concentration in 2% HSA in phosphate-buffered saline (PBS). Bound antibody was detected by horseradish peroxidase conjugated sheep anti-mouse IgG (Silenus, Melbourne, Australia) using ABTS (Sigma, Sydney, Australia) as a substrate and the absorbance measured at 405 nm.

Figure 1A:
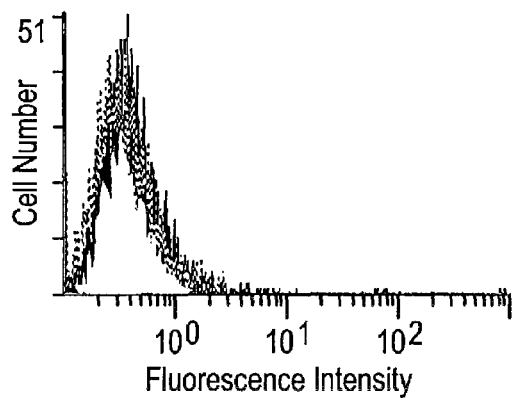
FIG. 1 presents the results of flow cytometric analysis of glioma cell lines. U87MG (light gray histograms) and U87MG.Δ2-7 (dark gray histograms) cells were stained with either an irrelevant IgG2b antibody (open histograms), DJ8.3 (specific for de2-7 EGFR), MAb 806 or 528 (binds both wild type and de2-7 EGFR) as indicated.
Figure 1B:
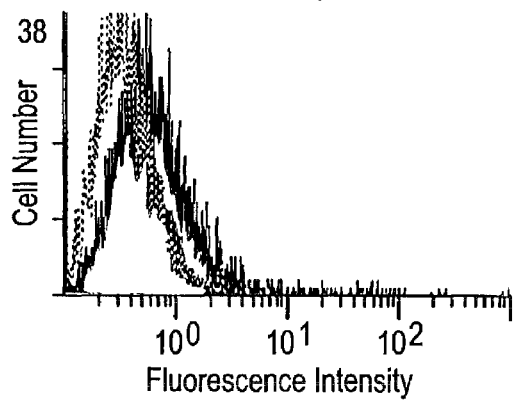
Figure 1C:
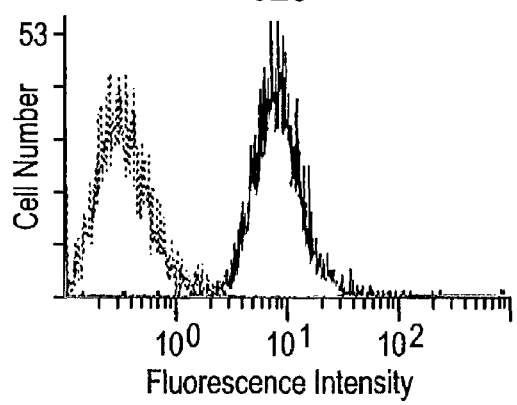
Figure 1D:
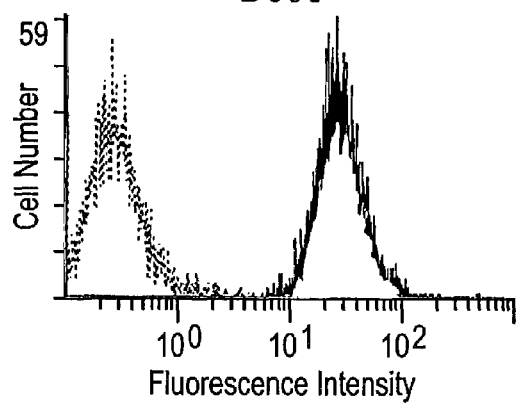
Figure 1E:
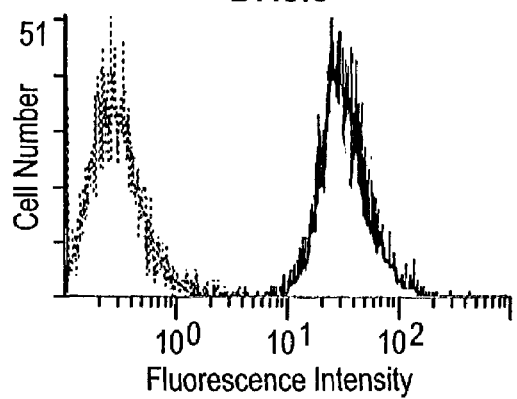
Figure 1F:
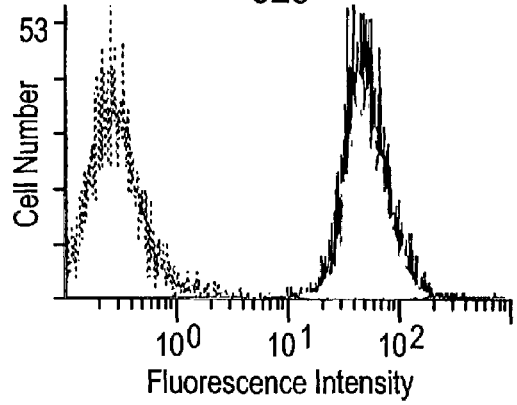
Figure 2A:
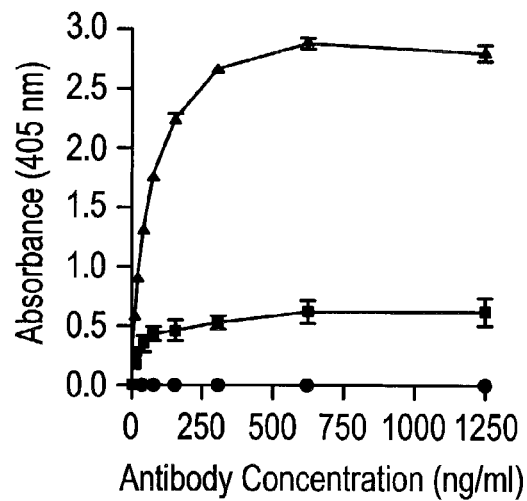
FIGS. 2A-C present the results of ELISA of MAb 806, DH8.3 and 528 antibodies. (A) binding of increasing concentrations of MAb 806 (▲) DH8.3 (●) or 528 (ζ) antibody to sEGFR coated ELISA plates. (B) inhibition of MAb 806 and 528 binding to sEGFR coated ELISA plates by increasing concentrations of sEGFR in solution. (C) binding of increasing concentrations of DH8.3 to the de2-7 junctional peptide illustrates binding curves for mAb 806 and 528 antibodies to immobilized wild-type sEGFR.
Figure 2B:
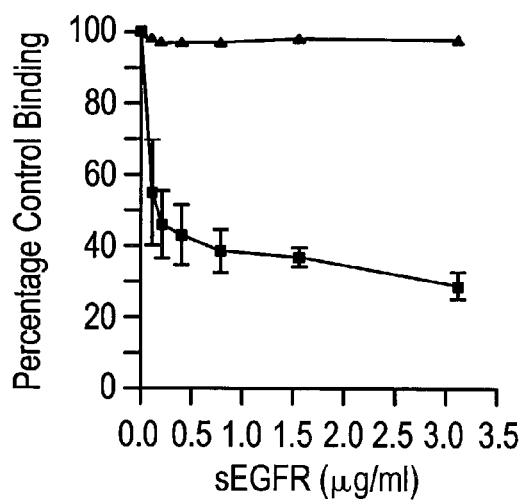
Figure 2C:
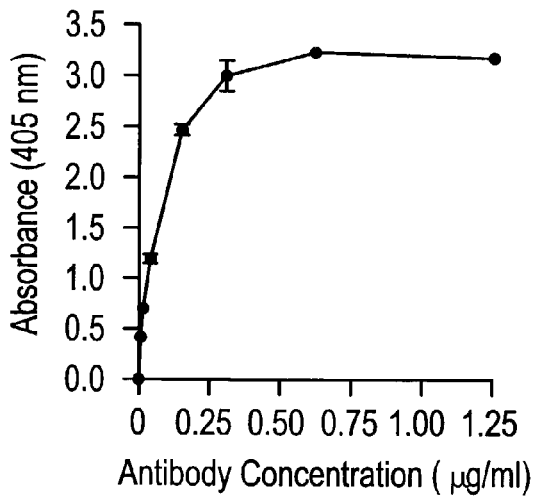

Both mAb 806 and the 528 antibody displayed dose-dependent and saturating binding curves to immobilized wild type sEGFR (FIG. 2A). As the unique junctional peptide found in the de2-7 EGFR is not contained within the sEGFR, mAb 806 must be binding to an epitope located within the wild type EGFR sequence. The binding of the 528 antibody was lower than that observed for mAb 806. As expected the DH8.3 antibody did not bind the wild type sEGFR even at concentrations up to 10 μg/ml (FIG. 2A). While sEGFR in solution inhibited the binding of the 528 antibody to immobilized sEGFR in a dose-dependent fashion, it was unable to inhibit the binding of mAb 806 (FIG. 2B). This suggests that mAb 806 can only bind wild type EGFR once immobilized on ELISA plates, a process that may induce conformational changes. Similar results were observed using a BIAcore whereby mAb 806 bound immobilized sEGFR but immobilized mAb 806 was not able to bind sEGFR in solution (data not shown). The DH8.3 antibody exhibited dose-dependent and saturable binding to the unique de2-7 EGFR peptide (FIG. 2C).

In the second assay, the biotinylated de2-7 specific peptide (Biotin-LEEKKGNYVVTDH (SEQ ID NO: 5)) was bound to ELISA plates precoated with streptavidin (Pierce, Rockford, Ill.). Antibodies were bound and detected as in the first assay. Neither mAb 806 nor the 528 antibody bound to the peptide, even at concentrations higher than those used to obtain saturation binding of DH8.3, further indicating that mAb 806 does not recognize an epitope determinant within this peptide.

To further demonstrate that mAb 806 recognizes an epitope distinct from the junction peptide, additional experiments were performed. C-terminal biotinylated de2-7 peptide (LEEKKGNYVVTDH-Biotin (SEQ ID NO: 6)) was utilized in studies with mAb806 and mAb L8A4, generated against the de2-7 peptide (Reist, C J et al (1995) Cancer Res. 55(19): 4375-4382; Foulon C F et al. (2000) Cancer Res. 60(16): 4453-4460).

Reagents Used in Peptide Studies:

Junction Peptide: LEEKKGNYVVTDH-OH (Biosource, Camarillo, Calif.) (SEQ ID NO: 13);

Peptide C: LEEKKGNYVVTDH(K-Biot)-OH (Biosource, Camarillo, Calif.) (SEQ ID NO: 14);

sEGFR: CHO-cell-derived recombinant soluble extracellular domain (aa 1-621) of the wild type EGFR (LICR Melbourne);

mAb 806: mouse monoclonal antibody, IgG2b (LICR NYB);

mAb L8A4: mouse monoclonal antibody, IgG, (Duke University);

IgG$_1$ isotype control mAb;

IgG$_{2b}$ isotype control mAb

Peptide C was immobilized on a Streptavidin microsensor chip at a surface density of 350RU (+/−30RU). Serial dilutions of mAbs were tested for reactivity with the peptide. Blocking experiments using non-biotinylated peptide were performed to assess specificity.

Figure 2D:
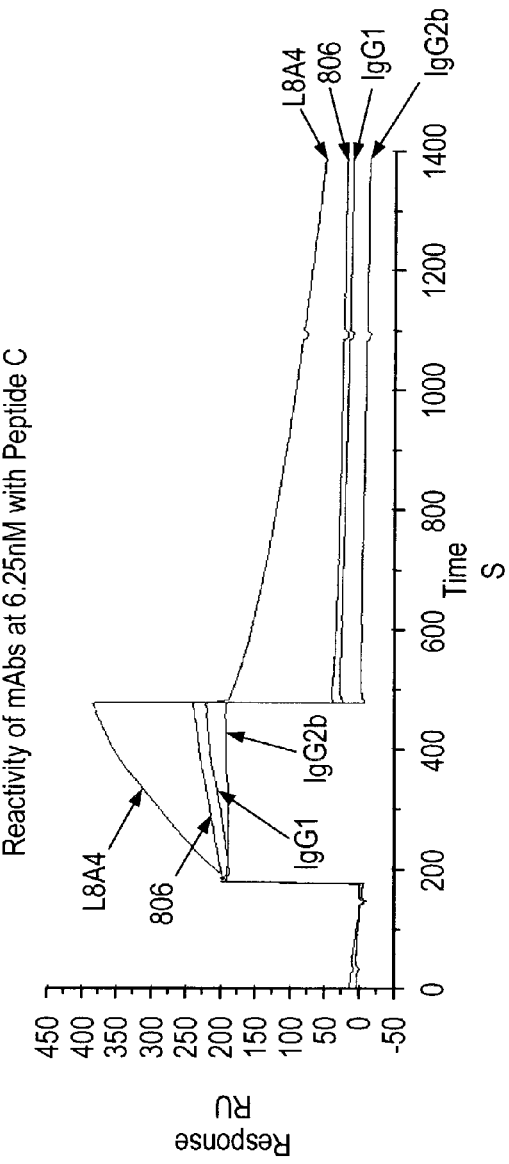
FIGS. 2D and 2E graphically present the results of BIAcore binding studies using C-terminal biotinylated peptide and including a monoclonal antibody of the invention, along with other known antibodies, among them the L8A4 antibody which recognizes the junction peptide of the de2-7 EGFR mutant, and controls.
Figure 2E:
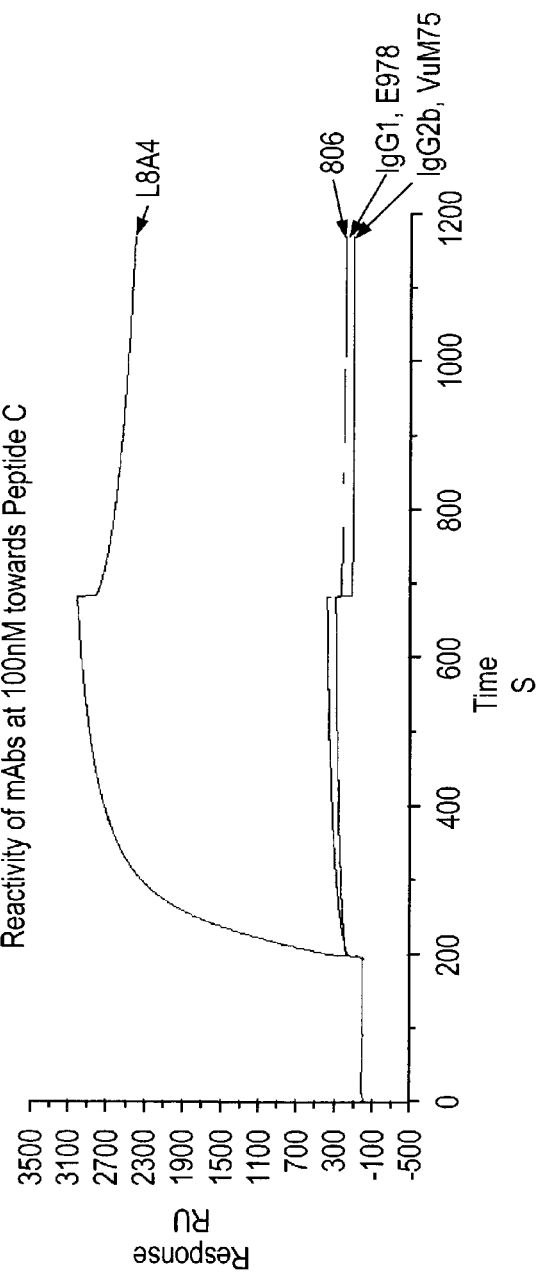

MAb L8A4 showed strong reactivity with Peptide C even at low antibody concentrations (6.25 nM) (FIG. 2D). mAb 806 did not show detectable specific reactivity with peptide C up to antibody concentrations of 100 nM (highest concentration tested) (FIGS. 2D and 2E). It was expected that mAb L8A4 would react with Peptide C because the peptide was used as the immunogen in the generation of mAb L8A4. Addition of the Junction Peptide (non-biotinylated, 50 ug/ml) completely blocks the reactivity of mAb L8A4 with Peptide C, confirming the antibody's specificity for the junction peptide epitope.

In a second set of BIAcore™ experiments, sEGFR was immobilized on a CM microsensor chip at a surface density of ~4000 RU. Serial dilutions of mAbs were tested for reactivity with sEGFR.

MAb 806 was strongly reactive with denatured sEGFR while mAb L8A4 did not react with denatured sEGFR. Reactivity of mAb 806 with denatured sEGFR decreases with decreasing antibody concentrations. It was expected that mAb L8A4 does not react with sEGFR because mAb L8A4 was generated using the junction peptide as the immunogen and sEGFR does not contain the junction peptide.

Dot-blot immune stain experiments were also performed. Serial dilutions of peptide were spotted in 0.5 µl onto a PVDF or nitrocellulose membranes. Membranes were blocked with 2% BSA in PBS, and then probed with 806, L8A4, DH8.3 and control antibodies. Antibodies L8A4 and DH8.3 bound to peptide on the membranes (data not shown). Mab806 did not bind peptide at concentrations where L8A4 clearly showed binding (data not shown). Control antibodies were also negative for peptide binding.

mAb 806 bound to the wtEGFR in cell lysates following immunoblotting (results not shown). This is different from the results obtained with DH8.3 antibody, which reacted with de2-7 EGFR but not wtEGFR. Thus, mAb 806 can recognize the wtEGFR following denaturation but not when the receptor is in its natural state on the cell surface.

EXAMPLE 4

Scatchard Analysis

A Scatchard analysis using U87MG.Δ2-7 cells was performed following correction for immunoreactivity in order to determine the relative affinity of each antibody. Antibodies were labelled with $^{125}$I (Amrad, Melbourne, Australia) by the chloramine T method and immunoreactivity determined by Lindmo assay (23). All binding assays were performed in 1% HSA/PBS on 1-2×10$^6$ live U87MG.Δ2-7 or A431 cells for 90 min at 4° C. with gentle rotation. A set concentration of 10 ng/ml $^{125}$I-labeled antibody was used in the presence of increasing concentrations of the appropriate unlabeled antibody. Non-specific binding was determined in the presence of 10,000-fold excess of unlabeled antibody. After the incubation was completed, cells were washed and counted for bound $^{125}$I-labeled antibody using a COBRA II gamma counter (Packard Instrument Company, Meriden, USA).

Both mAb 806 and the DH8.3 antibody retained high immunoreactivity when iodinated and was typically greater than 90% for mAb 806 and 45-50% for the DH8.3 antibody. mAb 806 had an affinity for the de2-7 EGFR receptor of $1.1 \times 10^9$ M$^{-1}$ whereas the affinity of DH8.3 was some 10-fold lower at $1.0 \times 10^8$ M$^{-1}$. Neither $^{125}$I-radiolabeled mAb 806 nor the $^{125}$I-radiolabeled DH8.3 antibody bound to parental U87MG cells. mAb 806 recognized an average of $2.4 \times 10^5$ binding sites per cell with the DH8.3 antibody binding an average of $5.2 \times 10^5$ sites. Thus, there was not only good agreement in receptor number between the antibodies, but also with a previous report showing $2.5 \times 10^5$ de2-7 receptors per cell as measured by a different de2-7 EGFR specific antibody on the same cell line (25).

EXAMPLE 5

Internalization of Antibodies by U87MG.Δ2-7 Cells

The rate of antibody internalization following binding to a target cell influences both its tumor targeting properties and therapeutic options. Consequently, the inventors examined the internalization of mAb 806 and the DH8.3 antibody following binding to U87MG.Δ2-7 cells by FACS. U87MG.Δ2-7 cells were incubated with either mAb 806 or the DH8.3 antibody (10 µg/ml) for 1 h in DMEM at 4° C. After washing, cells were transferred to DMEM pre-warmed to 37° C. and aliquots taken at various time points following incubation at 37° C. Internalization was stopped by immediately washing aliquots in ice-cold wash buffer (1% HSA/PBS). At the completion of the time course cells were stained by FACS as described above. Percentage internalization was calculated by comparing surface antibody staining at various time points to zero time using the formula: percent antibody internalized=(mean fluorescence at time×background fluorescence)/(mean fluorescence at time 0−background fluorescence)×100. This method was validated in one assay using an iodinated antibody (mAb 806) to measure internalization as previously described (24). Differences in internalization rate at different time points were compared using Student's t-test.

Both antibodies showed relatively rapid internalization reaching steady-state levels at 10 min for mAb 806 and 30 min for DH8.3 (FIG. 3). Internalization of DH8.3 was significantly higher both in terms of rate (80.5% of DH8.3 internalized at 10 min compared to 36.8% for mAb 806, p<0.01) and total amount internalized at 60 min (93.5% versus 30.4%, p<0.001). mAb 806 showed slightly lower levels of internalization at 30 and 60 min compared to 20 min in all 4 assays performed (FIG. 3). This result was also confirmed using an internalization assay based on iodinated mAb 806.

EXAMPLE 6

Electron Microscopy Analysis of Antibody Internalization

Given the above noted difference in internalization rates between the antibodies, a detailed analysis of antibody intracellular trafficking was performed using electron microscopy.

U87MG.Δ2-7 cells were grown on gelatin coated chamber slides (Nunc, Naperville, Ill.) to 80% confluence and then washed with ice cold DMEM. Cells were then incubated with mAb 806 or the DH8.3 antibody in DMEM for 45 min at 4° C. After washing, cells were incubated for a further 30 min with gold-conjugated (20 nm particles) anti-mouse IgG (BB International, Cardiff, UK) at 4° C. Following a further wash, pre-warmed DMEM/10% FCS was added to the cells, which were incubated at 37° C. for various times from 1-60 min. Internalization of the antibody was stopped by ice-cold media and cells fixed with 2.5% glutaraldehyde in PBS/0.1% HSA and then post-fixed in 2.5% osmium tetroxide. After dehydration through a graded series of acetone, samples were embedded in Epon/Araldite® resin, cut as ultra-thin sections with a Reichert Ultracut-S microtome (Leica) and collected on nickel grids. The sections were stained with uranyl acetate and lead citrate before being viewed on a Philips CM12 transmission electron microscope at 80 kV. Statistical analysis of gold grains contained within coated pits was performed using a Chi-square test.

While the DH8.3 antibody was internalized predominantly via coated-pits, mAb 806 appeared to be internalized by macropinocytosis (FIG. 19). In fact, a detailed analysis of 32 coated pits formed in cells incubated with mAb 806 revealed that none of them contained antibody. In contrast, around 20% of all coated-pits from cells incubated with DH8.3 were positive for antibody, with a number containing multiple gold grains. A statistical analysis of the total number of gold grains contained within coated-pits found that the difference was highly significant (p<0.01). After 20-30 min both antibodies could be seen in structures that morphologically resemble lysosomes. The presence of cellular debris within these structures was also consistent with their lysosome nature.

EXAMPLE 7

Biodistribution of Antibodies in Tumor Bearing Nude Mice

The biodistribution of mAb 806 and the DH8.3 antibody was compared in nude mice containing U87MG xenografts on one side and U87MG.Δ2-7 xenografts on the other. A relatively short time period was chosen for this study as a previous report demonstrated that the DH8.3 antibody shows peak levels of tumor targeting between 4-24 h (16).

Tumor xenografts were established in nude BALB/c mice by s.c. injection of $3 \times 10^6$ U87MG, U87MG.Δ2-7 or A431 cells. de2-7 EGFR expression in U87MG.Δ2-7 xenografts remained stable throughout the period of biodistribution. Also, A431 cells retained their mAb 806 reactivity when grown as tumor xenografts as determined by immunohistochemistry (data not shown). U87MG or A431 cells were injected on one side 7-10 days before U87MG.Δ2-7 cells were injected on the other side because of the faster growth rate observed for de2-7 EGFR expressing xenografts. Antibodies were radiolabeled and assessed for immunoreactivity as described above and were injected into mice by the retro-orbital route when tumors were 100-200 mg in weight. Each mouse received two different antibodies (2 µg per antibody): 2 µCi of $^{125}$I-labeled mAb 806 and 2 µCi of $^{131}$I labelled DH8.3 or 528. Unless indicated, groups of 5 mice were sacrificed at various time points post-injection and blood obtained by cardiac puncture. The tumors, liver, spleen, kidneys and lungs were obtained by dissection. All tissues were weighed and assayed for $^{125}$I and $^{131}$I activity using a dual-channel counting Window. Data was expressed for each antibody as % ID/g tumor determined by comparison to injected dose standards or converted into tumor to blood/liver ratios (i.e. % ID/g tumor divided by % ID/g blood or liver). Differences between groups were analysed by Student's t-test.

Figure 4A:
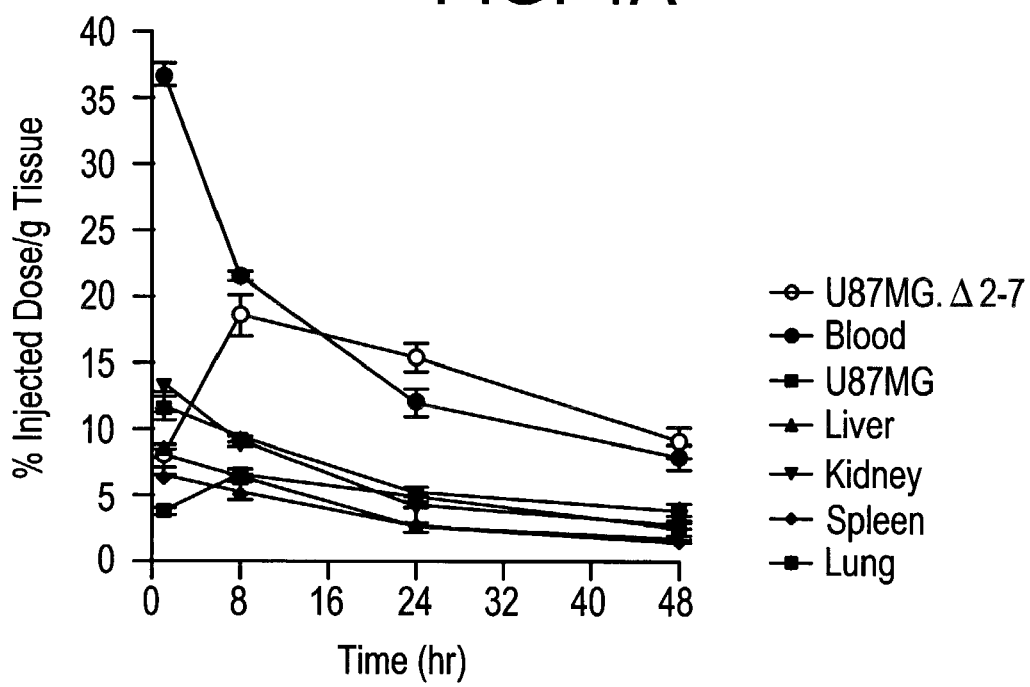
FIGS. 4A and 4B illustrate biodistribution (% ID/g tumor) of radiolabeled (a) $^{125}$I-MAb 806 and (b) $^{131}$I-DH8.3 in nude mice bearing U87MG and U87MG.Δ2-7 xenografts. Each point represents the mean of 5 mice ±SE except for 1 hr where n=4.
Figure 4B:
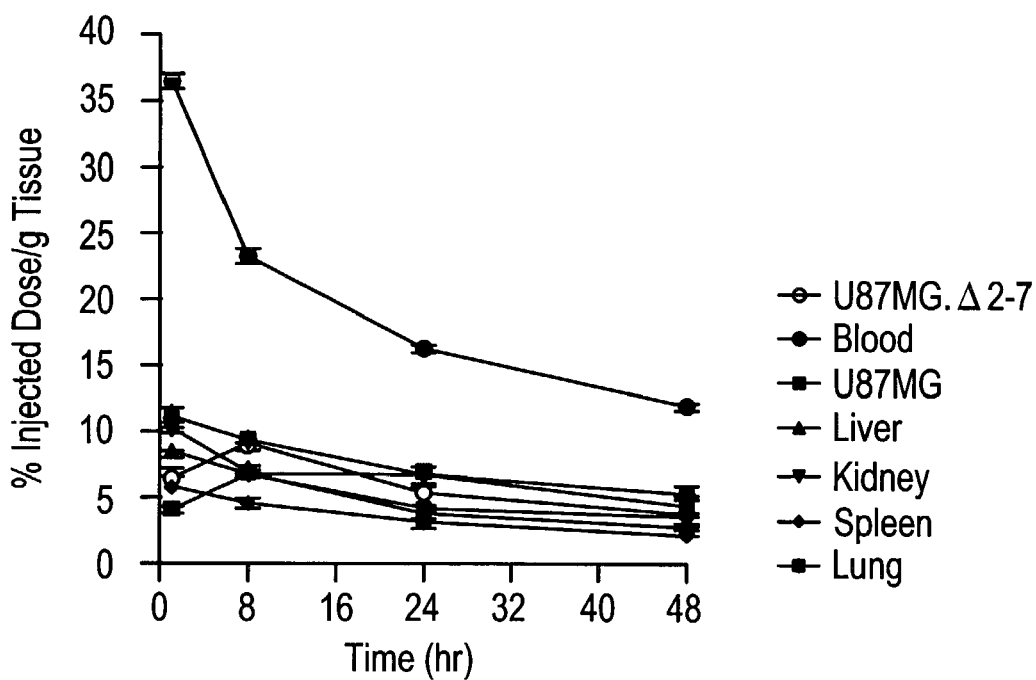
Figure 5A:
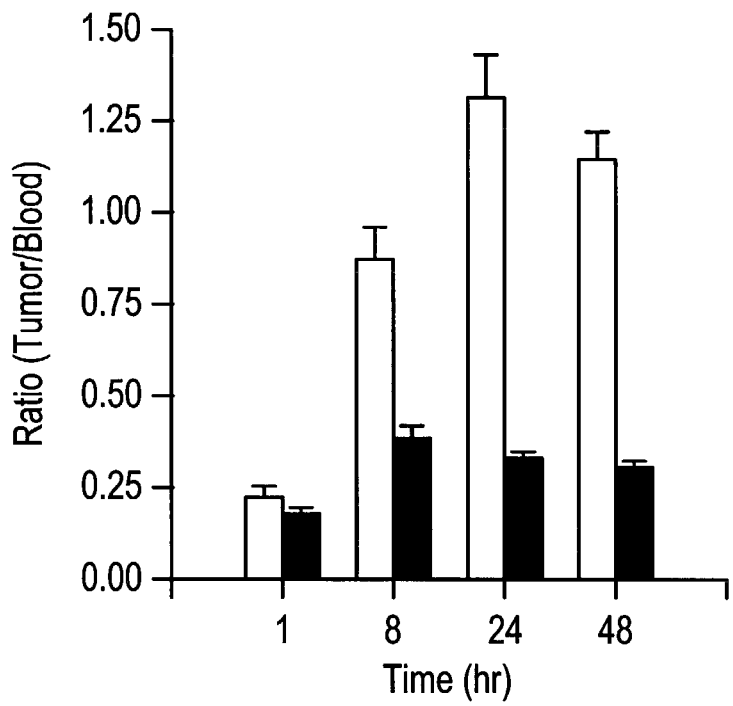
FIGS. 5A and 5B illustrate biodistribution of radiolabeled $^{125}$I-MAb 806 (open bar) and $^{131}$I-DH8.3 (filled bar) antibodies expressed as (a) tumor:blood or (b) tumor:liver ratios in nude mice bearing U87MG.Δ2-7 xenografts. Each bar represents the mean of 5 mice ±SE except for 1 hr where n=4

In terms of % ID/g tumor, mAb 806 reached its peak level in U87MG.Δ2-7 xenografts of 18.6% m/g tumor at 8 h (FIG. 4A), considerably higher than any other tissue except blood. While DH 8.3 also showed peak tumor levels at 8 h, the level was a statistically (p<0.001) lower 8.8% m/g tumor compared to mAb 806 (FIG. 4B). Levels of both antibodies slowly declined at 24 and 48 h. Neither antibody showed specific targeting of U87MG parental xenografts (FIGS. 4A,B). With regards to tumor to blood/liver ratios, mAb 806 showed the highest ratio at 24 h for both blood (ratio of 1.3) and liver (ratio of 6.1) (FIGS. 5A,B). The DH8.3 antibody had its highest ratio in blood at 8 h (ratio of 0.38) and at 24 h in liver (ratio of 1.5) (FIGS. 5 A,B), both of which are considerably lower than the values obtained for mAb 806.

As described above, levels of mAb 806 in the tumor peaked at 8 hours. While this peak is relatively early compared to many tumor-targeting antibodies, it is completely consistent with other studies using de2-7 EGFR specific antibodies which all show peaks at 4-24 hours post-injection when using a similar dose of antibody (16, 25, 33). Indeed, unlike the earlier reports, the 8 h time point was included on the assumption that antibody targeting would peak rapidly. The % ID/g tumor seen with mAb 806 was similar to that reported for other de2-7 EGFR specific antibodies when using standard iodination techniques (16, 24, 32). The reason for the early peak is probably two-fold. Firstly, tumors expressing the de2-7 EGFR, including the transfected U87MG cells, grow extremely rapidly as tumor xenografts. Thus, even during the relatively short period of time used in these biodistribution studies, the tumor size increases to such an extent (5-10 fold increase in mass over 4 days) that the % ID/g tumor is reduced compared with slow growing tumors. Secondly, while internalization of mAb 806 was relatively slow compared to DH8.3, it is still rapid with respect to many other tumor antibody/antigen systems. Internalized antibodies undergo rapid proteolysis with the degradation products being excreted from the cell (34). This process of internalization, degradation and excretion reduces the amount of iodinated antibody retained within the cell. Consequently, internalizing antibodies display lower levels of targeting than their non-internalizing counterparts. The electron microscopy data reported herein demonstrates that internalized mAb 806 is rapidly transported to lysosomes where rapid degradation presumably occurs. This observation is consistent with the swift expulsion of iodine from the cell.

The previously described L8A4 monoclonal antibody directed to the unique junctional peptide found in the de2-7 EGFR, behaves in a similar fashion to mAb 806 (35). Using U87MG cells transfected with the de2-7 EGFR, this antibody had a similar internalization rate (35% at 1 hour compared to 30% at 1 hour for mAb 806) and displayed comparable in vivo targeting when using 3T3 fibroblasts transfected with de2-7 EGFR (peak of 24% ID/g tumor at 24 hours compared to 18% ID/g tumor at 8 hours for mAb 806) (25). Interestingly, in vivo retention of this antibody in tumor xenografts was enhanced when labeled with N-succinimidyl 5-iodo-3-pyridine carboxylate (25). This labeled prosthetic group is positively charged at lysosmal pH and thus has enhanced cellular retention (33). Enhanced retention is potentially useful when considering an antibody for radioimmunotherapy and this method could be used to improve retention of iodinated mAb 806 or its fragments.

EXAMPLE 8

Binding of mAb 806 to Cells Containing Amplified EGFR

Figure 6A:
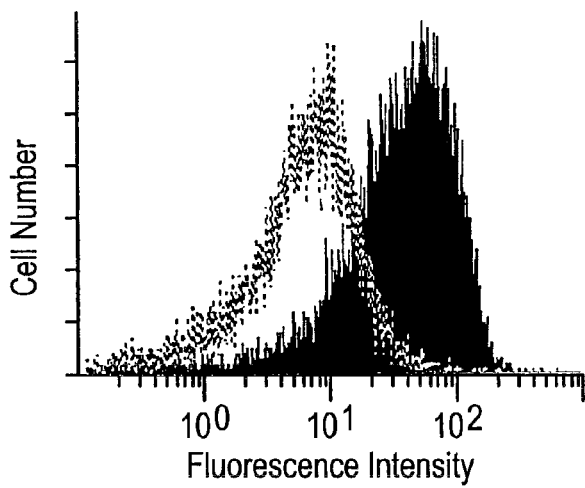
FIG. 6 illustrates flow cytometric analysis of cell lines containing amplification of the EGFR gene. A431 cells were stained with either MAb 806, DH8.3 or 528 (black histograms) and compared to an irrelevant IgG2b antibody (open histogram)
Figure 6B:
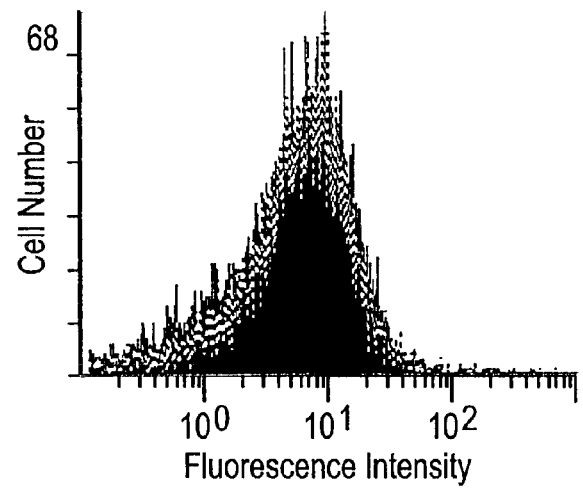
Figure 6C:
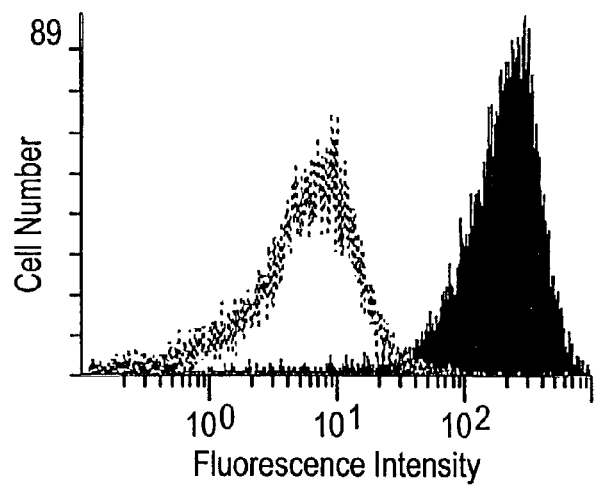

To examine if mAb 806 could recognize the EGFR expressed in cells containing an amplified receptor gene, its binding to A431 cells was analysed. As described previously, A431 cells are human squamous carcinoma cells and express high levels of wtEGFR. Low, but highly reproducible, binding of mAb 806 to A431 cells was observed by FACS analysis (FIG. 6). The DH8.3 antibody did not bind A431 cells, indicating that the binding of mAb 806 was not the result of low level de2-7 EGFR expression (FIG. 6). As expected, the anti-EGFR 528 antibody showed strong staining of A431 cells (FIG. 6). Given this result, binding of mAb 806 to A431 was characterized by Scatchard analysis. While the binding of iodinated mAb 806 was comparatively low, it was possible to get consistent data for Scatchard. The average of such experiments gave a value for affinity of $9.5 \times 10^7$ $M^{-1}$ with $2.4 \times 10^5$ receptors per cell. Thus the affinity for this receptor was some 10-fold lower than the affinity for the de2-7 EGFR. Furthermore, mAb 806 appears to only recognize a small portion of EGFR found on the surface of A431 cells. Using the 528 antibody, the inventors measured approximately $2 \times 10^6$ receptors per cell which is in agreement with numerous other studies(26).

Recognition of the wild type sEGFR by mAb 806 clearly requires some denaturation of the receptor in order to expose the epitope. The extent of denaturation required is only slight as even absorption of the wild type sEGFR on to a plastic surface induced robust binding of mAb 806 in ELISA assays. As mAb 806 only bound approximately 10% of the EGFR on the surface of A431 cells, it is tempting to speculate that this subset of receptors may have an altered conformation similar to that induced by the de2-7 EGFR truncation. Indeed, the extremely high expression of the EGFR mediated by gene amplification in A431 cells, may cause some receptors to be incorrectly processed leading to altered conformation. Interestingly, semi-quantitative immunoblotting of A431 cell lysates with mAb 806 showed that it could recognize most of the A431 EGF receptors following SDS-PAGE and western transfer. This result further supports the argument that mAb 806 is binding to a subset of receptors on the surface of A431 cells that have an altered conformation. These observations in A431 cells are consistent with the immunohistochemistry data demonstrating that mAb 806 binds gliomas containing amplification of the EGFR gene. As mAb 806 binding was completely negative on parental U87MG cells it would appear this phenomenon may be restricted to cells containing amplified EGFR although the level of "denatured" receptor on the surface of U87MG cells may be below the level of detection. However, this would seem unlikely as iodinated mAb 806 did not bind to U87MG cell pellets containing up to $1 \times 10^7$ cells.

EXAMPLE 9

In Vivo Targeting of A431 Cells by mAb 806

A second biodistribution study was performed with mAb 806 to determine if it could target A431 tumor xenografts. The study was conducted over a longer time course in order obtain more information regarding the targeting of U87MG.Δ2-7 xenografts by mAb 806, which were included in all mice as a positive control. In addition, the anti-EGFR 528 antibody was included as a positive control for the A431 xenografts, since a previous study demonstrated low but significant targeting of this antibody to A431 cells grown in nude mice (21).

Figure 7A:
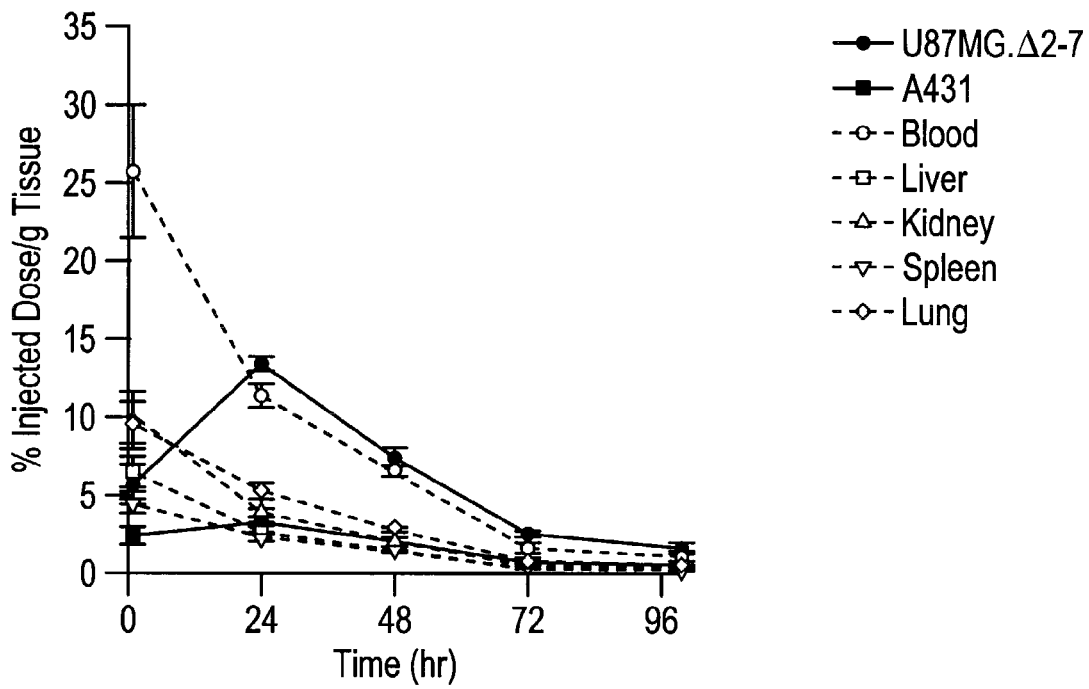
FIGS. 7A and 7B illustrate biodistribution (% ID/g tumor) of radiolabeled (a) $^{125}$I-MAb 806 and (b) $^{131}$I-528 in nude mice bearing U87MG.Δ2-7 nd A431 xenografts.
Figure 7B:
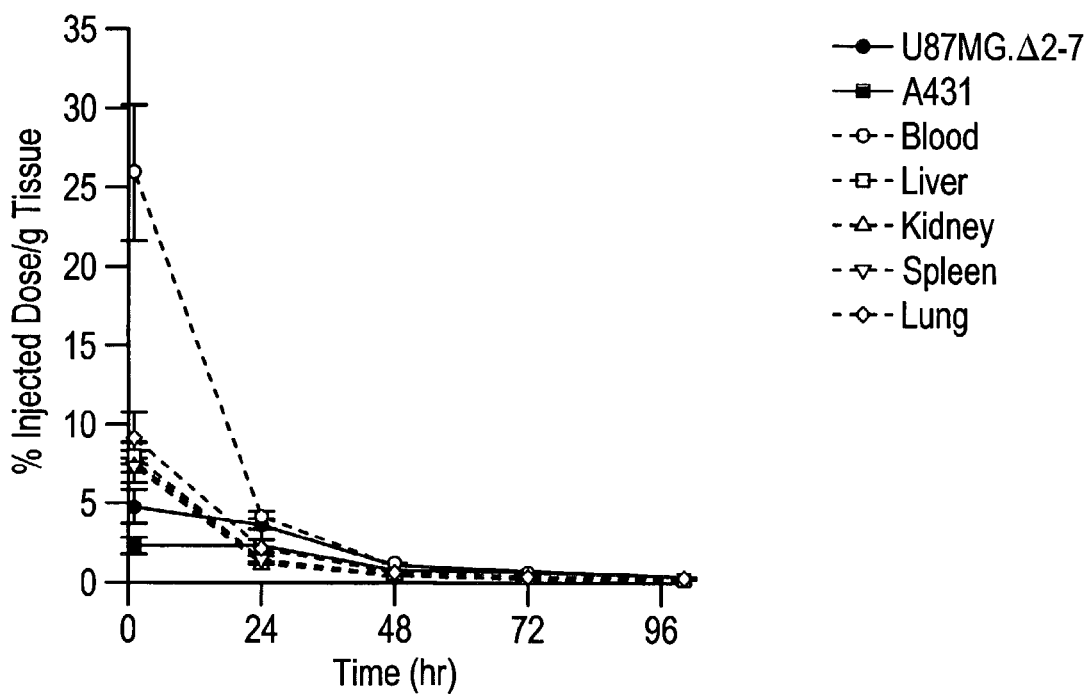
Figure 8A:
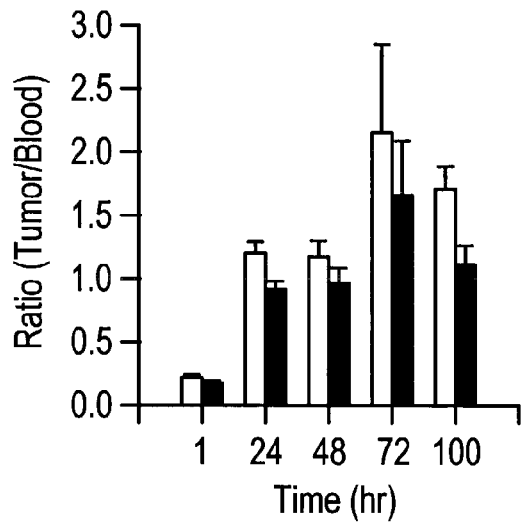
FIGS. 8A-8D illustrate biodistribution of radiolabeled $^{125}$I-MAb 806 (open bar) and $^{131}$-528 (filled bar) and antibodies expressed as (a,b) tumor:blood or (c,d) tumor:liver ratios in nude mice bearing (a,c) U87MGΔ2-7 and (b,d) A431 xenografts.

During the first 48 h, mAb 806 displayed almost identical targeting properties as those observed in the initial experiments (FIG. 7A compared with FIG. 4A). In terms of % ID/g tumor, levels of mAb 806 in U87MG.Δ2-7 xenografts slowly declined after 24 h but always remained higher than levels detected in normal tissue. Uptake in the A431 xenografts was comparatively low, however there was a small increase in % ID/g tumor during the first 24 h not observed in normal tissues such as liver, spleen, kidney and lung (FIG. 7A). Uptake of the 528 antibody was very low in both xenografts when expressed as % ID/g tumor (FIG. 7B) partially due to the faster clearance of this antibody from the blood. In terms of tumor to blood ratio mAb 806 peaked at 72 h for U87MG.Δ2-7 xenografts and 100 h for A431 xenografts (FIGS. 8A,B). While the tumor to blood ratio for mAb 806 never surpassed 1.0 with respect to the A431 tumor, it did increase throughout the entire time course (FIG. 8B) and was higher than all other tissues examined (data not shown) indicating low levels of targeting.

Figure 8B:
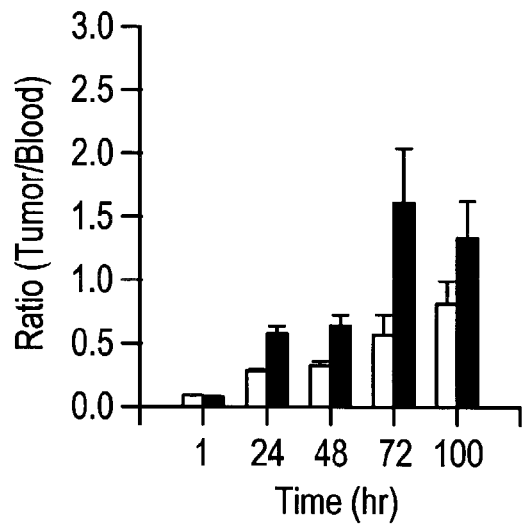
Figure 8C:
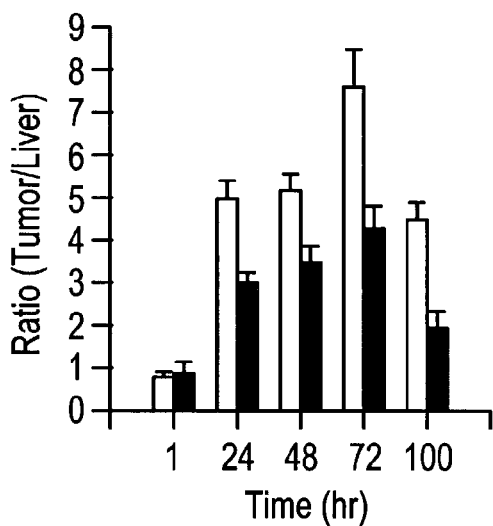
Figure 8D:
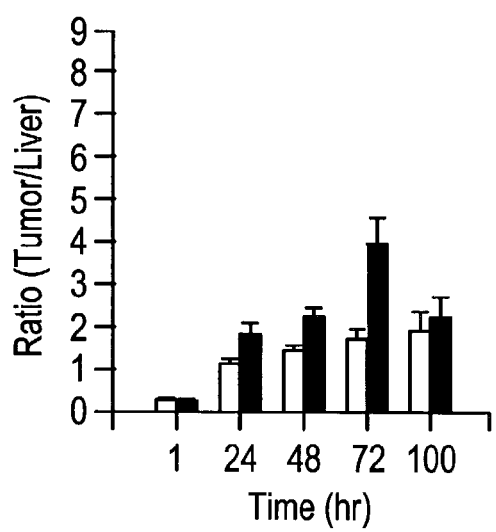

The tumor to blood ratio for the 528 antibody showed a similar profile to mAb 806 although higher levels were noted in the A431 xenografts (FIGS. 8A,B). mAb 806 had a peak tumor to liver ratio in U87MG.Δ2-7 xenografts of 7.6, at 72 h, clearly demonstrating preferential uptake in these tumors compared to normal tissue (FIG. 8C). Other tumor to organ ratios for mAb 806 were similar to those observed in the liver (data not shown). The peak tumor to liver ratio for mAb 806 in A431 xenografts was 2.0 at 100 h, again indicating a slight preferential uptake in tumor compared with normal tissue (FIG. 8D).

EXAMPLE 10

Therapy Studies

The effects of mAb806 were assessed in two xenograft models of disease—a preventative model and an established tumor model.

Xenograft Models

Consistent with previous reports (Nishikawa et al, Proc. Natl. Acad. Sci. USA, 91(16); 7727-7731) U87MG cells transfected with de2-7 EGFR grew more rapidly than parental cells and U87MG cells transfected with the wt EGFR. Therefore, it was not possible to grow both cell types in the same mice.

$3 \times 10^6$ tumor cells in 100 ml of PBS were inoculated subcutaneously. into both flanks of 4-6 week old female nude mice (Animal Research Centre, Western Australia, Australia). Therapeutic efficacy of mAb 806 was investigated in both preventative and established tumor models. In the preventative model, 5 mice with 2 xenografts each were treated intraperitoneally. with either 1 or 0.1 mg of mAb 806 or vehicle (PBS) starting the day before tumor cell inoculation. Treatment was continued for a total of 6 doses, 3 times per week for 2 weeks. In the established model, treatment was started when tumors had reached a mean volume of 65±6.42 $mm^3$ (U87MG.Δ2-7), 84±9.07 $mm^3$ (U87MG), 73±7.5 $mm^3$ (U87MG.wtEGFR) or 201±19.09 $mm^3$ (A431 tumors). Tumor volume in $mm^3$ was determined using the formula (length×width$^2$)/2, where length was the longest axis and width the measurement at right angles to the length (Scott et al, 2000). Data was expressed as mean tumor volume ±S.E. for each treatment group. Statistical analysis was performed at given time points using Student's t test. Animals were euthanased when the xenografts reached an approximate volume of 1.5 $cm^3$ and the tumors excised for histological examination. This research project was approved by the Animal Ethics Committee of the Austin and Repatriation Medical Centre.

Histological Examination of Tumor Xenografts

Xenografts were excised and bisected. One half was fixed in 10% formalin/PBS before being embedded in paraffin. Four micron sections were then cut and stained with haematoxylin and eosin (H&E) for routine histological examination. The other half was embedded in Tissue Tek® OCT compound (Sakura Finetek, Torrance, Calif.), frozen in liquid nitrogen and stored at −80° C. Thin (5 micron) cryostat sections were cut and fixed in ice-cold acetone for 10 min followed by air drying for a further 10 min. Sections were blocked in protein blocking reagent (Lipshaw Immunon, Pittsburgh U.S.A.) for 10 min and then incubated with biotinylated primary antibody (1 mg/ml), for 30 min at room temperature (RT). All antibodies were biotinylated using the ECL protein biotinylation module (Amersham, Baulkham Hills, Australia), as per the manufactures instructions. After rinsing with PBS, sections were incubated with a streptavidin horseradish peroxidase complex for a further 30 min (Silenus, Melbourne, Australia). Following a final PBS wash the sections were exposed to 3-amino-9-ethylcarbozole (AEC) substrate (0.1 M acetic acid, 0.1 M sodium acetate, 0.02 M AEC (Sigma Chemical Co., St Louis, Mo.)) in the presence of hydrogen peroxide for 30 min. Sections were rinsed with water and counterstained with hematoxylin for 5 min and mounted.

Efficacy of mAb 806 in Preventative Model

Figure 9A:
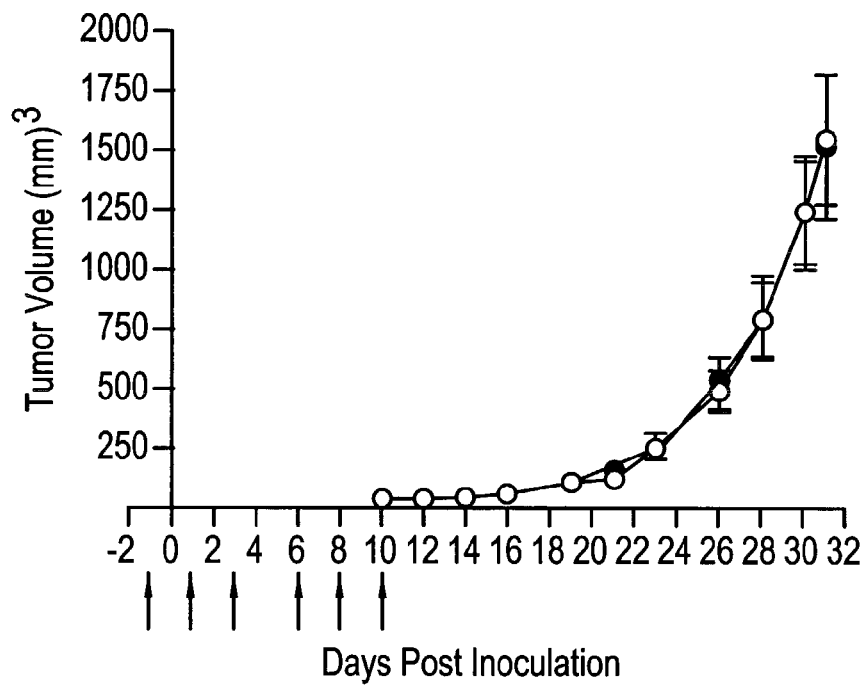
FIG. 9 illustrates anti-tumor effect of mAb 806 on A) U87MG and B) U87MG.Δ2-7 xenograft growth rates in a preventative model. 3×10$^6$ U87MG or U87MG.Δ2-7 cells were injected s.c. into both flanks of 4-6 week old BALB/c nude mice, (n=5) at day 0. Mice were injected i.p. with either 1 mg of mAb 806 (●); 0.1 mg of mAb 806 (▲); or vehicle (○) starting one day prior to tumor cell inoculation. Injections were given three times per week for two weeks as indicated by the arrows. Data are expressed as mean tumor volume ±S.E.
Figure 9B:
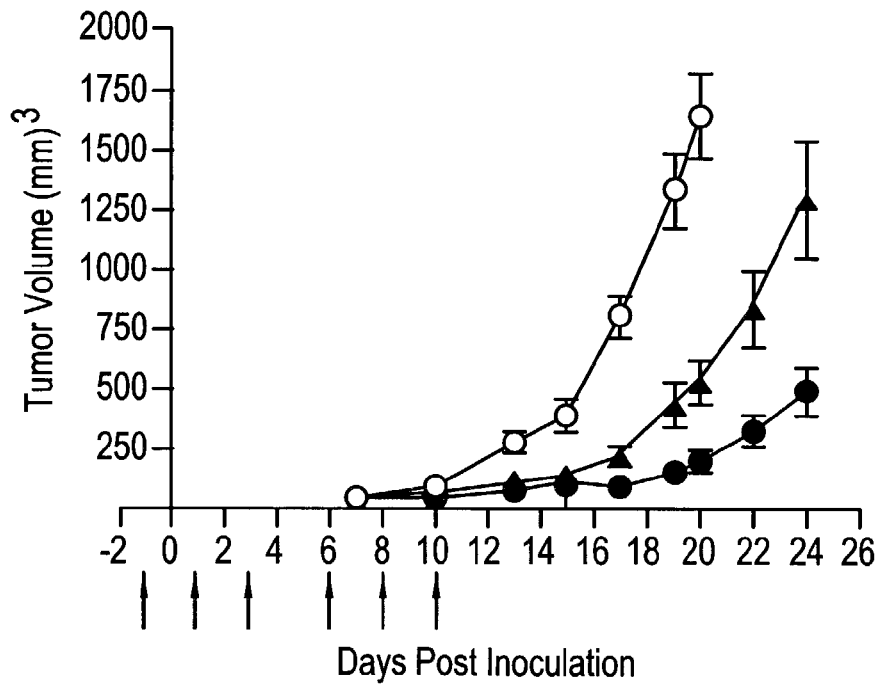

MAb 806 was examined for efficacy against U87MG and U87MG.Δ2-7 tumors in a preventative xenograft model. Antibody or vehicle were administered i.p. the day before tumor inoculation and was given 3 times per week for 2 weeks. MAb 806 had no effect on the growth of parental U87MG xenografts, which express the wt EGFR, at a dose of 1 mg per injection (FIG. 9A). In contrast, mAb 806 significantly inhibited the growth of U87MG.Δ2-7 xenografts in a dose dependent manner (FIG. 9B). At day 20, when control animals were sacrificed, the mean tumor volume was $1637\pm178.98$ mm$^3$ for the control group, a statistically smaller $526\pm94.74$ mm$^3$ for the 0.1 mg per injection group (p<0.0001) and $197\pm42.06$ mm$^3$ for the 1 mg injection group (p<0.0001). Treatment groups were sacrificed at day 24 at which time the mean tumor volumes was $1287\pm243.03$ mm$^3$ for the 0.1 mg treated group and $492\pm100.8$ mm$^3$ for the 1 mg group.

Efficacy of mAb 806 in Established Xenograft Model

Figure 10A:
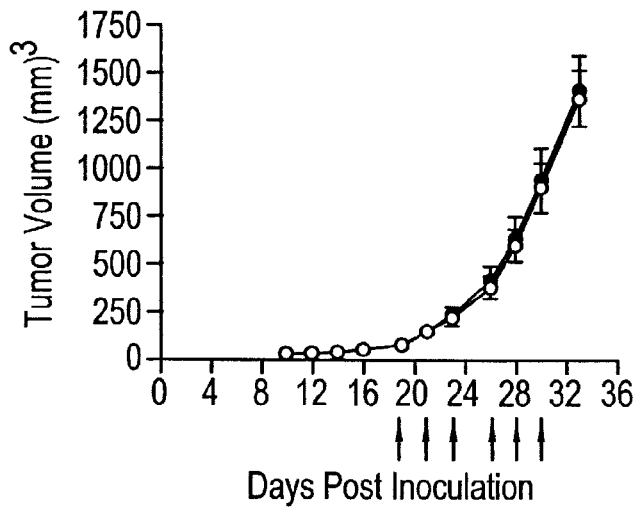
FIG. 10 illustrates the anti-tumor effect of mAb 806 on A) U87MG, B) U87MG.Δ2-7 and C) U87MG.wtEGFR xenografts in an established model. 3×10$^6$ U87MG, U87MG.Δ2-7, or U87MG.wtEGFR cells were injected s.c. into both flanks of 4-6 week old BALB/c nude mice, (n=5). Mice were injected i.p. with either 1 mg doses of mAb 806 (●); 0.1 mg doses of mAb 806 (▲); or vehicle (○) starting when tumors had reached a mean tumor volume of 65-80 mm3. Injections were given three times per week for two weeks as indicated by the arrows. Data are expressed as mean tumor volume ±S.E.
Figure 10B:
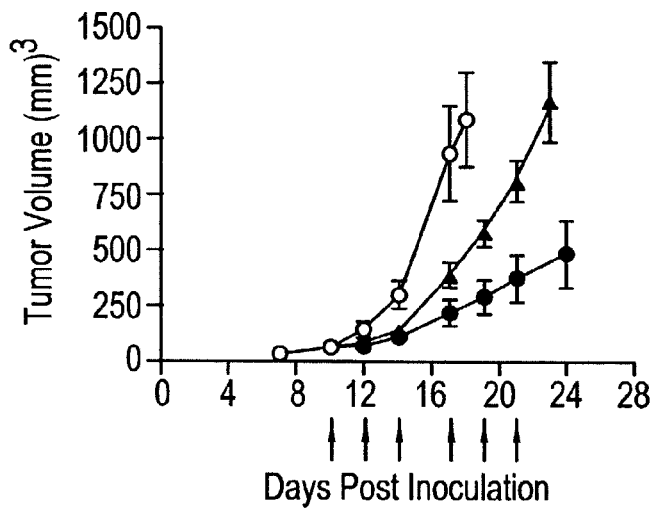

Given the efficacy of mAb 806 in the preventative xenograft model, its ability to inhibit the growth of established tumor xenografts was then examined. Antibody treatment was as described in the preventative model except that it commenced when tumors had reached a mean tumor volume of $65\pm6.42$ mm$^3$ for the U87MG.Δ2-7 xenografts and $84\pm9.07$ mm$^3$ for the parental U87MG xenografts. Once again, mAb 806 had no effect on the growth of parental U87MG xenografts at a dose of 1 mg per injection (FIG. 10A). In contrast, mAb 806 significantly inhibited the growth of U87MG.Δ2-7 xenografts in a dose dependent manner (FIG. 10B). At day 17, one day before control animals were sacrificed, the mean tumor volume was $935\pm215.04$ mm$^3$ for the control group, $386\pm57.51$ mm$^3$ for the 0.1 mg per injection group (p<0.01) and $217\pm58.17$ mm$^3$ for the 1 mg injection group (p<0.002).

Figure 10C:
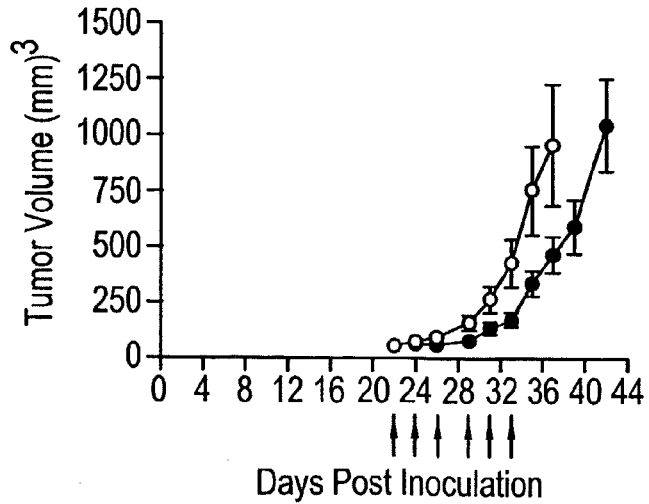

To examine whether the growth inhibition observed with mAb 806 was restricted to cell expressing de2-7 EGFR, its efficacy against U87MG.wtEGFR tumor xenografts was examined in an established model. These cells serve as a model for tumors containing amplification of the EGFR gene without de2-7 EGFR expression. MAb 806 treatment commenced when tumors had reached a mean tumor volume of $73\pm7.5$ mm$^3$. MAb 806 significantly inhibited the growth of established U87MG.wtEGFR xenografts when compared to control tumors treated with vehicle (FIG. 10C). On the day control animals were sacrificed, the mean tumor volume was $960\pm268.9$ mm$^3$ for the control group and $468\pm78.38$ mm$^3$ for the group treated with 1 mg injections (p<0.04).

Histological and Immunohistochemical Analysis of Established Tumors

To evaluate potential histological differences between mAb 806-treated and control U87MG.Δ2-7 and U87MG.wtEGFR xenografts (collected at days 24 and 42 respectively), formalin-fixed, paraffin embedded sections were stained with H&E. Areas of necrosis were seen in sections from both U87MG.Δ2-7 (collected 3 days after treatment finished), and U87MG.wtEGFR xenografts (collected 9 days after treatment finished) treated with mAb 806. This result was consistently observed in a number of tumor xenografts (n=4). However, analysis of sections from xenografts treated with control did not display the same areas of necrosis seen with mAb 806 treatment. Sections from mAb 806 or control treated U87MG xenografts were also stained with H&E and revealed no differences in cell viability between the two groups, further supporting the hypothesis that mAb 806 binding induces decreased cell viability/necrosis within tumor xenografts.

An immunohistochemical analysis of U87MG, U87MG.Δ2-7 and U87MG.wtEGFR xenograft sections was performed to determine the levels of de2-7 and wt EGFR expression following mAb806 treatment. Sections were collected at days 24 and 42 as above, and were immunostained with the 528 or 806 antibodies. As expected the 528 antibody stained all xenograft sections with no obvious decrease in intensity between treated and control tumors. Staining of U87MG sections was undetectable with the mAb 806, however positive staining of U87MG.Δ2-7 and U87MG.wtEGFR xenograft sections was observed. There was no difference in mAb 806 staining density between control and treated U87MG.Δ2-7 and U87MG.wtEGFR xenografts suggesting that antibody treatment does not down regulate de2-7 or wt EGFR expression.

Treatment of A431 Xenografts with mAb 806

Figure 11A:
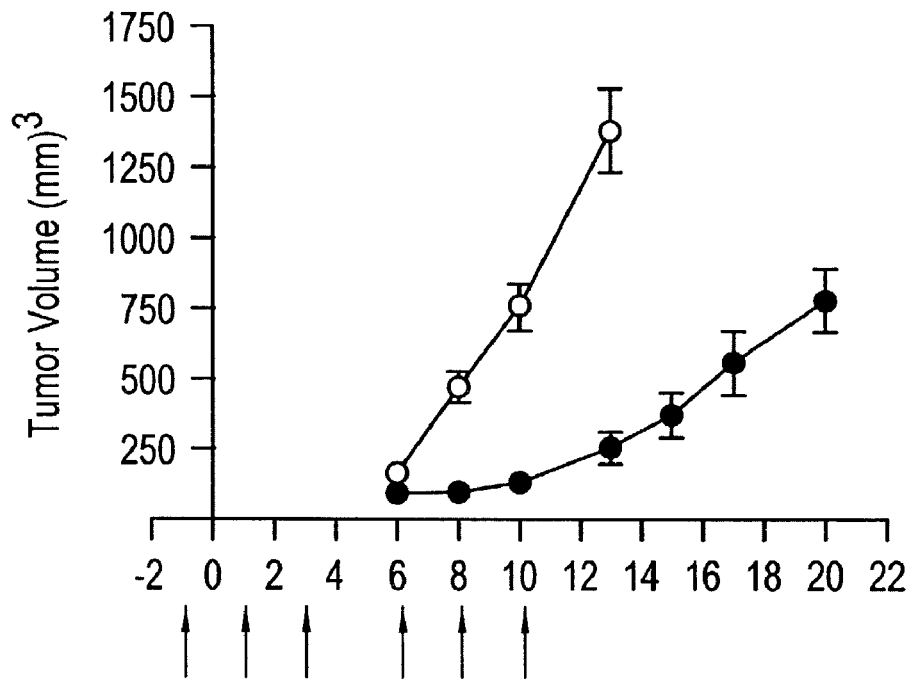
FIG. 11 illustrates anti-tumor effect of mAb 806 on A431 xenografts in A) preventative and B) established models. 3×10$^6$ A431 cells were injected s.c. into both flanks of 4-6 week old BALB/c nude mice (n=5). Mice were injected i.p. with either 1 mg doses of mAb 806 (●); or vehicle (○), starting one day prior to tumor cell inoculation in the preventative model, or when tumors had reached a mean tumor volume of 200 mm$^3$. Injections were given three times per week for two weeks as indicated by the arrows. Data are expressed as mean tumor volume ±S.E.

To demonstrate that the anti-tumor effects of mAb 806 were not restricted to U87MG cells, the antibody was administered to mice with A431 xenografts. These cells contain an amplified EGFR gene and express approximately $2\times10^6$ receptors per cell. As described above, mAb 806 binds about 10% of these EGFR and targets A431 xenografts. MAb 806 significantly inhibited the growth of A431 xenografts when examined in the previously described preventative xenograft model (FIG. 11A). At day 13, when control animals were sacrificed, the mean tumor volume was $1385\pm147.54$ mm$^3$ in the control group and $260\pm60.33$ mm$^3$ for the 1 mg injection treatment group (p<0.0001).

In a separate experiment, a dose of 0.1 mg mAb also significantly inhibited the growth of A431 xenografts in a preventative model.

Figure 11B:
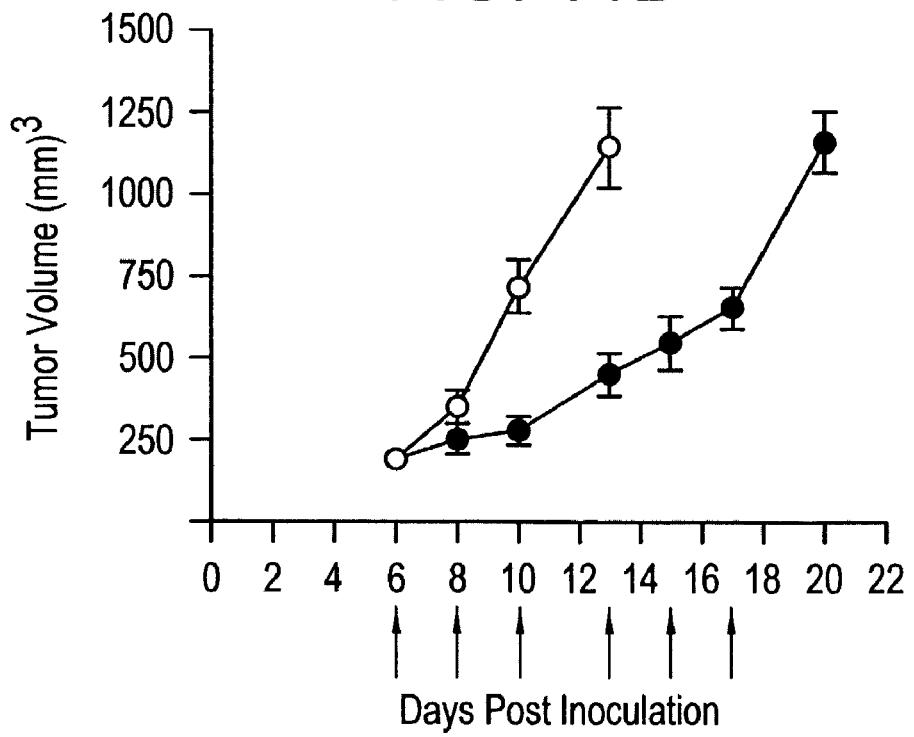

Given the efficacy of mAb 806 in the preventative A431 xenograft model, its ability to inhibit the growth of established tumor xenografts was examined. Antibody treatment was as described in the preventative model except it was not started until tumors had reached a mean tumor volume of $201\pm19.09$ mm$^3$. MAb 806 significantly inhibited the growth of established tumor xenografts (FIG. 11B). At day 13, when control animals were sacrificed, the mean tumor volume was $1142\pm120.06$ mm$^3$ for the control group and $451\pm65.58$ mm$^3$ for the 1 mg injection group (p<0.0001).

In summary, the therapy studies with mAb 806 described here clearly demonstrated dose dependent inhibition of U87MG.Δ2-7 xenograft growth. In contrast, no inhibition of parental U87MG xenografts was observed despite the fact they continue to express the wt EGFR in vivo. MAb 806 not only significantly reduced xenograft volume, it also induced significant necrosis within the tumor. This is the first report showing the successful therapeutic use of such an antibody in vivo against a human de2-7 EGFR expressing glioma xenografts.

Gene amplification of the EGFR has been reported in a number of different tumors and is observed in approximately 50% of gliomas (Voldberg et al, 1997). It has been proposed that the subsequent EGFR over-expression mediated by receptor gene amplification may confer a growth advantage by increasing intracellular signalling and cell growth (Filmus et al, 1987). The U87MG cell line was transfected with the wt EGFR in order to produce a glioma cell that mimics the process of EGFR gene amplification. Treatment of established U87MG.wtEGFR xenografts with mAb 806 resulted in significant growth inhibition. Thus, mAb 806 also mediates in vivo anti-tumor activity against cells containing amplification of the EGFR gene. Interestingly, mAb 806 inhibition of U87MG.wtEGFR xenografts appears to be less effective than that observed with U87MG.Δ2-7 tumors. This probably reflects the fact that mAb 806 has a lower affinity for the amplified EGFR and only binds a small proportion of receptors expressed on the cell surface. However, it should be noted that despite the small effect on U87MG.wtEGFR xenograft volumes, mAb 806 treatment produced large areas of necrosis within these xenografts. To rule out the possibility that mAb 806 only mediates inhibition of the U87MG derived cell lines we tested its efficacy against A431 xenografts. This squamous cell carcinoma derived cell line contains significant EGFR gene amplification which is retained both in vitro and in vivo. Treatment of A431 xenografts with mAb 806 produced significant growth inhibition in both a preventative and established model, indicating the anti-tumor effects of mAb 806 are not restricted to transfected U87MG cell lines.

EXAMPLE 11

Combination Therapy Treatment of A431 Xenografts with mAb806 and AG1478

The anti-tumor effects of mAb 806 combined with AG1478 was tested in mice with A431 xenografts. AG1478 (4-(3-Chloroanilino)-6,7-dimethoxyquinazoline) is a potent and selective inhibitor of the EGFR kinase versus HER2-neu and platelet-derived growth factor receptor kinase (Calbiochem Cat. No. 658552). Three controls were included: treatment with vehicle only, vehicle+mAb806 only and vehicle+AG1478 only. The results are illustrated in FIG. 12. 0.1 mg mAb806 was administered at 1 day prior to xenograft and 1, 3, 6, 8 and 10 days post xenograft. 400 μg AG1478 was administered at 0, 2, 4, 7, 9, and 11 days post xenograft.

Both AG1478 and mAb806, when administered alone produced a significant reduction of tumor volume. However, in combination, the reduction of tumor volume was greatly enhanced.

Figure 13:
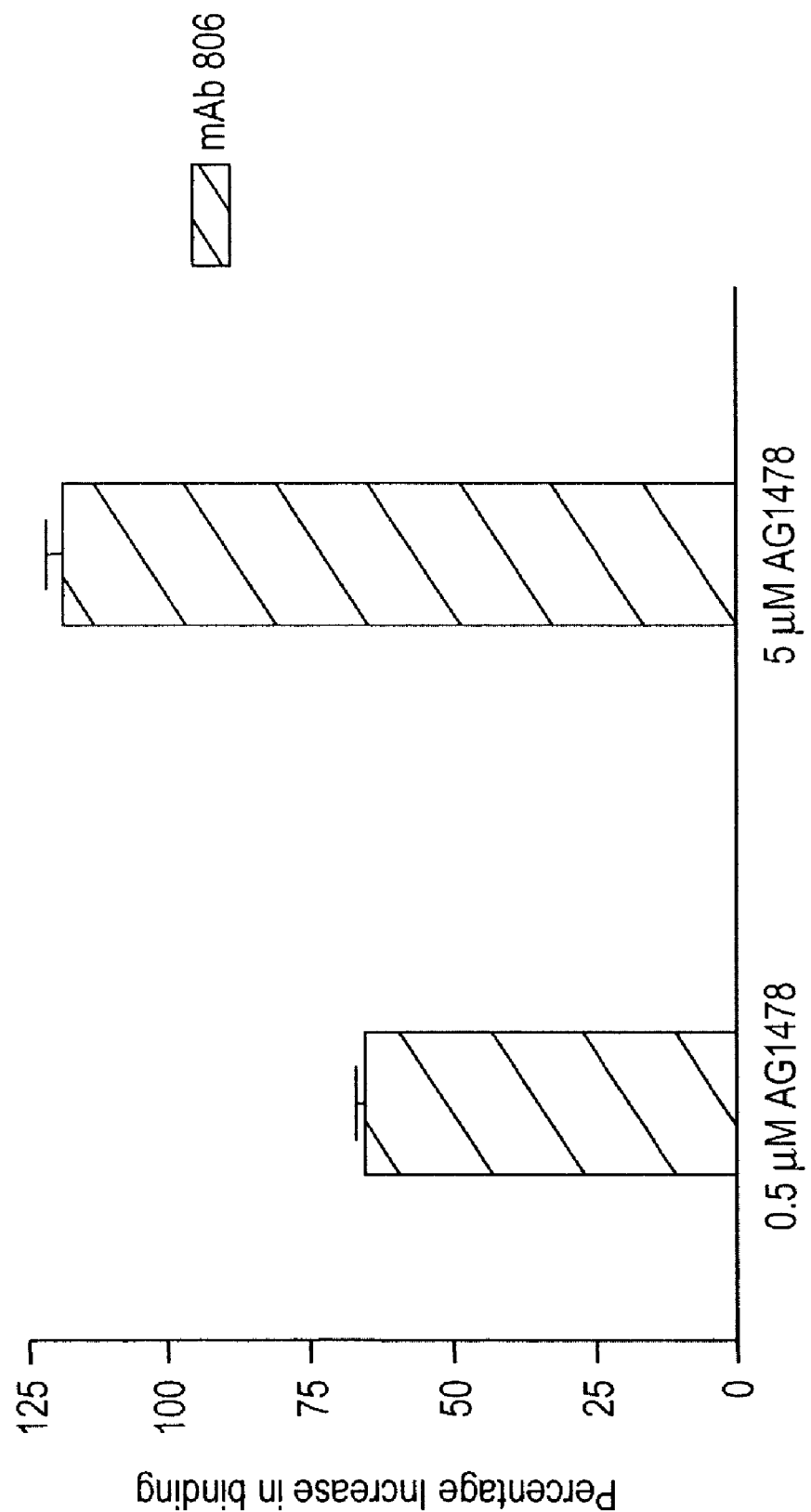
FIG. 13 depicts antibody 806 binding to A431 cells in the presence of increasing concentrations of AG1478 (0.5 uM and 5 uM).

In addition, the binding of mAb806 to EGFR of A431 cells was evaluated in the absence and presence of AG1478. Cells were placed in serum free media overnight, then treated with AG1478 for 10 min at 37° C., washed twice in PBS then lysed in 1% Triton and lysates prepared. The lysates were prepared as described in Example 20 herein. Lysate was then assessed for 806 reactivity by an ELISA is a modified version of an assay described by Schooler and Wiley, Analytical Biochemistry 277, 135-142 (2000). Plates were coated with 10 ug/ml of mAb 806 in PBS/EDTA overnight at room temperature and then washed twice. Plates were then blocked with 10% serum albumin/PBS for 2 hours at 37° C. and washed twice. A 1:20 cell lysate was added in 10% serum albumin/PBS for 1 hour at 37° C., then washed four times. Anti-EGFR (SC-03 (Santa Cruz Biotechnology Inc.)) in 10% serum albumin/PBS was reacted 90 min at room temperature, the plate washed four times, and anti-rabbit-HRP (1:2000 if from Silenus) in 10% serum albumin/PBS was added for 90 min at room temperature, washed four timed, and color developed using ABTS as a substrate. It was found that mAb806 binding is significantly increased in the presence of increasing amounts of AG1478 (FIG. 13).

EXAMPLE 12

Immunoreactivity in Human Glioblastomas Pre-Typed for EGFR Status

Given the high incidence of EGFR expression, amplification and mutation in glioblastomas, a detailed immunohistochemical study was performed in order to assess the specificity of 806 in tumors other than xenografts. A panel of 16 glioblastomas was analyzed by immunohistochemistry. This panel of 16 glioblastomas was pre-typed by RT-PCR for the presence of amplified wild-type EGFR and de2-7 EGFR expression. Six of these tumors expressed only the wt EGFR transcript, 10 had wtEGFR gene amplification with 5 of these showing wild-type EGFR transcripts only, and 5 both wild-type EGFR and de2-7 gene transcript. Immunohistochemical analysis was performed using 5 mm sections of fresh frozen tissue applied to histology slides and fixed for 10 minutes in cold acetone. Bound primary antibody was detected with biotylated horse anti-mouse antibody followed by an avidin-biotin-complex reaction. Diaminobenzidine tetrahydrochloride (DAB) was used as chromogen. The extent of the immunohistochemical reactivity in tissues was estimated by light microscopy and graded according to the number of immunoreactive cells in 25% increments as follows:

Focal=less than 5%
+=5-25%
++=25-50%
+++=50-75%
++++=>75%

The 528 antibody showed intense reactivity in all tumors, while DH 8.3 immunostaining was restricted to those tumors expressing the de2-7 EGFR (Table 2). Consistent with the previous observations in FACS and resetting assays, mAb 806 did not react with the glioblastomas expressing the wtEGFR transcript from non-amplified EGFR genes (Table 2). This pattern of reactivity for mAb 806 is similar to that observed in the xenograft studies and again suggests that this antibody recognizes the de2-7 and amplified EGFR but not the wtEGFR when expressed on the cell surface.

TABLE 2

Immunoreactivity of MAbs 528, DH8.3 and 806 on glioblastomas pretyped for the presence of wild type EGFR and mutated de2-7 EGFR and for their amplification status.

| Amplification | de2-7 EGFR Expression | 528 | DH 8.3 | 806 |
|---|---|---|---|---|
|  | No | ++++ | − | − |
|  | No | ++++ | − | −* |
|  | No | ++++ | − | − |
|  | No | ++ | − | − |
|  | No | +++ | − | − |
|  | No | ++++ | − | − |
| Yes | No | ++++ | − | ++++ |
| Yes | No | ++++ | − | + |
| Yes | No | ++++ | − | +++ |
| Yes | No | ++++ | − | ++++ |
| Yes | No | ++++ | − | +−++++ |
| Yes | Yes | ++++ | ++++ | ++++ |
| Yes | Yes | ++++ | ++++ | ++++ |
| Yes | Yes | ++++ | ++++ | ++++ |

TABLE 2-continued

Immunoreactivity of MAbs 528, DH8.3 and 806 on glioblastomas pretyped for the presence of wild type EGFR and mutated de2-7 EGFR and for their amplification status.

| Amplification | de2-7 EGFR Expression | 528 | DH 8.3 | 806 |
|---|---|---|---|---|
| Yes | Yes | ++++ | ++++ | ++++ |
| Yes | Yes | ++++ | ++ | ++ |

*focal staining

EXAMPLE 13

EGFR Immunoreactivity in Normal Tissue

In order to determine if the de2-7 EGFR is expressed in normal tissue, an immunohistochemical study with mAb 806 and DH8.3 was conducted in a panel of 25 tissues. There was no strong immunoreactivity with either mAb 806 or DH8.3 in any tissue tested suggesting that the de2-7 EGFR is absent in normal tissues (Table 3). There was some variable staining present in tonsils with mAb 806 that was restricted to the basal cell layer of the epidermis and mucosal squamous cells of the epithelium. In placenta, occasional immunostaining of the trophoblast epithelium was observed. Interestingly, two tissues that express high endogenous levels of wtEGFR, the liver and skin, failed to show any significant mAb 806 reactivity. No reactivity was observed with the liver samples at all, and only weak and inconsistent focal reactivity was detected occasionally (in no more than 10% of all samples studied) in basal keratinocytes in skin samples and in the squamous epithelium of the tonsil mucosa, further demonstrating that this antibody does not bind the wtEGFR expressed on the surface of cells to any significant extent (Table 3). All tissues were positive for the wtEGFR as evidenced by the universal staining seen with the 528 antibody (Table 3).

TABLE 3

Reactivity of 582, DH8.3 and 806 on normal tissues.

| TISSUE | 528 | DH8-3 | 806 |
|---|---|---|---|
| Esophagus | pos | – | – |
| Stomach | pos | – | – |
| Duodenum | pos | – | – |
| Small intestine/duodenum | pos | – | – |
| Colon | pos | – | – |
| Liver | pos | – | – |
| Salivary glands (parotid) | pos | – | – |
| Kidney | pos | – | – |
| Urinary bladder | pos | – | – |
| Prostate | pos | – | – |
| Testis | pos | – | – |
| Uterus (cx/endom) | pos | –* | – |
| Fallopian tube | pos | – | – |
| Ovary | pos | – | – |
| Breast | pos | –* | – |
| Placenta | pos | – | – |
| Peripheral nerve | pos | – | – |
| Skeletal muscle | pos | – | – |
| Thyroid gland | pos | – | – |
| Lymph node | pos | – | – |
| Spleen | pos | – | – |
| Tonsil | pos | – | – occ. weak reactivity of basal layer of squamous epithelium |
| Heart | pos | – | – |
| Lung | pos | – | – |
| Skin | pos | – | – occ. weak reactivity of basal layer of squamous epithelium |

*some stromal staining in various tissue

EXAMPLE 14

EGFR Immunoreactivity in Various Tumors

The extent of de2-7 EGFR in other tumor types was examined using a panel of 12 different malignancies. The 528 antibody showed often homogeneous staining in many tumors analysed except melanoma and seminoma. When present, DH8.3 immunoreactivity was restricted to the occasional focal tumor cell indicating there is little if any de2-7 EGFR expression in tumors outside the brain using this detection system (Table 4). There was also focal staining of blood vessels and a varying diffuse staining of connective tissue with the DH8.3 antibody in some tumors (Table 4). This staining was strongly dependent on antibody concentration used and was considered nonspecific background reactivity. The mAb 806 showed positive staining in 64% of head and neck tumors and 50% of lung carcinomas (Table 4). There was little mAb 806 reactivity elsewhere except in urinary tumors that were positive in 30% of cases. Since the head and neck and lung cancers were negative for the DH8.3 antibody the reactivity seen with the mAb in these tumors maybe associated with EGFR gene amplification.

TABLE 4

Monoclonal antibodies 528, DH8.3 and 806 on tumor panel.

| Tumor | 528 | DH8.3 | 806 |
|---|---|---|---|
| Malignant melanoma metastases | 0/10 | 0/10 | 0/10 |
| Urinary bladder (tcc, sqcc, adeno) | 10/10 (7x++++, 2x+++, 1x+) | 0/10* | 3/10* (2x++++, 1x++) |
| Mammary gland | 6/10 (3x++++, 3x++) | 1/10 (1x+) | 1/10 (foc) |
| Head + neck cancer (sqcc) | 11/11 1x+++-10x++++) | 0/11* | 7/11 (3x++++, 3x+++, 1x+) |
| Lung (sqcc, adeno, neuroend) | 12/12 10x++++-1x+++) | 0/12* | 6/12 (3x++++ 3x+++) |

TABLE 4-continued

Monoclonal antibodies 528, DH8.3 and 806 on tumor panel.

| Tumor | 528 | DH8.3 | 806 |
|---|---|---|---|
| Leiomyosarcoma | 5/5 (4x++++, 1x+) | 0/5 | 0/5 |
| Liposarcoma | 5/5 (2x + 3x+++) | 0/5 | 0/5* |
| Synovial sarcoma | 4/5* (4x++++) | 0/5 | 0/5* |
| Mfh Malignant fibrous histiocytoma | 4/5* | 0/5* | 0/5* |
| Colonic carcinoma | 10/10 (9x++++, 1x+) | 0/10* | 0/10 |
| Seminoma | 1/10* | 1/10* | 0/10 |
| Ovary (serous-papillary) | 4/5 (3x++++, 1x+) | 0/5* | 0/5 |

*focal staining

EXAMPLE 15

Immunoreactivity in Human Glioblastomas Unselected for EGFR Status

In order to confirm the unique specificity and to evaluate the reactivity of mAb 806, it was compared to the 528 and DH8.3 antibodies in a panel of 46 glioblastomas not preselected for their EGFR status. The 528 antibody was strongly and homogeneously positive in all samples except two (No. 27 and 29) (44/46, 95.7%). These two cases were also negative for mAb806 and mAb DH8.3. The mAb 806 was positive in 27/46 (58.7%) cases, 22 of which displayed homogeneous immunoreactivity in more than 50% of the tumor. The DH8.3 antibody was positive in 15/46 (32.6%) glioblastomas, 9 of which showed homogeneous immunoreactivity. The immunochemical staining of these unselected tumors is tabulated in Table 5.

There was concordance between mAb 806 and DH8.3 in every case except one (No. 35).

A molecular analysis for the presence of EGFR amplification was done in 44 cases (Table 5). Of these, 30 cases co-typed with the previously established mAb 806 immunoreactivity pattern: e.g. 16 mAb 806-negative cases revealed no EGFR amplification and 14 EGFR-amplified cases were also mAb 806 immunopositive. However, 13 cases, which showed 806 immunoreactivity, were negative for EGFR amplification while 1 EGFR-amplified case was mAb 806 negative. Further analysis of the mutation status of these amplification negative and 806 positive cases is described below and provides explanation for most of the 13 cases which were negative for EGFR amplification and were recognized by 806.

Subsequently, a molecular analysis of the deletion mutation by RT-PCR was performed on 41/46 cases (Table 5). Of these, 34 cases co-typed with DH8.3 specific for the deletion mutation: 12 cases were positive in both RT-PCR and immunohistochemistry and 22 cases were negative/negative. Three cases (#2, #34, #40) were DH8.3 positive/RT-PCR negative for the deletion mutation and three cases (#12, #18, #39) were DH8.3 negative/RT-PCR positive. As expected based on our previous specificity analysis, mAb 806 immunoreactivity was seen in all DH8.3-positive tissues except in one case (#35).

Case #3 also revealed a mutation (designated A2 in Table 5), which included the sequences of the de2-7 mutation but this did not appear to be the classical de2-7 deletion with loss of the 801 bases (data not shown). This case was negative for DH8.3 reactivity but showed reactivity with 806, indicating that 806 may recognize an additional and possibly unique EGFR mutation.

TABLE 5

Immunohistochemical analysis of 46 unselected glioblastomas with mAbs 528, 806, and DH8.3

| # | 528 | 806 | DH8.3 | EGFR Amp.* | 5' MUT |
|---|---|---|---|---|---|
| 1 | ++++ | ++++ | ++ | A | 5' MUT |
| 2 | ++++ | ++++ | ++++ | N | WT |
| 3 | ++++ | ++++ (det.) | neg. | N | A2 |
| 4 | ++++ | ++++ | neg. | N | WT |
| 5 | ++++ | ++++ | ++++ | N | 5' MUT |
| 6 | ++++ | ++++ | neg. | A | WT |
| 7 | ++++ | ++++ | ++++ | N | 5' MUT |
| 8 | ++++ | ++++ | ++++ | A | 5' MUT |
| 9 | ++++ | ++++ | neg. | A | WT |
| 10 | ++++ | neg. | neg. | N | WT |
| 11 | ++ | ++ | ++ | A | 5' MUT |
| 12 | ++++ | ++ | neg. | A | 5' MUT |
| 13 | ++++ | ++++ | neg | N | WT |
| 14 | ++ | neg. | neg. | Nd | nd |
| 15 | ++ | ++ | neg | N | WT |
| 16 | + | neg. | neg. | N | nd |
| 17 | ++++ | neg. | neg. | N | WT |
| 18 | ++++ | ++++ | neg. | A | 5' MUT |
| 19 | ++++ | ++++ | neg. | N | WT |
| 20 | ++++ | neg. | neg | N | WT |
| 21 | ++++ | ++++ | neg. | N | WT |
| 22 | +++ | neg. | neg. | N | WT |
| 23 | ++++ | ++++ | ++ | N | 5' MUT |
| 24 | ++++ | ++++ | neg. | A | WT |
| 25 | ++++ | neg. | neg. | N | WT |
| 26 | ++++ | ++++ | +++ | A | 5' MUT |
| 27 | neg. | neg. | neg. | N | WT |
| 28 | +++ | neg. | neg. | N | WT |
| 29 | neg. | neg. | neg. | N | WT |
| 30 | ++++ | ++++ | neg. | N | WT |
| 31 | ++++ par det | neg. | neg. | N | nd |
| 32 | ++ | ++ | ++ | N | 5' MUT |
| 33 | +++ | ++++ | ++++ | A | 5' MUT |
| 34 | ++++ | +++ | ++++ | N | WT |
| 35 | ++++ | neg. | ++++ | A | 5' MUT |
| 36 | +++ | ++ | +++ | A | 5' MUT |
| 37 | ++++ | + | + | A | 5' MUT |
| 38 | ++++ | neg. | neg. | N | WT |
| 39 | ++ | neg. | neg. | N | 5' MUT |
| 40 | ++++ | ++++ | + | A | WT |
| 41 | ++ | neg. | neg. | N | WT |
| 42 | ++++ | ++++ | neg. | A | WT |
| 43 | ++++ | neg. | neg. | nd | nd |

TABLE 5-continued

Immunohistochemical analysis of 46 unselected glioblastomas with mAbs 528, 806, and DH8.3

| # | 528 | 806 | DH8.3 | EGFR Amp.* | 5' MUT |
|---|-----|-----|-------|------------|--------|
| 44 | ++++ | neg. | neg. | N | WT |
| 45 | ++++ | neg. | neg. | N | WT |
| 46 | ++++ | neg. | neg. | N | nd |

*N = not amplified, A-amplified,
+WT = wildtype, 5'-mut
nd = not done

The 806 antibody reactivity co-typed with amplified or de2-7 mutant EGFR in 19/27 or over 70% of the cases. It is notable that 2 of these 8 cases were also DH8.3 reactive.

EXAMPLE 16

Systemic Treatment and Analysis of Intracranial Glioma Tumors

To test the efficacy of the anti-ΔEGFR monoclonal antibody, mAb 806, we treated nude mice bearing intracranial ΔEGFR-overexpressing glioma xenografts with intraperitoneal injections of mAb806, the isotype control IgG or PBS.

The human glioblastoma cell lines U87MG, LN-Z308 and A1207 (gift from Dr. S. Aaronson, Mount Sinai Medical Center, New York, N.Y.) were infected with ΔEGFR, kinase-deficient ΔEGFR (DK), or wild-type EGFR (wtEGFR) viruses. Populations expressing similar high levels of EGFRs were selected by fluorescence-activated cell sorting and designated as U87MG.ΔEGFR, U87MG.DK, U87MG.wtEGFR, LN-Z308.ΔEGFR, LN-Z308.DK, LN-Z308. wtEGFR, A1207.ΔEGFR, A1207.DK and A1207.wtEGFR, respectively. Each was maintained in medium containing G418 (U87MG cell lines, 400 µg/ml; LN-Z308 and A1207 cell lines, 800 µg/ml).

U87MG.ΔEGFR cells were implanted intracranially into nude mice and the treatments began on the same day. $10^5$ cells in 51 µl PBS were implanted into the right corpus striatum of nude mice brains. Systemic therapy with mAb 806, or the IgG2b isotype control, was accomplished by i.p. injection of 1 mg of mAbs in a volume of 100 µl every other day from post-implantation day 0 through 14. For direct therapy of intracerebral U87MG.ΔEGFR tumors, 10 µg of mAb 806, or the IgG2b isotype control, in a volume of 5 µl were injected at the tumor-injection site every other day starting at day 1 for 5 days.

Animals treated with PBS or isotype control IgG had a median survival of 13 days, whereas mice treated with mAb 806 had a 61.5% increase in median survival up to 21 days (P<0.001).

Treatment of mice 3 days post-implantation, following tumor establishment, also extended the median survival of the mAb 806 treated animals by 46.1% (from 13 days to 19 days; P<0.01) compared to that of the control groups.

To determine whether these antitumor effects of mAb 806 extended beyond U87MG.ΔEGFR xenografts, similar treatments were administered to animals bearing other glioma cell xenografts of LN-Z308.ΔEGFR and A 1207.ΔEGFR. The median survival of mAb 806 treated mice bearing LN-Z308.ΔEGFR xenografts was extended from 19 days for controls to 58 days (P<0.001). Remarkably, four of eight mAb 806 treated animals survived beyond 60 days. The median survival of animals bearing A1207.ΔEGFR xenografts was also extended from 24 days for controls to 29 days (P<0.01).

MAb 806 Treatment Inhibits ΔEGFR-overexpressing Brain Tumor Growth.

Mice bearing U87MG.ΔEGFR and LN-Z308.ΔEGFR xenografts were euthanized at day 9 and day 15, respectively. Tumor sections were histopathologically analyzed and tumor volumes were determined. Consistent with the results observed for animal survival, mAb 806 treatment significantly reduced the volumes by about 90% of U87MG.ΔEGFR. (P<0.001) and LN-Z308.ΔEGFR by more than 95% (P<0.001) xenografts in comparison to that of the control groups. Similar results were obtained for animals bearing A1207.ΔEGFR tumors (65% volume reduction, P<0.01).

Intratumoral Treatment with mAb 806 Extends Survival of Mice Bearing U87MG.ΔEGFR Brain Tumors.

The efficacy of direct intratumoral injection of mAb 806 for the treatment of U87MG.ΔEGFR xenografts was also determined. Animals were given intratumoral injections of mAb 806 or isotype control IgG one day post-implantation. Control animals survived for 15 days, whereas mAb 806 treated mice remained alive for 18 days (P<0.01). While the intratumoral treatment with mAb 806 was somewhat effective, it entailed the difficulties of multiple intracranial injections and increased risk of infection. We therefore focused on systemic treatments for further studies.

MAb 806 Treatment Slightly Extends Survival of Mice Bearing U87MG.wtEGFR but not U87MG or U87MG.DK Intracranial Xenografts.

To determine whether the growth inhibition by mAb 806 was selective for tumors expressing ΔEGFR, we treated animals bearing U87MG, U87MG.DK (kinase-deficient ΔEGFR) and U87MG.wtEGFR brain xenografts. MAb 806 treatment did not extend survival of mice implanted with U87MG tumors which expressed a low level of endogenous wild-type EGFR (wtEGFR), or animals bearing U87MG.DK xenografts which overexpressed a kinase-deficient ΔEGFR in addition to a low level of endogenous wtEGFR. The mAb 806 treatment slightly extended the survival of mice bearing U87MG.wtEGFR tumors (P<0.05, median survival 23 days versus 26 days for the control groups) which overexpressed wtEGFR MAb 806 Reactivity Correlates with In Vivo Anti-Tumor Efficacy.

To understand the differential effect of mAb 806 on tumors expressing various levels or different types of EGFR, we determined mAb 806 reactivity with various tumor cells by FACS analysis. Consistent with previous reports, the anti-EGFR monoclonal antibody 528 recognized both ΔEGFR and wtEGFR, and demonstrated stronger staining for U87MG.ΔEGFR cells compared to U87MG cells. In contrast, antibody EGFR. 1 reacted with wtEGFR but not ΔEGFR, as U87MG.ΔEGFR cells were as weakly reactive as U87MG cells. This EGFR.1 antibody reacted with U87MG.wtEGFR more intensively than U87MG cells, as U87MG.wtEGFR cells overexpressed wtEGFR. While mAb 806 reacted intensely with U87MG.ΔEGFR and U87MG.DK cells and not with U87MG cells, it reacted weakly with U87MG.wtEGFR, indicating that mAb 806 is selective for ΔEGFR with a weak cross-activity to overexpressed wtEGFR. This level of reactivity with U87MG.wtEGFR was quantitatively and qualitatively similar to the extension of survival mediated by the antibody treatment.

We further determined mAb 806 specificity by immunoprecipitation. EGFRs in various cell lines were immunoprecipitated with antibody 528, EGFR.1 and mAb 806. Blots of electrophoretically-separated proteins were then probed with the anti-EGFR antibody, C13, which recognizes wtEGFR as well as ΔEGFR and DK. Consistent with the FACS analysis antibody 528 recognized wtEGFR and mutant receptors, while antibody EGFR.1 reacted with wtEGFR but not the mutant species. Moreover, the levels of mutant receptors in U87MG.ΔEGFR and U87MG.DK cells are comparable to those of wtEGFR in the U87MG.wtEGFR cells. However, antibody mAb 806 was able to precipitate only a small amount of the wtEGFR from the U87MG.wtEGFR cell lysates as compared with the larger amount of mutant receptor precipitated from U87MG.ΔEGFR and U87MG.DK cells, and an undetectable amount from the U87MG cells. Collectively, these data suggest that mAb 806 recognizes an epitope in ΔEGFR which also exists in a small fraction of wtEGFR only when it is overexpressed on cell surface.

MAb 806 Treatment Reduces ΔEGFR Autophosphorylation and Down-Regulates Bcl.$X_L$ Expression in U87MG.ΔEGFR Brain Tumors.

We next investigated the mechanisms underlying the growth inhibition by mAb 806. Since the constitutively active kinase activity and autophosphorylation of the carboxyl terminus of ΔEGFR are essential for its biological functions we determined ΔEGFR phosphorylation status in tumors from treated and control animals. It was found that mAb 806 treatment dramatically reduced ΔEGFR autophosphorylation, even though receptor levels were only slightly decreased in the mAb 806 treated xenografts. We have previously shown that receptor autophosphorylation causes up-regulation of the antiapoptotic gene, Bcl-$X_L$, which plays a key role in reducing apoptosis of ΔEGFR overexpressing tumors. Therefore, we next determined the effect of mAb 806 treatment on Bcl-$X_L$, expression. ΔEGFR tumors from mAb 806 treated animals did indeed show reduced levels of Bcl-$X_L$.

MAb 806 Treatment Decreases Growth and Angiogenesis, and Increases Apoptosis in U87MG.ΔEGFR Tumors.

In light of the in vivo suppression caused by mAb 806 treatment and its biochemical effects on receptor signaling, we determined the proliferation rate of tumors from control or treated mice. The proliferative index, measured by Ki-67 staining of the mAb 806-treated tumors, was significantly lower than that of the control tumors (P<0.001). In addition, analysis of the apoptotic index through TUNEL staining demonstrated a significant increase in the number of apoptotic cells in mAb 806 treated tumors as compared with the control tumors (P<0.001). The extent of tumor vascularization was also analyzed by immunostaining of tumors from treated and control specimens for CD31. To quantify tumor vascularization, microvascular areas (MVA) were measured using computerized image analysis. MAb 806 treated tumors showed 30% less MVA than control tumors (P<0.001). To understand whether interaction between receptor and antibody may elicit an inflammatory response, we stained tumor sections for the macrophage marker, F4/80, and the NK cell marker, asialo GM1. Macrophages were identified throughout the tumor matrix and especially accumulated around the mAb 806 treated-U87MG.ΔEGFR tumor periphery. We observed a few NK cells infiltrated in and around the tumors and no significant difference between mAb 806 treated and isotype-control tumors.

EXAMPLE 17

Combination Immunotherapy with mAb806 and mAb528

The experiments set forth herein describe in vivo work designed to determine the efficacy of antibodies in accordance with this invention.

Female nude mice, 4-6 weeks old, were used as the experimental animals. Mice received subcutaneous inoculations of $3 \times 10^6$ tumor cells in each of their flanks.

The animals received either U87MG.D2-7, U87MG.DK, or A431 cells, all of which are described, supra. Therapy began when tumors had grown to a sufficient size.

Mice then received injections of one of (i) phosphate buffered saline, (ii) mAb 806 (0.5 mg/injection), (iii) mAb 528 (0.5 mg/injection), or (iv) a combination of both mAbs. With respect to "(iv)," different groups of mice received either 0.5 mg/injection of each mAb, or 0.25 mg/injection of each mAb.

The first group of mice examined were those which had received U87MG.D2-7 injections. The treatment protocol began 9 days after inoculation, and continued, 3 times per week for 2 weeks (i.e., the animals were inoculated 9, 11, 13, 16, 18 and 20 days after they were injected with the cells). At the start of the treatment protocol, the average tumor diameter was 115 mm$^3$. Each group contained 50 mice, each with two tumors.

Figure 18B:
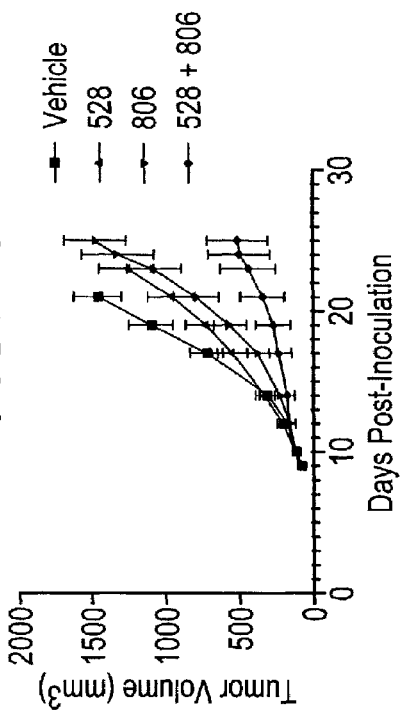
FIGS. 18A-18D shows the results of in vivo studies designed to determine the therapeutic effect of combination antibody therapy, particularly mAb806 and the 528 antibody. Mice received inoculations of U87MG.D2-7 (A and B), U87MG.DK (C), or A431 (D) cells.

Within the group of mice which received the combination of antibodies (0.5 mg/injection of each), there were three complete regressions. There were no regressions in any of the other groups. FIG. 18A shows the results graphically.

In a second group of mice, the injected materials were the same, except the combination therapy contained 0.25 mg of each antibody per injection. The injections were given 10, 12, 14, 17, 19 and 21 days after inoculation with the cells. At the start of the therapy the average tumor size was 114 mm$^3$. Results are shown in FIG. 18B.

The third group of mice received inoculations of U87MG.DK. Therapeutic injections started 18 days after inoculation with the cells, and continued on days 20, 22, 25, 27 and 29. The average tumor size at the start of the treatment was 107 mm$^3$. FIG. 18C summarizes the results. The therapeutic injections were the same as in the first group.

Finally, the fourth group of mice, which had been inoculated with A431 cells, received injections as in groups I and III, at 8, 10, 12 and 14 days after inoculation. At the start, the average tumor size was 71 mm$^3$. Results are shown in FIG. 18D.

The results indicated that the combination antibody therapy showed a synergistic effect in reducing tumors. See FIG. 18A. A similar effect was seen at a lower dose, as per FIG. 18B, indicating that the effect is not simply due to dosing levels.

The combination therapy did not inhibit the growth of U87MG.DK (FIG. 18C), indicating that antibody immune function was not the cause for the decrease seen in FIGS. 18A and 18B.

Figure 18D:
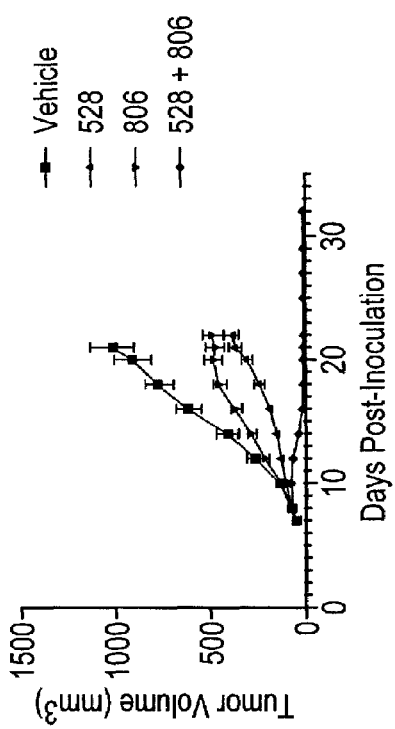
Figure 18A:
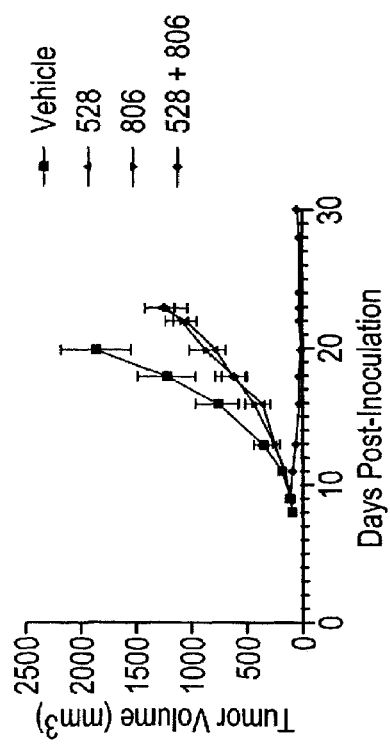
Figure 18C:
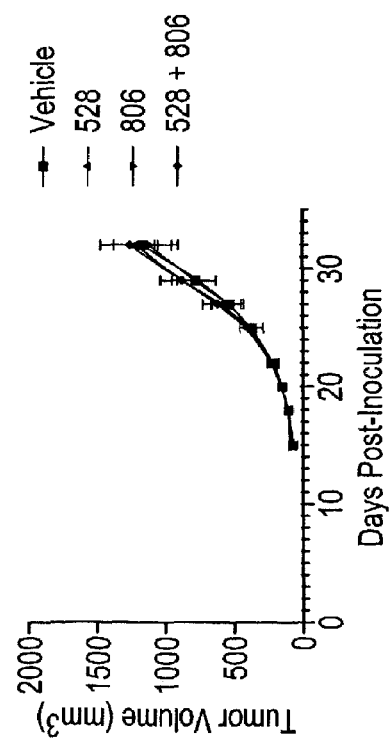

It is noted that, as shown in FIG. 18D, the combination therapy also exhibited synergistic efficacy on A431 tumors, with 4 doses leading to a 60% complete response rate. These data suggest that the EGFR molecule recognized by mAb806 is functionally different from that inhibited by 528.

REFERENCES

1. Wikstrand, C. J., McLendon, R. E., Friedman, A. H., and Bigner, D. D. Cell surface localization and density of the tumor-associated variant of the epidermal growth factor receptor, EGFRvIII, Cancer Res. 57: 4130-40, 1997.
2. Olapade-Olaopa, E. O., Moscatello, D. K., MacKay, E. H., Horsburgh, T., Sandhu, D. P., Terry, T. R., Wong, A. J., and Habib, F. K. Evidence for the differential expression of a variant EGF receptor protein in human prostate cancer, Br J Cancer. 82: 186-94, 2000.
3. Wikstrand, C. J., Hale, L. P., Batra, S. K., Hill, M. L., Humphrey, P. A., Kurpad, S. N., McLendon, R. E., Moscatello, D., Pegram, C. N., Reist, C. J., and et al. Monoclonal antibodies against EGFRvIII are tumor specific and react with breast and lung carcinomas and malignant gliomas, Cancer Res. 55: 3140-8, 1995.
4. Garcia de Palazzo, I. E., Adams, G. P., Sundareshan, P., Wong, A. J., Testa, J. R., Bigner, D. D., and Weiner, L. M. Expression of mutated epidermal growth factor receptor by non-small cell lung carcinomas, Cancer Res. 53: 3217-20, 1993.
5. Ekstrand, A. J., Sugawa, N., James, C. D., and Collins, V. P. Amplified and rearranged epidermal growth factor receptor genes in human glioblastomas reveal deletions of sequences encoding portions of the N- and/or C-terminal tails, Proc Natl Acad Sci USA. 89: 4309-13, 1992.
6. Wong, A. J., Ruppert, J. M., Bigner, S. H., Grzeschik, C. H., Humphrey, P. A., Bigner, D. S., and Vogelstein, B. Structural alterations of the epidermal growth factor receptor gene in human gliomas, Proc Natl Acad Sci USA. 89: 2965-9, 1992.
7. Yamazaki, H., Ohba, Y., Tamaoki, N., and Shibuya, M. A deletion mutation within the ligand binding domain is responsible for activation of epidermal growth factor receptor gene in human brain tumors, Jpn J Cancer Res. 81: 773-9, 1990.
8. Yamazaki, H., Fukui, Y., Ueyama, Y., Tamaoki, N., Kawamoto, T., Taniguchi, S., and Shibuya, M. Amplification of the structurally and functionally altered epidermal growth factor receptor gene (c-erbB) in human brain tumors, Mol Cell Biol. 8: 1816-20, 1988.
9. Sugawa, N., Ekstrand, A. J., James, C. D., and Collins, V. P. Identical splicing of aberrant epidermal growth factor receptor transcripts from amplified rearranged genes in human glioblastomas, Proc Natl Acad Sci USA. 87: 8602-6, 1990.
10. Nishikawa, R., Ji, X. D., Harmon, R. C., Lazar, C. S., Gill, G. N., Cavenee, W. K., and Huang, H. J. A mutant epidermal growth factor receptor common in human glioma confers enhanced tumorigenicity, Proc Natl Acad Sci USA. 91: 7727-31, 1994.
11. Batra, S. K., Castelino-Prabhu, S., Wikstrand, C. J., Zhu, X., Humphrey, P. A., Friedman, H. S., and Bigner, D. D. Epidermal growth factor ligand-independent, unregulated, cell-transforming potential of a naturally occurring human mutant EGFRvIII gene, Cell Growth Differ. 6: 1251-9, 1995.
12. Nagane, M., Coufal, F., Lin, H., Bogler, O., Cavenee, W. K., and Huang, H. J. A common mutant epidermal growth factor receptor confers enhanced tumorigenicity on human glioblastoma cells by increasing proliferation and reducing apoptosis, Cancer Res. 56: 5079-86, 1996.
13. Wikstrand, C. J., Reist, C. J., Archer, G. E., Zalutsky, M. R., and Bigner, D. D. The class III variant of the epidermal growth factor receptor (EGFRvIII): characterization and utilization as an immunotherapeutic target, J Neurovirol. 4: 148-58, 1998.
14. Humphrey, P. A., Wong, A. J., Vogelstein, B., Zalutsky, M. R., Fuller, G. N., Archer, G. E., Friedman, H. S., Kwatra, M. M., Bigner, S. H., and Bigner, D. D. Anti-synthetic peptide antibody reacting at the fusion junction of deletion-mutant epidermal growth factor receptors in human glioblastoma, Proc Natl Acad Sci USA. 87: 4207-11, 1990.
15. Okamoto, S., Yoshikawa, K., Obata, Y., Shibuya, M., Aoki, S., Yoshida, J., and Takahashi, T. Monoclonal antibody against the fusion junction of a deletion-mutant epidermal growth factor receptor, Br J Cancer. 73: 1366-72, 1996.
16. Hills, D., Rowlinson-Busza, G., and Gullick, W. J. Specific targeting of a mutant, activated EGF receptor found in glioblastoma using a monoclonal antibody, Int J Cancer. 63: 537-43, 1995.
17. Moscatello, D. K., Holgado-Madruga, M., Godwin, A. K., Ramirez, G., Gunn, G., Zoltick, P. W., Biegel, J. A., Hayes, R. L., and Wong, A. J. Frequent expression of a mutant epidermal growth factor receptor in multiple human tumors, Cancer Res. 55: 5536-9, 1995.
18. Baselga, J., Pfister, D., Cooper, M. R., Cohen, R., Burtness, B., Bos, M., D'Andrea, G., Seidman, A., Norton, L., Gunnett, K., Falcey, J., Anderson, V., Waksal, H., and Mendelsohn, J. Phase I Studies of Anti-Epidermal Growth Factor Receptor Chimeric Antibody C225 Alone and in Combination With Cisplatin, J Clin Oncol. 18: 904, 2000.
19. Faillot, T., Magdelenat, H., Mady, E., Stasiecki, P., Fohanno, D., Gropp, P., Poisson, M., and Delattre, J. Y. A phase I study of an anti-epidermal growth factor receptor monoclonal antibody for the treatment of malignant gliomas, Neurosurgery. 39: 478-83, 1996.
20. Ponten, J. and Macintyre, E. H. Long term culture of normal and neoplastic human glia, Acta Pathol Microbiol Scand. 74: 465-86, 1968.
21. Masui, H., Kawamoto, T., Sato, J. D., Wolf, B., Sato, G., and Mendelsohn, J. Growth inhibition of human tumor cells in athymic mice by anti-epidermal growth factor receptor monoclonal antibodies, Cancer Res. 44: 1002-7, 1984.
22. Domagala, T., Konstantopoulos, N., Smyth, F., Jorissen, R. N., Fabri, L., Geleick, D., Lax, I., Schlessinger, J., Sawyer, W., Howlett, G. J., Burgess, A. W., and Nice, E. C. Stoichiometry, kinetic and binding analysis of the interaction between Epidermal Growth Factor (EGF) and the Extracellular Domain of the EGF receptor., Growth Factors. 18: 11-29, 2000.
23. Lindmo, T., Boven, E., Cuttitta, F., Fedorko, J., and Bunn, P. A., Jr. Determination of the immunoreactive fraction of radiolabeled monoclonal antibodies by linear extrapolation to binding at infinite antigen excess, J Immunol Methods. 72: 77-89, 1984.
24. Huang, H. S., Nagane, M., Klingbeil, C. K., Lin, H., Nishikawa, R., Ji, X. D., Huang, C. M., Gill, G. N., Wiley, H. S., and Cavenee, W. K. The enhanced tumorigenic activity of a mutant epidermal growth factor receptor common in human cancers is mediated by threshold levels of constitutive tyrosine phosphorylation and unattenuated signaling, J Biol Chem. 272: 2927-35, 1997.
25. Reist, C. J., Archer, G. E., Wikstrand, C. J., Bigner, D. D., and Zalutsky, M. R. Improved targeting of an anti-epidermal growth factor receptor variant III monoclonal antibody in tumor xenografts after labeling using N-succinimidyl 5-iodo-3-pyridinecarboxylate, Cancer Res. 57: 1510-5, 1997.

26. Santon, J. B., Cronin, M. T., MacLeod, C. L., Mendelsohn, J., Masui, H., and Gill, G. N. Effects of epidermal growth factor receptor concentration on tumorigenicity of A431 cells in nude mice, Cancer Res. 46: 4701-5, 1986.
27. Voldborg, B. R., Damstrup, L., Spang-Thomsen, M., and Poulsen, H. S. Epidermal growth factor receptor (EGFR) and EGFR mutations, function and possible role in clinical trials, Ann Oncol. 8: 1197-206, 1997.
28. den Eynde, B. and Scott, A. M. Tumor Antigens. In: P. J. Delves and I. M. Roitt (eds.), Encyclopedia of Immunology, Second Edition edition, pp. 2424-31. London: Academic Press, 1998.
29. Seymour, L. Novel anti-cancer agents in development: exciting prospects and new challenges, Cancer Treat Rev. 25: 301-12, 1999.
30. Sturgis, E. M., Sacks, P. G., Masui, H., Mendelsohn, J., and Schantz, S. P. Effects of antiepidermal growth factor receptor antibody 528 on the proliferation and differentiation of head and neck cancer, Otolaryngol Head Neck Surg. 111: 633-43, 1994.
31. Goldstein, N. I., Prewett, M., Zuklys, K., Rockwell, P., and Mendelsohn, J. Biological efficacy of a chimeric antibody to the epidermal growth factor receptor in a human tumor xenograft model, Clin Cancer Res. 1: 1311-8, 1995.
32. Reist, C. J., Archer, G. E., Kurpad, S, N., Wikstrand, C. J., Vaidyanathan, G., Willingham, M. C., Moscatello, D. K., Wong, A. J., Bigner, D. D., and Zalutsky, M. R. Tumor-specific anti-epidermal growth factor receptor variant III monoclonal antibodies: use of the tyramine-cellobiose radioiodination method enhances cellular retention and uptake in tumor xenografts, Cancer Res. 55: 4375-82, 1995.
33. Reist, C. J., Garg, P. K., Alston, K. L., Bigner, D. D., and Zalutsky, M. R. Radioiodination of internalizing monoclonal antibodies using N-succinimidyl 5-iodo-3-pyridinecarboxylate, Cancer Res. 56: 4970-7, 1996.
34. Press, O. W., DeSantes, K., Anderson, S. K., and Geissler, F. Inhibition of catabolism of radiolabeled antibodies by tumor cells using lysosomotropic amines and carboxylic ionophores, Cancer Res. 50: 1243-50, 1990.
35. Reist, C. J., Batra, S. K., Pegram, C. N., Bigner, D. D., and Zalutsky, M. R. In vitro and in vivo behavior of radiolabeled chimeric anti-EGFRvIII monoclonal antibody: comparison with its murine parent, Nucl Med Biol. 24: 639-47, 1997.
36. Mineo, C., Gill, G. N., and Anderson, R. G. Regulated migration of epidermal growth factor receptor from caveolae, J Biol Chem. 274: 30636-43, 1999.
37. Gunther, N., Betzel, C., and Weber, W. The secreted form of the epidermal growth factor receptor. Characterization and crystallization of the receptor-ligand complex, J Biol Chem. 265: 22082-5, 1990.

EXAMPLE 18

Novel Monoclonal Antibody Specific for the De2-7 Epidermal Growth Factor Receptor (EGFR) that Also Recognizes the EGFR Expressed in Cells Containing Amplification of the EGFR Gene The following experiments were presented in Johns et al, (2002) Int. J. Cancer, 98, and in co-pending application Ser. No. 60/342,258 filed Dec. 21, 2001, the entire disclosure of both of which are incorporated herein by reference with cross referencing to the Figures herein where appropriate. The monoclonal antibody mAb 806 was studied and additional data respecting its binding characteristics as to the EGF receptor were developed, which is in addition to and corroborative of the data presented earlier herein. Accordingly, the following represents a review and presentation of the material set forth in the patent application and corresponding publication.

Monoclonal antibody (MAb 806) potentially overcomes the difficulties associated with targeting the EGFR expressed on the surface of tumor cells. MAb 806 bound to de2-7 EGFR transfected U87MG glioma cells (U87MG.Δ2-7) with high affinity ($\sim 1\times 10^9$ $M^{-1}$), but did not bind parental cells that express the wild type EGFR. Consistent with this observation, MAb 806 was unable to bind a soluble version of the wild type EGFR containing the extracellular domain. In contrast, immobilization of this extracellular domain to ELISA plates induced saturating and dose response binding of MAb 806, suggesting that MAb 806 can bind the wild type EGFR under certain conditions. MAb 806 also bound to the surface of A431 cells, which due to an amplification of the EGFR gene express large amounts of the EGFR. Interestingly, MAb 806 only recognized 10% of the total EGFR molecules expressed by A431 cells and the binding affinity was lower than that determined for the de2-7 EGFR. MAb 806 specifically targeted U87MG.Δ2-7 and A431 xenografts grown in nude mice with peak levels in U87MG.Δ2-7 xenografts detected 8 h after injection. No specific targeting of parental U87MG xenografts was observed. Following binding to U87MG.Δ2-7 cells, MAb 806 was rapidly internalized by macropinocytosis and subsequently transported to lysosomes, a process that probably contributes to the early targeting peak observed in the xenografts. Thus, MAb 806 can be used to target tumor cells containing amplification of the EGFR gene or de2-7 EGFR but does not bind to the wild type EGFR when expressed on the cell surface.

As discussed above, MAb 806 is specific for the de2-7 EGFR yet binds to an epitope distinct from the unique junctional peptide. Interestingly, while MAb 806 did not recognize the wild type EGFR expressed on the cell surface of glioma cells, it did bind to the extracellular domain of the wild type EGFR immobilized on the surface of ELISA plates. Furthermore, MAb 806 bound to the surface of A431 cells, which have an amplification of the EGFR gene but do not express the de2-7 EGFR. Therefore, it is possible that MAb 806 could be used to specifically target tumors with amplified EGFR regardless of their de2-7 EGFR status, although our results suggest tumors coexpressing the mutated receptor would still show preferential targeting. As MAb 806 does not bind wild type receptor in the absence of gene amplification, there would be no uptake in normal tissue, a potential problem associated with EGFR antibodies currently being developed.[18,19]

Material and Methods

MAbs and Cell Lines

The U87MG astrocytoma cell line has been described in detail previously.[20] This cell line was infected with a retrovirus containing the de2-7 EGFR to produce the U87MG.Δ2-7 cell line.10 Human squamous carcinoma A431 cells were obtained from ATCC (Rockville, Md.). These cell lines were cultured in DMEM/F-12 with GlutaMAX™ (Life Technologies, Melbourne, Australia) supplemented with 10% FCS (CSL, Melbourne, Australia). The murine pro-B cell line BaF/3, which does not express any known EGFR related molecules, was transfected with de2-7 EGFR as described above. The DH8.3 antibody (IgG1) has been described previously and was obtained following immunization of mice with the unique junctional peptide found in de2-7 EGFR.[16] MAb 806 (IgG2b) was produced following immunization of mice with NR6 mouse fibroblasts transfected with the de2-7 EGFR. It was selected for further characterization as hemagglutination assays showed a high titer against NR6.ΔEGFR cells but low backgrounds on NR6.wtEGFR cells. The 528 antibody, which recognizes both de2-7 and wild type EGFR, has been described previously 1 and was produced in the Biological Production Facility (Ludwig Institute for Cancer Research, Melbourne) using a hybridoma obtained from ATCC. The polyclonal antibody sc-03 directed to the COOH-terminal domain of the EGFR was purchased from Santa Cruz Biotechnology (Santa Cruz, Calif.).

Other Reagents

The recombinant extracellular domain (amino acids 1-621) of the wild type EGFR (sEGFR) was produced as previously described[22]. The biotinylated unique junctional peptide (Biotin-LEEKKGNYVVTDH) (SEQ ID NO:5) from de2-7 EGFR was synthesized by standard Fmoc chemistry and purity (>96%) determined by re-verse phase HPLC and mass spectral analysis (Auspep, Melbourne, Australia).

FACS Analysis

Cells were labeled with the relevant antibody (10 μg/ml) followed by fluorescein-conjugated goat anti-mouse IgG (1:100 dilution; Calbiochem, San Diego, Calif.). FACS data was obtained on a Coulter Epics Elite™ ESP by observing a minimum of 5,000 events and analyzed using EXPO (version 2) for Windows.

ELISA Assays

Two types of ELISA were used to determine the specificity of the antibodies. In the first assay, plates were coated with Segfr (10 μg/ml in 0.1 M carbonate buffer pH 9.2) for 2 hr and then blocked with 2% human serum albumin (HSA) in PBS. Antibodies were added to wells in triplicate at increasing concentration in 2% HSA in phosphate-buffered saline (PBS). Bound antibody was detected by horseradish peroxidase conjugated sheep anti-mouse IgG (Silenus, Melbourne, Australia) using ABTS (Sigma, Sydney, Australia) as a substrate and the absorbance measured at 405 nm. In the second assay, the biotinylated de2-7 specific peptide was bound to ELISA plates precoated with streptavidin (Pierce, Rock-ford, Ill.). Antibodies were bound and detected as in the first assay.

Scatchard Analysis

Antibodies were labeled with $^{125}$I (Amrad, Melbourne, Australia) by the chloramine T method and immunoreactivity determined by Lindmo assay.23 All binding assays were performed in 1% HSA/PBS on 1-2×10$^6$ live U87MG.Δ2-7 or A431 cells for 90 min at 4° C. with gentle rotation. A set concentration of 10 ng/ml $^{125}$I-labeled antibody was used in the presence of increasing concentrations of the appropriate unlabeled antibody. Non-specific binding was determined in the presence of 10,000-fold excess of unlabeled antibody. Neither $^{125}$I-radiolabeled MAb 806 or the DH8.3 antibody bound to parental U87MG cells. After the incubation was completed, cells were washed and counted for bound $^{125}$I-labeled antibody using a COBRA II™ gamma counter (Packard Instrument Company, Meriden, Conn.). Scatchard analysis was done following correction for immunoreactivity.

Internalization Assay

U87MG.Δ2-7 cells were incubated with either MAb 806 or the DH8.3 antibody (10 μg/ml) for 1 hr in DMEM at 4° C. After washing, cells were transferred to DMEM pre-warmed to 37° C. and aliquots taken at various time points following incubation at 37° C. Internalization was stopped by immediately washing aliquots in ice-cold wash buffer (1% HSA/PBS). At the completion of the time course cells were stained by FACS as described above. Percentage internalization was calculated by comparing surface antibody staining at various time points to zero time using the formula: percent antibody internalized=(mean fluorescence at time$_x$–background fluorescence)/(mean fluorescence at time0_background fluorescence)×100. This method was validated in 1 assay using an iodinated antibody (MAb 806) to measure internalization as previously described.[24] Differences in internalization rate at different time points were compared using Student's t-test.

Electron Microscopy of U87MG.Δ2-7 Cells

U87MG.Δ2-7 cells were grown on gelatin coated chamber slides (Nunc, Naperville, Ill.) to 80% confluence and then washed with ice cold DMEM. Cells were then incubated with MAb 806 or the DH8.3 antibody in DMEM for 45 min at 4° C. After washing, cells were incubated for a further 30 min with gold-conjugated (20 nm particles) anti-mouse IgG (BBInternational, Cardiff, UK) at 4° C. Following a further wash, pre-warmed DMEM/10% FCS was added to the cells, which were incubated at 37° C. for various times from 1-60 min. Internalization of the antibody was stopped by ice-cold media and cells fixed with 2.5% glutaraldehyde in PBS/0.1% HSA and then postfixed in 2.5% osmium tetroxide. After dehydration through a graded series of acetone, samples were embedded in Epon/Araldite resin, cut as ultrathin sections with a Reichert Ultracut-S microtome (Leica) and collected on nickel grids. The sections were stained with uranyl acetate and lead citrate before being viewed on a Philips CM12 transmission electron microscope at 80 kV. Statistical analysis of gold grains contained within coated pits was performed using a $\chi^2$ test.

Immunoprecipitation Studies

Cells were labeled for 16 hr with 100 μCi/ml of Tran$^{35}$S-Label (ICN Biomedicals, CA) in DMEM without methionine/cysteine supplemented with 5% dialyzed FCS. After washing with PBS, cells were placed in lysis buffer (1% Triton X-100, 30 mM HEPES, 150 mM NaCl, 500 μM AEBSF, 150 nM aprotinin, 1 μM E-64 protease inhibitor, 0.5 mM EDTA and 1 μM leupeptin, pH 7.4) for 1 hr at 4° C. Lysates were clarified by centrifugation for 10 min at 12,000 g, then incubated with 5 μg of appropriate antibody for 30 min at 4° C. before the addition of Protein A-Sepharose. Immunoprecipitates were washed 3 times with lysis buffer, mixed with SDS sample buffer, separated by gel electrophoresis using a 4-20% Tris/glycine gel that was then dried and exposed to X-ray film.

Biodistribution in Tumor Bearing Nude Mice

Tumor xenografts were established in nude BALB/c mice by s.c. injection of 3×10$^6$ U87MG, U87MG.Δ2-7 or A431 cells. de2-7 EGFR expression in U87MG.Δ2-7 xenografts remains stable throughout the period of biodistribution as measured by immunohistochemistry at various time points (data not shown). A431 cells also retained their MAb 806 reactivity when grown as tumor xenografts as determined by immunohistochemistry. U87MG or A431 cells were injected on 1 side 7-10 days before U87MG.Δ2-7 cells were injected on the other side because of the faster growth rate observed for de2-7 EGFR expressing xenografts. Antibodies were radiolabeled and assessed for immunoreactivity as described above and were injected into mice by the retro-orbital route when tumors were 100-200 mg in weight. Each mouse received 2 different antibodies (2 μg per antibody): 2 μCi of $^{125}$I-labeled MAb 806 and 2 μCi of $^{131}$I-labeled DH8.3 or 528. Unless indicated, groups of 5 mice were sacrificed at various time points post-injection and blood obtained by cardiac puncture. The tumors, liver, spleen, kidneys and lungs were obtained by dissection. All tissues were weighed and assayed for $^{125}$I and $^{131}$I activity using a dual-channel counting window. Data was expressed for each antibody as percentage injected dose per gram tumor (% ID/g tumor) determined by comparison to injected dose standards or converted into tumor to blood/liver ratios (i.e., % ID/g tumor÷% ID/g blood or liver). Differences between groups were analyzed by Student's t-test. After injection of radiolabeled MAb 806, some tumors were fixed in formalin, embedded in paraffin, cut into 5 μm sections and then exposed to X-ray film (AGFA, Mortsel, Belgium) to determine antibody localization by autoradiography.

Results

Binding of Antibodies to Cell Lines

In order to confirm the specificity of MAb 806 and the DH8.3 antibody, binding to U87MG and U87MG.Δ2-7 cells was analyzed by FACS. An irrelevant murine IgG2b was included as an isotype control for MAb 806 and the 528 antibody was included as it recognizes both the de2-7 and wild type EGFR. Only the 528 antibody was able to stain the U87MG cell line (FIG. 1) consistent with previous reports demonstrating that these cells express the wild type EGFR.[10] Both MAb 806 and the DH8.3 antibody had binding levels similar to the irrelevant antibody, clearly demonstrating they are unable to bind the wild type receptor (FIG. 1). Binding of the isotype control antibody to U87MG.Δ2-7 cells was similar as that observed for the U87MG cells. MAb 806 and the DH8.3 antibody immunostained U87MG.Δ2-7 cells, indicating that these antibodies specifically recognize the de2-7 EGFR (FIG. 1). The 528 antibody stained U87MG.Δ2-7 with a higher intensity than the parental cell as it binds both the de2-7 and wild type receptors that are co-expressed in these cells (FIG. 1). Importantly, MAb 806 also bound the BaF/3.Δ2-7 cell line, demonstrating that the co-expression of wild type EGFR is not a requirement for MAb 806 reactivity (FIG. 1 but data not shown herein).

Binding of Antibodies in ELISA Assays

To further characterize the specificity of MAb 806 and the DH8.3 antibody, their binding was examined by ELISA. Both MAb 806 and the 528 antibody displayed dose-dependent and saturating binding curves to immobilized wild type sEGFR (FIG. 2A). As the unique junctional peptide found in the de2-7 EGFR is not contained within the sEGFR, MAb 806 must be binding to an epitope located within the wild type EGFR sequence. The binding of the 528 antibody was probably lower than that observed for MAb 806 as it recognizes a conformational determinant. As expected the DH8.3 antibody did not bind the wild type sEGFR even at concentrations up to 10 μg/ml (FIG. 2A). Although sEGFR in solution inhibited the binding of the 528 antibody to immobilized sEGFR in a dose-dependent fashion, it was unable to inhibit the binding of MAb 806 (FIG. 2B). This suggests that MAb 806 can only bind wild type EGFR once immobilized on ELISA plates, a process that may induce conformational changes. Similar results were observed using a BIAcore whereby MAb 806 bound immobilized sEGFR but immobilized MAb 806 was not able to bind sEGFR in solution (data not shown). Following denaturation by heating for 10 min at 95° C., sEGFR in solution was able to inhibit the binding of MAb 806 to immobilized sEGFR (FIG. 2C but data not shown herein), confirming that MAb 806 can bind the wild type EGFR under certain conditions. Interestingly, the denatured sEGFR was unable to inhibit the binding of the 528 antibody (FIG. 2C but data not shown herein), demonstrating that this antibody recognizes a conformational epitope. The DH8.3 antibody exhibited dose-dependent and saturable binding to the unique de2-7 EGFR peptide (FIG. 2D). Neither MAb 806 or the 528 antibody bound to the peptide, even at concentrations higher than those used to obtain saturation binding of DH8.3, further indicating MAb 806 does not recognize an epitope determinant within this peptide.

Scatchard Analysis of Antibodies

A Scatchard analysis was performed using U87MG.Δ2-7 cells in order to determine the relative affinity of each antibody. Both MAb 806 and the DH8.3 antibody retained high immunoreactivity when iodinated and was typically greater than 90% for MAb 806 and 45-50% for the DH8.3 antibody. MAb 806 had an affinity for the de2-7 EGFR receptor of $1.1 \times 10^9$ $M^{-1}$ whereas the affinity of DH8.3 was some 10-fold lower at $1.0 \times 10^8$ $M^{-1}$. Neither iodinated antibody bound to U87MG parental cells. MAb 806 recognized an average of $2.4 \times 10^5$ binding sites per cell with the DH8.3 antibody binding an average of $5.2 \times 10^5$ sites. Thus, there was not only good agreement in receptor number between the antibodies, but also with a previous report showing $2.5 \times 10^5$ de2-7 receptors per cell as measured by a different de2-7 EGFR specific antibody on the same cell line.25

Internalization of Antibodies by U87MG.Δ2-7 Cells

The rate of antibody internalization following binding to a target cell influences both its tumor targeting properties and therapeutic options. Consequently, we examined the internalization of MAb 806 and the DH8.3 antibody following binding to U87MG.Δ2-7 cells by FACS. Both antibodies showed relatively rapid internalization reaching steady-state levels at 10 min for MAb 806 and 30 min for DH8.3 (FIG. 3). Internalization of DH8.3 was significantly higher both in terms of rate (80.5% of DH8.3 internalized at 10 min compared to 36.8% for MAb 806, $p<0.01$) and total amount internalized at 60 min (93.5% vs. 30.4%, $p<0.001$). MAb 806 showed slightly lower levels of internalization at 30 and 60 min compared to 20 min in all 4 assays performed (FIG. 3). This result was also confirmed using an internalization assay based on iodinated MAb 806 (data not shown).

Electron Microscopy Analysis of Antibody Internalization

Figure 19A:
FIG. 19 A-D Analysis of internalization by electron microscopy. U87MG.Δ2-7 cells were pre-incubated with MAb 806 or DH8.3 followed by gold conjugated anti-mouse IgG at 4° C., transferred to 37° C. and internalization examined at various time points by electron microscopy. (A) localization of the DH8.3 antibody to a coated pit (arrow) after 5 min; (B) internalization of MAb 806 by macropinocytosis (arrow) after 2 min; (C) localization of DH8.3 to lysosomes (arrow) after 20 min; (D) localization of MAb 806 to lysosomes (arrow) after 30 min. Original magnification for all images is ×30,000.
Figure 19B:
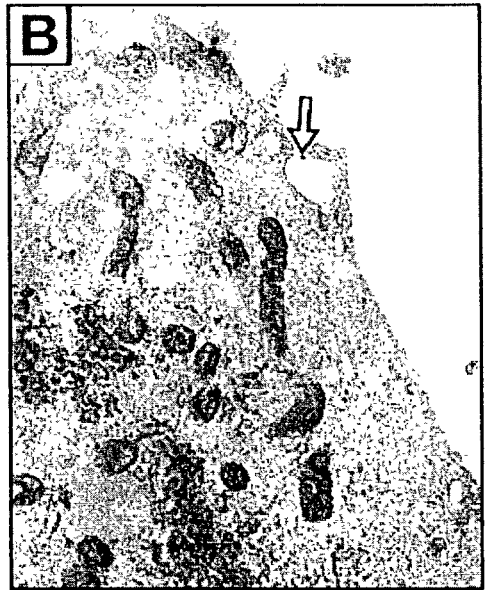
Figure 19C:
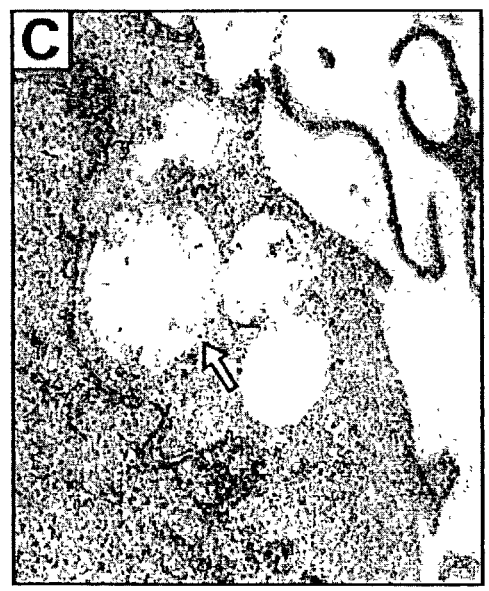
Figure 19D:

Given this difference in internalization rates between the antibodies, a detailed analysis of antibody intracellular trafficking was performed using electron microscopy. Although the DH8.3 anti-body was internalized predominantly via coated-pits (FIG. 19A), MAb 806 appeared to be internalized by macropinocytosis (FIG. 19B). In fact, a detailed analysis of 32 coated pits formed in cells incubated with MAb 806 revealed that none of them contained antibody. In contrast, around 20% of all coated-pits from cells incubated with DH8.3 were positive for antibody, with a number containing multiple gold grains. A statistical analysis of the total number of gold grains contained within coated-pits found that the difference was highly significant ($p<0.01$). After 20-30 min both antibodies could be seen in structures that morphologically resemble lysosomes (FIG. 19C). The presence of cellular debris within these structures is also consistent with their lysosome nature.

Biodistribution of Antibodies in Tumor Bearing Nude Mice

Figure 5B:
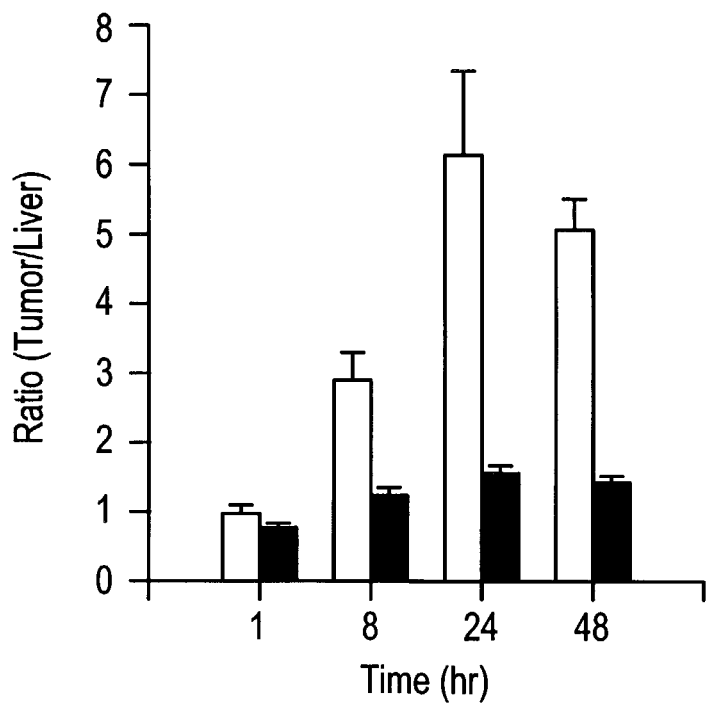

The biodistribution of MAb 806 and the DH8.3 antibody was compared in nude mice containing U87MG xenografts on 1 side and U87MG.Δ2-7 xenografts on the other. A relatively short time period was chosen for this study as a previous report demonstrated that the DH8.3 antibody shows peak levels of tumor targeting between 4-24 hr.[16] In terms of % ID/g tumor, MAb 806 reached its peak level in U87MG.Δ2-7 xenografts of 18.6% ID/g tumor at 8 hr (FIG. 4A), considerably higher than any other tissue except blood. Although DH 8.3 also showed peak tumor levels at 8 hr, the level was a statistically (p<0.001) lower 8.8% ID/g tumor compared to MAb 806 (FIG. 4B). Levels of both antibodies slowly declined at 24 and 48 hr. Autoradiography of U87MG.Δ2-7 xenograft tissue sections collected 8 hr after injection with $^{125}$I-labeled MAb 806 alone, clearly illustrates localization of antibody to viable tumor (FIG. 20). Neither antibody showed specific targeting of U87MG parental xenografts (FIGS. 4A, 4B). With regards to tumor to blood/liver ratios, MAb 806 showed the highest ratio at 24 hr for both blood (ratio of 1.3) and liver (ratio of 6.1) (FIGS. 5A, 5B). The DH8.3 antibody had its highest ratio in blood at 8 hr (ratio of 0.38) and at 24 hr in liver (ratio of 1.5) (FIGS. 5A, 5B), both of which are considerably lower than the values obtained for MAb 806.

Binding of MAb 806 to Cells Containing Amplified EGFR

Figure 21B:
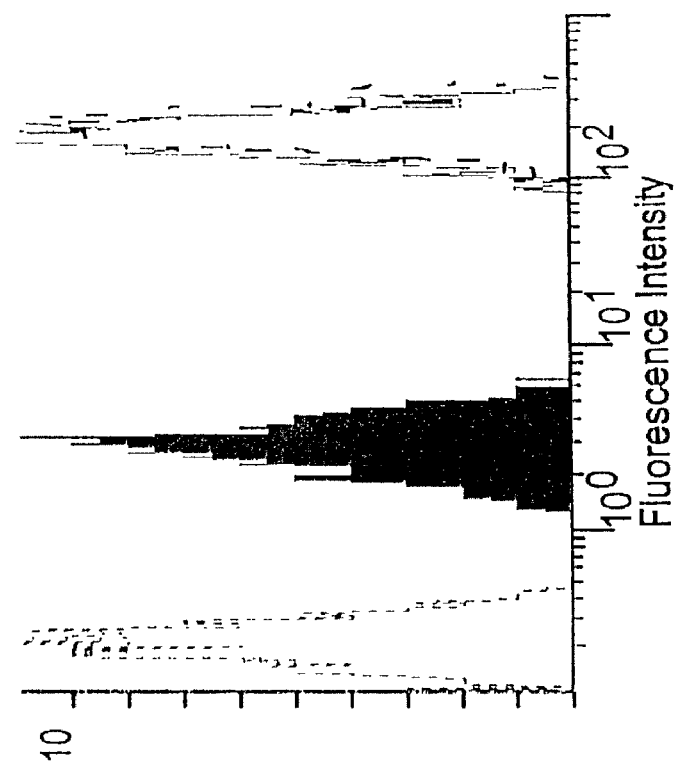
FIG. 21 Flow cytometric analysis of cell lines containing amplification of the EGFR gene. HN5 and MDA-468 cells were stained with an irrelevant IgG2b antibody (open histogram with dashed line), MAb 806 (black histogram) or 528 (open histogram with closed lines). The DH8.3 antibody was completely negative on both cell lines (data not shown).
Figure 21A:
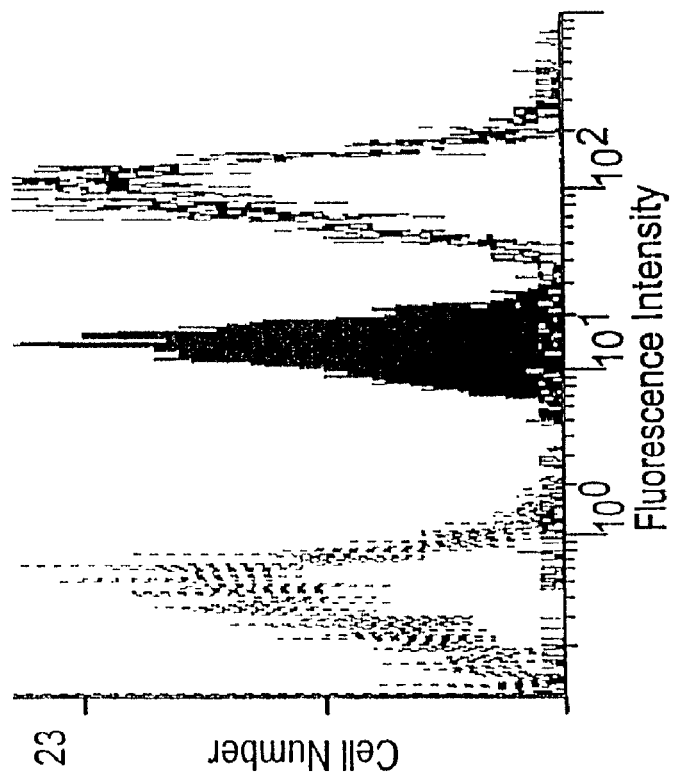

To examine if MAb 806 could recognize the EGFR expressed in cells containing an amplified receptor gene, its binding to A431 cells was analyzed. Low, but highly reproducible, binding of MAb 806 to A431 cells was observed by FACS analysis (FIG. 6). The DH8.3 antibody did not bind A431 cells, indicating that the binding of MAb 806 was not the result of low level de2-7 EGFR expression (FIG. 6). As expected, the anti-EGFR 528 antibody showed strong staining of A431 cells (FIG. 6). The average of 3 such experiments gave a value for affinity of $9.5 \times 10^7$ M$^{-1}$ with $2.4 \times 10^5$ receptors per cell. Thus the affinity for this receptor was some 10-fold lower than the affinity for the de2-7 EGFR. Furthermore, MAb 806 appears to only recognize a small portion of EGFR found on the surface of A431 cells. Using the 528 antibody approximately $2 \times 10^6$ receptors per cell were measured, which is in agreement with numerous other studies.[26] To ensure that these results were not simply restricted to the A431 cell line, MAb 806 reactivity was examined in 2 other cells lines exhibiting amplification of the EGFR gene. Both the HN5 head and neck cell line[27] and the MDA-468 breast cancer cell line 28 have been reported to contain multiple copies of the EGFR gene. Consistent with these reports, the 528 antibody displayed intense staining of both cell lines (FIG. 21). As with the A431 cell line, the MAb 806 clearly stained both cell lines but at a lower level than that observed with the 528 antibody (FIG. 21). Thus, MAb 806 binding is not simply restricted to A431 cells but appears to be a general observation for cells containing amplification of the EGFR gene.

Immunoprecipitations

Figure 22:
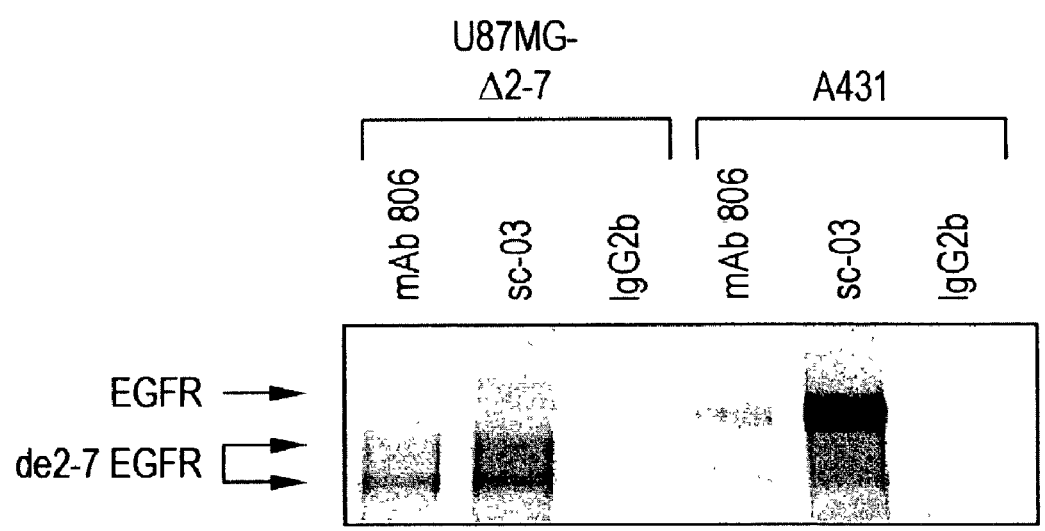
FIG. 22 Immunoprecipitation of EGFR from cell lines. The EGFR was immunoprecipitated from $^{35}$S-labeled U87MG.Δ2-7 or A431 cells with MAb 806, sc-03 antibody or a IgG2b isotype control. Arrows at the side indicate the position of the de2-7 and wt EGFR. Identical banding patterns were obtained in 3 independent experiments.

MAb 806 reactivity was further characterized by immunoprecipitation using $^{35}$S-labeled cells. The sc-03 antibody (a commercial polyclonal antibody specific for the c-terminal domain of the EGFR) immunoprecipitated 3 bands from U87MG.Δ2-7 cells; a doublet corresponding to the 2 de2-7 EGFR bands observed in these cells and a higher molecular weight band corresponding to the wt EGFR (FIG. 22). In contrast, while MAb 806 immunoprecipitated the 2 de2-7 EGFR bands, the wt EGFR was completely absent. The sc-03 antibody immunoprecipitated a single band corresponding to the wt EGFR from A431 cells (FIG. 22). The MAb 806 also immunoprecipitated a single band corresponding to the wt EGFR from A431 cells (FIG. 22) but consistent with the FACS and Scatchard data, the amount of EGFR immunoprecipitated by MAb 806 was substantially less than the total EGFR present on the cell surface. Given that MAb 806 and the sc-03 immunoprecipitated similar amounts of the de2-7 EGFR, this result supports the notion that the MAb 806 antibody only recognizes a portion of the EGFR in cells overexpressing the receptor. An irrelevant IgG2b (an isotype control for MAb 806) did not immunoprecipitate EGFR from either cell line (FIG. 22). Using identical conditions, MAb 806 did not immunoprecipitate the EGFR from the parental U87MG cells (data not shown).

In Vivo Targeting of A431 Cells by MAb 806

Figure 23:
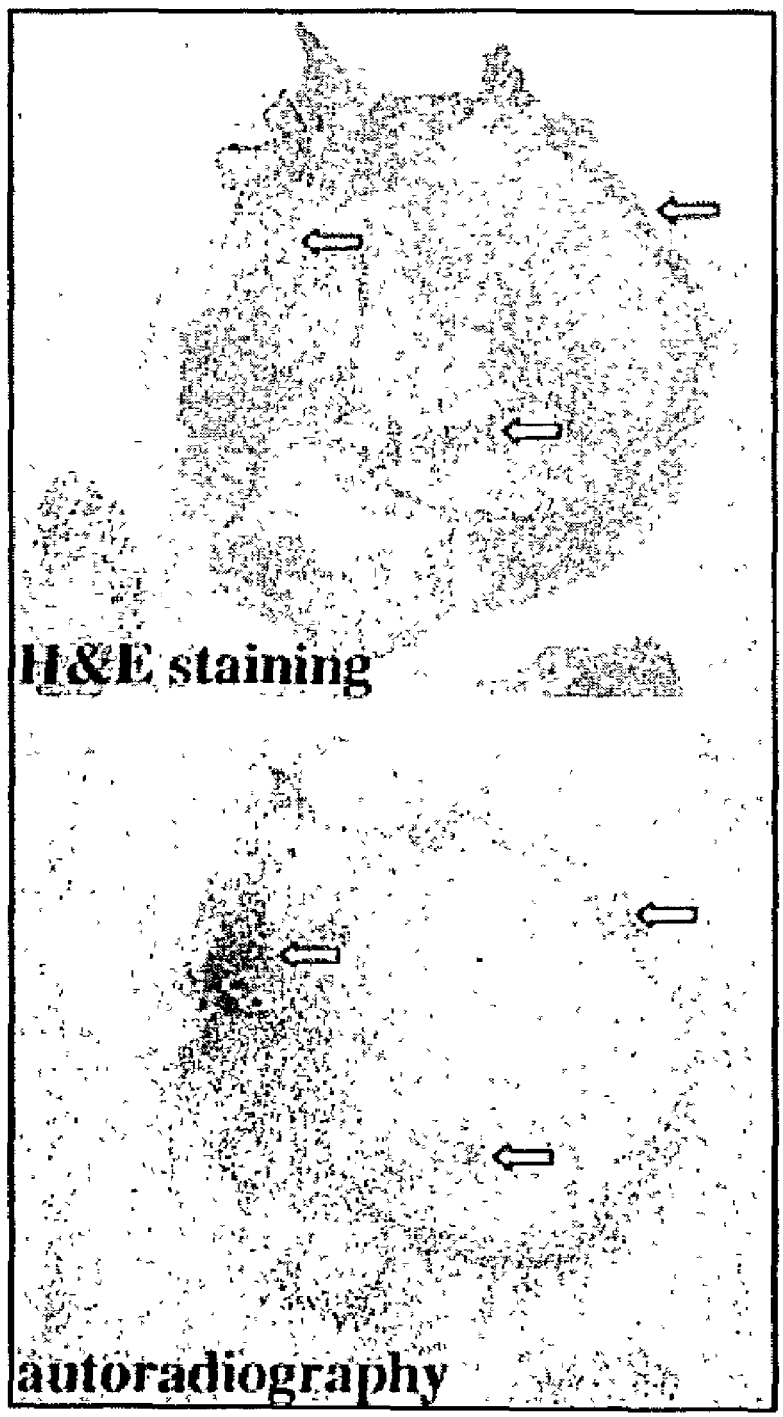
FIG. 23 Autoradiography of an A431 xenograft section collected 24 hr after injection of $^{125}$I-MAb 806, areas of localization to viable tissue are indicated (arrows).

A second biodistribution study was performed with MAb 806 to determine if it could target A431 tumor xenografts. The study was conducted over a longer time course in order to obtain more information regarding the targeting of U87MG.Δ2-7 xenografts by MAb 806, which were included in all mice as a positive control. In addition, the anti-EGFR 528 antibody was included as a positive control for the A431 xenografts, since a previous study demonstrated low but significant targeting of this antibody to A431 cells grown in nude mice.[21] During the first 48 hr, MAb 806 displayed almost identical targeting properties as those observed in the initial experiments (FIG. 7A compared with FIG. 4A). In terms of % ID/g tumor, levels of MAb 806 in U87MG.Δ2-7 xenografts slowly declined after 24 hr but always remained higher than levels detected in normal tissue. Uptake in the A431 xenografts was comparatively low, however, there was a small increase in % ID/g tumor during the first 24 hr not observed in normal tissues such as liver, spleen, kidney and lung (FIG. 7A). Uptake of the 528 antibody was low in both xenografts when expressed as % ID/g tumor (FIG. 7B). Autoradiography of A431 xenograft tissue sections collected 24 hr after injection with $^{125}$I-labeled MAb 806 alone, clearly illustrates localization of antibody to viable tumor around the periphery of the tumor and not central areas of necrosis (FIG. 23). In terms of tumor to blood ratio MAb 806 peaked at 72 hr for U87MG.Δ2-7 xenografts and 100 hr for A431 xenografts (FIG. 8A, 8B). Although the tumor:blood ratio for MAb 806 never surpassed 1.0 with respect to the A431 tumor, it did increase through-out the entire time course (FIG. 8B) and was higher than all other tissues examined (data not shown) indicating low levels of targeting. The tumor to blood ratio for the 528 antibody showed a similar profile to MAb 806 although higher levels were noted in the A431 xenografts (FIG. 8A, 8B). MAb 806 had a peak tumor to liver ratio in U87MG.Δ2-7 xenografts of 7.6 at 72 hr, clearly demonstrating preferential uptake in these tumors compared to normal tissue (FIG. 8C). Other tumor to organ ratios for MAb 806 were similar to those observed in the liver (data not shown). The peak tumor to liver ratio for MAb 806 in A431 xenografts was 2.0 at 1 od hr, again indicating a slight preferentially uptake in tumor compared with normal tissue (FIG. 8D).

Discussion

The previously described L8A4 monoclonal antibody directed to the unique junctional peptide found in the de2-7 EGFR, behaves in a similar fashion to MAb 806.[38] Using U87MG cells transfected with the de2-7 EGFR, this antibody had a similar internalization rate (35% at 1 hr compared to 30% at 1 hr for MAb 806) and displayed comparable in vivo targeting when using 3T3 fibroblasts transfected with de2-7 EGFR (peak of 24% ID/g tumor at 24 hr compared to 18% ID/g tumor at 8 hr for MAb 806).[25].

Perhaps the most important advantage of MAb 806 compared to current EGFR antibodies, is that MAb 806 can be directly conjugated to cytotoxic agents. This approach is not feasible with current EGFR specific antibodies as they target the liver and cytotoxic conjugation would almost certainly induce severe toxicity. Conjugation of cytotoxic agents such as drugs 41 or radioisotopes 42 to antibodies has the potential to improve efficacy and reduce the systemic toxicity of these agents. The ability of a conjugated antibody to mediate tumor kill is dependent upon its potential to be internalized. Thus, the rapid internalization observed with MAb 806 in U87MG.Δ2-7 cells, suggests MAb 806 is an ideal candidate for this type of approach.

MAb 806 is novel in that it is the first de2-7 EGFR specific antibody directed to an epitope not associated with the unique junctional peptide. It has superior affinity and better tumor targeting properties than DH8.3, a previously described de2-7 EGFR antibody. An important property, however, is its ability to recognize a subset of EGFR molecules expressed on the surface of tumor cells exhibiting amplification of the EGFR gene. This suggests that MAb 806 may possess a unique clinical property; the ability to target both de2-7 and amplified EGFR but not wild type receptors. If proven correct, this antibody would not target organs such as liver and therefore would be more versatile than current antibodies directed to the EGFR,[18,19] which cannot be used for the coupling of cytotoxic agents. Finally, MAb 806 may be a useful reagent for analyzing the conformational changes induced by the truncation found in de2-7 EGFR.

REFERENCES

1. Wikstrand C J, McLendon R E, Friedman A H, et al. Cell surface localization and density of the tumor-associated variant of the epidermal growth factor receptor, EGFRvIII. Cancer Res 1997; 57:4130-40.
2. Olapade-Olaopa E O, Moscatello D K, MacKay E H, et al. Evidence for the differential expression of a variant EGF receptor protein in human prostate cancer. Br Cancer 2000; 82:186-94.
3. Wikstrand C J, Hale L P, Batra S K, et al. Monoclonal antibodies against EGFRvIII are tumor specific and react with breast and lung carcinomas and malignant gliomas. Cancer Res 1995; 55:3140-8.
4. Garcia de Palazzo I E, Adams G P, Sundareshan P, et al. Expression of mutated epidermal growth factor receptor by non-small cell lung carcinomas. Cancer Res 1993; 53:3217-20.
5. Ekstrand A J, Sugawa N, James C D, et al. Amplified and rearranged epidermal growth factor receptor genes in human glioblastomas reveal deletions of sequences encoding portions of the N- or C-terminal tails. Proc Natl Acad Sci USA 1992; 89:4309-13.
6. Wong A J, Ruppert J M, Bigner S H, et al. Structural alterations of the epidermal growth factor receptor gene in human gliomas. Proc Natl Acad Sci USA 1992; 89:2965-9.
7. Yamazaki H, Ohba Y, Tamaoki N, et al. A deletion mutation within the ligand binding domain is responsible for activation of epidermal growth factor receptor gene in human brain tumors. Jpn J Cancer Res 1990; 81:773-9.
8. Yamazaki H, Fukui Y, Ueyama Y, et al. Amplification of the structurally and functionally altered epidermal growth factor receptor gene (c-erbB) in human brain tumors. Mol Cell Biol 1988; 8:1816-20.
9. Sugawa N, Ekstrand A J, James C D, et al. Identical splicing of aberrant epidermal growth factor receptor transcripts from amplified re-arranged genes in human glioblastomas. Proc Natl Acad Sci USA 1990; 87:8602-6.
10. Nishikawa R, Ji X D, Harmon R C, et al. A mutant epidermal growth factor receptor common in human glioma confers enhanced tumorigenicity. Proc Natl Acad Sci USA 1994; 91:7727-31.
11. Batra S K, Castelino-Prabhu S, Wikstrand C J, et al. Epidermal growth factor ligand-independent, unregulated, cell-transforming potential of a naturally occurring human mutant EGFRvIII gene. Cell Growth Differ 1995; 6: 1251-9.
12. Nagane M, Coufal F, Lin H, et al. A common mutant epidermal growth factor receptor confers enhanced tumorigenicity on human glioblastoma cells by increasing proliferation and reducing apoptosis. Cancer Res 1996; 56:5079-86.
13. Wikstrand C J, Reist C J, Archer G E, et al. The class III variant of the epidermal growth factor receptor (EGFRvIII): characterization and utilization as an immunotherapeutic target. J Neurovirol 1998; 4: 148-58.
14. Humphrey P A, Wong A J, Vogelstein B, et al. Anti-synthetic peptide antibody reacting at the fusion junction of deletion-mutant epidermal growth factor receptors in human glioblastoma. Proc Natl Acad Sci USA 1990; 87:4207-11.
15. Okamoto S, Yoshikawa K, Obata Y, et al. Monoclonal antibody against the fusion junction of a deletion-mutant epidermal growth factor receptor. Br J Cancer 1996; 73:1366-72.
16. Hills D, Rowlinson-Busza G, Gullick W J. Specific targeting of a mutant, activated EGF receptor found in glioblastoma using a monoclonal antibody. Int J Cancer 1995; 63:537-43.
17. Moscatello D K, Holgado-Madruga M, Godwin A K, et al. Frequent expression of a mutant epidermal growth factor receptor in multiple human tumors. Cancer Res 1995; 55:5536-9.
18. Baselga J, Pfister D, Cooper M R, et al. Phase I studies of anti-epidermal growth factor receptor chimeric antibody C225 alone and in combination with cisplatin. J Clin Oncol 2000; 18:904-14.
19. Faillot T, Magdelenat H, Mady E, et al. A phase I study of an anti-epidermal growth factor receptor monoclonal antibody for the treatment of malignant gliomas. Neurosurgery 1996; 39:478-83.
20. Ponten J, Macintyre E H. Long term culture of normal and neoplastic human glia. Acta Pathol Microbiol Scand 1968; 74:465-86.
21. Masui H, Kawamoto T, Sato J D, et al. Growth inhibition of human tumor cells in athymic mice by anti-epidermal growth factor receptor monoclonal antibodies. Cancer Res 1984; 44:1002-7.
22. Domagala T, Konstantopoulos N, Smyth F, et al. Stoichiometry, kinetic and binding analysis of the interaction between epidermal growth factor (EGF) and the extracellular domain of the EGF receptor. Growth Factors 2000; 18:11-29.
23. Lindmo T, Boven E, Cuttitta F, et al. Determination of the immunoreactive fraction of radiolabeled monoclonal antibodies by linear extrapolation to binding at infinite antigen excess. J Immunol Methods 1984; 72:77-89.
24. Huang H S, Nagane M, Klingbeil C K, et al. The enhanced tumorigenic activity of a mutant epidermal growth factor receptor common in human cancers is mediated by threshold levels of constitutive tyrosine phosphorylation and unattenuated signaling. J Biol Chem 1997; 272:2927-35.
25. Reist C J, Archer G E, Wikstrand C J, et al. Improved targeting of an anti-epidermal growth factor receptor variant III monoclonal antibody in tumor xenografts after labeling using N-succinimidyl 5-iodo-3-pyridinecarboxylate. Cancer Res 1997; 57:1510-5.
26. Santon J B, Cronin M T, MacLeod C L, et al. Effects of epidermal growth factor receptor concentration on tumorigenicity of A431 cells in nude mice. Cancer Res 1986; 46:4701-5.

27. Kwok T T, Sutherland R M. Differences in EGF related radiosensitisation of human squamous carcinoma cells with high and low numbers of EGF receptors. Br J Cancer 1991; 64:251-4.
28. Filmus J, Pollak M N, Cailleau R, et al. MDA-468, a human breast cancer cell line with a high number of epidermal growth factor (EGF) receptors, has an amplified EGF receptor gene and is growth inhibited by EGF. Biochem Biophys Res Commun 1985; 128:898-905.
29. Voldborg B R, Damstrup L, Spang-Thomsen M, et al. Epidermal growth factor receptor (EGFR) and EGFR mutations, function and possible role in clinical trials. Ann Oncol 1997; 8:1197-206.
30. den Eynde B, Scott A M. Tumor antigens. In: Delves P J, Roitt I M, eds. Encyclopedia of immunology. London: Academic Press, 1998. 2424-31.
31. Seymour L. Novel anti-cancer agents in development: exciting prospects and new challenges. Cancer Treat Rev 1999; 25:301-12.
32. Sturgis E M, Sacks P G, Masui H, et al. Effects of anti-epidermal growth factor receptor antibody 528 on the proliferation and differentiation of head and neck cancer. Otolaryngol Head Neck Surg 1994; 111:633-43.
33. Goldstein N I, Prewett M, Zuklys K, et al. Biological efficacy of a chimeric antibody to the epidermal growth factor receptor in a human tumor xenograft model. Clin Cancer Res 1995; 1: 1311-8.
34. Fernandes H, Cohen S, Bishayee S. Glycosylation-induced conformational modification positively regulates receptor-receptor association: a study with an aberrant epidermal growth factor receptor (EGFRvIII/DEGFR) expressed in cancer cells. J Biol Chem 2001; 276:5375-83.
35. Reist C J, Garg P K, Alston K L, et al. Radioiodination of internalizing monoclonal antibodies using N-succinimidyl 5-iodo-3-pyridinecar-boxylate. Cancer Res 1996; 56:4970-7.
36. Reist C J, Archer G E, Kurpad S N, et al. Tumor-specific anti-epidermal growth factor receptor variant III monoclonal antibodies: use of the tyramine-cellobiose radio iodination method enhances cellular retention and uptake in tumor xenografts. Cancer Res 1995; 55:4375-82.
37. Press O W, DeSantes K, Anderson S K, et al. Inhibition of catabolism of radiolabeled antibodies by tumor cells using lysosomotropic amines and carboxylic ionophores. Cancer Res 1990; 50:1243-50.
38. Reist C J, Batra S K, Pegram C N, et al. In vitro and in vivo behavior of radiolabeled chimeric anti-EGFRvIII monoclonal antibody: comparison with its murine parent. Nucl Med Biol 1997; 24:639-47.
39. Mineo C, Gill G N, Anderson R G. Regulated migration of epidermal growth factor receptor from caveolae. J Biol Chem 1999; 274:30636-43.
40. Luwor R B, Johns T G, Murone C, et al. Monoclonal antibody 806 inhibits the growth of tumor xenografts expressing either the de2-7 or amplified epidermal growth factor receptor (EGFR) but not wild-type EGFR. Cancer Res 2001; 61:5355-61.
41. Trail P A, Bianchi A B. Monoclonal antibody drug conjugates in the treatment of cancer. Curr Opin Immunol 1999; 11:584-8.
42. DeNardo S J, Kroger L A, DeNardo G L. A new era for radiolabeled antibodies in cancer? Curr Opin Immunol 1999; 11:563-9.

EXAMPLE 19

Growth Suppression of Intracranial Xenografted Glioblastomas Overexpressing Mutant Epidermal Growth Factor Receptors by Systemic Administration of Monoclonal Antibody (mAb) 806, a Novel Monoclonal Antibody Directed to the Receptor This example presents the evaluation of mAb 806 on the growth of intracranial xenografted gliomas in nude mice. The following corresponds to and was presented in Mishima et al, (2001) Cancer Research, 61:5349-5354, and the entire publication is incorporated herein by reference with cross referencing to the Figures herein where appropriate. and made a part hereof. The data and findings of Mishima et al. are set forth below.

Systemic treatment with mAb 806 significantly reduced the volume of tumors and increased the survival of mice bearing xenografts of U87 MG.ΔEGFR, LN-Z308.ΔEGFR, or A1207 gliomas, each of which expresses high levels of ΔEGFR. In contrast, mAb 806 treatment was ineffective with mice bearing the parental U87 MG tumors, which expressed low levels of endogenous wild-type EGFR, or U87 MG.DK tumors, which expressed high levels of kinase-deficient ΔEGFR. A slight increase of survival of mice xenografted with a wild-type EGFR-overex-pressing U87 MG glioma (U87 MG.wtEGFR) was effected by mAb 806 concordant with its weak cross-reactivity with such cells. Treatment of U87 MG.ΔEGFR tumors in mice with mAb 806 caused decreases in both tumor growth and angiogenesis, as well as increased apoptosis. Mechanistically, in vivo mAb 806 treatment resulted in reduced phosphorylation of the constitutively active ΔEGFR and caused down-regulated expression of the apoptotic protector, Bcl-XL. These data provide preclinical evidence that mAb 806 treatment may be a useful biotherapeutic agent for those aggressive gliomas that express ΔEGFR.

The present example demonstrates that systemic treatment with the novel ΔEGFR-specific mAb, mAb 806, causes reduced phosphorylation of the constitutively active ΔEGFR and thereby suppresses growth of intracranially implanted gliomas overexpressing this mutant receptor in nude mice and extends their survival. The inhibition of tumor growth was mediated by a decrease in proliferation and angiogenesis and increased apoptosis of the tumor cells. This suppression affected active signaling by ΔEGFR because intracranial xenografts that were derived from cells overexpressing kinase-deficient ΔEGFR (DK), which are recognized equally well by mAb 806, were not significantly suppressed after the same therapy.

Materials and Methods

Cell Lines. Because primary explants of human glioblastomas rapidly lose expression of amplified, rearranged receptors in culture, no existing glioblastoma cell lines exhibit such expression. To force maintenance of expression levels comparable with those seen in human tumors, U87 MG, LN-Z308, and A1207 (gift from Dr. S. Aaronson, Mount Sinai Medical Center, New York, N.Y.) cells were infected with ΔEGFR, kinase-deficient ΔEGFR (DK), or wtEGFR viruses which also conferred resistance to G418 as described previously (21). Populations expressing similar levels of the various EGFR alleles (these expression levels correspond approximately to an amplification level of 25 gene copies; human glioblastomas typically have amplification levels from 10 to 50 gene copies of the truncated receptor) were selected by FACS as described previously (21) and designated as U87 MG.ΔEGFR, U87 MG.DK, U87 MG.wtEGFR, LN-Z308.ΔEGFR, LN-Z308.DK, LN-Z308.wtEGFR, A1207.ΔEGFR, A1207.DK, and A1207.wtEGFR, respectively. Each was maintained in medium containing G418 (U87 MG cell lines, 400 mg/ml; LN-Z308 and A1207 cell lines, 800 mg/ml). mAbs. mAb 806 (IgG2b, k), a ΔEGFR specific mAb, was produced after immunization of mice with NR6 mouse fibroblasts expressing the ΔEGFR. It was selected from several clones because hemagglutination assays showed that it had a high reactivity against NR6.ΔEGFR cells, low reactivity for NR6.wtEGFR cells, and none for NR6 cells.

Immunoprecipitation and Western Blot Analysis. Cells were lysed with lysis buffer containing 50 mM HEPES (pH 7.5), 150 mM NaCl, 10% glycerol, 1% Triton X-100, 2 mM EDTA, 0.1% SDS, 0.5% sodium deoxycholate, 10 mM sodium $PP_i$, 1 mM phenylmethlsulfonyl fluoride, 2 mM $Na_3VO_4$, 5 μg/ml leupeptin, and 5 μg/ml aprotinin. Antibodies were incubated with cell lysates at 4° C. for 1 h before the addition of protein-A and -G Sepharose. Immuno-precipitates were washed twice with lysis buffer and once with HNTG buffer [50 mM HEPES (pH 7.5), 150 mM NaCl, 0.1% Triton X-100, and 10% glycerol], electrophoresed, and transferred to nitrocellulose membranes. Blots were probed with the anti-EGFR antibody, C13, and proteins were visualized using the ECL chemiluminescent detection system (Amersham Pharmacia Biotech.). The mAbs used for precipitation were mAb 806, anti-EGFR mAb clone 528 (Oncogene Research Products, Boston, Mass.), or clone EGFR.1 (Oncogene Research Products). A mAb, C13, used for detection of both wild-type and ΔEGFR on immunoblots was provided by Dr. G. N. Gill (University of California, San Diego, Calif.). Antibodies to Bcl-X (rabbit poly-clonal antibody; Transduction Laboratories, Lexington, Ky.) and phosphotyrosine (4G10, Upstate Biotechnology, Lake Placid, N.Y.) were used for Western blot analysis as described previously (26).

Flow Cytometry Analysis. Cells were labeled with the relevant antibody followed by fluorescein-conjugated goat antimouse IgG (1:100 dilution; Becton-Dickinson PharMingen, San Diego, Calif.) as described previously (21). Stained cells were analyzed with a FACSCalibur using Cell Quest software (Becton-Dickinson PharMingen). For the first antibody, the following mAbs were used: mAb 806, anti-EGFR mAb clone 528, and clone EGFR. 1. Mouse IgG2a or IgG2b was used as an isotype control.

Tumor Therapy. U87 MG.ΔEGFR cells ($1\times10^5$) or $5\times10^5$ LN-Z308.ΔEGFR, A1207. ΔEGFR, U87 MG, U87 MG.DK, and U87 MG.wtEGFR cells in 5 μl of PBS were implanted into the right corpus striatum of nude mice brains as described previously (27). Systemic therapy with mAb 806, or the IgG2b isotype control, was accomplished by i.p. injection of 1 μg of mAbs in a volume of 100 μl every other day from postimplantation day 0 through 14. For direct therapy of intracerebral U87 MG.ΔEGFR tumors, 10 μg of mAb 806, or the IgG2b isotype control, in a volume of 5 μl were injected at the tumor-injection site every other day starting at day 1 for 5 days.

Immunohistochemistry. To assess angiogenesis in tumors, they were fixed in a solution containing zinc chloride, paraffin embedded, sectioned, and immunostained using a monoclonal rat antimouse CD31 antibody (Becton-Dickinson PharMingen; 1:200). Assessment of tumor cell proliferation was performed by Ki-67 immunohistochemistry on formalin-fixed paraffin-embedded tumor tissues. After deparaffinization and rehydration, the tissue sections were incubated with 3% hydrogen peroxide in methanol to quench endogenous peroxidase. The sections were blocked for 30 min with goat serum and incubated overnight with the primary antibody at 4° C. The sections were then washed with PBS and incubated with a biotinylated secondary antibody for 30 min. After several washes with PBS, products were visualized using streptavidin horseradish peroxidase with diaminobenzidine as chromogen and hematoxylin as the counterstain. As a measure of proliferation, the Ki-67 labeling index was determined as the ratio of labeled:total nuclei in high-power (3400) fields. Approximately 2000 nuclei were counted in each case by systematic random sampling. For macrophage and NK cell staining, frozen sections, fixed with buffered 4% paraformaldehyde solution, were immunostained using bio-tinylated mAb F4/80 (Serotec, Raleigh, N.C.) and polyclonal rabbit antiasialo GM1 antibody (Dako Chemicals, Richmond, Va.), respectively. Angiogenesis was quantitated as vessel area using computerized analysis. For this purpose, sections were immunostained using anti-CD31 and were analyzed using a computerized image analysis system without counterstain. MVAs were determined by capturing digital images of the sections at 3200 magnification using a CCD color camera as described previously (27). Images were then analyzed using Image Pro Plus version 4.0 software (Media Cybernetics, Silver Spring, Md.) and MVA was determined by measuring the total amount of staining in each section. Four fields were evaluated for each slide. This value was represented as a percentage of the total area in each field. Results were confirmed in each experiment by at least two observers (K. M., H-J. S. H.).

TUNEL Assay. Apoptotic cells in tumor tissue were detected by using the TUNEL method as described previously (27). TUNEL-positive cells were counted at ×400. The apoptotic index was calculated as a ratio of apoptotic cell number:total cell number in each field.

Statistical Analysis. The data were analyzed for significance by Student's t test, except for the in vivo survival assays, which were analyzed by Wilcoxon analysis.

Results

Systemic Treatment of mAb 806 Extends the Survival of Mice Bearing ΔEGFR-Overexpressing Intracranial Glioma Tumors.

To test the efficacy of the anti-ΔEGFR mAb, mAb 806, we treated nude mice bearing intracranial ΔEGFR-overexpressing glioma xenografts with i.p. injections of mAb 806, the isotype control IgG, or PBS. U87 MG.ΔEGFR cells were implanted intracranially into nude mice, and the treatments began on the same day as described in "Materials and Methods."

Figure 24A:
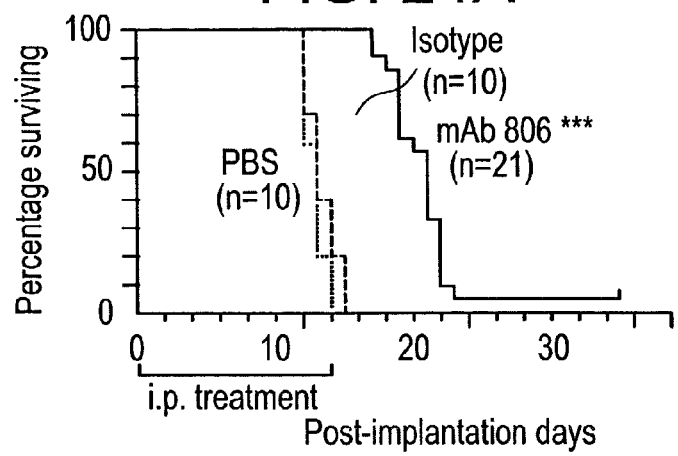
FIGS. 24 A and B, extended survival of nude mice bearing intracranial U87 MG.ΔEGFR (A) and LN-Z308.ΔEGFR (B) xenografts with systemic mAb 806 treatment. U87 MG.ΔEGFR cells (1×10$^5$) or LN-Z308.ΔEGFR cells (5×10$^5$) were implanted into nude mice brains, and the animals were treated with either mAb 806, PBS, or isotype IgG from postimplantation days 0 through 14. C and D, growth inhibition of intracranial tumors by mAb 806 treatment. Nude mice (five per group), treated with either mAb 806 or the isotype IgG control, were euthanized on day 9 for U87 MG.ΔEGFR(C) and on day 15 for LN-Z308.ΔEGFR (D), and their brains were harvested, fixed, and sectioned. Data were calculated by taking the tumor volume of control as 100%. Values are mean±SD. * * *, P<0.001; control versus mAb 806. Arrowheads, tumor tissue. E, extended survival of nude mice bearing intracranial U87 MG.ΔEGFR xenografts with intratumoral mAb 806 treatment. U87 MG.ΔEGFR cells were implanted as described. Ten mg of mAb 806 or isotype IgG control in a volume of 5 μl were injected at the tumor-injection site every other day starting at day 1 for five times.
Figure 24B:
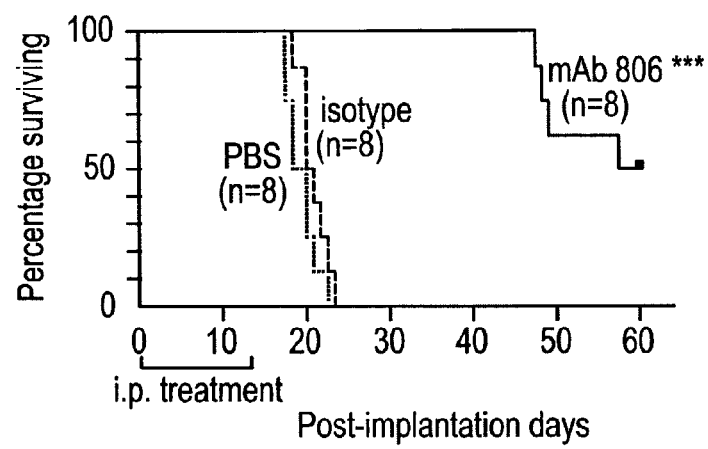

Animals treated with PBS or isotype control IgG had a median survival of 13 days, whereas mice treated with mAb 806 had a 61.5% increase in median survival up to 21 days ($P<0.001$; FIG. 24A). Treatment of mice 3 days postimplantation, after tumor establishment, also extended the median survival of the mAb 806-treated animals by 46.1% (from 13 days to 19 days; $P<0.01$) compared with that of the control groups (data not shown). To determine whether these antitumor effects of mAb 806 extended beyond U87 MG.ΔEGFR xenografts, we also did similar treatments of animals bearing other glioma cell xenografts of LN-Z308.ΔEGFR and A1207.ΔEGFR. The median survival of mAb 806-treated mice bearing LN-Z308.ΔEGFR xenografts was extended from 19 days for controls to 58 days ($P<0.001$; FIG. 24B).

Remarkably, four of eight mAb 806-treated animals survived beyond 60 days (FIG. 24B). The median survival of animals bearing A1207.ΔEGFR xenografts was also extended from 24 days for controls to 29 days (P<0.01; data not shown).

mAb 806 Treatment Inhibits ΔEGFR-overexpressing Brain Tumor Growth.

Figure 24E:
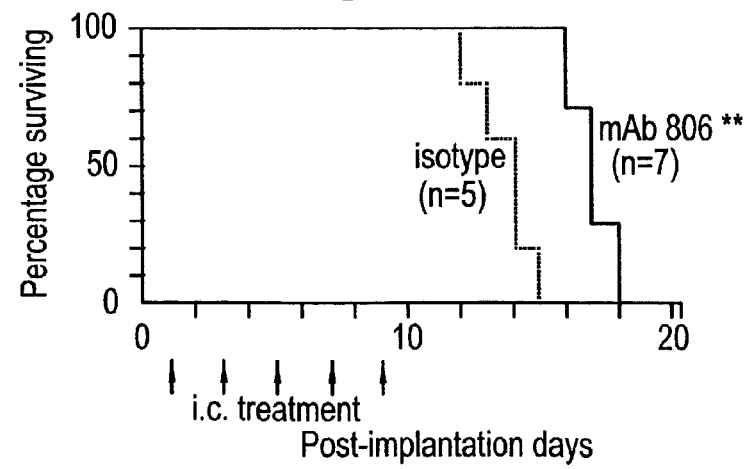
Figure 24C:
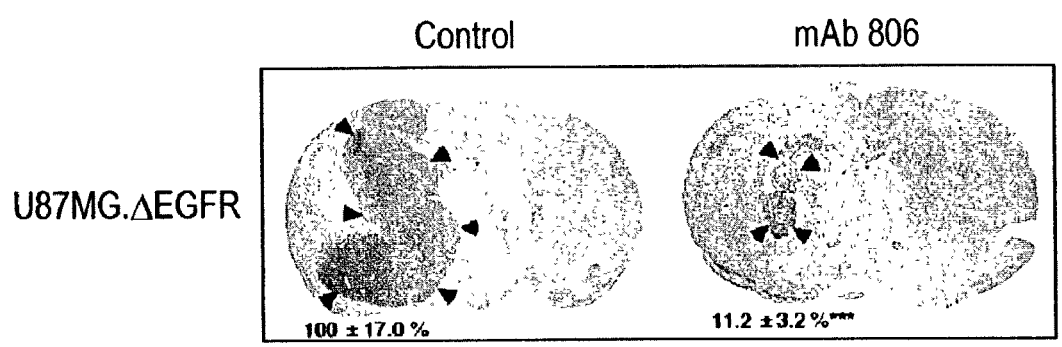
Figure 24D:
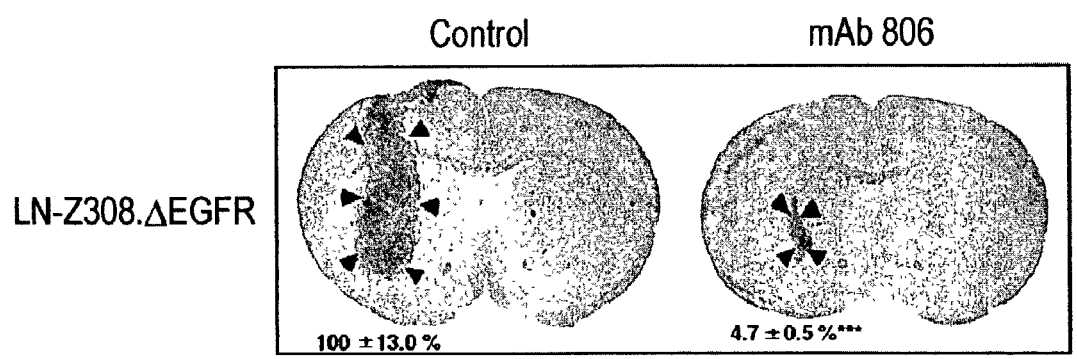

Mice bearing U87 MG.ΔEGFR and LN-Z308. ΔEGFR xenografts were killed at day 9 and day 15, respectively. Tumor sections were histopathologically analyzed, and tumor volumes were determined as described in "Materials and Methods." Consistent with the results observed for animal survival, mAb 806 treatment significantly reduced the volumes of U87 MG.ΔEGFR by 90% (P<0.001; FIG. 24C), and of LN-Z308.ΔEGFR by 0.95% (P<0.001; FIG. 24D), of xenografts in comparison with those of the control groups. Similar results were obtained for animals bearing A1207.ΔEGFR tumors (65% volume reduction; P<0.01; data not shown).

Intratumoral Treatment with mAb 806 Extends Survival of Mice Bearing U87 MG.ΔEGFR Brain Tumors.

We also determined the efficacy of direct intratumoral injection of mAb 806 for the treatment of U87 MG.ΔEGFR xenografts. Animals were given intratumoral injections of mAb 806 or isotype control IgG at 1 day postimplantation, as described in "Materials and Methods." Control animals survived for 15 days, whereas mAb 806 treated mice remained alive for 18 days (P<0.01; FIG. 24E). Although the intratumoral treatment with mAb 806 was somewhat effective, it entailed the difficulties of multiple intracranial injections and of increased risk of infection. We, therefore, focused on systemic treatments for additional studies.

mAb 806 Treatment Slightly Extends Survival of Mice Bearing U87 MG.wtEGFR but not of Mice Bearing U87 MG or U87 MG.DK Intracranial Xenografts.

Figure 25A:
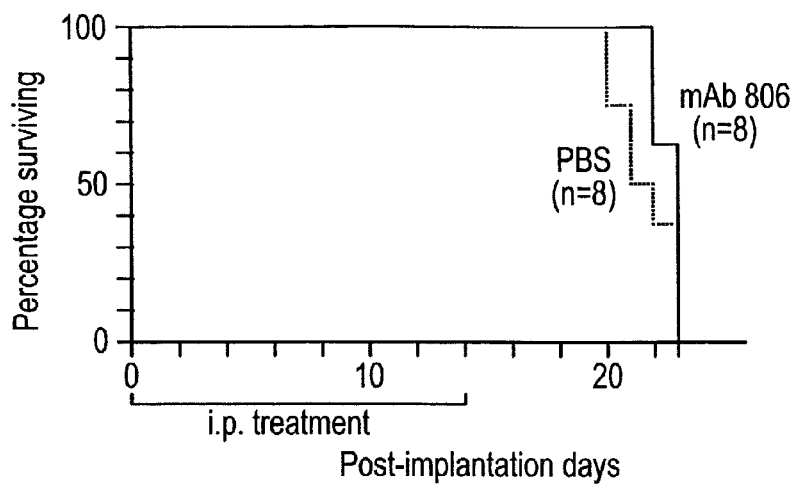
FIG. 25 mAb 806 extends survival of mice with U87 MG.wtEGFR brain tumors but not with U87 MG.DK. or U87 MG brain tumors. U87 MG (A), U87 MG.DK (B), or U87 MG.wtEGFR(C) cells (5×10$^5$) were implanted into nude mice brains, and the animals were treated with mAb 806 from postimplantation days 0 through 14 followed by observation after discontinuation of therapy.
Figure 25B:
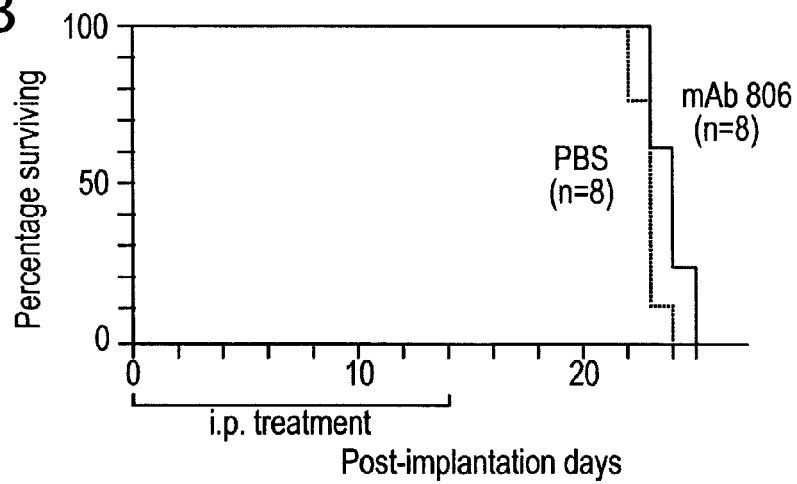
Figure 25C:
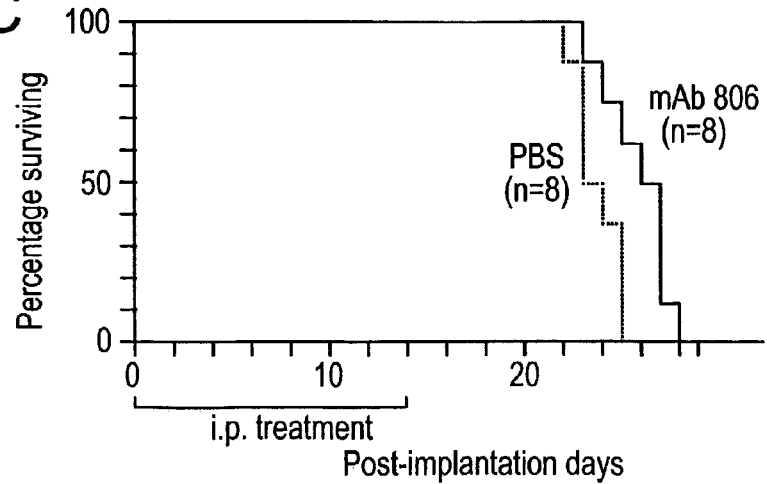

To determine whether the growth inhibition by mAb 806 was selective for tumors expressing ΔEGFR, we treated animals bearing U87 MG, U87 MG.DK (kinase-deficient ΔEGFR) or U87 MG.wtEGFR brain xenografts. mAb 806. treatment did not extend the survival of mice implanted with U87 MG tumors (FIG. 25A), which expressed a low level of endogenous wtEGFR (22), or of animals bearing U87 MG.DK xenografts, which overexpressed a kinase-deficient ΔEGFR in addition to a low level of endogenous wtEGFR (FIG. 25B). The mAb 806 treatment slightly extended the survival of mice bearing U87 MG.wtEGFR tumors (P<0.05; median survival, 23 days versus 26 days for the control groups), which overexpressed wtEGFR (FIG. 25C).

mAb 806 Reactivity Correlates with In Vivo Antitumor Efficacy.

To understand the differential effect of mAb 806 on tumors expressing various levels or different types of EGFR, we determined mAb 806 reactivity with various tumor cells by FACS analysis. Consistent with previous reports (21), the anti-EGFR mAb 528 recognized both ΔEGFR and wtEGFR and demonstrated stronger staining for U87 MG.ΔEGFR cells compared with U87 MG cells (FIG. 26A, 528). In contrast, antibody EGFR.1 reacted with wtEGFR but not with ΔEGFR (21), because U87 MG.ΔEGFR cells were as weakly reactive as U87 MG cells (FIG. 26A, panel EGFR-1). This EGFR.1 antibody reacted with U87 MG.wtEGFR more intensively than with U87 MG cells, because U87 MG.wtEGFR cells overexpressed wtEGFR (FIG. 26A, panel EGFR.1). Although mAb 806 reacted intensely with U87 MG.ΔEGFR and U87 MG.DK cells and not with U87 MG cells, it reacted weakly with U87 MG.wtEGFR, which indicated that mAb 806 is selective for ΔEGFR with a weak cross-activity to overexpressed wtEGFR (FIG. 26A, panel mAb 806). This level of reactivity with U87 MG.wtEGFR was quantitatively and qualitatively similar to the extension of survival mediated by the antibody treatment (FIG. 25C)

We further determined mAb 806 specificity by immunoprecipitation. EGFRs in various cell lines were immunoprecipitated with antibody 528, EGFR.1, and mAb 806. Blots of electrophoretically separated proteins were then probed with the anti-EGFR antibody, C13, which recognizes wtEGFR as well as ΔEGFR and DK (22). Consistent with the FACS analysis, antibody 528 recognized wtEGFR and mutant receptors (FIG. 26B—panel IP: 528), whereas antibody EGFR.1 reacted with wtEGFR but not with the mutant species (FIG. 26B, panel IP: EGFR. 1). Moreover, the levels of mutant receptors in U87 MG.ΔEGFR and U87 MG.DK cells are comparable with those of wtEGFR in the U87 MG.wtEGFR cells (FIG. 26B, panel IP: 528).

However, antibody mAb 806 was able to precipitate only a small amount of the wtEGFR from the U87 MG.wtEGFR cell lysates as compared with the larger amount of mutant receptor precipitated from U87 MG.ΔEGFR and U87 MG.DK cells, and an undetectable amount from the U87 MG cells (FIG. 26B, panel IP: mAb 806). Collectively, these data suggest that mAb 806 recognizes an epitope in ΔEGFR that also exists in a small fraction of wtEGFR only when it is overexpressed on the cell surface.

mAb 806 Treatment Reduces ΔEGFR Autophosphorylation and Down-Regulates Bcl-XL Expression in U87 MG.ΔEGFR Brain Tumors.

The mechanisms underlying the growth inhibition by mAb 806 were next investigated. Because the constitutively active kinase activity and autophosphorylation of the COOH terminus of ΔEGFR are essential for its biological functions (21, 22, 28, 29), ΔEGFR phosphorylation status was determined in tumors from treated and control animals. As shown in FIG. 27A, mAb 806 treatment dramatically reduced ΔEGFR autophosphorylation, although receptor levels were only slightly decreased in the mAb 806-treated xenografts. We have previously shown that receptor autophosphorylation causes upregulation of the antiapoptotic gene, Bcl-$X_L$, which plays a key role in reducing apoptosis of ΔEGFR-overexpressing tumors (28, 29). Therefore, the effect of mAb 806 treatment on Bcl-$X_L$ expression was next determined. ΔEGFR tumors from mAb 806-treated animals did indeed show reduced levels of Bcl-XL (FIG. 27A).

mAb 806 Treatment Decreases Growth and Angiogenesis and Increases Apoptosis in U87 MG.ΔEGFR Tumors.

In light of the in vivo suppression caused by mAb 806 treatment and its biochemical effects on receptor signaling, we determined the proliferation rate of tumors from control or treated mice. The proliferative index, measured by Ki-67 staining of the mAb 806-treated tumors, was significantly lower than that of the control tumors (P<0.001; FIG. 28). In addition, analysis of the apoptotic index through TUNEL staining demonstrated a significant increase in the number of apoptotic cells in mAb 806-treated tumors as compared with the control tumors (P<0.001; FIG. 28). The extent of tumor vascularization was also analyzed by immunostaining of tumors from treated and control specimens for CD31. To quantify tumor vascularization, MVAs were measured using computerized image analysis. mAb 806-treated tumors showed 30% less MVA than did control tumors (P<0.001; FIG. 28). To understand whether interaction between receptor and antibody may elicit an inflammatory response, we stained tumor sections for the macrophage marker, F4/80, and the NK cell marker, asialo GM1. Macrophages were identified throughout the tumor matrix and especially accumulated around the mAb 806-treated-U87 MG. ΔEGFR-tumor periphery (FIG. 28). We observed few NK cells infiltrated in and around the tumors and no significant difference between mAb 806-treated and isotype-control tumors (data not shown).

Discussion

ΔEGFR appears to be an attractive potential therapeutic target for cancer treatment of gliomas. It is correlated with poor prognosis (25), whereas its genetic or pharmacological inhibition effectively suppresses growth of ΔEGFR-overexpressing cells both in vitro and in vivo (29, 30). Because this mutant EGFR is expressed on the cell surface, it represents a potential target for antibody-based therapy, and, here, we tested the efficacy of a novel anti-ΔEGFR mAb, mAb 806, on the treatment of intracranial xenografts of ΔEGFR-overexpressing gliomas of different cellular backgrounds in nude mice. The systemic administration of mAb 806 inhibited tumor growth and extended animal survival. The effect of mAb 806 was evident for each cell line and was independent of the p53 status of the tumors, because U87 MG. ΔEGFR and A1207. ΔEGFR expressed wild-type p53, whereas LN-Z308. ΔEGFR was p53-null.

The enhanced tumorigenicity of ΔEGFR is mediated through its constitutively active kinase activity and tyrosine autophosphorylation at the COOH terminus (22, 28, 29). Phosphorylation of ΔEGFR in mAb 806-treated tumors was significantly decreased, proliferation was reduced, and apoptosis was elevated, which suggests that the antitumor effect of mAb 806 is, at least in part, attributable to the inhibition of the intrinsic function of the receptor. The ΔEGFR signaling caused up-regulation of the antiapoptotic gene, Bcl-XL (28), and treatment with mAb 806 resulted in down-regulation of Bcl-XL expression, which further suggests that the antitumor effect of mAb 806 is mediated through the inhibition of ΔEGFR signaling. The level of ΔEGFR in the mAb 806-treated tumors was also slightly reduced (FIG. 27A), but not to a degree that was consistent with the degree of dephosphorylation of the mutant receptor or sufficient to explain the magnitude of its biological effect. The antitumor effect of mAb 806 is likely to result, at least in part, from the inhibition of the intrinsic signaling function of ΔEGFR. This assertion is also supported by the lack of antitumor effects on DK tumors, which bind to the antibody but are kinase deficient.

Intratumoral injection of a different anti-ΔEGFR antibody, mAbY10, inhibited the growth of ΔEGFR-expressing B16 melanoma tumors in mouse brains through a Fc/Fc receptor-dependent mechanism (31). In conjunction with this, mAbY10 was shown to mediate antibody-dependent macrophage cytotoxicity in vitro with both murine and human effector cells (17), although it had little effect with macrophage infiltration found in our mAb 806-treated tumors raises the question as to whether the antitumor effect of mAb 806 may be accomplished by macrophage-mediated cytotoxicity. We believe this to be unlikely, because macrophage infiltration also occurred on mAb 806 treatment of U87 MG.DK (kinase-deficient ΔEGFR) tumors, in which it was ineffective in regulating tumor growth.

mAb 806 appears to be selective for ΔEGFR with a weak cross-reactivity with overexpressed wtEGFR. Consistent with the in vitro specificity, mAb 806 treatment was very effective in ΔEGFR-over-expressed tumors, whereas it showed a much less robust, but reproducible, growth inhibition for tumors overexpressing wtEGFR. However, the simple interaction between mAb 806 and its target molecules is insufficient to inhibit tumor growth because, although mAb 806 is capable of binding equally well to kinase-deficient ΔEGFR (DK) receptors and ΔEGFR, it is ineffective in affecting DK-expressing tumor growth. The inability of mAb 806 to interact with the low-level of wtEGFR normally present in cells suggests a large therapeutic window for ΔEGFR-over-expressed as well as, to a lesser extent, wtEGFR-overexpressed cancers when compared with normal tissues.

Although the mAb 806 treatment was effective for suppression of intracranial xenografts, it should be noted that the ΔEGFR-tumors eventually grew, and durable remissions were not achieved. This may have resulted from inefficient distribution of antibody in the tumor mass. mAbs in combination with other therapeutic modalities such as toxins, isotopes or drugs, for cancer treatments have been shown to be more effective than antibody alone in many cases (2, 3, 32-34). Chemotherapeutic drugs such as doxorubicin and cisplatin in conjunction with wtEGFR antibodies have also shown enhanced antitumor activity (35, 36). Combination treatments targeted at tumor growth as well as angiogenic development have more effectively inhibited glioblastoma growth than either treatment alone (27). This raises the possibility that mAb 806 in combination with chemotherapeutic drugs or compounds modulating angiogenesis may be even more effective than mAb 806 alone.

REFERENCES

1. Old, L. J. Immunotherapy for cancer. Sci. Am., 275: 102-109, 1996.
2. Weiner, L. M. An overview of monoclonal antibody therapy of cancer. Semin. Oncol., 26 (Suppl. 12): 41-50, 1999.
3. Green, M. C., Murray, J. L., and Hortobagyi, G. N. Monoclonal antibody therapy for solid tumors. Cancer Treat. Rev., 26: 269-286, 2000.
4. Ashley, D. M., Batra, S. K., and Bigner, D. D. Monoclonal antibodies to growth factors and growth factor receptors: their diagnostic and therapeutic potential in brain tumors. J. Neurooncol., 35: 259-273, 1997.
5. Fan, Z., and Mendelsohn, J. Therapeutic application of anti-growth factor receptor antibodies. Curr. Opin. Oncol., 10: 67-73, 1998.
6. Slamon, D. J., Godolphin, W., Jones, L. A., Holt, J. A., Wong, S. G., Keith, D. E., Levin, W. J., Stuart, S. G., Udove, J., Ullrich, A., and Press, M. F. Studies of the HER-2/neu proto-oncogene in human breast and ovarian cancer. Science (Wash. DC), 244: 707-712, 1989.
7. Harari, D., and Yarden, Y. Molecular mechanisms underlying ErbB2/HER2 action in breast cancer. Oncogene, 19: 6102-6114, 2000.
8. Sliwkowski, M. X., Lofgren, J. A., Lewis, G. D., Hotaling, T. E., Fendly, B. M., and Fox, J. A. Nonclinical studies addressing the mechanism of action of trastuzumab (Herceptin). Semin. Oncol., 26 (Suppl. 12): 60-70, 1999.
9. Baselga, J., Tripathy, D., Mendelsohn, J., Baughman, S., Benz, C. C, Dantis, L., Sklarin, N. T., Seidman, A. D., Hudis, C. A., Moore, J., Rosen, P. P., Twaddell, T., Henderson, I. C., and Norton, L. Phase II study of weekly intravenous recombinant humanized anti-p185HER2 monoclonal antibody in patients with HER2/neu-overexpressing metastatic breast cancer. J. Clin. Oncol., 14: 737-744, 1996.
10. Baselga, J. Clinical trials of Herceptin(R) (trastuzumab). Eur. J. Cancer, 37: 18-24, 2001.

11. Salomon, D. S., Brandt, R., Ciardiello, F., and Normanno, N. Epidermal growth factor-related peptides and their receptors in human malignancies. Crit. Rev. Oncol. Hematol., 19: 183-232, 1995.
12. Mendelsohn, J. Epidermal growth factor receptor inhibition by a monoclonal antibody as anticancer therapy. Clin. Cancer Res., 3: 2703-2707, 1997.
13. Waksal, H. W. Role of an anti-epidermal growth factor receptor in treating cancer. Cancer Metastasis Rev., 18: 427-436, 1999.
14. Faillot, T., Magdelenat, H., Mady, E., Stasiecki, P., Fohanno, D., Gropp, P., Poisson, M., and Delattre, J. Y. A Phase I study of an anti-epidermal growth factor receptor monoclonal antibody for the treatment of malignant gliomas. Neurosurgery (Baltimore), 39: 478-83, 1996.
15. Wikstrand, C. J., Reist, C. J., Archer, G. E., Zalutsky, M. R., and Bigner, D. D. The class III variant of the epidermal growth factor receptor (EGFRvIII): characterization and utilization as an immunotherapeutic target. J. Neurovirol., 4: 148-158, 1998.
16. Wong, A. J., Ruppert, J. M., Bigner, S. H., Grzeschik, C. H., Humphrey, P. A., Bigner, D. S., and Vogelstein, B. Structural alterations of the epidermal growth factor receptor gene in human gliomas. Proc. Natl. Acad. Sci. USA, 89: 2965-2969, 1992.
17. Wikstrand, C. J., Cokgor, I., Sampson, J. H., and Bigner, D. D. Monoclonal antibody therapy of human gliomas: current status and future approaches. Cancer Metastasis Rev., 18: 451-464, 1999.
18. Garcia de Palazzo, I. E., Adams, G. P., Sundareshan, P., Wong, A. J, Testa, J. R., Bigner, D. D., and Weiner, L. M. Expression of mutated epidermal growth factor receptor by non-small cell lung carcinomas. Cancer Res., 53: 3217-3220, 1993.
19. Moscatello, D. K., Holgado-Madruga, M., Godwin, A. K., Ramirez, G., Gunn, G., Zoltick, P. W., Biegel, J. A., Hayes, R. L., and Wong, A. J. Frequent expression of a mutant epidermal growth factor receptor in multiple human tumors. Cancer Res., 55: 5536-5539, 1995.
20. Olapade-Olaopa, E. O., Moscatello, D. K., MacKay, E. H., Horsburgh, T., Sandhu, D. P., Terry, T. R., Wong, A. J., and Habib, F. K. Evidence for the differential expression of a variant EGF receptor protein in human prostate cancer. Br. J. Cancer, 82: 186-194, 2000.
21. Nishikawa, R., Ji, X. D., Harmon, R. C., Lazar, C. S, Gill, G. N., Cavenee, W. K., and Huang, H. J. A mutant epidermal growth factor receptor common in human glioma confers enhanced tumorigenicity. Proc. Natl. Acad. Sci. USA, 91: 7727-7731, 1994.
22. Huang, H.-J. S., Nagane, M., Klingbeil, C. K., Lin, H., Nishikawa, R., Ji, X. D., Huang, C. M., Gill, G. N., Wiley, H. S., and Cavenee, W. K. The enhanced tumorigenic activity of a mutant epidermal growth factor receptor common in human cancers is mediated by threshold levels of constitutive tyrosine phosphorylation and unattenuated signaling. J. Biol. Chem., 272: 2927-2935, 1997.
23. Mishima, K. Nagane, M., Lin, H., Cavenee, W. K., and Huang, H-J. S. Expression of a tumor-specific mutant epidermal growth factor receptor mediates glioma cell invasion in vivo. Proc. Am. Assoc. Cancer Res., 40: 519, 1999.
24. Han, Y., Caday, C. G., Nanda, A., Cavenee, W. K., and Huang, H. J. Tyrphostin AG1478 preferentially inhibits human glioma cells expressing truncated rather than wild-type epidermal growth factor receptors. Cancer Res., 56: 3859-3861, 1996.
25. Feldkamp, M. M., Lala, P., Lau, N., Roncari, L., and Guha, A. Expression of activated epidermal growth factor receptors, Ras-guanosine triphosphate, and mitogen-activated protein kinase in human glioblastoma multiforme specimens. Neurosurgery (Baltimore), 45: 1442-1453, 1999.
26. Nagane, M., Levitzki, A., Gazit, A., Cavenee, W. K., and Huang, H-J. S. Drug resistance of human glioblastoma cells conferred by a tumor-specific mutant epidermal growth factor receptor through modulation of Bcl-XL and caspase-3-like pro-teases. Proc. Natl. Acad. Sci. USA, 95: 5724-5729, 1998.
27. Mishima, K., Mazar, A. P., Gown, A., Skelly, M., Ji, X. D., Wang, X. D., Jones, T. R., Cavenee, W. K., and Huang, H-J. S. A peptide derived from the non-receptor-binding region of urokinase plasminogen activator inhibits glioblastoma growth and angiogenesis in vivo in combination with cis-platin. Proc. Natl. Acad. Sci. USA, 97: 8484-8489, 2000.
28. Nagane, M., Coufal, F., Lin, H., Bogler, O., Cavenee, W. K., and Huang, H-J. S. A common mutant epidermal growth factor receptor confers enhanced tumorigenicity on human glioblastoma cells by increasing proliferation and reducing apoptosis. Cancer Res., 56: 5079-5086, 1996.
29. Nagane, M., Lin, H., Cavenee, W. K., and Huang, H-J. S. Aberrant receptor signaling in human malignant gliomas: mechanisms and therapeutic implications. Cancer Lett., 162 (Suppl. 1): S17-S21, 2001.
30. Halatsch, M. E., Schmidt, U., Botefur, I. C., Holland, J. F., and Ohnuma, T. Marked inhibition of glioblastoma target cell tumorigenicity in vitro by retrovirus-mediated transfer of a hairpin ribozyme against deletion-mutant epidermal growth factor receptor messenger RNA. J. Neurosurg., 92: 297-305, 2000.
31. Sampson, J. H, Crotty, L. E., Lee, S., Archer, G. E., Ashley, D. M., Wikstrand, C. J., Hale, L. P., Small, C., Dranoff, G., Friedman, A. H., Friedman, H. S., and Bigner, D. D. Unarmed, tumor-specific monoclonal antibody effectively treats brain tumors. Proc. Natl. Acad. Sci. USA, 97: 7503-7508, 2000.
32. Trail, P. A, and Bianchi, A. B. Monoclonal antibody drug conjugates in the treatment of cancer. Curr. Opin. Immunol., 11: 584-588, 1999.
33. Pietras, R. J., Pegram, M. D., Finn, R. S., Maneval, D. A., and Slamon, D. J. Remission of human breast cancer xenografts on therapy with humanized monoclonal antibody to HER-2 receptor and DNA-reactive drugs. Oncogene, 17: 2235-2249, 1998.
34. Baselga, J., Norton, L., Albanell, J., Kim, Y. M., and Mendelsohn, J. Recombinant humanized anti-HER2 antibody (Herceptin) enhances the antitumor activity of paclitaxel and doxorubicin against HER2/neu overexpressing human breast cancer xenografts. Cancer Res., 58: 2825-2831, 1998.
35. Baselga, J., Norton, L., Masui, H., Pandiella, A., Coplan, K., Miller, W. H., and Mendelsohn, J. Antitumor effects of doxorubicin in combination with anti-epidermal growth factor receptor monoclonal antibodies. J. Natl. Cancer Inst. (Bethesda), 85: 1327-1333, 1993.
36. Fan, Baselga, J., Masui, H., and Mendelsohn, J. Antitumor effect of anti-epidermal growth factor receptor monoclonal antibodies plus cis-diamminedichloroplatinum on well established A431 cell xenografts. Cancer Res., 53: 4637-4642, 1993.

EXAMPLE 20

Monoclonal Antibody 806 Inhibits the Growth of Tumor Xenografts Expressing Either the DE 2-70R Amplified Epidermal Growth Factor Receptor (EGFR) But Not Wild-Type EGFR The following example presents findings by the present inventors that is also set forth in Luwor et al., (2001) Cancer Research, 61:5355-5361. The disclosure of this publication is incorporated herein in its entirety with cross referencing to the Figures herein where appropriate and made a part hereof.

The monoclonal antibody (mAb) 806 was raised against the delta2-7 epidermal growth factor receptor (de2-7 EGFR or EGFRvIII), a truncated version of the EGFR commonly expressed in glioma. Unexpectedly, mAb 806 also bound the EGFR expressed by cells exhibiting amplification of the EGFR gene but not to cells or normal tissue expressing the wild-type receptor in the absence of gene amplification. The unique specificity of mAb 806 offers an advantage over current EGFR antibodies, which all display significant binding to the liver and skin in humans. Therefore, we examined the antitumor activity of mAb 806 against human tumor xenografts grown in nude mice. The growth of U87 MG xenografts, a glioma cell line that endogenously expresses ~$10^5$ EGFRs in the absence of gene amplification, was not inhibited by mAb 806. In contrast, mAb 806 significantly inhibited the growth of U87 MG xenografts transfected with the de2-7 EGFR in a dose-dependent manner using both preventative and established tumor models. Significantly, U87 MG cells transfected with the wild-type EGFR, which increased expression to ~$10^6$ EGFRs/cell and mimics the situation of gene amplification, were also inhibited by mAb 806 when grown as xenografts in nude mice. Xenografts treated with mAb 806 all displayed large areas of necrosis that were absent in control tumors. This reduced xenograft viability was not mediated by receptor down-regulation or clonal selection because levels of antigen expression were similar in control and treated groups. The antitumor effect of mAb 806 was not restricted to U87 MG cells because the antibody inhibited the growth of new and established A431 xenografts, a cell line expressing>$10^6$ EGFRs/cell. This study demonstrates that mAb 806 possesses significant antitumor activity.

The de2-7 EGFR specific mAb 806 was produced after immunization of mice with NR6 mouse fibroblasts expressing the truncated de2-7 EGFR. mAb 806 binds the U87 MG glioma cell line transfected with the de2-7 EGFR but not the parental U87 MG cell line, which expresses the wt EGFR without gene amplification.[3] Similar results were observed in vivo with mAb 806 showing specific targeting of de2-7 EGFR expressing U87 MG xenografts but not parental U87 MG tumors.[3] Interestingly, mAb 806 was capable of binding an EGFR subset (~10%) on the surface of the A431 cell line, which contains an amplified EGFR gene. Therefore, unlike all other de2-7 EGFR-specific antibodies, which recognize the unique peptide junction that is generated by the de2-7 EGFR truncation, mAb 806 binds to an epitope also found in overexpressed wt EGFR. However, it would appear that this epitope is preferentially exposed in the de2-7 EGFR and a small proportion of receptors expressed in cells containing wt EGFR gene amplification. Importantly, normal tissues that expresses high levels of endogenous wt EFGR, such as liver and skin, show no significant mAb 806 binding. On the basis of the unique property of the mAb 806 to bind both the de2-7 and amplified wt EGFR but not the native wt EGFR when expressed at normal levels, we decided to examine the efficacy of mAb 806 against several tumor cell lines grown as xenografts in nude mice.

Materials and Methods

Cell Lines and Monoclonal Antibodies. The human glioblastoma cell line U87 MG, which endogenously expresses the wt EGFR, and the transfected cell lines U87 MG.Δ2-7 and U87 MG.wtEGFR, which express the de2-7 EGFR and overexpress the wt EGFR, respectively, have been described previously (16, 23). The epidermoid carcinoma cell line A431 has been described previously (24).

All cell lines were maintained in DMEM (DMEM/F12; Life Technologies, Inc., Grand Island, N.Y.) containing 10% FCS(CSL, Melbourne, Victoria, Australia), 2 mM glutamine (Sigma Chemical Co., St. Louis, Mo.), and peni-cillin/streptomycin (Life Technologies, Inc., Grand Island, N.Y.). In addition, the U87 MG.D2-7 and U87 MG.wtEGFR cell lines were maintained in 400 mg/ml of Geneticin™ geneticin (Life Technologies, Inc., Melbourne, Victoria, Australia).

Cell lines were grown at 37° C. in a humidified atmosphere of 5% $CO_2$. The mAb 806 (IgG2b) was produced after immunization of mice with NR6 mouse fibroblasts expressing the de2-7 EGFR. mAb 806 was selected after rosette assays showed binding to NR6 cells, which overexpressed the de2-7 EGFR (titer of 1:2500). mAb 528, which recognizes both de2-7 and wt EGFR, has been described previously (10) and was produced in the Biological Production Facility (Ludwig Institute for Cancer Research, Melbourne, Victoria, Australia) using a hybridoma obtained from American Type Culture Collection (Rockville, Md.). The DH8.3 mAb, which is specific for the de2-7 EGFR, was kindly provided by Prof. William Gullick (University of Kent and Canterbury, Kent, United Kingdom) (19). The polyclonal antibody sc-03 directed to the COOH-terminal domain of the EGFR was purchased from Santa Cruz Bio-technology (Santa Cruz Bio-technology, Santa Cruz, Calif.).

FACS Analysis of Receptor Expression. Cultured parental and trans-fected U87 MG cell lines were analyzed for wt and de2-7 EGFR expression using the 528, 806, and DH8.3 antibodies. Cells (1 3 10 6) were incubated with 5 mg/ml of the appropriate antibody or an isotype-matched negative control in PBS containing 1% HSA for 30 min at 4° C. After three washes with PB S/1% HSA, cells were incubated an additional 30 min at 4° C. with FITC-coupled goat antimouse antibody (1:100 dilution; Calbiochem, San Diego, Calif.). After three subsequent washes, cells were analyzed on an Epics Elite ESP (Beckman Coulter, Hialeah, Fla.) by observing a minimum of 20,000 events and analyzed using EXPO (version 2) for Windows.

Scatchard Analysis. The mAb 806 was labeled with 125 I (Amrad, MeI-bourne, Victoria, Australia) by the Chloramine T method. All binding assays were performed in 1% HSA/ PBS on 1-2×$10^6$ live U87 MG.Δ2-7 or A431 cells for 90 min at 4° C. with gentle rotation. A set concentration of 10 ng/ml 125 I-labeled mAb 806 was used in the presence of increasing concentrations of unlabeled antibody. Nonspecific binding was determined in the presence of 10,000-fold excess of unlabeled antibody. After incubation, cells were washed and counted for bound 125 I-labeled mAb 806 using a COBRA II gamma counter (Packard Instrument Company, Meriden, Conn.). Scatchard analysis was done after correction for immunoreactivity.

Immunoprecipitation Studies. Cells were labeled for 16 h with 100 mCi/ml of Tran 35 S-Label (ICN Biomedicals, Irvine, Calif.) in DMEM without methionine/cysteine supplemented with 5% dialyzed FCS. After washing with PBS, cells were placed in lysis buffer (1% Triton X-100, 30 mM HEPES, 150 mM NaCl, 500 mM 4-(2-aminoethyl)benzenesulfonylfluoride, 150 nM aprotinin, 1 mM E-64 protease inhibitor, 0.5 mM EDTA, and 1 mM leupeptin, pH 7.4) for 1 h at 4° C. Lysates were clarified by centrifugation for 10 min at 12,000 3 g and then incubated with 5 mg of appropriate antibody for 30 min at 4° C. before the addition of protein A-Sepharose. Immunoprecipitates were washed three times with lysis buffer, mixed with SDS sample buffer, separated by gel electrophoresis using a 7.5% gel that was then dried, and exposed to X-ray film.

Xenograft Models. Consistent with previous reports (23, 25), U87 MG cells transfected with de2-7 EGFR grew more rapidly then parental cells and U87 MG cells transfected with the wt EGFR. Tumor cells ($3\times10^6$) in 100 ml of PBS were inoculated s.c. into both flanks of 4-6-week-old, female nude mice (Animal Research Center, Western Australia, Perth, Australia). Therapeutic efficacy of mAb 806 was investigated in both preventative and established tumor models. In the preventative model, five mice with two xenografts each were treated i.p. with either 0.1 or 1 mg of mAb 806 or vehicle (PBS) starting the day before tumor cell inoculation. Treatment was continued for a total of six doses, three times per week for 2 weeks. In the established model, treatment was started when tumors had reached a mean volume of 65 mm 3 (U87 MG.Δ2-7), 84 mm 3 (U87 MG), 73 mm 3 (U87 MG.wtEGFR), or 201 mm 3 (A431 tumors). Tumor volume in mm 3 was determined using the formula (length 3 width 2)/2, where length was the longest axis and width the measurement at right angles to the length (26). Data were expressed as mean tumor volume 6 SE for each treatment group. This research project was approved by the Animal Ethics Committee of the Austin and Repatriation Medical Centre.

Histological Examination of Tumor Xenografts. Xenografts were excised at the times indicated and bisected. One half was fixed in 10% formalin/BS before being embedded in paraffin. Four-mm sections were then cut and stained with H&E for routine histological examination. The other half was embedded in Tissue Tek OCT compound (Sakura Finetek, Torrance, Calif.), frozen in liquid nitrogen, and stored at 280° C. Thin (5-mm) cryostat sections were cut and fixed in ice-cold acetone for 10 min, followed by air drying for an additional 10 min. Sections were blocked in protein blocking reagent (Lipshaw Immunon, Pittsburgh, Pa.) for 10 min and then incubated with biotinylated primary antibody (1 mg/ml) for 30 min at room temperature. All antibodies were biotinylated using the ECL protein biotinylation module (Amersham, Baulkham Hills, NSW, Australia), as per the manufacturer's instructions. After rinsing with PBS, sections were incubated with a streptavidin-horseradish peroxidase complex for an additional 30 min (Silenus, Melbourne, Victoria, Australia). After a final PBS wash, the sections were exposed to 3-amino-9-ethylcarbazole substrate [0.1 M acetic acid, 0.1 M sodium acetate, 0.02 M 3-amino-9-ethylcarbazole (Sigma Chemical Co., St. Louis, Mo.)] in the presence of hydrogen peroxide for 30 min. Sections were rinsed with water and counterstained with hematoxylin for 5 min and mounted.

Statistical Analysis. The in vivo tumor measurements in mm 3 are ex-pressed as the mean 6 SE. Differences between treatment groups at given time points were tested for statistical significance using Student's t test.

Results

Binding of Antibodies to Cell Lines. To determine the specificity of mAb 806, its binding to U87 MG, U87 MG.D2-7, and U87 MG.wtEGFR cells was analyzed by FACS. An irrelevant IgG2b (mAb 100-310 directed to the human antigen A33) was included as an isotype control for mAb 806, and the 528 antibody was included because it recognizes both the de2-7 and wt EGFR. Only the 528 antibody was able to stain the parental U87 MG cell line (FIG. 29), consistent with previous reports demonstrating that these cells express the wt EGFR (16). mAb 806 had binding levels similar to the control antibody, clearly demonstrating that it is unable to bind the wt EGFR (FIG. 29). Binding of the isotype control antibody to the U87 MG.D2-7 and U87 MG.wtEGFR cell lines was similar to that observed for the U87 MG cells. mAb 806 stained U87 MG.D2-7 and U87 MG. wtEGFR cells, indicating that mAb 806 specifically recognized the de2-7 EGFR and a subset of the overexpressed EGFR (FIG. 29). As expected, the 528 antibody stained both the U87 MG.D2-7 and U87 MG.wtEGFR cell lines (FIG. 29). The intensity of 528 antibody staining on U87 MG.wtEGFR cells was much higher than mAb 806, suggesting that mAb 806 only recognizes a portion of the overexpressed EGFR. The mAb 806 reactivity observed with U87 MG.wtEGFR cells is similar to that obtained with A431 cells, another cell line that overexpresses the wt EGFR.3

A Scatchard analysis was performed using U87 MG.D2-7 and A431 cells to determine the relative affinity and binding sites for mAb 806 on each cell line. mAb 806 had an affinity for the de2-7 EGFR receptor of $1.1\times10^9$ $M^{-1}$ and recognized an average (three separate experiments) of $2.4\times10^5$ binding sites/cell. In contrast, the affinity of mAb 806 for the wt EGFR on A431 cells was only $9.5\times10^7$ $M^{-1}$. Interestingly, mAb 806 recognized $2.3\times10^5$ binding sites on the surface of A431, which is some 10-fold lower than the reported number of EGFR found in these cells. To confirm the number of EGFR on the surface of our A431 cells, we performed a Scatchard analysis using $^{125}$I-labeled 528 antibody. As expected, this antibody bound to approximately $2\times10^6$ sites on the surface of A431 cells. Thus, it appears that mAb 806 only binds a portion of the EGFR receptors on the surface of A431 cells. Importantly, $^{125}$I-labeled mAb 806 did not bind to the parental U87 MG cells at all, even when the number of cells was increased to $1\times10^7$.

Immunoprecipitations. We further characterized mAb 806 reactivity in the various cell lines by immunoprecipitation after 35 S-labeling using mAb 806, sc-03 (a commercial polyclonal antibody specific for the COOH-terminal domain of the EGFR) and a IgG2b isotype control. The sc-03 antibody immunoprecipitated three bands from U87 MG.Δ2-7 cells, a doublet corresponding to the two de2-7 EGFR bands observed in these cells and a higher molecular weight band corresponding to the wt EGFR (FIG. 30). In contrast, although mAb 806 immunoprecipitated the two de2-7 EGFR bands, the wt EGFR was completely absent (FIG. 30). The pattern seen in U87 MG.wtEGFR and A431 cells was essentially identical. The sc-03 antibody immunoprecipitated a single band corresponding to the wt EGFR from both cell lines (FIG. 30). The mAb 806 also immunoprecipitated a single band corresponding to the wt EGFR from both U87 MG.wtEGFR and A431 cells (FIG. 30). Consistent with the FACS and Scatchard data, the amount of EGFR immunoprecipitated by mAb 806 was substantially less than the total EGFR present on the cell surface. Given that mAb 806 and the sc-03 immunoprecipitated similar amounts of the de2-7 EGFR, this result supports the notion that the mAb 806 antibody only recognizes a portion of the EGFR in cells overexpressing the receptor. Comparisons between mAb 806 and the 528 antibody showed an identical pattern of reactivity (data not shown). An irrelevant IgG2b (an isotype control for mAb 806) did not immunoprecipitate EGFR from any of the cell lines (FIG. 30). Using identical conditions, mAb 806 did not immunoprecipitate the EGFR from the parental U87 MG cells (data not shown).

Efficacy of mAb 806 in Preventative Models. mAb 806 was examined for efficacy against U87 MG and U87 MG.Δ2-7 tumors in a preventative xenograft model. Antibody or vehicle was administered i.p. the day before tumor inoculation and was given three times per week for 2 weeks (see "Materials and Methods"). At a dose of 1 mg/injection, mAb 806 had no effect on the growth of parental U87 MG xenografts that express the wt EGFR (FIG. 9A). In contrast, mAb 806 inhibited significantly the growth of U87 MG.Δ2-7 xenografts in a dose-dependent manner (FIG. 9B). Twenty days after tumor inoculation, when control animals were sacrificed, the mean tumor volume was 1600±180 mm$^3$ for the control group, a significantly smaller 500±95 mm$^3$ for the 0.1 mg/injection group (P<0.0001) and 200±42 mm$^3$ for the 1 mg/injection group (P<0.0001). Treatment groups were sacrificed at day 24, at which time the mean tumor volumes were 1300±240 mm 3 for the 0.1 mg treated group and 500±100 mm$^3$ for the 1 mg group (P<0.005).

Efficacy of mAb 806 in Established Xenograft Models. Given the efficacy of mAb 806 in the preventative xenograft model, its ability to inhibit the growth of established tumor xenografts was examined. Antibody treatment was as described in the preventative model, except that it commenced when tumors had reached a mean tumor volume of 65 mm$^3$ (10 days after implantation) for the U87 MG.Δ2-7 xenografts and 84 mm$^3$ (19 days after implantation) for the parental U87 MG xenografts. Once again, mAb 806 had no effect on the growth of parental U87 MG xenografts, even at a dose of 1 mg/injection (FIG. 10A). In contrast, mAb 806 significantly inhibited the growth of U87 MG.Δ2-7 xenografts in a dose-dependent manner (FIG. 10B). At day 17, 1 day before control animals were sacrificed, the mean tumor volume was 900±200 mm$^3$ for the control group, 400±60 mm$^3$ for the 0.1 mg/injection group (P<0.01), and 220±60 mm$^3$ for the 1 mg/injection group (P<0.002). Treatment of U87 MG.Δ2-7 xenografts with an IgG2b isotype control had no effect on tumor growth (data not shown).

To examine whether the growth inhibition observed with mAb 806 was restricted to cells expressing de2-7 EGFR, its efficacy against the U87 MG.wtEGFR xenografts was also examined in an established model. These cells serve as a model for tumors containing amplification of the EGFR gene without de2-7 EGFR expression. mAb 806 treatment commenced when tumors had reached a mean tumor volume of 73 mm 3 (22 days after implantation). mAb 806 significantly inhibited the growth of established U87 MG.wtEGFR xenografts when compared with control tumors treated with vehicle (FIG. 10C). On the day control animals were sacrificed, the mean tumor volume was 1000±300 mm$^3$ for the control group and 500±80 mm$^3$ for the group treated with 1 mg/injection (P<0.04).

Histological and Immunohistochemical Analysis of Established Tumors. To evaluate potential histological differences between mAb 806-treated and control U87 MG.Δ2-7 and U87 MG.wtEGFR xenografts, formalin-fixed, paraffin-embedded sections were stained with H&E (FIG. 31). Areas of necrosis were seen in sections from mAb 806-treated U87 MG.Δ2-7 (mAb 806-treated xenografts were collected 24 days after tumor inoculation and vehicle treated xenografts at 18 days), and U87 MG.wtEGFR xenografts (mAb 806 xenografts were collected 42 days after tumor inoculation and vehicle treated xenografts at 37 days; FIG. 31). This result was consistently observed in a number of tumor xenografts (n 5 4 for each cell line). However, sections from U87 MG.Δ2-7 and U87 MG.wtEGFR xenografts treated with vehicle (n 5 5) did not display the same areas of necrosis seen after mAb 806 treatment (FIG. 31). Vehicle and mAb 806-treated xenografts removed at identical times also showed these differences in tumor necrosis (data not shown). Thus, the increase in necrosis observed was not caused by the longer growth periods used for the mAb 806-treated xenografts. Furthermore, sections from mAb 806-treated U87 MG xenografts were also stained with H&E and did not reveal any areas of necrosis (data not shown), further supporting the hypothesis that mAb 806 binding induces decreased cell viability, resulting in increased necrosis within tumor xenografts.

An immunohistochemical analysis of U87 MG, U87 MG.Δ2-7, and U87 MG.wtEGFR xenograft sections was performed to determine the levels of de2-7 and wt EGFR expression after mAb 806 treatment (FIG. 32). As expected, the 528 antibody stained all xenografts sections with no obvious decrease in intensity between treated and control tumors (FIG. 32). Staining of U87 MG sections was undetectable with the mAb 806; however, positive staining of U87 MG.Δ2-7 and U87 MG.wtEGFR xenograft sections was observed (FIG. 32). There was no difference in mAb 806 staining intensity between control and treated U87 MG.Δ2-7 and U87 MG.wtEGFR xenografts, suggesting that antibody treatment does not lead to the selection of clonal variants lacking mAb 806 reactivity.

Treatment of A431 Xenografts with mAb 806. To demonstrate that the antitumor effects of mAb 806 were not restricted to U87 MG cells, the antibody was administrated to mice containing A431 xe-nografts. These cells contain an amplified EGFR gene and express approximately $2 \times 10^6$ receptors/cells. We have previously shown that mAb 806 binds 10% of these EGFRs and targets A431 xenografts.(3) mAb 806 significantly inhibited the growth of A431 xenografts when examined in the preventative xenograft model described previously (FIG. 11A). At day 13, when control animals were sacrificed, the mean tumor volume was 1400±150 mm$^3$ in the vehicle-treated group and 260±60 mm$^3$ for the 1 mg/injection treatment group (P<0.0001). In a separate experiment, a dose of 0.1 mg of mAb also inhibited significantly (P<0.05) the growth of A431 xenografts in a preventative model (data not shown).

Given the efficacy of mAb 806 in the preventative A431 xenograft model, its ability to inhibit the growth of established tumor xenografts was examined. Antibody treatment was as described in the preventative model, except it was not started until tumors had reached a mean tumor volume of 200±20 mm$^3$. mAb 806 significantly inhibited the growth of established A431 xenografts (FIG. 11B). At day 13, the day control animals were sacrificed, the mean tumor volume was 1100±100 mm 3 for the control group and 450±70 mm$^3$ for the 1 mg/injection group (P<0.0001).

We have shown previously[3] that mAb 806 targets both de2-7 EGFR-transfected U87 MG xenografts and A431 xenografts that over express the wt EGFR. mAb 806 did not target parental U87 MG cells, which express ~$10^5$ EGFR[3] (16). As assessed by FACS, immunohistochemistry, and immunoprecipitation, we now demonstrate that mAb 806 is also able to specifically bind U87 MG.wtEGFR cells, which express>$10^6$ EGFRs/cell. Thus, the previous observed binding of mAb 806 to A431 cells is not the result of some unusual property of these cells but rather appears to be a more general phenomenon related to over expression of the wt EGFR.

(a) We were unable to detect mAb 806 binding to the parental U87 MG cell line, which expresses $1 \times 10^5$ wt EGFRs/cell (16), either by FACS, immunoprecipitation, immunohistochemistry, or with iodinated antibody. Indeed, iodinated mAb 806 did not bind to U87 MG cell pellets containing 1×10$^7$ cells, which based on the Scatchard data using 1×10$^6$ A431 cells, are conditions that should detect low level antibody binding (i.e., the total number of receptors being similar in both cases).

(b) Scatchard analysis clearly showed that mAb 806 only bound to 10% of the total EGFR on the surface of A431 cells. If mAb 806 simply binds to the wt EGFR with low affinity, then it should have bound to a considerably higher percentage of the receptor.

(c) Comparative immunoprecipitation of the A431 and U87 MG. wtEGFR cell lines with mAb 806 and the sc-03 antibody also supported the hypothesis that only a subset of receptors are recognized by mAb 806. Taken together, these results support the notion that mAb 806 recognizes a EGFR subset on the surface of cells overexpressing the EGFR. We are currently analyzing the EGFR immunoprecipitated by mAb 806 to see if it displays altered biochemical properties related to glycosylation or kinase activity.

The xenograft studies with mAb 806 described here demonstrate dose-dependent inhibition of U87 MG.D2-7 xenograft growth. In contrast, no inhibition of parental U87 MG xenografts was observed, despite the fact that they continue to express the wt EGFR in vivo. mAb 806 not only significantly reduced xenograft volume, it also induced significant necrosis within the tumor. As noted above, other de2-7 EGFR-specific mAbs have been generated (20-22), but this is the first report showing the successful therapeutic use of such an antibody in vivo against a human de2-7 EGFR-expressing glioma xenograft. A recent report demonstrated that the de2-7 EGFR-specific Y10 mAb had in vivo antitumor activity against murine B16 melanoma cells transfected with a murine homologue of the human de2-7 EGFR (33). Y10 mediated in vitro cell lysis (>90%) of B16 melanoma cells expressing the de2-7 EGFR in the absence of complement or effector cells. In contrast to their in vitro observations, the in vivo Y10 antibody efficacy was completely mediated through Fc function when using B16 melanoma cells grown as xenografts in an immuno-competent model. Thus, the direct effects observed in vitro do not seem to be replicated when cells are grown as tumor xenografts.

Overexpression of the EGFR has been reported in a number of different tumors and is observed in most gliomas (4, 14). It has been proposed that the subsequent EGFR over expression mediated by receptor gene amplification may confer a growth advantage by increasing intracellular signaling and cell growth (34). The U87 MG cell line was transfected with the wt EGFR to produce a glioma cell that mimics the process of EGFR gene amplification. Treatment of established U87 MG.wtEGFR xenografts with mAb 806 resulted in significant growth inhibition. Thus, mAb 806 also mediates in vivo antitumor activity against cells overexpressing the EGFR. Interestingly, mAb 806 inhibition of U87 MG.wtEGFR xenografts was less pronounced than that observed with U87 MG.Δ2-7 tumors. This probably reflects the fact that mAb 806 has a lower affinity for the overexpressed wt EGFR and only binds a small proportion of receptors expressed on the cell surface.(3) However, it should be noted that despite the small effect on U87 MG.wtEGFR xenograft volumes, mAb 806 treatment produced large areas of necrosis within these xenografts. To exclude the possibility that mAb 806 only mediates inhibition of the U87 MG-derived cell lines, we tested its efficacy against A431 xenografts. This squamous cell carcinoma-derived cell line contains significant EGFR gene amplification, which is retained both in vitro and in vivo. Treatment of A431 xenografts with mAb 806 produced significant growth inhibition in both a preventative and established model, indicating the antitumor effects of mAb 806 are not restricted to transfected U87 MG cell lines.

Complete prevention of A431 xenograft growth by antibody treatment has been reported previously. The wt EGFR mAbs 528, 225, and 425 all prevented the formation of A431 xenografts when administered either on the day or 1 day after tumor inoculation (9, 10). The reason for this difference in efficacy between these wt EGFR anti-bodies and mAb 806 is not known but may be related to the mechanism of cell growth inhibition. The wt EGFR antibodies function by blocking ligand binding to the EGFR, but this is probably not the case with mAb 806 because it only binds a small EGFR subset on the surface of A431 cells. The significant efficacy of mAb 806 against U87 MG cells expressing the ligand-independent de2-7 EGFR further supports the notion that this antibody mediates its antitumor activity by a mechanism not involving ligand blockade. Therefore, we are currently investigating the nonimmunological and immunological mechanisms that contribute to the antitumor effects of mAb 806. Nonimmunological mechanisms may include subtle changes in receptor levels, blockade of signaling, or induction of inappropriate signaling.

Previously, agents such as doxorubicin and cisplatin in conjunction with wt EGFR antibodies have produced enhanced antitumor activity (35, 36). The combination of doxorubicin and mAb 528 resulted in total eradication of established A431 xenografts, whereas treatment with either agent alone caused only temporary in vivo growth inhibition (36). Likewise, the combination of cisplatin and either mAb 528 or 225 also led to the eradication of well-established A431 xenografts, which was not observed when treatment with either agent was used (35). Thus, future studies involving the combination of chemotherapeutic agents with mAb 806 are planned using xenograft models.

Maybe the most important advantage of mAb 806 compared with current EGFR antibodies is that it should be possible to directly conjugate cytotoxic agents to mAb 806. This approach is not feasible with current EGFR-specific antibodies because they target the liver and cytotoxic conjugation would almost certainly induce severe toxicity. Conjugation of cytotoxic agents such as drugs (37) or radioisotopes (38) to antibodies has the potential to improve efficacy and reduce the systemic toxicity of these agents. This study clearly demonstrates that mAb 806 has significant in vivo antitumor activity against de2-7 EGFR-positive xenografts and tumors overexpressing the EGFR. The unique specificity of mAb 806 suggests immunotherapeutic potential in targeting a number of tumor types, particularly head and neck tumors and glioma, without the restrictions associated with normal tissue uptake.

REFERENCES

1. Scott, A. M., and Welt, S. Antibody-based immunological therapies. Curr. Opin. Immunol., 9: 717-722, 1997.
2. Fan, Z., and Mendelsohn, J. Therapeutic application of anti-growth factor receptor antibodies. Curr. Opin. Oncol., 10: 67-73, 1998.
3. Garcia de Palazzo, I. E., Adams, G. P., Sundareshan, P., Wong, A. J., Testa, J. R., Bigner, D. D., and Weiner, L. M. Expression of mutated epidermal growth factor receptor by non-small cell lung carcinomas. Cancer Res., 53: 3217-3220, 1993.
4. Wikstrand, C. J., Reist, C. J., Archer, G. E., Zalutsky, M. R., and Bigner, D. D. The class III variant of the epidermal growth factor receptor (EGFRvIII): characterization and utilization as an immunotherapeutic target. J. Neurovirol., 4: 148-158, 1998.

5. Korshunov, A., Golanov, A., Sycheva, R., and Pronin, I. Prognostic value of tumor associated antigen immunoreactivity and apoptosis in cerebral glioblastomas: an analysis of 168 cases. J. Clin. Pathol., 52: 574-580, 1999.

6. Grandis, J. R., Melhem, M. F., Gooding, W. E., Day, R., Holst, V. A., Wagener, M. M., Drenning, S. D., and Tweardy, D. J. Levels of TGF-a and EGFR protein in head and neck squamous cell carcinoma and patient survival. J. Natl. Cancer Inst., 90: 824-832, 1998.

7. Fan, Z., Masui, H., Altas, I., and Mendelsohn, J. Blockade of epidermal growth factor receptor function by bivalent and monovalent fragments of 225 anti-epidermal growth factor receptor monoclonal antibodies. Cancer Res., 53: 4322-4328, 1993.

8. Teramoto, T., Onda, M., Tokunaga, A., and Asano, G. Inhibitory effect of anti-epidermal growth factor receptor antibody on a human gastric cancer. Cancer (Phila.), 77: 1639-1645, 1996.

9. Rodeck, U., Herlyn, M., Herlyn, D., Molthoff, C., Atkinson, B., Varello, M., Steplewski, Z., and Koprowski, H. Tumor growth modulation by a monoclonal antibody to the epidermal growth factor receptor: immunologically mediated and effector cell-independent effects. Cancer Res., 47: 3692-3696, 1987.

10. Masui, H., Kawamoto, T., Sato, J. D., Wolf, B., Sato, G., and Mendelsohn, J. Growth inhibition of human tumor cells in athymic mice by anti-epidermal growth factor receptor monoclonal antibodies. Cancer Res., 44: 1002-1007, 1984.

11. Faillot, T., Magdelenat, H., Mady, E., Stasiecki, P., Fohanno, D., Gropp, P., Poisson, M., and Delattre, J. Y. A Phase I study of an anti-epidermal growth factor receptor monoclonal antibody for the treatment of malignant gliomas. Neurosurgery, 39: 478-483, 1996.

12. Divgi, C. R., Welt, S., Kris, M., Real, F. X., Yeh, S. D., Gralla, R., Merchant, B., Schweighart, S., Unger, M., Larson, S. M., et al. Phase I and imaging trial of indium 11-labeled anti-epidermal growth factor receptor monoclonal antibody 225 in patients with squamous cell lung carcinoma. J. Natl. Cancer Inst., 83: 97-104, 1991.

13. Baselga, J., Pfister, D., Cooper, M. R., Cohen, R., Burtness, B., Bos, M., D'Andrea, G., Seidman, A., Norton, L., Gunnett, K., Falcey, J., Anderson, V., Waksal, H., and Mendelsohn, J. Phase I studies of anti-epidermal growth factor receptor chimeric antibody C225 alone and in combination with cisplatin. J. Clin. Oncol., 18: 904, 2000.

14. Voldborg, B. R., Damstrup, L., Spang-Thomsen, M., and Poulsen, H. S. Epidermal growth factor receptor (EGFR) and EGFR mutations, function and possible role in clinical trials. Ann. Oncol., 8: 1197-1206, 1997.

15. Sugawa, N., Ekstrand, A. J., James, C. D., and Collins, V. P. Identical splicing of aberrant epidermal growth factor receptor transcripts from amplified rearranged genes in human glioblastomas. Proc. Natl. Acad. Sci. USA, 87: 8602-8606, 1990.

16. Nishikawa, R., Ji, X. D., Harmon, R. C., Lazar, C. S., Gill, G. N., Cavenee, W. K., and Huang, H. J. A mutant epidermal growth factor receptor common in human glioma confers enhanced tumorigenicity. Proc. Natl. Acad. Sci. USA, 91: 7727-7731, 1994.

17. Tang, C. K., Gong, X. Q., Moscatello, D. K., Wong, A. J., and Lippman, M. E. Epidermal growth factor receptor vIII enhances tumorigenicity in human breast cancer. Cancer Res., 60: 3081-3087, 2000.

18. Olapade-Olaopa, E. O., Moscatello, D. K., MacKay, E. H., Horsburgh, T., Sandhu, D. P., Terry, T. R., Wong, A. J., and Habib, F. K. Evidence for the differential expression of a variant EGF receptor protein in human prostate cancer. Br. J. Cancer, 82:186-194, 2000.

19. Moscatello, D. K., Holgado-Madruga, M., Godwin, A. K., Ramirez, G., Gunn, G., Zoltick, P. W., Biegel, J. A., Hayes, R. L., and Wong, A. J. Frequent expression of a mutant epidermal growth factor receptor in multiple human tumors. Cancer Res., 55: 5536-5539, 1995.

20. Wikstrand, C. J., Hale, L. P., Batra, S. K., Hill, M. L., Humphrey, P. A., Kurpad, S. N., McLendon, R. E., Moscatello, D., Pegram, C. N., Reist, C. J., et al. Monoclonal antibodies against EGFRvIII are tumor specific and react with breast and lung carcinomas and malignant gliomas. Cancer Res., 55: 3140-3148, 1995.

21. Hills, D., Rowlinson-Busza, G., and Gullick, W. J. Specific targeting of a mutant, activated FGF receptor found in glioblastoma using a monoclonal antibody. Int. J. Cancer, 63: 537-543, 1995.

22. Okamoto, S., Yoshikawa, K., Obata, Y., Shibuya, M., Aoki, S., Yoshida, J., and Takahashi, T. Monoclonal antibody against the fusion junction of a deletion-mutant epidermal growth factor receptor. Br. J. Cancer, 73: 1366-1372, 1996.

23. Nagane, M., Coufal, F., Lin, H., Bogler, O., Cavenee, W. K., and Huang, H. J. A common mutant epidermal growth factor receptor confers enhanced tumorigenicity on human glioblastoma cells by increasing proliferation and reducing apoptosis. Cancer Res., 56: 5079-5086, 1996.

24. Sato, J. D., Le, A. D., and Kawamoto, T. Derivation and assay of biological effects of monoclonal antibodies to epidermal growth factor receptors. Methods Enzymol., 146: 63-81, 1987.

25. Huang, H. S., Nagane, M., Klingbeil, C. K., Lin, H., Nishikawa, R., Ji, X. D., Huang, C. M., Gill, G. N., Wiley, H. S., and Cavenee, W. K. The enhanced tumorigenic activity of a mutant epidermal growth factor receptor common in human cancers is mediated by threshold levels of constitutive tyrosine phosphorylation and unattenuated signaling. J. Biol. Chem., 272: 2927-2935, 1997.

26. Clarke, K., Lee, F. T., Brechbiel, M. W., Smyth, F. E., Old, L. J., and Scott, A. M. Therapeutic efficacy of anti-Lewis (y) humanized 3S193 radioimmunotherapy in a breast cancer model: enhanced activity when combined with Taxol chemotherapy. Clin. Cancer Res., 6: 3621-3628, 2000.

27. Atlas, I., Mendelsohn, J., Baselga, J., Fair, W. R., Masui, H., and Kumar, R. Growth regulation of human renal carcinoma cells: role of transforming growth factor a. Cancer Res., 52: 3335-3339, 1992.

28. Perez-Soler, R., Donato, N. J., Shin, D. M., Rosenblum, M. G., Zhang, H. Z., Tornos, C., Brewer, H., Chan, J. C., Lee, J. S., Hong, W. K., et al. Tumor epidermal growth factor receptor studies in patients with non-small-cell lung cancer or head and neck cancer treated with monoclonal antibody RG 83852. J. Clin. Oncol., 12: 730-739, 1994.

29. Wersall, P., Ohlsson, I., Biberfeld, P., Collins, V. P., von Krusenstjema, S., Larsson, S., Mellstedt, H., and Boethius, J. Intratumoral infusion of the monoclonal antibody, mAb 425, against the epidermal-growth-factor receptor in patients with advanced malignant glioma. Cancer Immunol. Immunother., 44: 157-164, 1997.

30. Brady, L. W., Miyamoto, C., Woo, D. V., Rackover, M., Enrich, J., Bender, H., Dadparvar, S., Steplewski, Z., Koprowski, H., Black, P., et al. Malignant astrocytomas treated with iodine-125 labeled monoclonal antibody 425 against epidermal growth factor receptor: a Phase II trial. Int. J. Radiat. Oncol. Biol. Phys., 22: 225-230, 1992.
31. Reist, C. J., Archer, G. E., Kurpad, S, N., Wikstrand, C. J., Vaidyanathan, G., Willingham, M. C., Moscatello, D. K., Wong, A. J., Bigner, D. D., and Zalutsky, M. R. Tumor-specific anti-epidermal growth factor receptor variant III monoclonal antibodies: use of the tyramine-cellobiose radioiodination method enhances cellular retention and uptake in tumor xenografts. Cancer Res., 55: 4375-4382, 1995.
32. Reist, C. J., Archer, G. E., Wikstrand, C. J., Bigner, D. D., and Zalutsky, M. R. Improved targeting of an anti-epidermal growth factor receptor variant III monoclonal antibody in tumor xenografts after labeling using N-succinimidyl 5-iodo-3-pyridin-ecarboxylate. Cancer Res., 57: 1510-1515, 1997.
33. Sampson, J. H., Crotty, L. E., Lee, S., Archer, G. E., Ashley, D. M., Wikstrand, C. Hale, L. P., Small, C., Dranoff, G., Friedman, A. H., Friedman, H. S., and Bigner, D. D. Unarmed, tumor-specific monoclonal antibody effectively treats brain tumors. Proc. Natl. Acad. Sci. USA, 97: 7503-7508, 2000.
34. Filmus, J., Trent, J. M., Pollak, M. N., and Buick, R. N. Epidermal growth factor receptor gene-amplified MDA-468 breast cancer cell line and its nonamplified variants. Mol. Cell. Biol., 7: 251-257, 1987.
35. Fan, Z., Baselga, J., Masui, H., and Mendelsohn, J. Antitumor effect of anti-epidermal growth factor receptor monoclonal antibodies plus cis-diamminedichloroplatinum on well established A431 cell xenografts. Cancer Res., 53: 4637-4642, 1993.
36. Baselga, J., Norton, L., Masui, H., Pandiella, A., Coplan, K., Miller, W. H., Jr., and Mendelsohn, J. Antitumor effects of doxorubicin in combination with anti-epidermal growth factor receptor monoclonal antibodies. J. Natl. Cancer Inst., 85: 1327-1333, 1993.
37. Trail, P. A., and Bianchi, A. B. Monoclonal antibody drug conjugates in the treatment of cancer. Curr. Opin. Immunol., 11: 584-588, 1999.
38. DeNardo, S. J., Kroger, L. A., and DeNardo, G. L. A new era for radiolabeled antibodies in cancer? Curr. Opin. Immunol., 11: 563-569, 1999.

EXAMPLE 21

Construction, Expression and Analysis of Chimeric 806 Antibody

Chimeric antibodies are a class of molecules in which heavy and light chain variable regions of for instance, a mouse, rat or other species are joined onto human heavy and light chain regions. Chimeric antibodies are produced recombinantly. One advantage of chimeric antibodies is that they can reduce xenoantigenic effects, the inherent immunogenicity of non-human antibodies (for instance, mouse, rat or other species). In addition, recombinantly prepared chimeric antibodies can often be produced in large quantities, particularly when utilizing high level expression vectors.

For high level production, the most widely used mammalian expression system is one which utilizes the gene amplification procedure offered by dehydrofolate reductase deficient ("dhfr-") Chinese hamster ovary cells. The system is well known to the skilled artisan. The system is based upon the dehydrofolate reductase "dhfr" gene, which encodes the DHFR enzyme, which catalyzes conversion of dehydrofolate to tetrahydrofolate. In order to achieve high production, dhfr-CHO cells are transfected with an expression vector containing a functional DHFR gene, together with a gene that encodes a desired protein. In this case, the desired protein is recombinant antibody heavy chain and/or light chain.

By increasing the amount of the competitive DHFR inhibitor methotrexate (MTX), the recombinant cells develop resistance by amplifying the dhfr gene. In standard cases, the amplification unit employed is much larger than the size of the dhfr gene, and as a result the antibody heavy chain is co-amplified.

When large scale production of the protein, such as the antibody chain, is desired, both the expression level, and the stability of the cells being employed, are critical. In long term culture, recombinant CHO cell populations lose homogeneity with respect to their specific antibody productivity during amplification, even though they derive from a single, parental clone.

Bicistronic expression vectors were prepared for use in recombinant expression of the chimeric antibodies. These bicistronic expression vectors, employ an "internal ribosomal entry site" or "IRES." In these constructs for production of chimeric antiEGFR, the immunoglobulin chains and selectable markers cDNAs are linked via an IRES. IRES are cis-acting elements that recruit the small ribosomal subunits to an internal initiator codon in the mRNA with the help of cellular trans-acting factors. IRES facilitate the expression of two or more proteins from a polycistronic transcription unit in eukaryotic cells. The use of bicistronic expression vectors in which the selectable marker gene is translated in a cap dependent manner, and the gene of interest in an IRES dependent manner has been applied to a variety of experimental methods. IRES elements have been successfully incorporated into vectors for cellular transformation, production of transgenic animals, recombinant protein production, gene therapy, gene trapping, and gene targeting.

Synopsis of Chimeric Antibody 806 (ch806) Construction

The chimeric 806 antibody was generated by cloning the VH and VL of the 806 antibody from the parental murine hybridoma using standard molecular biology techniques. The VH and VL were then cloned into the pREN mammalian expression vectors, the construction of which are set forth in Table 6 and Table 7, and transfected into CHO (DHFR −/−ve) cells for amplification and expression. Briefly, following trypsinization 4×10$^6$ CHO cells were co-transferred with 10 μg of each of the LC and HC expression vectors using electroporation under standard conditions. Following a 10 min rest period at room temperature, the cells were added to 15 ml medium (10% fetal calf serum, hypoxanthine/thymidine supplement with additives) and transferred to 15×10 cm cell culture petri dishes. The plates were then placed into the incubator under normal conditions for 2 days. At this point, the addition of gentamycin, 5 nM methotrexate, the replacement of fetal calf serum with dialyzed fetal calf serumand the removal of hypoxanthine/thymidine, initiated the selection for clones that were successfully transfected with both the LC and HC from the medium. At day 17 following transfection, individual clones growing under selection were picked and screened for expression of the chimeric 806 antibody. An ELISA was utilized for screening and consisted of coating an ELISA plate with denatured soluble EGF receptor (denatured EGFR is known to allow 806 binding). This assay allows for the screening of production levels by individual clones and also for the functionality of the antibody being screened. All clones were shown to be proding functional ch806 and the best producer was taken and expanded for amplification. To amplify the level of ch806 being produced, the highest producing clone was subjected to reselection under a higher methotrexate concentration (100 nM vs 5 nM). This was undertaken using the aforementioned procedures.

Clones growing at 100 nM MTX were then passed onto the Biological Procution Facility, Ludwig Institute, Melbourne, Australia for measurement of production levels, weaning off serum, cell banking. The cell line has been shown to stably produce ~10 mg/liter in roller bottles.

The nucleic acid sequence of the pREN ch806 LC neo vector is provided in SEQ ID NO:7, while the corresponding amino acid sequence is set forth in SEQ ID NO:8. The nucleic acid sequence of the pREN ch806 HC DHFR vector is provided in SEQ ID NO:9, and the corresponding amino acid sequence is set forth in SEQ ID NO: 10.

FIG. 33 depicts the vectors pREN-HC and pREN-LC, which employ an IRES. The pREN bicistronic vector system is described and disclosed in copending U.S. Ser. No. 60/355, 838 filed Feb. 13, 2002, which is incorporated herein by reference in its entirety.

Ch806 was assessed by FACS analysis to demonstrate that the chimeric 806 displays identical binding specificity to that of the murine parental antibody. Analysis was performed using wild type cells (U87 MG parental cells), cells overexpressing the EGF receptor (A431 cells and UA87 wt EGFR cells) and UA87 A2-7 cells (data not shown). Similar binding specificity of Mab806 and ch806 was obtained using cells overexpressing EGFR and cells expressing the de2-7 EGFR. No binding was observed in wild type cells. Scatchard analysis revealed a binding affinity for radiolabeled ch806 of $6.4 \times 10^9$ M$^{-1}$ using U87MGde2-7 cells (data not shown).

Biodistribution analysis of the ch806 antibody was performed in BALB/c nude mice bearing U87MG-de2-7 xenograft tumors and the results are shown in FIG. 34. Mice were injected with 5 ug of radiolabelled antibody and were sacrificed in groups of four per time point at 8, 24, 48 and 74 hours. Organs were collected, weighed and radioactivity measured in a gamma counter. $^{125}$I-labelled ch806 displays reduced targeting to the tumor compared to $^{111}$In-labelled ch806, which has high tumor uptake and cumulative tumor retention over the 74 hour time period. At 74 hours, the $^{111}$In-labelled antibody displays approximately 30% ID/gram tissue and a tumor to blood ratio of 4.0 (FIG. 35). The $^{111}$In-labelled ch806 shows some nonspecific retention in the liver, spleen and kidneys. This is common for the use of this isotope and decreases with time, which supports that this binding is non-specific to ch806 and due to $^{111}$In binding.

Chimeric antibody ch806 was assessed for theraeutic efficacy in an established tumor model. $3 \times 10^6$ U87MG.Δ2-7 cells in 100 ul of PBS were inoculated s.c. into both flanks of 4-6 week old female nude mice (Aminal Research Center, Western Australia, Australia). The mAb806 was included as a positive control. The results are depicted in FIG. 36. Treatment was started when tumors had reached a mean volume of 50 mm$^3$ and consisted of 1 mg of ch806 or mAb806 given i.p. for a total of 5 injections on the days indicated. Tumor volume in mm$^3$ was determined using the formula (length×width$^2$)/2, where length was the longest axis and width the measurement at right angles to the length. Data was expressed as mean tumor volume+/−S.E. for each treatment group. The ch806 and mAb806 displayed nearly identical anti-tumor activity against U87MG.Δ2-7 xenografts.

Analysis of Ch806 Immune Effector Function

Materials and Methods

Antibodies and Cell Lines:

Murine anti-de2-7 EGFR monoclonal mAb 806, chimeric antibody ch806 (IgG$_1$) and control isotype matched chimeric anti-G250 monoclonal antibody cG250 were prepared by the Biological Production Facility, Ludwig Institute for Cancer Research, Melbourne, Australia. Both complement-dependant cytotoxicity (CDC) and antibody-dependent cellular-cytotoxicity (ADCC) assays utilised U87MG.de2-7 and A431 cells as target cells. The previously described U87MG.de2-7 cell line is a human astrocytoma cell line infected with a retrovirus containing the de2-7EGFR (Nishikawa, R. et al. (1994) Proc Natl Acad Sci USA. 91: 7727-31). Human squamous carcinoma A431 cells were purchased from the American Type Culture Collection (Manassas, Va.). All cell lines were cultured in DMEM/F-12 with GLUTAMAX™ (Life Technologies, Melbourne, Australia) supplemented with 10% heat-inactivated FCS(CSL, Melbourne, Australia), 100 units/ml penicillin and 100 ug/ml streptomycin. To maintain selection for retrovirally transfected U87MG.de2-7 cells, 400 ug/ml G418 was included in the media.

Preparation of human peripheral blood mononuclear cells (PBMC) Effector Cells: PBMCs were isolated from healthy volunteer donor blood. Heparinised whole blood was fractionated by density centrifugation on Ficoll-Hypaque (ICN Biomedical Inc., Ohio, USA). PBMC fractions was collected and washed three times with RPMI+1640 supplemented with 100 U/ml penicillin and 100 ug/ml streptomycin, 2 mM L-glutamine, containing 5% heat-inactivated FCS.

Preparation of Target Cells:

CDC and ADCC assays were performed by a modification of a previously published method ((Nelson, D. L. et al. (1991) In: J. E. Colignan, A. M. Kruisbeek, D. D. Margulies, E. M. Shevach, and W. Strober (eds.), Current Protocols in Immunology, pp. 7.27.1. New York: Greene Publishing Wiley Interscience). Briefly, $5 \times 10^6$ target U87MG.de2-7 and A431 cells were labeled with 50 μCi $^{51}$Cr (Geneworks, Adelaide, Australia) per $1 \times 10^6$ cells and incubated for 2 hr at 37° C. The cells were then washed three time with PBS (0.05M, pH 7.4) and a fourth wash with culture medium. Aliquots ($1 \times 10^4$ cells/50 ul) of the labeled cells were added to each well of 96-well microtitre plates (NUNC, Roskilde, Denmark).

CDC Assay:

To 50 ul labeled target cells, 50 ul ch806 or isotype control antibody cG250 were added in triplicate over the concentration range 0.00315-10 ug/ml, and incubated on ice 5 min. Fifty ul of freshly prepared healthy donor complement (serum) was then added to yield a 1:3 final dilution of the serum. The microtitre plates were incubated for 4 hr at 37° C. Following centrifugation, the released $^{51}$Cr in the supernatant was counted (COBRA II™ automated Gamma Counter, Canberra Packard, Melbourne, Australia). Percentage specific lysis was calculated from the experimental $^{51}$Cr release, the total (50 ul target cells+100 ul 10% Tween 20) and spontaneous (50 ul target cells+100 ul medium) release.

ADCC Assay:

Ch806-mediated ADCC effected by healthy donor PBMCs was measured by two 4-hr $^{51}$Cr release assays. In the first assay, labelled target cells were plated with the effector cells in 96-well "U" bottom microplates (NUNC, Roskilde, Denmark) at effector/target (E:T) cell ratios of 50:1. For ADCC activity measurements, 0.00315-10 ug/ml (final concentration) test and control antibodies were added in triplicate to each well. In the second ADCC assay, the ADCC activity of ch806 was compared with the parental murine mAb 806 over a range of Effector:Target cell ratios with the test antibody concentration constant at 1 ug/ml. In both assays, micotitre plates were incubated at 37° C. for 4 hours, then 50 ul supernatant was harvested from each well and released $^{51}$Cr was determined by gamma counting (COBRA II™ automated Gamma Counter, Canberra Packard, Melbourne, Australia). Controls included in the assays corrected for spontaneous release (medium alone) and total release (10% Tween20™/ PBS). Appropriate controls with the same subclass antibody were run in parallel.

The percentage cell lysis (cytotoxicity) was calculated according to the formula:

$$\text{Percentage Cytotoxicity} = \frac{\text{Sample Counts} - \text{Spontaneous Release}}{\text{Total Release} - \text{Spontaneous Release}} \times 100$$

The percent (%) cytotoxicity was plotted versus concentration of antibody (µg/ml).

Results

The results of the CDC analyses are presented in FIG. 37. Minimal CDC activity was observed in the presence of up to 10 ug/ml ch806 with CDC comparable to that observed with isotype control cG250.

Ch806 mediated ADCC on target U87MG.de2-7 and A431 cells at E:T ratio of 50:1 is presented in FIG. 38. Effective ch806 specific cytotoxicity was displayed against target U87MG.de2-7 cells, but minimal ADCC was mediated by ch806 on A431 cells. The levels of cytotoxicity achieved reflect the number of ch806 binding sites on the two cell populations. Target U87MG.de2-7 cells express ~1×10$^6$ de2-7EGFR which are specifically recognised by ch806, while only a subset of the 1×10$^6$ wild-type EGFR molecules expressed on A431 cells are recognised by ch806 (see above Examples).

Further ADCC analyses were performed to compare the ADCC mediated by 1 ug/ml ch806 on target U87MG.de2-7 cells with that effected by 1 ug/ml parental murine mAb 806. Results are presented in FIG. 39. Chimerisation of mAb 806 has effected marked improvement of the ADCC achieved by the parental murine mAb with greater than 30% cytotoxicity effected at E:T ratios 25:1 and 50:1.

The lack of parental murine mAb 806 immune effector function has been markedly improved upon chimerisation. Ch806 mediates good ADCC, but minimal CDC activity.

EXAMPLE 22

Generation of Anti-Idiotype Antibodies to Chimeric Antibody ch806

To assist the clinical evaluation of mAb806 or ch806, laboratory assays are required to monitor the serum pharmacokinetics of the antibodies and quantitate any immune responses to the mouse-human chimeric antibody. Mouse monoclonal anti-idiotypic antibodies (anti-ids) were generated and characterised for suitability as ELISA reagents for measuring ch806 in patient sera samples and use as positive controls in human anti-chimeric antibody immune response analyses. These antiidiotype antibodies may also be useful as therapeutic or prophylactic vaccines, generating a natural anti-EGFR antibody response in patients.

Methods for generating anti-idiotype antibodies are well known in the art (Bhattacharya-Chatterjee, Chatterjee et al. 2001, Uemura et al. 1994, Steffens, Boerman et al. 1997, Safa and Foon 2001, Brown and Ling 1988).

Mouse monoclonal anti-idiotypic antibodies (anti-ids) were, briefly, generated as follows. Splenocytes from mice immunized with ch806 were fused with SP2/0-AG14 plasmacytoma cells and antibody producing hybridomas were selected through ELISA for specific binding to ch806 and competitive binding for antigen (FIG. 40). Twenty-five hybridomas were initially selected and four, designated LMH-11, -12-13 and -14, secreted antibodies that demonstrated specific binding to ch806, mAb 806 and were able to neutralise ch806 or mAb 806 antigen binding activity (FIG. 41). The recognition of the ch806/mAb 806 idiotope or CDR region was demonstrated by lack of cross-reactivity with purified polyclonal human IgG.

In the absence of readily available recombinant antigen de2-7 EGFR to assist with the determination of ch806 in serum samples, the ability of the novel anti-idiotype ch806 antibodies to concurrently bind 806 variable regions was exploited in the development of a sensitive, specific ELISA for measuring ch806 in clinical samples (FIG. 42). Using LMH-12 for capture and Biotinylated-LMH-12 for detection, the validated ELISA demonstrated highly reproducible binding curves for measuring ch806 (2 ug/ml-1.6 ng/ml) in sera with a 3 ng/ml limit of detection. (n=12; 1-100 ng/ml, Coefficient of Variation<25%; 100 ng/ml-5 ug/ml, Coefficient of Variation<15%). No background binding was evident with the three healthy donor sera tested and negligible binding was observed with isotype control hu3S193. The hybridoma produces high levels of antibody LMH-12, and larger scale production is planned to enable the measurement of ch806 and quantitation of any immune responses in clinical samples. (Brown and Ling 1988)

Results

Mice Immunization and Hybridoma Clone Selection

Immunoreactivity of pre- and post-immunization sera samples indicated the development of high titer mouse anti-ch806 and anti-huIgG mAbs. Twenty-five hybridomas producing antibodies that bound ch806, but not huIgG, were initially selected. The binding characteristics of some of these hybridomas are shown in FIGS. 42A and 42B. Four of these anti-ch806 hybridomas with high affinity binding (clones 3E3, 5B8, 9D6 and 4D8) were subsequently pursued for clonal expansion from single cells by limiting dilution and designated Ludwig Institute for Cancer Research Melbourne Hybridoma (LMH)-11, -12, -13, and -14, respectively (FIG. 42).

Binding and Blocking Activities of Selected Anti-Idiotype Antibodies

The ability of anti-ch806 antibodies to concurrently bind two ch806 antibodies is a desirable feature for their use as reagents in an ELISA for determining serum ch806 levels. Clonal hybridomas, LMH-11, -12, -13, and -14 demonstrated concurrent binding (data not shown).

After clonal expansion, the hybridoma culture supernatants were examined by ELISA for the ability to neutralise ch806 or mAb 806 antigen binding activity with sEGFR621. Results demonstrated the antagonist activity of anti-idiotype mAbs LMH-11, -12, -13, and -14 with the blocking in solution of both ch806 and murine mAb 806 binding to plates coated with sEGFR (FIG. 41 for LMH-11, -12, -13).

Following larger scale culture in roller bottles the binding specificity's of the established clonal hybridomas, LMH-11, -12, -13, and -14 were verified by ELISA. LMH-11 through -14 antibodies were identified as isotype IgG1κ by mouse monoclonal antibody isotyping kit.

ch806 in Clinical Serum Samples: Pharmacokinetic ELISA Assay Development

To assist with the determination of ch806 in serum samples, the ability of the anti-idiotype ch806 antibodies to concurrently bind the 806 variable region was exploited in the development of a sensitive and specific ELISA assay for ch806 in clinical samples. The three purified clones LMH-11, -12, and -13 (FIGS. 49, B, and C respectively) were compared for their ability to capture and then detect bound ch806 in sera. Results indicated using LMH-12 (10 µg/ml) for capture and biotinylated-LMH-12 for detection yielded the highest sensitivity for ch806 in serum (3 ng/ml) with negligible background binding.

Having established the optimal pharmacokinetic ELISA conditions using 1 µg/ml anti-idiotype LMH-12 and 1 µg/ml biotinylated LMH-12 for capture and detection, respectively, validation of the method was performed. Three separate ELISAs were performed in quadruplicate to measure ch806 in donor serum from three healthy donors or 1% BSA/media with isotype control hu3S193. Results of the validation are presented in FIG. 43 and demonstrate highly reproducible binding curves for measuring ch806 (2 µg/ml-1.6 ng/ml) in sera with a 3 ng/ml limit of detection. (n=12; 1-100 ng/ml, Coefficient of Variation<25%; 100 ng/ml-5 µg/ml, Coefficient of Variation<15%). No background binding was evident with any of the three sera tested and negligible binding was observed with isotype control hu3S193.

REFERENCES

These should really be incorporated with those at the end of Example 17 and put to the end of all the examples Brown, G. and N. Ling (1988). Murine Monoclonal Antibodies. Antibodies, Volume I. A Practical Approach. D. Catty. Oxford, England, IRL Press: 81-104.

Bhattacharya-Chatterjee, M., S. K. Chatterjee, et al. (2001). "The anti-idiotype vaccines for immunotherapy." Curr Opin Mol Ther 3(1): 63-9.

Domagala, T., N. Konstantopoulos, et al. (2000). "Stoichiometry, kinetic and binding analysis of the interaction between epidermal growth factor (EGF) and the extracellular domain of the EGF receptor." Growth Factors 18(1): 11-29

Safa, M. M. and K. A. Foon (2001). "Adjuvant immunotherapy for melanoma and colorectal cancers." Semin Oncol 28(1): 68-92.

Uemura, H., E. Okajima, et al. (1994). "Internal image anti-idiotype antibodies related to renal-cell carcinoma-associated antigen G250." Int J Cancer 56(4): 609-14.

EXAMPLE 23

Assessment of Carbohydrate Structures and Antibody Recognition

Experiments were undertaken to further assess the role of carbohydrate structures in the binding and recognition of the EGFR, both amplified and de2-7 EGFR, by the mAb806 antibody.

To determine if carbohydrate structures are directly involved in the mAb 806 epitope, the recombinant sEGFR expressed in CHO cells was treated with PNGase F to remove N-linked glycosylation. Following treatment, the protein was run on SDS-PAGE, transferred to membrane and immunoblotted with mAb 806 (FIG. 44). As expected, the deglycosylated sEGFR ran faster on SDS-PAGE, indicating that the carbohydrates had been successfully removed. The mAb 806 antibody clearly bound the deglycosylated material demonstrating the antibody epitope is peptide in nature and not solely a glycosylation epitope.

Lysates, prepared from cell lines metabolically labelled with $^{35}$S, were immunoprecipitated with different antibodies directed to the EGFR (FIG. 45). As expected, the 528 antibody immunoprecipitated 3 bands from U87MG.Δ2-7 cells, an upper band corresponding to the wild type (wt) EGFR and two lower bands corresponding to the de2-7 EGFR. These two de2-7 EGFR bands have been reported previously and are assumed to represent differential glycosylation (Chu et al. (1997) Biochem. J. June 15; 324 (Pt 3):885-861). In contrast, mAb 806 only immunoprecipitated the two de2-7 EGFR bands, with the wt receptor being completely absent even after over-exposure (data not shown). Interestingly, mAb806 showed increased relative reactivity with the lower de2-7 EGFR band but decreased reactivity with the upper band when compared to the 528 antibody. The SC-03 antibody, a commercial rabbit polyclonal antibody directed to C-terminal domain of the EGFR, immunoprecipitated the three EGFR bands as seen with the 528 antibody although the total amount of receptor immunoprecipitated by this antibody was considerably less. No bands were observed when using an irrelevant IgG2b antibody as a control for mAb 806.

The 528 antibody immunoprecipitated a single band from U87MG.wtEGFR cells corresponding to the wt receptor (FIG. 45). MAb 806 also immunoprecipitated a single band from these cells, however, this EGFR band clearly migrated faster than the 528 reactive receptor. The SC-03 antibody immunoprecipitated both EGFR reactive bands from U87MG.wtEGFR cells, further confirming that the mAb 806 and 528 recognize different forms of the EGFR in whole cell lysates from these cells.

As observed with U87MG.wtEGFR cells, the 528 antibody immunoprecipitated a single EGFR band from A431 cells (FIG. 45). The 528 reactive EGFR band is very broad on these low percentage gels (6%) and probably reflects the diversity of receptor glycosylation. A single EGFR band was also seen following immunoprecipitation with mAb 806. While this EGFR band did not migrate considerably faster than the 528 overall broad reactive band, it was located at the leading edge of the broad 528 band in a reproducible fashion. Unlike U87MG.Δ2-7 cell lysates, the total amount of EGFR immunoprecipitated by mAb 806 from A431 lysates was considerably less than with the 528 antibody, a result consistent with our Scatchard data showing mAb 806 only recognizes a portion of the EGFR on the surface of these cells (see Example 4 above). Immunoprecipitation with SC-03 resulted in a single broad EGFR band as for the 528 antibody. Similar results were obtained with HN5 cells (data not shown). Taken together, this data indicates that mAb 806 preferentially reacts with faster migrating species of the EGFR, which may represent differentially glycosylated forms of the receptor.

In order to determine at what stage of receptor processing mAb 806 reactivity appeared a pulse/chase experiment was conducted. A431 and U87MG.Δ2-7 cells were pulsed for 5 min with $^{35}$S methionine/cysteine, then incubated at 37° C. for various times before immunoprecipitation with mAb 806 or 528 (FIG. 46). The immunoprecipitation pattern in A431 cells with the 528 antibody was typical for a conformational dependent antibody specific for the EGFR. A small amount of receptor was immunoprecipitated at 0 min (i.e. after 5 min pulse) with the amount of labelled EGFR increasing at each time point. There was also a concurrent increase in the molecular weight of the receptor with time. In contrast, the mAb 806 reactive EGFR material was present at high levels at 0 min, peaked at 20 min and then reduced at each further time point. Thus, it appears that mAb 806 preferentially recognizes a form of the EGFR found at an early stage of processing.

The antibody reactivity observed in pulse-labelled U87MG.Δ2-7 cells was more complicated. Immunoprecipitation with the 528 antibody at 0 min revealed that a small amount of the lower de2-7 EGFR band was labelled (FIG. 46). The amount of 528 reactive de2-7 EGFR lower band increased with time, peaking at 60 min and declining slowly at 2 and 4 h. No significant amount of the labelled upper band of de2-7 EGFR was detected until 60 min, after which the level continued to increase until the end of the time course. This clearly indicates that the upper de2-7 EGFR is a more mature form of the receptor. MAb 806 reactivity also varied during the time course study, however mAb 806 preferentially precipitated the lower band of the de2-7 EGFR. Indeed, there were no significant levels of mAb 806 upper band seen until 4 h after labelling.

The above experiments suggest that mab 806 preferentially reacts with a more immature glycosylation form of the de2-7 and wt EGFR. This possibility was tested by immunoprecipitating the EGFR from different cells lines labelled overnight with $^{35}$S methionine/cysteine and then subjecting the resultant precipitates to Endoglycosidase H (Endo H) digestion. This enzyme preferentially removes high mannose type carbohydrates (i.e. immature glycosylation) from proteins while leaving complex carbohydrates (i.e. mature glycoslation) intact. Immunoprecipitation and digestion with Endo H of labelled U87MG.Δ2-7 cell lysates with 528, mAb 806 and SC-03 gave similar results (FIG. 47). As predicted, the lower de2-7 EGFR band was fully sensitive to Endo H digestion, migrating faster on SDS-PAGE after Endo H digestion, demonstrating that this band represents the high mannose form of the de2-7 EGFR. The upper de2-7 EGFR band was essentially resistant to Endo H digestion, showing only a very slight difference in migration after Endo H digestion, indicating that the majority of the carbohydrate structures are of the complex type. The small but reproducible decrease in the molecular weight of the upper band following enzyme digestion suggests that while the carbohydrates on the upper de2-7 EGFR band are predominantly of the complex type, it does possess some high mannose structures. Interestingly, these cells also express low amounts of endogenous wt EGFR that is clearly visible following 528 immunopreciptitation. There was also a small but noticeable reduction in molecular weight of the wt receptor following Endo H digestion, indicating that it also contains high mannose structures.

The sensitivity of the immunoprecipitated wt EGFR to Endo H digestion was similar in both U87MG.wtEGFR and A431 cells (FIG. 47). The bulk of the material precipitated by the 528 antibody was resistant to the Endo H enzyme although a small amount of the material was of the high mannose form. Once again there was a small decrease in the molecular weight of the wt EGFR following Endo H digestion suggesting that it does contain some high mannose structures. The results using the SC-03 antibody were similar to the 528 antibody. In contrast, the majority of the EGFR precipitated by mAb 806 was sensitive to Endo H in both U87MG.wtEGFR and A431 cells, confirming that mAb 806 preferentially recognizes the high mannose form of the EGFR. Similar results were obtained with HN-5 cells, wherein the majority of the material precipitated by mAb 806 was sensitive to Endo H digestion, while the majority of the material precipitated by mAb528 and SC-03 was resistant to Endo H digestion (data not shown).

Cell surface iodination of the A431 celline, was performed with $^{125}$, followed by immunoprecipitation with the 806 antibody. The protocol for surface iodination was as follows: The cell lysis, immunoprecipitation, Endo H digestion, SDS PAGE and autoradiography are as described above herein. For labeling, cells were grown in media with 10% FCS, detached with EDTA, washed twice with PBS then resuspended in 400 ul of PBS (approx 2-3×10$^6$ cells). To this was added 15 ul of $^{125}$I (100 mCi/ml stock), 100 ul bovine lactoperoxidase (1 mg/ml) stock, 10 ul H$_2$O$_2$ (0.1% stock) and this was incubated for 5 min. A further 10 ul of H$_2$O$_2$ was then added and the incubation continued for a further 3 min. Cells were then washed again 3 times with PBS and lysed in 1% Triton™. Cell surface iodination of the A431 cell line with lactoperoxidase, followed by immunoprecipitation with the 806 antibody, showed that, similar to the whole cell lysates described above, the predominant form of the EGFR recognized by 806 bound on the cell surface of A431 cells was sensitive to EndoH digestion (FIG. 48). This confirms that the form of EGFR bound by 806 on the cell surface of A431 cells is an EndoH sensitive form and thus is the high mannose type.

This invention may be embodied in other forms or carried out in other ways without departing from the spirit or essential characteristics thereof. The present disclosure is therefore to be considered as in all aspects illustrated and not restrictive, the scope of the invention being indicated by the appended Claims, and all changes which come within the meaning and range of equivalency are intended to be embraced therein.

Various references are cited throughout this Specification, each of which is incorporated herein by reference in its entirety.

TABLE 6 pREN ch806 LC Neo Vector

```
         Xho I
       1 CTCGAGAGCGGGCAGTGAGCGCAACGCAATTAATGTGAGTTAGCTCACTC

51 ATTAGGCACCCCAGGCTTTACACTTTATGCTCCCGGCTCGTATGTTGTGT

EcoRI    EF1α promoter
     101 GGAGATTGTGAGCGGATAACAATTTCACACAGAATTCGTGAGGCTCCGGT

151 GCCCGTCAGTGGGCAGAGCGCACATCGCCCACAGTCCCCGAGAAGTTGGG

201 GGGAGGGGTCGGCAATTGAACCGGTGCCTAGAGAAGGTGGCGCGGGGTAA

251 ACTGGGAAAGTGATGTCGTGTACTGGCTCCGCCTTTTTCCCGAGGGTGGG

301 GGAGAACCGTATATAAGTGCAGTAGTCGCCGTGAACGTTCTTTTTCGCAA

351 CGGGTTTGCCGCCAGAACACAGGTAAGTGCCGTGTGTGGTTCCCGCGGGC
```

TABLE 6-continued pREN ch806 LC Neo Vector

```
 401 CTGGCCTCTTTACGGGTTATGGCCCTTGCGTGCCTTGAATTACTTCCACG

451 CCCCTGGCTGCAGTACGTGATTCTTGATCCCGAGCTTCGGGTTGGAAGTG

501 GGTGGGAGAGTTCGAGGCCTTGCGCTTAAGGAGCCCCTTCGCCTCGTGCT

551 TGAGTTGAGGCCTGGCCTGGGCGCTGGGGCCGCCGCGTGCGAATCTGGTG

601 GCACCTTCGCGCCTGTCTCGCTGCTTTCGATAAGTCTCTAGCCATTTAAA

651 ATTTTTGATGACCTGCTGCGACGCTTTTTTTCTGGCAAGATAGTCTTGTA

701 AATGCGGGCCAAGATCTGCACACTGGTATTTCGGTTTTTGGGGCCGCGGG

751 CGGCGACGGGGCCCGTGCGTCCCAGCGCACATGTTCGGCGAGGCGGGGCC

801 TGCGAGCGCGGCCACCGAGAATCGGACGGGGGTAGTCTCAAGCTGGCCGG

851 CCTGCTCTGGTGCCTGGCCTCGCGCCGCCGTGTATCGCCCCGCCCTGGGC

901 GGCAAGGCTGGCCCGGTCGGCACCAGTTGCGTGAGCGGAAAGATGGCCGC

951 TTCCCGGCCCTGCTGCAGGGAGCTCAAAATGGAGGACGCGGCGCTCGGGA

1001 GAGCGGGCGGGTGAGTCACCCACACAAAGGAAAAGGGCCTTTCCGTCCTC

1051 AGCCGTCGCTTCATGTGACTCCACGGAGTACCGGGCGCCGTCCAGGCACC

1101 TCGATTAGTTCTCGAGCTTTTGGAGTACGTCGTCTTTAGGTTGGGGGAG

1151 GGGTTTTATGCGATGGAGTTTCCCCACACTGAGTGGGTGGAGACTGAAGT

1201 TAGGCCAGCTTGGCACTTGATGTAATTCTCCTTGGAATTTGCCCTTTTTG

1251 AGTTTGGATCTTGGTTCATTCTCAAGCCTCAGACAGTGGTTCAAAGTTTT

MluI     HindIII    PmeI
1301 TTTCTTCCATTTCAGGTGTACGCGTCTCGGGAAGCTTTAGTTTAAACGCC 1351 GCCACCATGGTGTCCACAGCTCAGTTCCTTGCATTCTTGTTGCTTTGGTTT
             M  V  S  T  A  Q  F  L  A  F  L  L  L  W  F 1401 CCAGGTGCAAGATGTGACATCCTGATGACCCAATCTCCATCCTCCATGTCT
      P  G  A  R  C  D  I  L  M  T  Q  S  P  S  S  M  S 1451 GTATCTCTGGGAGACACAGTCAGCATCACTTGCCATTCAAGTCAGGACATT
      V  S  L  G  D  T  V  S  I  T  C  H  S  S  Q  D  I 1501 AACAGTAATATAGGGTGGTTGCAGCAGAGACCAGGGAAATCATTTAAGGGC
      N  S  N  I  G  W  L  Q  Q  R  P  G  K  S  F  K  G 1551 CTGATCTATCATGGAACCAACTTGGACGATGAAGTTCCATCAAGGTTCAGT
      L  I  Y  H  G  T  N  L  D  D  E  V  P  S  R  F  S 1601 GGCAGTGGATCTGGAGCCGATTATTCTCTCACCATCAGCAGCCTGGAATCT
      G  S  G  S  G  A  D  Y  S  L  T  I  S  S  L  E  S 1651 GAAGATTTTGCAGACTATTACTGTGTACAGCATGCTCAGTTTCCGTGGACG
      E  D  F  A  D  Y  Y  C  V  Q  H  A  Q  F  P  W  T BamHI
1701 TTCGGTGGAGGCACCAAGCTGGAAATCAAACGGGTGAGTGGATCCATCTGGG
      F  G  G  G  T  K  L  K  I  K  R

1751 ATAAGCATGCTGTTTTCTGTCTGTCCCTAACATGCCCTGTGATTATGCGCAAA

1801 CAACACACCCAAGGGCAGAACTTTGTTACTTAAACACCATCCTGTTTGCTTCTT

1851 TCCTCAGGAACTGTGGCTGCACCA
         T  V  A  A  P

1876 TCTGTCTTCATCTTCCCGCCATCTGATGAGCAGTTGAAATCTGGAACTGC
      S  V  F  I  F  P  P  S  D  E  Q  L  K  S  G  T  A

1926 CTCTGTTGTGTGCCTGCTGAATAACTTCTATCCCAGAGAGGCCAAAGTAC
      S  V  V  C  L  L  N  N  F  Y  P  R  E  A  K  V  Q
```

TABLE 6-continued pREN ch806 LC Neo Vector

```
1976 AGTGGAAGGTGGATAACGCCCTCCAATCGGGTAACTCCCAGGAGAGTGTC
       W   K   V   D   N   A   L   Q   S   G   N   S   Q   E   S   V

2026 ACAGAGCAGGACAGCAAGGACAGCACCTACAGCCTCAGCAGCACCCTGAC
       T   E   Q   D   S   K   D   S   T   Y   S   L   S   S   T   L   T

2076 GCTGAGCAAAGCAGACTACGAGAAACACAAAGTCTACGCCTGCGAAGTCA
       L   S   K   A   D   Y   E   K   H   K   V   Y   A   C   E   V   T

2126 CCCATCAGGGCCTGAGCTCGCCCGTCACAAAGAGCTTCAACAGGGGAGAG
       H   Q   G   L   S   S   P   V   T   K   S   F   N   R   G   E

Nhe/Xba
2176 TGTTGAGCTAGAACTAACTAACTAAGCTAGCAACGGTTTCCCTCTAGCGG
       C   *

2226 GATCAATTCCGCCCCCCCCCCCTAACGTTACTGGCCGAAGCCGCTTGGAA

2276 TAAGGCCGGTGTGCGTTTGTCTATATGTTATTTTCCACCATATTGCCGTC

2326 TTTTGGCAATGTGAGGGCCCGGAAACCTGGCCCTGTCTTCTTGACGAGCA

2376 TTCCTAGGGGTCTTTCCCCTCTCGCCAAAGGAATGCAAGGTCTGTTGAAT

2426 GTCGTGAAGGAAGCAGTTCCTCTGGAAGCTTCTTGAAGACAAACAACGTC

2476 TGTAGCGACCCTTTGCAGGCAGCGGAACCCCCCACCTGGCGACAGGTGCC

2526 TCTGCGGCCAAAAGCCACGTGTATAAGATACACCTGCAAAGGCGGCACAA

2576 CCCCAGTGCCACGTTGTGAGTTGGATAGTTGTGGAAAGAGTCAAATGGCT

2626 CTCCTCAAGCGTATTCAACAAGGGGCTGAAGGATGCCCAGAAGGTACCCC

2676 ATTGTATGGGATCTGATCTGGGGCCTCGGTGCACATGCTTTACGTGTGTT

2751 TAGTCGAGGTTAAAAAACGTCTAGGCCCCCCGAACCACGGGGACGTGGTT

2801 TTCCTTTGAAAAACACGATAATACCATGGTTGAACAAGATGGATTGCACG

2851 CAGGTTCTCCGGCCGCTTGGGTGGAGAGGCTATTCGGCTATGACTGGGCA

2901 CAACAGACAATCGGCTGCTCTGATGCCGCCGTGTTCCGGCTGTCAGCGCA

2951 GGGGCGCCCGGTTCTTTTTGTCAAGACCGACCTGTCCGGTGCCCTGAATG

3001 AACTGCAGGACGAGGCAGCGCGGCTATCGTGGCTGGCCACGACGGGCGTT

3051 CCTTGCGCAGCTGTGCTCGACGTTGTCACTGAAGCGGGAAGGGACTGGCT

3101 GCTATTGGGCGAAGTGCCGGGGCAGGATCTCCTGTCATCTCACCTTGCTC

3151 CTGCCGAGAAAGTATCCATCATGGCTGATGCAATGCGGCGGCTGCATACG

3201 CTTGATCCGGCTACCTGCCCATTCGACCACCAAGCGAAACATCGCATCGA

3251 GCGAGCACGTACTCGGATGGAAGCCGGTCTTGTCGATCAGGATGATCTGG

3301 ACGAAGAGCATCAGGGGCTCGCGCCAGCCGAACTGTTCGCCAGGCTCAAG

3351 GCGCGCATGCCCGACGGCGAGGATCTCGTCGTGACCCATGGCGATGCCTG

3401 CTTGCCGAATATCATGGTGGAAAATGGCCGCTTTTCTGGATTCATCGACT

3451 GTGGCCGGCTGGGTGTGGCGGACCGCTATCAGGACATAGCGTTGGCTACC

3501 CGTGATATTGCTGAAGAGCTTGGCGGCGAATGGGCTGACCGCTTCCTCGT

3551 GCTTTACGGTATCGCCGCTCCCGATTCGCAGCGCATCGCCTTCTATCGCC blunt end SalI/SalI
3601 TTCTTGACGAGTTCTTCTGAGTCGATCGACCTGGCGTAATAGCGAAGAGG

3651 CCCGCACCGATCGCCCTTCCCAACAGTTGCGCAGCCTGAATGGCGAATGG

3701 GACGCGCCCTGTAGCGGCGCATTAAGCGCGGCGGGTGTGGTGGTTACGCG
```

TABLE 6-continued pREN ch806 LC Neo Vector

```
3751 CAGCGTGACCGCTACACTTGCCAGCGCCCTAGCGCCCGCTCCTTTCGCTT

3801 TCTTCCCTTCCTTTCTCGCCACGTTCGCCGGCTTTCCCCGTCAAGCTCTA

3851 AATCGGGGGCTCCCTTTAGGGTTCCGATTTAGTGCTTTACGGCACCTCGA

3901 CCCCAAAAAACTTGATTAGGGTGATGGTTCACGTAGTGGGCCATCGCCCT

3951 GATAGACGGTTTTTCGCCTTTGACGTTGGAGTCCACGTTCTTTAATAGTG

4001 GACTCTTGTTCCAAACTGGAACAACACTCAACCCTATCTCGGTCTATTTA

4051 TAAGGGATTTTGCCGATTTCGGCCTATTGGTTAAAAAATGAGCTGATTTA

4101 ACAAAATTTAACGCGAATTTTAACAAAATATTAACGCTTACAATTTAGGT

4151 GGCACTTTTCGGGGAAATGTGCGCGGAACCCCTATATTTGTTTATTTTTC

4201 TAAATACATTCAAATATGTATCCGCTCATGAGACAATAACCCTGATAAAT

4251 GCTTCAATAATATTGAAAAAGGAAGAGTATGAGTATTCAACATTTCCGTG

4301 TCGCCCTTATTCCCTTTTTTGCGGCATTTTGCCTTACTGTTTTTGCTCAC

4351 CCAGAAACGCTGGTGAAAGTAAAAGATGCTGAAGATCAGTTGGGTGCACG

4401 AGTGGGTTACATCGAACTGGATCTCAACAGCGGTAAGATCCTTGAGAGTT

4451 TTCGCCCCGAAGAACGTTTTCCAATGATGAGCACTTTTAAAGTTCTGCTA

4501 TGTGGCGCGGTATTATCCCGTATTGACGCCGGGCAAGAGCAACTCGGTCG

4551 CCGCATACACTATTCTCAGAATGACTTGGTTGAGTACTCACCAGTCACAG

4601 AAAAGCATATTACGGATGGCATGACAGTAAGAGAATTATGCAGTGCTGCC

4651 ATAACCATGAGTGATAACACTGCGGCCAACTTACTTCTGACAACGATCGG

4701 AGGACCGAAGGAGCTAACCGCTTTTTTGCACAACATGGGGGATCATGTAA

4751 CTCGCCTTGATCGTTGGGAACCGGAGCTGAATGAAGCCATACCAAACGAC

4801 GAGCGTGACACCACGATGCCTGTAGCAATGGCAACAACGTTGCGCAAACT

4851 ATTAACTGGCGAACTACTTACTCTAGCTTCCCGGCAACAATTAATAGACT

4901 GGATGGAGGCGGATAAAGTTGCAGGACCACTTCTGCGCTCGGCCCTTCCG

4951 GCTGGCTGGTTTATTGCTGATAAATCTGGAGCCGGTGAGCGTGGGTCTCG

5001 CGGTATCATTGCAGCACTGGGGCCAGATGGTAAGCCCTCCCGTATCGTAG

5051 TTATCTACACGACGGGGAGTCAGGCAACTATGGATGAACGAAATAGACAG

5101 ATCGCTGAGATAGGTGCCTCACTGATTAAGCATTGGTAACTGTCAGACCA

5151 AGTTTACTCATATATACTTTAGATTGATTTAAAACTTCATTTTTAATTTA

5201 AAAGGATCTAGGTGAAGATCCTTTTTGATAATCTCATGACCAAAATCCCT

5251 TAACGTGAGTTTTCGTTCCACTGAGCGTCAGACCCCGTAGAAAAGATCAA

5301 AGGATGTTCTTGAGATCCTTTTTTTCTGCACGTAATCTGCTGCTTGCAAA

5351 CAAAAAACCACCGCTACCAGCGGTGGTTTGTTTGCCGGATCAAGAGCTAC

5401 CAACTCTTTTTCCGAAGGTAACTGGCTTCAGCAGAGCGCAGATACCAAAT

5451 ACTGTCCTTCTAGTGTAGCCGTAGTTAGGCCACCACTTCAAGAACTCTGT

5501 AGCACCGCCTACATACCTCGCTCTGCTAATCCTGTTACCAGTGGCTGCTG

5551 CCAGTGGCGATAAGTCGTGTCTTACCGGGTTGGACTCAAGACGATAGTTA

5601 CCGGATAAGGCGCAGCGGTCGGGCTGAACGGGGGGTTCGTGCACACAGCC
```

TABLE 6-continued pREN ch806 LC Neo Vector

5651  CAGCTTGGAGCGAACGACCTACACCGAACTGAGATACCTACAGCGTGAGC

5701  TATGAGAAAGCGCCACGCTTCCCGAAGGGAGAAAGGCGGACAGGTATCCG

5751  GTAAGCGGCAGGGTCGGAACAGGAGAGCGCACGAGGGAGCTTCCAGGGGG

5801  AAACGCCTGGTATCTTTATAGTCCTGTCGGGTTTCGCCACCTCTGACTTG

5851  AGCGTCGATTTTTGTGATGCTCGTCAGGGGGCGGAGCCTATGGAAAAAC

5901  GCCAGCAACGCGGCCTTTTTACGGTTCCTGGCCTTTTGCTGGCCTTTTGC

5951  TCACATGTTCTTTCCTGCGTTATCCCCTGATTCTGTGGATAACCGTATTA

6001  CCGCCTTTGAGTGAGCTGATACCGCTCGCCGCAGCCGAACGACCGAGCGC

6051  AGCGAGTCAGTGAGCGAGGAAGCGGAAGAGCGCCCAATACGCAAACCGCC

6101  TCTCCCCGCGCGTTGGCCGATTCATTAATGCAGGTATCACGAGGCCCTTT

6151  CGTCTTCAC

The above nucleic acid sequence corresponds to SEQ ID NO:7. The above amino acid sequence including any underlined amino acid sequence, corresponds to the sequence of SEQ ID NO:9.

TABLE 7 pREN 806 HC DHFR Vector
    Xho I
   1  CTCGAGAGCGGGCAGTGAGCGCAACGCAATTAATGTGAGTTAGCTCACTC

52  ATTAGGCACCCCAGGCTTTACACTTTATGCTCCCGGCTCGTATGTTGTGT

EcoRI    EF1µ    promoter
 102  GGAGATTGTGAGCGGATAACAATTTCACACAGAATTCGTGAGGCTCCGGT

152  GCCCGTCAGTGGGCAGAGCGCACATCGCCCACAGTCCCCGAGAAGTTGGG

202  GGCAGGGGTCGGCAATTGAACCGGTGCCTAGAGAAGGTGGCGCGGGGTAA

252  ACTGGGAAAGTGATGTCGTGTACTGGCTCCGCCTTTTTCCCGAGGGTGGG

302  GGAGAACCGTATATAAGTGCAGTAGTCGCCGTGAACGTTCTTTTTCGCAA

352  CGGGTTTGCCGCCAGAACACAGGTAAGTGCCGTGTGTGGTTCCCGCGGGC

402  CTGCCCTCTTTACCGGTTATGGCCCTTGCGTGCCTTGAATTACTTCCACG

452  CCCCTGGCTGCAGTACGTGATTCTTGATCCCGAGCTTCGGGTTGGAAGTG

502  GGTGGGAGAGTTCGAGGCCTTGCGCTTAAGGAGCCCCTTCGCCTCGTGCT

552   TGAGTTGAGGCCTGGCCTGGGCGCTGGGGCCGCCGCGTGCGAATCTGGTG

602  GCACCTTCGCGCCTGTCTCGCTGCTTTCGATAAGTCTCTAGCCATTTAAA

652  ATTTTTGATGACCTGCTGCGACGCTTTTTTTCTGGCAAGATAGTCTTGTA

702  AATGCGGGCCAAGATCTGCACACTGGTATTTCGGTTTTTGGGGCCGCGGG

752  CGGCGACCGGGCCCGTGCGTCCCAGCGCACATGTTCGGCGAGGCGGGGCC

802  TGCGAGCGCGGCCACCGAGAATCGGACGGGGGTAGTCTCAAGCTGGCCGG

852  CCTGCTCTGGTGCCTGGCCTCGCGCCGCCGTGTATCGCCCCGCCCTGGGC

902  GGCAAGGCTGGCCCGGTCGGCACCAGTTGCGTGAGCGGAAAGATGGCCGC

952  TTCCCGGCCCTGCTGCAGGGAGCTCAAAATGGAGGACGCGGCGCTCGGGA

1002  GAGCGGGCGGGTGAGTCACCCACACAAAGGAAAAGGGCCTTTCCGTCCTC

TABLE 7-continued

```
1052 AGCCGTCGCTTCATGTGACTCCACGGAGTACCGGGCGCCGTCCAGGCACC

1102 TCGATTAGTTCTCGAGCTTTTGGAGTACGTCGTCTTTAGGTTGGGGGGAG

1152 GGGTTTTATGCGATGGAGTTTCCCCACACTGAGTGGGTGGAGACTGAAGT

1202 TAGGCCAGCTTGGCACTTGATGTAATTCTCCTTGGAATTTGCCCTTTTTG

1251 AGTTTGGATCTTGGTTCATTCTCAAGCCTCAGACAGTGGTTCAAAGTTTT

MluI        HindIII    PmeI
1302 TTTCTTCCATTTCAGGTGTACGCGTCTCGGGAAGCTTTAGTTTAAACGCC 1352 GCCACCATGAGAGTGCTGATTCTTTTGTGGCTGTTCACAGCCTTTCCTGGT
            M   R   V  L  I  L  L  W  L  F  T  A  F  P  G 1401 GTCCTGTCTGATGTGCAGCTTCAGGAGTCGGGACCTAGCCTGGTGAAACCT
      V  L  S  D  V  Q  L  Q  E  S  G  P  S  L  V  K  P 1451 TCTCAGACTCTGTCCCTCACCTGCACTGTCACTGGCTACTCAATCACCAGT
      S  Q  T  L  S  L  T  C  T  V  T  G  Y  S  I  T  S 1501 GATTTTGCCTGGAACTGGATCCGGCAGTTTCCAGGAAACAAGCTGGAGTGG
      D  F  A  W  N  W  I  R  Q  F  P  G  N  K  L  E  W 1551 ATGGGCTACATAAGTTATAGTGGTAACACTAGGTACAACCCATCTCTCAAA
      M  G  Y  I  S  Y  S  G  N  T  R  Y  N  P  S  L  K 1601 AGTCGAATCTCTATCACTCGAGACACATCCAAGAACCAATTCTTCCTGCAG
      S  R  I  S  I  T  R  D  T  S  K  N  Q  F  L  Q 1651 TTGAATTCTGTGACTATTGAGGACACAGCCACATATTACTGTGTAACGGCG
       L  N  S  V  T  I  E  D  T  A  T  Y  Y  C  V  T  A 1701 GGACGCGGGTTTCCTTATTGGGGCCAAGGGACTCTGGTCACTGTCTCTGCA
      G  R  G  F  P  Y  W  G  Q  G  T  L  V  T  V  S  A

1751 CAGTGAGTGGATCCTCTGCGCCTGGGCCCAGCTCTGTC

1801 CCACACCGCGGTCACATGGCACCACCTCTCTTGCAGCCTCCACCAAGGGC
                                              S  T  K  G

1851 CCATCGGTCTTCCCCCTGGCACCCTCCTCCAAGAGCACCTCTGGGGGCAC
     p  s  v  f  p  l  a  p  s  s  k  s  t  s  g  g  t

1901 AGCGGCCCTGGGCTGCCTGGTCAAGGACTACTTCCCCGAACCGGTGACGG
      A  A  L  G  C  L  V  K  D  Y  F  P  E  P  V  T  V

1951 TGTCGTGGAACTCAGGCGCCCTGACCAGCGGCGTGCACACCTTCCCGGCT
     s  w  n   s  g   a  l  t  s  g  v   h  t   f  p   a

2001 GTCCTACAGTCCTCAGGACTCTACTCCCTCAGCAGCGTGGTGACCGTGCC
     v  l   q  s   s  g   l  y   s  l   s  s  v  y  s  v  p

2051 CTCCAGCAGCTTGGGCACCCAGACCTACATCTGCAACGTGAATCACAAGC
         S  S  S  L  G  T  Q  T  Y  I  C  N  V  N  H  K  P

2101 CCAGCAACACCAAGGTGGACAAGAAAGTTGAGCCCAAATCTTGTGACAAA
         S  N  T  K  V  D  K  K  V  E  P  K  S  C  D  K

2151 ACTCACACATGCCCACCGTGCCCAGCACCTGAACTCCTGGGGGGACCGTC
         T  H  T  C  P  P  C  P  A  P  E  L  L  C  G  P  S

2201 AGTCTTCCTCTTCCCCCCAAAACCCAACGACACCCTCATGATCTCCCGGA
         V  F  L  F  P  P  K  P  K  D  T  L  M  I  S  R  T

2251 CCCCTGAGGTCACATGCGTGGTGGTCGACGTGAGCCACGAACACCCTGAG
         P  E  V  T  C  V  V  V  D  V  S  H  E  D  P  E

2301 GTCAAGTTCAACTGCTACGTGGACGCCCTGCAGGTGCATAACGCCAACAC
         V  K  F  N  W  Y  V  D  C  V  E  V  H  N  A  K  T
```

TABLE 7-continued

```
2351 AAACCCCCGGACCACCAGTACAACAGCACGTACCGCGTGCTCAGCGTCC
      K  P  R  E  E  Q  Y  N  S  T  Y  R  V  V  S  V  L

2401 TCACCCTCCTCCACCAGCACTGGCTGAATGCCAAGCACTACAAGTGCAAG
       T  V  L  H  Q  D  W  L  N  G  K  E  Y  K  C  K

2451 GTCTCCAACAAAGCCCTCCCAGCCCCCATCGAGAAAACCATCTCCAAAGC
      V  S  N  K  A  L  P  A  P  I  E  K  T  I  S  K  A

2501 CAAAGGGCAGCCCCGAGAACCACAGGTGTACACCCTGCCCCCATCCCGGG
       K  G  Q  P  R  E  P  Q  V  Y  T  L  P  P  S  R  E

2551 AGGAGATGACCAAGAACCAGGTCAGCCTGACCTGCCTGGTCAAAGGCTTC
       E  M  T  K  N  Q  V  S  L  T  C  L  V  K  G  F

2601 TATCCCAGCGACATCGCCGTGGAGTGGGAGAGCAATGGGCAGCCGCAGAA
      Y  P  S  D  I  A  V  E  W  E  S  N  G  Q  P  E  N

2651 CAACTACAACACCACGCCTCCCGTGCTGGACTCCGACGGCTCCTTCTTCC
       N  Y  K  T  T  P  P  V  L  D  S  D  G  S  F  F  L

2701 TCTACAGCAAGCTCACCGTGGACAAGAGCAGGTGGCAGCAGGGGAACGTC
       Y  S  K  L  T  V  D  K  S  R  W  Q  Q  G  N  V

2751 TTCTCATGCTCCGTGATGCATGAGGCTCTGCACAACCACTACACGCAGAA
       F  S  C  S  V  M  H  E  A  L  H  N  H  Y  T  Q  K

Nhe/Xba
2801 GAGCCTCTCCCTGTCTCCGGGTAAATGAGCTAGAAACTAACTAAGCTAGC
      S  L  S  L  S  P  G  K  *

2851 AACGGTTTCCCTCTAGCGGGATCAATTCCGCCCCCCCCCCCTAACGTTAC

2901 TGGCCGAAGCCGCTTGGAATAAGGCCGGTGTGCGTTTGTCTATATGTTAT

2951 TTTCCACCATATTGCCGTCTTTTGGCAATGTGAGGGCCCGGAAACCTGGC

3001 CCTGTCTTCTTGACGAGCATTCCTAGGGGTCTTTCCCCTCTCGCCAAAGG

3051 AATGCAAGGTCTGTTGAATGTCGTGAAGGAAGCAGTTCCTCTGGAAGCTT

3101 CTTGAAGACAAACAACGTCTGTAGCGACCCTTTGCAGGCAGCGGAACCCC

3151 CCACCTGGCGACAGGTGCCTCTGCGGCCAAAAGCCACGTGTATAAGATAC

3201 ACCTGCAAAGGCGGCACAACCCCAGTGCCACGTTGTGAGTTGGATAGTTG

3251 TGGAAAGAGTCAAATGGCTCTCCTCAAGCGTATTCAACAAGGGGCTGAAG

3301 GATGCCCAGAAGGTACCCCATTGTATGGGATCTGATCTGGGGCCTCGGTG

3351 CACATGCTTTACGTGTGTTTAGTCGAGGTTAAAAAACGTCTAGGCCCCCC

3401 GAACCACGGGGACGTGGTTTTCCTTTGAAAAACACGATAATACCATGGTT

3451 CGACCATTGAACTGCATCGTCGCCGTGTCCCAAAATATGGGGATTGGCAA

3501 GAACGGAGACCTACCCTGGCCTCCGCTCAGGAACGAGTTCAAGTACTTCC

3551 AAAGAATGACCACAACCTCTTCAGTGGAAGGTAAACAGAATCTGGTGATT

3601 ATGGGTAGGAAAACCTGGTTCTCCATTCCTGAGAAGAATCGACCTTTAAA

3651 GGACAGAATTAATGGTTCGATATAGTTCTCAGTAGAGAACTCAAAGAACC

3701 ACCACGAGGAGCTCATTTTCTTGCCAAAAGTTTGGATGATGCCTTAAGAC

3751 TTATTGAACAACCGGAATTGGCAAGTAAAGTAGACATGGTTTGGATAGTC

3801 GGAGGCAGTTCTGTTTACCAGGAAGCCATGAATCAACCAGGCCACCTCAG

3851 ACTCTTTGTGACAAGGATCATGCAGGAATTTGAAAGTGACACGTTTTTCC

3901 CAGAAATTGATTTGGGGAAATATAAACTTCTCCCAGAATACCCAGGCGTC

3951 CTCTCTGAGGTCCAGCAGGAAAAAGGCATCAAGTATAAGTTTGAAGTCTA

4001 CGAGAAGAAAGACTAACAGGAAGATGCTTTCAAGTTCTCTGCTCCCCTCC
                                                   Blunt end
```

TABLE 7-continued

```
SalI/SalI
4051 TAAAGCTATGCATTTTTATAAGACCATGGGACTTTTGCTGGTCGATCGAC

4101 CTGGCGTAATAGCGAAGAGGCCCGCACCGATCGCCCTTCCCAACAGTTGC

4151 GCACCCTGAATGGCGAATGGGACGCGCCCTGTAGCGGCGCATTAAGCGCG

4201 GCGGGTGTGGTGGTTACGCGCAGCGTGACCGCTACACTTGCCAGCGCCCT

4251 AGCGCCCGCTCCTTTCGCTTTCTTCCCTTCCTTTCTCGCCACGTTCGCCG

4301 GCTTTCCCCGTCAAGCTCTAAATCGGGGGCTCCCTTTAGGGTTCCGATTT

4351 AGTGCTTTACGGCACCTCGACCCCAAAAAACTTGATTAGGGTGATGGTTC

4401 ACGTAGTGGGCCATCGCCCTGATAGACGGTTTTTCGCCTTTGACGTTGGA

4451 GTCCACGTTCTTTAATAGTCGACTCTTGTTCCAAACTGGAACAACACTCA

4501 ACCCTATCTCGGTCTATTTATAAGGGATTTTGCCGATTTCGGCCTATTGG

4551 TTAAAAAATGAGCTGATTTAACAAAATTTAACGCGAATTTTAACAAAATA

4601 TTAACGCTTACAATTTAGGTGGCACTTTTCGGGGAAATGTGCGCGGAACC

4651 CCTATATTTGTTTATTTTTCTAAATACATTCAAATATGTATCCGCTCATG

4701 AGACAATAACCCTGATAAATGCTTCAATAATATTGAAAAAGGAAGAGTAT

4751 GAGTATTCAACATTTCCGTGTCGCCCTTATTCCCTTTTTTGCGGCATTTT

4801 GCCTTACTGTTTTTGCTCACCCAGAAACGCTGGTGAAAGTAAAAGATGCT

4851 GAAGATCAGTTGGGTGCACGAGTGGGTTACATCGAACTGGATCTCAACAG

4901 CGGTAAGATCCTTGAGAGTTTTCGCCCCGAAGAACGTTTTCCAATGATGA

4951 GCACTTTTAAAGTTCTGCTATGTGGCGCGGTATTATCCCGTATTGACGCC

5001 GGGCAAGAGCAACTCGGTCGCCGCATACACTATTCTCAGAATGACTTGGT

5051 TGAGTACTCACCAGTCACAGAAAAGCATATTACGGATGGCATGACAGTAA

5101 GAGAATTATGCAGTGCTGCCATAACCATGAGTGATAACACTGCGGCCAAC

5151 TTACTTCTGACAACGATCGGAGGACCGAAGGAGCTAACCGCTTTTTTGCA

5201 CAACATGGGGGATCATGTAACTCGCCTTGATCGTTGGGAACCGGAGCTGA

5251 ATGAAGCCATACCAAACGACGAGCGTGACACCACGATCCCTGTAGCAATG

5301 GCAACAACGTTGCGCAAACTATTAACTGGCGAACTACTTACTCTAGCTTC

5351 CCGGCAACAATTAATAGACTGGATGGAGGCGGATAAAGTTGCAGGACCAC

5401 TTCTGCGCTCGGCCCTTCCGGCTGGCTGGTTTATTGCTGATAAATCTGGA

5451 GCCGGTGAGCGTGGGTCTCGCGGTATCATTGCAGCACTGGGGCCACATGG

5501 TAAGCCCTCCCGTATCGTAGTTATCTACACGACGGGGAGTCAGGCAACTA

5551 TGGATGAACGAAATAGACAGATCGCTGAGATAGGTGCCTCACTGATTAAG

5601 CATTGGTAACTGTCAGACCAAGTTTACTCATATATACTTTAGATTGATTT

5651 AAAACTTCATTTTTAATTTAAAAGGATCTAGGTGAAGATCCTTTTTGATA

5701 ATCTCATGACCAAAATCCCTTAACGTGAGTTTTCGTTCCACTGAGCGTCA

5751 GACCCCGTAGAAAAGATCAAAGGATGTTCTTGAGATCCTTTTTTTCTGCA

5801 CGTAATCTGCTGCTTGCAAACAAAAAACCACCGCTACCAGCGGTGGTTTG

5851 TTTGCCGGATCAAGAGCTACCAACTCTTTTTCCGAAGGTAACTGGCTTCA

5901 CCAGAGCGCAGATACCAAATACTGTCCTTCTAGTGTAGCCGTAGTTAGGC

5951 CACCACTTCAAGAACTCTGTAGCACCGCCTACATACCTCGCTCTGCTAAT
```

TABLE 7-continued

```
6001  CCTGTTACCAGTGGCTGCTGCCAGTGGCGATAACTCGTGTCTTACCGGGT

6051  TGGACTCAAGACGATAGTTACCGGATAAGGCGCAGCGGTCGGGCTGAACG

6101  GGGGGTTCGTGCACACAGCCCAGCTTGGAGCGAACGACCTACACCGAACT

6151  GAGATACCTACAGCGTGAGCTATGAGAAAGCGCCACGCTTCCCGAAGGGA

6201  GAAAGGCGGACAGGTATCCGGTAAGCGGCAGGGTCGGAACAGGAGAGCGC

6251  ACGAGGGAGCTTCCAGGGGAAACGCCTGGTATCTTTATAGTCCTGTCGG

6301  GTTTCGCCACCTCTGACTTGAGCGTCGATTTTTGTGATGCTCGTCAGGGG

6351  GGCGGAGCCTATGGAAAAACGCCAGCAACGCGGCCTTTTTACGGTTCCTG

6401  GCCTTTTGCTGGCCTTTTGCTCACATGTTCTTTCCTGCGTTATCCCCTGA

6451  TTCTGTGGATAACCGTATTACCGCCTTTGAGTGAGCTGATACCGCTCGCC

6501  GCAGCCGAACGACCGAGCGCAGCGAGTCAGTGAGCGAGGAAGCGGAAGAG

6551  CGCCCAATACGCAAACCGCCTCTCCCCGCGCGTTGGCCGATTCATTAATG

6601  CAGGTATCACGAGGCCCTTTCGTCTTCAC
```

The above nucleic acid sequence corresponds to SEQ ID NO:8. The above amino acid sequence, including any underlined amino acid sequence, corresponds to the sequence of SEQ ID NO:10.

---

What is claimed is:

1. An antibody capable of binding EGFR on tumors containing amplifications of the EGFR gene, wherein cells of the tumor contain multiple copies of the EGFR gene, and on tumors that express the truncated version of the EGFR receptor de2-7, wherein said antibody does not bind to the de2-7 EGFR junctional peptide consisting of the amino acid sequence of SEQ ID NO: 13, wherein said antibody comprises a heavy chain and light chain and the heavy chain variable region sequence comprises polypeptide binding domain CDRs corresponding to amino acids 26-36, 50-65, and 97-105 of SEQ ID NO: 11 and the light chain variable region sequence comprises polypeptide binding domain CDRs corresponding to residues 24-34, 50-56, and 89-97 of SEQ ID NO: 12.

2. The antibody of claim 1 which is humanized or chimerized.

3. An F (ab')$_2$ or scFv fragment of an antibody according to claim 1.

4. An antibody according to claim 1 which carries a detectable or functional label.

* * * * *

UNITED STATES PATENT AND TRADEMARK OFFICE
CERTIFICATE OF CORRECTION

PATENT NO. : 7,589,180 B2
APPLICATION NO. : 10/145598
DATED : September 15, 2009
INVENTOR(S) : L. J. Old et al.

It is certified that error appears in the above-identified patent and that said Letters Patent is hereby corrected as shown below:

Title page, Item (73)
Assignee, "Abbott Laboratories Inc." should read -- Ludwig Institute for Cancer Research --.

Signed and Sealed this
Eleventh Day of January, 2011

David J. Kappos
*Director of the United States Patent and Trademark Office*